United States Patent
Olivera et al.

(10) Patent No.: US 6,727,226 B2
(45) Date of Patent: Apr. 27, 2004

(54) MU-CONOPEPTIDES

(75) Inventors: Baldomero M. Olivera, Salt Lake City, UT (US); J. Michael McIntosh, Salt Lake City, UT (US); James E. Garrett, Salt Lake City, UT (US); Lourdes J. Cruz, Manila (PH); Robert M. Jones, Salt Lake City, UT (US); G. Edward Cartier, Salt Lake City, UT (US); John D. Wagstaff, Salt Lake City, UT (US)

(73) Assignees: University of Utah Research Foundation, Salt Lake City, UT (US); Cognetix, Inc., Salt Lake City, UT (US)

( * ) Notice: Subject to any disclaimer, the term of this patent is extended or adjusted under 35 U.S.C. 154(b) by 0 days.

(21) Appl. No.: 09/910,009

(22) Filed: Jul. 23, 2001

(65) Prior Publication Data

US 2003/0050234 A1 Mar. 13, 2003

Related U.S. Application Data

(60) Provisional application No. 60/277,270, filed on Mar. 21, 2001, provisional application No. 60/264,319, filed on Jan. 29, 2001, provisional application No. 60/245,157, filed on Nov. 3, 2000, and provisional application No. 60/219,619, filed on Jul. 21, 2000.

(51) Int. Cl.[7] .................. C07K 7/08; C07K 14/435; A61K 38/10
(52) U.S. Cl. .............. 514/13; 514/2; 530/326; 530/300
(58) Field of Search ................ 530/300, 326; 514/2, 13

(56) References Cited

U.S. PATENT DOCUMENTS 5,670,622 A  9/1997  Shon et al. ............... 530/324

OTHER PUBLICATIONS

McIntosh et al. Conus peptides as probes for Ion channels. 1999. Methods in Enzymology 294: 605–624.*
Cruz, L.J. et al. (1985). "*Conus geographics* Toxins That Discriminate Between Neuronal and Muscle Sodium Channels," *J. Biol. Chem.* 260(16), Aug. 5, pp. 9280–9288.
Fainzilber, M. et al. (1995). "A New Cysteine Framework in Sodium Channel Blocking Conotoxins," *Biochemistry* 34:8649–8656.
Shon, K–J. et al. (1998). "μ–Conotoxin PIIIA, a New Peptide for Discriminating Among Tetrodotoxin–Sensitive Na Channel Subtypes," *J. Neurosci.* 18(12), Jun. 15, 1998:4473–4481.
Jones, R.M. et al. (2000). "Conus peptides—Combinatorial Chemistry at a Cone Snail's Pace," *Current Opn. Drug Discov& Devel.* 3(2):141–154.
Nakamura, M. et al. (2001). "Modification of Arg–13 of μ–Conotoxin GIIIA with Piperidinyl–Arg Analogs and Their Relation to the Inhibition of Sodium Channels," *FEBS Letters.* 503:107–110.
West, P.J. et al. (2002). "μu–Conotoxin SmIIA, a Potent Inhibitor of Tetrodotoxin–Resistant Sodium Channels in Amphibian Sympathetic and Sensory Neurons," *Biochem.* 41:15388–15393.
Waxman, S.G. et al. (2000). "Voltage–gated sodium channels and the molecular pathogenesis of pain: A review," *J. Rehabil. Res. Devel.* 37(5):517–528.
Wakamatsu, K. et al. (1992). "Structure–Activity Relationships of μ–Conotoxin GIIIA: Structure Determination of Active and Inactive Sodium Channel Blocker Peptides by NMR and Simulated Annealing Calculations," *Biochemistry* 31:12577–12584.
Olivera, B.M. et al. (1990). "Diversity of *Conus* Neuropeptides," *Science* 249:257–263.
Cruz, L.J. et al. (1989). "μ–Conotoxin GIIIA, aPeptide Ligand for Muscle Sodium Channels: Chemical Synthesis, Radiolabeling, and Receptor Characterization," *Biochemistry* 28: 3437–3442.
Olivera, B.M. et al. (1985). "Peptide Neurotoxins from Fish–Hunting Cone Snails," *Science* 230:1338–1343.

* cited by examiner

*Primary Examiner*—Gabriele Bugaisky
(74) *Attorney, Agent, or Firm*—Rothwell, Figg, Ernst & Manbeck, p.c.

(57) ABSTRACT

The present invention is to μ-conopeptides, derivatives or pharmaceutically acceptable salts thereof. The present invention is further directed to the use of this peptide, derivatives thereof and pharmaceutically acceptable salts thereof for the treatment of disorders associated with voltage-gated sodium channels. Thus, the μ-conopeptides or derivatives are useful as neuromuscular blocking agents, local anesthetic agents, analgesic agents and neuroprotective agents. The μ-conopeptides are also useful for treating neuromuscular disorders. The invention is further directed to nucleic acid sequences encoding the μ-conopeptides and encoding propeptides, as well as the propeptides.

18 Claims, No Drawings

SEQUENCE LISTING

<160> NUMBER OF SEQ ID NOS: 520

<210> SEQ ID NO 1
<211> LENGTH: 280
<212> TYPE: DNA
<213> ORGANISM: Conus arentus

<400> SEQUENCE: 1
caagaaggat cgatagcagt tcatgatgtc taaactggga gtcttcttga ccatctgtat     60
gcttctgttt ccccttactg ctcttccgct ggatggggat caacctgcag accgacctgc    120
agagcgtatg caggacgact ttataactga gcatcatccc ctgtttgatc ctgtcaaacg    180
gtgttgcgag aggccatgca acataggatg cgtaccttgt tgttaatgac cagctttgtc    240
atcgcggcct catcaagcga ataagtaaaa cgattgcagt                          280

<210> SEQ ID NO 2
<211> LENGTH: 67
<212> TYPE: PRT
<213> ORGANISM: Conus arentus

<400> SEQUENCE: 2

Met Met Ser Lys Leu Gly Val Phe Leu Thr Ile Cys Met Leu Leu Phe
1               5                   10                  15

Pro Leu Thr Ala Leu Pro Leu Asp Gly Asp Gln Pro Ala Asp Arg Pro
            20                  25                  30

Ala Glu Arg Met Gln Asp Asp Phe Ile Thr Glu His His Pro Leu Phe
        35                  40                  45

Asp Pro Val Lys Arg Cys Cys Glu Arg Pro Cys Asn Ile Gly Cys Val
    50                  55                  60

Pro Cys Cys
65

<210> SEQ ID NO 3
<211> LENGTH: 14
<212> TYPE: PRT
<213> ORGANISM: Conus arentus
<220> FEATURE:
<221> NAME/KEY: PEPTIDE
<222> LOCATION: (1)..(14)
<223> OTHER INFORMATION: Xaa at residue 3 is Glu or gamma-carboxy Glu;
      Xaa at residue 5 an d 12 is Pro or Hyp

<400> SEQUENCE: 3

Cys Cys Xaa Arg Xaa Cys Asn Ile Gly Cys Val Xaa Cys Cys
1               5                   10

<210> SEQ ID NO 4
<211> LENGTH: 244
<212> TYPE: DNA
<213> ORGANISM: Conus atlanticus

<400> SEQUENCE: 4
ggatccatga tgtctaaact gggagtcttg ttgaccatct gtctgcttct gtttccactt     60
actgctcttc cgctggatga agatcaaccg gtacaccgac tgcagagcg tatgcaggac    120 atttcatctg atcaacatct cttctttgat ctcatcaaac ggtgctgcga gttgccatgc    180
gggccaggct tttgcgtccc ttgttgctga catcaataac gtgttgatga ccaactttct    240
cgag                                                                 244

```
<210> SEQ ID NO 5
<211> LENGTH: 69
<212> TYPE: PRT
<213> ORGANISM: Conus atlanticus

<400> SEQUENCE: 5
```

Gly Ser Met Met Ser Lys Leu Gly Val Leu Leu Thr Ile Cys Leu Leu
1               5                   10                  15

Leu Phe Pro Leu Thr Ala Leu Pro Leu Asp Glu Asp Gln Pro Val His
            20                  25                  30

Arg Pro Ala Glu Arg Met Gln Asp Ile Ser Ser Asp Gln His Leu Phe
        35                  40                  45

Phe Asp Leu Ile Lys Arg Cys Cys Glu Leu Pro Cys Gly Pro Gly Phe
    50                  55                  60

Cys Val Pro Cys Cys
65

```
<210> SEQ ID NO 6
<211> LENGTH: 15
<212> TYPE: PRT
<213> ORGANISM: Conus atlanticus
<220> FEATURE:
<221> NAME/KEY: PEPTIDE
<222> LOCATION: (1)..(15)
<223> OTHER INFORMATION: Xaa at residue 3 is Glu or gamma-carboxy Glu;
      Xaa at residue 5, 8 and 13 is Pro or Hyp

<400> SEQUENCE: 6
```

Cys Cys Xaa Leu Xaa Cys Gly Xaa Gly Phe Cys Val Xaa Cys Cys
1               5                   10                  15

```
<210> SEQ ID NO 7
<211> LENGTH: 310
<212> TYPE: DNA
<213> ORGANISM: Conus aurisiacus

<400> SEQUENCE: 7
```
caagagggat cgatagcagt tcatgatgtc taaactggga gtcttgttga ccatctgttt      60
gcttctgttt ccccttactg ctcttccgat ggatggagat caatctgtag accgacctga     120
agagcgtatg caggacgaca tttcatctga gcagcatccc ttgtttaatc agaaaagaat     180
gtgttgcggc gaaggccgga aatgccccag ctatttcaga aacagtcaga tttgtcattg     240
ttgttaaatg acaacgtgtc gatgaccaac ttcgttatca cgactaatga ataagtaaaa     300
cgattgcagt                                                            310

```
<210> SEQ ID NO 8
<211> LENGTH: 74
<212> TYPE: PRT
<213> ORGANISM: Conus aurisiacus

<400> SEQUENCE: 8
```

Met Met Ser Lys Leu Gly Val Leu Leu Thr Ile Cys Leu Leu Leu Phe
1               5                   10                  15

Pro Leu Thr Ala Leu Pro Met Asp Gly Asp Gln Ser Val Asp Arg Pro
            20                  25                  30

Glu Glu Arg Met Gln Asp Asp Ile Ser Ser Glu Gln His Pro Leu Phe
        35                  40                  45

Asn Gln Lys Arg Met Cys Cys Gly Glu Gly Arg Lys Cys Pro Ser Tyr
    50                  55                  60

```
Phe Arg Asn Ser Gln Ile Cys His Cys Cys
65                  70
```

<210> SEQ ID NO 9
<211> LENGTH: 22
<212> TYPE: PRT
<213> ORGANISM: Conus aurisiacus
<220> FEATURE:
<221> NAME/KEY: PEPTIDE
<222> LOCATION: (1)..(22)
<223> OTHER INFORMATION: Xaa at residue 5 is Glu or gamma-carboxy Glu;
    Xaa at residue 10 is Pro or Hyp; Xaa at residue 12 is Tyr,
    125I-Tyr, mono-iodo-Tyr, di-iodo-Tyr, O-sulpho-Tyr or
    O-phospho-Tyr

<400> SEQUENCE: 9

```
Met Cys Cys Gly Xaa Gly Arg Lys Cys Xaa Ser Xaa Phe Arg Asn Ser
1               5                   10                  15

Gln Ile Cys His Cys Cys
            20
```

<210> SEQ ID NO 10
<211> LENGTH: 257
<212> TYPE: DNA
<213> ORGANISM: Conus aurisiacus

<400> SEQUENCE: 10

```
ggatccatga tgtctaaact gggagtcttg ttgaccatct gtttgcttct gtttcccctt     60
actgctcttc cgatcgatgg agatcaatct gtagaccgac ctgcagagcg tatgcaggat    120
gacatttcat ctgagcagca tcgcttgttc aatcagaaaa gaaggtgctg ccggtggcca    180
tgcccccgac aaatcgacgg tgaatattgt ggctgttgcc ttggatgata accgtgttga    240
tgaccaactt tctcgag                                                   257
```

<210> SEQ ID NO 11
<211> LENGTH: 75
<212> TYPE: PRT
<213> ORGANISM: Conus aurisiacus

<400> SEQUENCE: 11

```
Gly Ser Met Met Ser Lys Leu Gly Val Leu Leu Thr Ile Cys Leu Leu
1               5                   10                  15

Leu Phe Pro Leu Thr Ala Leu Pro Ile Asp Gly Asp Gln Ser Val Asp
            20                  25                  30

Arg Pro Ala Glu Arg Met Gln Asp Asp Ile Ser Ser Glu Gln His Arg
        35                  40                  45

Leu Phe Asn Gln Lys Arg Arg Cys Cys Arg Trp Pro Cys Pro Arg Gln
    50                  55                  60

Ile Asp Gly Glu Tyr Cys Gly Cys Cys Leu Gly
65                  70                  75
```

<210> SEQ ID NO 12
<211> LENGTH: 19
<212> TYPE: PRT
<213> ORGANISM: Conus aurisiacus
<220> FEATURE:
<221> NAME/KEY: PEPTIDE
<222> LOCATION: (1)..(19)
<223> OTHER INFORMATION: Xaa at residue 13 is Glu or gamma-carboxy Glu;
    Xaa at residue 5 and 7 is Pro or Hyp; Xaa at residue 4 is Trp or
    Bromo Trp; Xaa at residue 14 is Tyr, 125I-Tyr, mono-iodo-Tyr,
    di-iodo-Tyr, O-sulpho-Tyr or O-phospho-Tyr

<400> SEQUENCE: 12

Cys Cys Arg Xaa Xaa Cys Xaa Arg Gln Ile Asp Gly Xaa Xaa Cys Gly
1               5                   10                  15

Cys Cys Leu

<210> SEQ ID NO 13
<211> LENGTH: 262
<212> TYPE: DNA
<213> ORGANISM: Conus aurisiacus

<400> SEQUENCE: 13
ggatccatga tgtctaaact gggagtcttg ttgaccatct gtctacttct gtttcccctt      60
actgcttttc cgatggatgg agatcaacct gcagaccaac ctgcagatcg tatgcaggac     120
gacatttcat ctgagcagta tcccttgttt gataagagac aaaagtgttg cactgggaag     180 aagggtcat gctccggcaa agcatgcaaa aatctcaaat gttgctctgg acgataacgt      240
gttgatgacc aactttctcg ag                                             262

<210> SEQ ID NO 14
<211> LENGTH: 78
<212> TYPE: PRT
<213> ORGANISM: Conus aurisiacus

<400> SEQUENCE: 14

Gly Ser Met Met Ser Lys Leu Gly Val Leu Leu Thr Ile Cys Leu Leu
1               5                   10                  15

Leu Phe Pro Leu Thr Ala Phe Pro Met Asp Gly Asp Gln Pro Ala Asp
                20                  25                  30

Gln Pro Ala Asp Arg Met Gln Asp Asp Ile Ser Ser Glu Gln Tyr Pro
            35                  40                  45

Leu Phe Asp Lys Arg Gln Lys Cys Cys Thr Gly Lys Lys Gly Ser Cys
        50                  55                  60

Ser Gly Lys Ala Cys Lys Asn Leu Lys Cys Cys Ser Gly Arg
65                  70                  75

<210> SEQ ID NO 15
<211> LENGTH: 23
<212> TYPE: PRT
<213> ORGANISM: Conus aurisiacus
<220> FEATURE:
<221> NAME/KEY: PEPTIDE
<222> LOCATION: (1)..(23)
<223> OTHER INFORMATION: Xaa at residue 1 is Gln or pyro-Glu

<400> SEQUENCE: 15

Xaa Lys Cys Cys Thr Gly Lys Lys Gly Ser Cys Ser Gly Lys Ala Cys
1               5                   10                  15

Lys Asn Leu Lys Cys Cys Ser
            20

<210> SEQ ID NO 16
<211> LENGTH: 232
<212> TYPE: DNA
<213> ORGANISM: Conus aurisiacus

<400> SEQUENCE: 16
ggatccatga tgtctaaact gggagtcttg ctgaccatct gtctgcttct gtttccactt      60
actgctgttc cgctggatgg agatcaacct ctagaccgac acgcggagcg tatgcatgat     120
ggcatttcac ctaaacgcca tccctggttt gatcccgtca acggtgttg caaggtgcaa      180

```
tgcgagtctt gcacccettg ttgctaacgt gttgatgacc aactttctcg ag         232
```

```
<210> SEQ ID NO 17
<211> LENGTH: 68
<212> TYPE: PRT
<213> ORGANISM: Conus aurisiacus

<400> SEQUENCE: 17
```

Gly Ser Met Met Ser Lys Leu Gly Val Leu Leu Thr Ile Cys Leu Leu
1               5                   10                  15

Leu Phe Pro Leu Thr Ala Val Pro Leu Asp Gly Asp Gln Pro Leu Asp
            20                  25                  30

Arg His Ala Glu Arg Met His Asp Gly Ile Ser Pro Lys Arg His Pro
        35                  40                  45

Trp Phe Asp Pro Val Lys Arg Cys Cys Lys Val Gln Cys Glu Ser Cys
    50                  55                  60

Thr Pro Cys Cys
65

```
<210> SEQ ID NO 18
<211> LENGTH: 13
<212> TYPE: PRT
<213> ORGANISM: Conus aurisiacus
<220> FEATURE:
<221> NAME/KEY: PEPTIDE
<222> LOCATION: (1)..(13)
<223> OTHER INFORMATION: Xaa at residue 7 is Glu or gamma-carboxy Glu;
      Xaa at residue 11 is Pro or Hyp

<400> SEQUENCE: 18
```

Cys Cys Lys Val Gln Cys Xaa Ser Cys Thr Xaa Cys Cys
1               5                   10

```
<210> SEQ ID NO 19
<211> LENGTH: 241
<212> TYPE: DNA
<213> ORGANISM: Conus bandus

<400> SEQUENCE: 19
ggatccatga tgtctaaact gggagtcttg ttgaccatct gtatgcttct gtttccctc    60 actgctcttc cgatggatgg agatcaacct gcagaccgac ctgcagagcg tagtcaggac  120
gtttcatctg aacagcatcc cttgtttgat cccgtcaaac ggtgttgcaa ctggccatgc  180
tccatgggat gcatcccttg ttgctactat taataacgtg ttgatgacca actttctcga  240
g                                                                  241
```

```
<210> SEQ ID NO 20
<211> LENGTH: 70
<212> TYPE: PRT
<213> ORGANISM: Conus bandus

<400> SEQUENCE: 20
```

Gly Ser Met Met Ser Lys Leu Gly Val Leu Leu Thr Ile Cys Met Leu
1               5                   10                  15

Leu Phe Pro Leu Thr Ala Leu Pro Met Asp Gly Asp Gln Pro Ala Asp
            20                  25                  30

Arg Pro Ala Glu Arg Ser Gln Asp Val Ser Ser Glu Gln His Pro Leu
        35                  40                  45

Phe Asp Pro Val Lys Arg Cys Cys Asn Trp Pro Cys Ser Met Gly Cys
    50                  55                  60

```
Ile Pro Cys Cys Tyr Tyr
65                  70

<210> SEQ ID NO 21
<211> LENGTH: 16
<212> TYPE: PRT
<213> ORGANISM: Conus bandus
<220> FEATURE:
<221> NAME/KEY: PEPTIDE
<222> LOCATION: (1)..(16)
<223> OTHER INFORMATION: Xaa at residue 5 and 12 is Pro or Hyp; Xaa at
      residue 4 is Trp or bromo-Trp; Xaa at residue 15 and 16 is Tyr,
      125I-Tyr, mono-iodo-Tyr, di-iodo-Tyr, O-sulpho-Tyr or
      O-phospho-Tyr

<400> SEQUENCE: 21

Cys Cys Asn Xaa Xaa Cys Ser Met Gly Cys Ile Xaa Cys Cys Xaa Xaa
1               5                   10                  15

<210> SEQ ID NO 22
<211> LENGTH: 298
<212> TYPE: DNA
<213> ORGANISM: Conus betulinus

<400> SEQUENCE: 22
caagagggat cgatagcagt tcatgatgtc taaactggga gtcttgttga ccttctgtct    60
gcttctgttt ccctgactg ctcttccgct ggatgaagat caacctgcag accgacctgc   120
agagcgtatg caggacattt catctgaaca gcatcccttg tttgatcccg tcaaacggtg   180
ttgcgaattg ccatgccatg gatgcgtccc ttgttgctgg ccttaataac gtgtggatga   240
ccaactgtgt tatcacggcc ac

<210> SEQ ID NO 25
<211> LENGTH: 298
<212> TYPE: DNA
<213> ORGANISM: Conus betulinus

<400> SEQUENCE: 25

```
caagagggat cgatagcagt tcatgatgtc taaactggga gtcttgttga ccttctgtct     60
gcttctgttt cccctgactg ctcttccgct ggatgaagat caacctgcag accgacatgc    120
agagcgtatg caggacattt cacctgaaca gcatccctcg tttgatcccg tcaaacggtg    180
ttgcgggctg ccatgcaatg gatgcgtccc ttgttgctgg ccttcataac gtgtggacga    240
ccaactttgt tatcacggcc acgtcaagtg tctgatgaat aagtaaaacg attgcagt      298
```

<210> SEQ ID NO 26
<211> LENGTH: 68
<212> TYPE: PRT
<213> ORGANISM: Conus betulinus

<400> SEQUENCE: 26

```
Met Met Ser Lys Leu Gly Val Leu Leu Thr Phe Cys Leu Leu Leu Phe
1               5                   10                  15

Pro Leu Thr Ala Leu Pro Leu Asp Glu Asp Gln Pro Ala Asp Arg His
            20                  25                  30

Ala Glu Arg Met Gln Asp Ile Ser Pro Glu Gln His Pro Ser Phe Asp
        35                  40                  45

Pro Val Lys Arg Cys Cys Gly Leu Pro Cys Asn Gly Cys Val Pro Cys
    50                  55                  60

Cys Trp Pro Ser
65
```

<210> SEQ ID NO 27
<211> LENGTH: 16
<212> TYPE: PRT
<213> ORGANISM: Conus betulinus
<220> FEATURE:
<221> NAME/KEY: PEPTIDE
<222> LOCATION: (1)..(16)
<223> OTHER INFORMATION: Xaa at residue 5, 11 and 15 is Pro or Hyp;
      Xaa at residue 14 is Trp or bromo-Trp

<400> SEQUENCE: 27

```
Cys Cys Gly Leu Xaa Cys Asn Gly Cys Val Xaa Cys Cys Xaa Xaa Ser
1               5                   10                  15
```

<210> SEQ ID NO 28
<211> LENGTH: 282
<212> TYPE: DNA
<213> ORGANISM: Conus betulinus

<400> SEQUENCE: 28

```
caagagggat cgatagcagt tcatgatgtt taaactggga gtcttgttga ccatctatat     60
gcttctgttt ccctttactg ctcttccgct ggatggagat caacctgcag accaacctct    120
agagcgcatg cagtatgaca tgttacgtgc agtgaatccc tggtttgatc ccgtcaaaag    180
gtgctgctcg aggaactgcg cagtatgcat cccttgttgc ccgaattggc cagcttgatt    240
atcgcggcca agagtctaat gaataagtaa aacgattgca gt                       282
```

<210> SEQ ID NO 29
<211> LENGTH: 71
<212> TYPE: PRT

-continued

<213> ORGANISM: Conus betulinus

<400> SEQUENCE: 29

Met Met Phe L

<210> SEQ ID NO 33
<211> LENGTH: 23
<212> TYPE: PRT
<213> ORGANISM: Conus bullatus
<220> FEATURE:
<221> NAME/KEY: PEPTIDE
<222> LOCATION: (1)..(23)
<223> OTHER INFORMATION: Xaa at residue 11 is Glu or gamma-carboxy Glu;
      Xaa at residue 15 is Trp or bromo-Trp

<400> SEQUENCE: 33

Val Thr Asp Arg Cys Cys Lys Gly Lys Arg Xaa Cys Gly Arg Xaa Cys
1               5                   10                  15

Arg Asp His Ser Arg Cys Cys
            20

<210> SEQ ID NO 34
<211> LENGTH: 326
<212> TYPE: DNA
<213> ORGANISM: Conus bullatus

<400> SEQUENCE: 34
caagagggat cgatagcagt tcatgatgtc taaactggga gtcttgttga ccatctgtct      60
gcttctgttt ccccttttg ctcttcggca ggatggagat caacctgcag accgacctgc     120
agagcgtatg caggatgaca tttcatctga gcagaatccc ttgcttgaga agagagttgg    180
tgacaggtgc tgcaaaggga gaggggtg cggcagatgg tgcagagatc actcacgttg     240
ttgcggtcga cgataacgtg ttgatgacca gctttgttat cacggctaca tcaagtgtct    300
tagtgattaa gtaaaacgat tgcagt                                         326

<210> SEQ ID NO 35
<211> LENGTH: 77
<212> TYPE: PRT
<213> ORGANISM: Conus bullatus

<400> SEQUENCE: 35

Met Met Ser Lys Leu Gly Val Leu Leu Thr Ile Cys Leu Leu Leu Phe
1               5                   10                  15

Pro Leu Phe Ala Leu Arg Gln Asp Gly Asp Gln Pro Ala Asp Arg Pro
            20                  25                  30

Ala Glu Arg Met Gln Asp Asp Ile Ser Ser Glu Gln Asn Pro Leu Leu
        35                  40                  45

Glu Lys Arg Val Gly Asp Arg Cys Cys Lys Gly Lys Arg Gly Cys Gly
    50                  55                  60

Arg Trp Cys Arg Asp His Ser Arg Cys Cys Gly Arg Arg
65                  70                  75

<210> SEQ ID NO 36
<211> LENGTH: 23
<212> TYPE: PRT
<213> ORGANISM: Conus bullatus
<220> FEATURE:
<221> NAME/KEY: PEPTIDE
<222> LOCATION: (1)..(23)
<223> OTHER INFORMATION: Xaa at residue 15 is Trp or bromo-Trp

<400> SEQUENCE: 36

Val Gly Asp Arg Cys Cys Lys Gly Lys Arg Gly Cys Gly Arg Xaa Cys
1               5                   10                  15

Arg Asp His Ser Arg Cys Cys

-continued

20

<210> SEQ ID NO 37
<211> LENGTH: 331
<212> TYPE: DNA
<213> ORGANISM: Conus bullatus

<400> SEQUENCE: 37

| caagaaggat cgatagcagt tcatgatgtc taaactggga gtcttgttga ccatctgtct | 60 |
| gcttctgttt cccctttttg ctcttccgca ggatggagat caacctgcag accgacctgc | 120 |
| agagcgtatg caggacgaca tttcatctga gcagaatccc ttgcttgaga agagagttgg | 180 |
| tgaaaggtgc tgcaaaaacg ggaagagggg gtgcggcaga tggtcagag atcactcacg | 240 |
| ttgttgcggt cgacgataac gtgttgatga ccgaggcttt cgttatcacg gctacatcaa | 300 |
| gtgtctagtg aataagtaaa acgattgcag t | 331 |

<210> SEQ ID NO 38
<211> LENGTH: 78
<212> TYPE: PRT
<213> ORGANISM: Conus bullatus

<400> SEQUENCE: 38

Met Met Ser Lys Leu Gly Val Leu Leu Thr Ile Cys Leu Leu Leu Phe
1               5                   10                  15

Pro Leu Phe Ala Leu Pro Gln Asp Gly Asp Gln Pro Ala Asp Arg Pro
            20                  25                  30

Ala Glu Arg Met Gln Asp Asp Ile Ser Ser Glu Gln Asn Pro Leu Leu
        35                  40                  45

Glu Lys Arg Val Gly Glu Arg Cys Cys Lys Asn Gly Lys Arg Gly Cys
    50                  55                  60

Gly Arg Trp Cys Arg Asp His Ser Arg Cys Cys Gly Arg Arg
65                  70                  75

<210> SEQ ID NO 39
<211> LENGTH: 24
<212> TYPE: PRT
<213> ORGANISM: Conus bullatus
<220> FEATURE:
<221> NAME/KEY: PEPTIDE
<222> LOCATION: (1)..(24)
<223> OTHER INFORMATION: Xaa at residue 3 is Glu or gamma-carboxy Glu;
      Xaa at residue 16 is Trp or bromo-Trp

<400> SEQUENCE: 39

Val Gly Xaa Arg Cys Cys Lys Asn Gly Lys Arg Gly Cys Gly Arg Xaa
1               5                   10                  15

Cys Arg Asp His Ser Arg Cys Cys
            20

<210> SEQ ID NO 40
<211> LENGTH: 337
<212> TYPE: DNA
<213> ORGANISM: Conus bullatus

<400> SEQUENCE: 40

| caagagggat cgatagcagt tcatgatgtc taaactggga gtcttgttga ccatctgtct | 60 |
| gcttctgttt cccctttttg ctcttccgca ggacggagat caacctgcag accgacctgc | 120 |
| agagcgtatg caggacgacc tttcatctga gcagcatccc ttgtttgaga agagaattgt | 180 |
| tgacaggtgc tgcaacaaag ggaacgggaa gaggggtgc agcagatggt gcagagatca | 240 |

```
ctcacgttgt tgcggtcgac gatgaactgt tgatgaccga ggctttggtt atcacggcta    300
catcaagtgt ctagtgaata agtaaaacga ttgcagt                            337
```

<210> SEQ ID NO 41
<211> LENGTH: 80
<212> TYPE: PRT
<213> ORGANISM: Conus bullatus

<400> SEQUENCE: 41

Met Met Ser Lys Leu Gly Val Leu Leu Thr Ile Cys Leu Leu Leu Phe
1               5                   10                  15

Pro Leu Phe Ala Leu Pro Gln Asp Gly Asp Gln Pro Ala Asp Arg Pro
            20                  25                  30

Ala Glu Arg Met Gln Asp Asp Leu Ser Ser Glu Gln His Pro Leu Phe
        35                  40                  45

Glu Lys Arg Ile Val Asp Arg Cys Cys Asn Lys Gly Asn Gly Lys Arg
    50                  55                  60

Gly Cys Ser Arg Trp Cys Arg Asp His Ser Arg Cys Cys Gly Arg Arg
65                  70                  75                  80

<210> SEQ ID NO 42
<211> LENGTH: 26
<212> TYPE: PRT
<213> ORGANISM: Conus bullatus
<220> FEATURE:
<221> NAME/KEY: PEPTIDE
<222> LOCATION: (1)..(26)
<223> OTHER INFORMATION: Xaa at residue 18 is Trp or bromo-Trp

<400> SEQUENCE: 42

Ile Val Asp Arg Cys Cys Asn Lys Gly Asn Gly Lys Arg Gly Cys Ser
1               5                   10                  15

Arg Xaa Cys Arg Asp His Ser Arg Cys Cys
            20                  25

<210> SEQ ID NO 43
<211> LENGTH: 337
<212> TYPE: DNA
<213> ORGANISM: Conus bullatus

<400> SEQUENCE: 43

```
caagaaggat cgatagcagt tcatgatgtc taaactggga gtcttgttga ccatctgtct    60
gcttctgttt ccccttttg ctcttccgca ggatggagat caacctgcag accgacctgc    120
tgagcgtatg caggacgaca tttcatctga gcggaatccc ttgtttgaga agagcgttgg    180
tttatattgc tgccgaccca aacccaacgg gcagatgatg tgcgacagat ggtgcgaaaa    240
aaactcacgt tgttgcggtc gacgataatg tgttgatgac cagctttgtt atcaaggcta    300
catcaagtat ctagtgaata agtaaaacga ttgcagt                            337
```

<210> SEQ ID NO 44
<211> LENGTH: 77
<212> TYPE: PRT
<213> ORGANISM: Conus bullatus

<400> SEQUENCE: 44

Met Met Ser Lys Leu Gly Val Leu Leu Thr Ile Cys Leu Leu Leu Phe
1               5                   10                  15

Pro Leu Phe Ala Leu Pro Gln Asp Gly Asp Gln Pro Ala Asp Arg Pro
            20                  25                  30

```
Ala Glu Arg Met Gln Asp Asp Ile Ser Ser Asn Pro Leu Phe Glu Lys
        35                  40                  45

Ser Val Gly Cys Cys Arg Pro Lys Pro Asn Gly Gln Met Met Cys Asp
    50                  55                  60

Arg Trp Cys Glu Lys Asn Ser Arg Cys Cys Gly Arg Arg
65                  70                  75
```

<210> SEQ ID NO 45
<211> LENGTH: 27
<212> TYPE: PRT
<213> ORGANISM: Conus bullatus
<220> FEATURE:
<221> NAME/KEY: PEPTIDE
<222> LOCATION: (1)..(27)
<223> OTHER INFORMATION: Xaa at residue 21 is Glu or gamma-carboxy Glu;
      Xaa at residue 8 and 10 is Pro or Hyp; Xaa at residue 19 is Trp or
      bromo-Trp; Xaa at residue 4 is Tyr, 125I-Tyr, mono-iodo-Tyr,
      di-iodo-Tyr, O-sulpho-Tyr or O-phospho-Tyr

<400> SEQUENCE: 45

```
Val Gly Leu Xaa Cys Cys Arg Xaa Lys Xaa Asn Gly Gln Met Met Cys
1               5                   10                  15

Asp Arg Xaa Cys Xaa Lys Asn Ser Arg Cys Cys
            20                  25
```

<210> SEQ ID NO 46
<211> LENGTH: 323
<212> TYPE: DNA
<213> ORGANISM: Conus bullatus

<400> SEQUENCE: 46

```
caagaaggat cgatagcagt tcatgatgtc taaactggga gttttgttga ccatctgtct      60
gcttctgttt ccccttactg ctcttccgat ggatggagat caatctgtag accgacctgc     120
agaacgtatg caggacgacc tttcatctga gcagcatccc ttgtttgttc agaaaagaag     180
gtgttgcggc gaaggcttga catgccccag atattggaaa acagtcaga tttgtgcttg     240 ttgttaaatg acaacgtgtc gatgaccaac ttcggtatca cgactacgcc aagtgtctaa     300
tgaataagta aaacgattgc agt                                             323
```

<210> SEQ ID NO 47
<211> LENGTH: 74
<212> TYPE: PRT
<213> ORGANISM: Conus bullatus

<400> SEQUENCE: 47

```
Met Met Ser Lys Leu Gly Val Leu Leu Thr Ile Cys Leu Leu Leu Phe
1               5                   10                  15

Pro Leu Thr Ala Leu Pro Met Asp Gly Asp Gln Ser Val Asp Arg Pro
            20                  25                  30

Ala Glu Arg Met Gln Asp Asp Leu Ser Ser Glu Gln His Pro Leu Phe
        35                  40                  45

Val Gln Lys Arg Arg Cys Cys Gly Glu Gly Leu Thr Cys Pro Arg Tyr
    50                  55                  60

Trp Lys Asn Ser Gln Ile Cys Ala Cys Cys
65                  70
```

<210> SEQ ID NO 48
<211> LENGTH: 22
<212> TYPE: PRT
<213> ORGANISM: Conus bullatus

```
<220> FEATURE:
<221> NAME/KEY: PEPTIDE
<222> LOCATION: (1)..(22)
<223> OTHER INFORMATION: Xaa at residue 5 is Glu or gamma-carboxy Glu;
      Xaa at residue 10 is Pro or Hyp; Xaa at residue 13 is Trp or
      bromo-Trp; Xaa at residue 12 is Tyr, 125I-Tyr, mono-iodo-Tyr,
      di-iodo-Tyr, O-sulpho-Tyr or O-phospho-Tyr

<400> SEQUENCE: 48

Arg Cys Cys Gly Xaa Gly Leu Thr Cys Xaa Arg Xaa Xaa Lys Asn Ser
1               5                   10                  15

Gln Ile Cys Ala Cys Cys
            20

<210> SEQ ID NO 49
<211> LENGTH: 322
<212> TYPE: DNA
<213> ORGANISM: Conus bullatus

<400> SEQUENCE: 49
caagagggat cgatagcagt tcatgatgtc taaactggga gtcttgttga ccatctgtct      60
gcttctgttt cccctttttg ctcttccgca ggatggagat caacctgcag accgacctgc    120
tgagcgtatg caggacgaca tttcatctga gcaggatccc ttgtttgttc agaaaagaag    180
gtgttgcggc gaaggcttga catgccccag atattggaaa acagtcaga tttgtgcttg     240 ttgttaaatg acaacgtgtg atgaccaact tcggtatcac gactacgcca agtgtctaat    300
gaataagtaa aacgattgca gt                                              322

<210> SEQ ID NO 50
<211> LENGTH: 74
<212> TYPE: PRT
<213> ORGANISM: Conus bullatus

<400> SEQUENCE: 50

Met Met Ser Lys Leu Gly Val Leu Leu Thr Ile Cys Leu Leu Leu Phe
1               5                   10                  15

Pro Leu Phe Ala Leu Pro Gln Asp Gly Asp Gln Pro Ala Asp Arg Pro
            20                  25                  30

Ala Glu Arg Met Gln Asp Asp Ile Ser Ser Glu Gln Asp Pro Leu Phe
        35                  40                  45

Val Gln Lys Arg Arg Cys Cys Gly Glu Gly Leu Thr Cys Pro Arg Tyr
    50                  55                  60

Trp Lys Asn Ser Gln Ile Cys Ala Cys Cys
65                  70

<210> SEQ ID NO 51
<211> LENGTH: 22
<212> TYPE: PRT
<213> ORGANISM: Conus bullatus
<220> FEATURE:
<221> NAME/KEY: PEPTIDE
<222> LOCATION: (1)..(22)
<223> OTHER INFORMATION: Xaa at residue 5 is Glu or gamma-carboxy Glu;
      Xaa at residue 10 is Pro or Hyp; Xaa at residue 13 is Trp or
      bromo-Trp; Xaa at residue 12 is Tyr, 125I-Tyr, mono-iodo-Tyr,
      di-iodo-Tyr, O-sulpho-Tyr or O-phospho-Tyr

<400> SEQUENCE: 51

Arg Cys Cys Gly Xaa Gly Leu Thr Cys Xaa Arg Xaa Xaa Lys Asn Ser
1               5                   10                  15

Gln Ile Cys Ala Cys Cys
            20
```

<210> SEQ ID NO 52
<211> LENGTH: 238
<212> TYPE: DNA
<213> ORGANISM: Conus capitaneus

<400> SEQUENCE: 52

```
ggatccatga tgtctaaact gggagtcttg gtgaccatct gcctgcttct gtttcccctt      60
gctgcttttc cactggatgg aaatcaacct gcagaccacc ctgcaaagcg tacgcaagat     120
gacagttcag ctgccctgat caatacctgg attgatcatt cccattcttg ctgcagggac     180
tgcggtgaag attgtgttgg ttgttgccgg taacgtgttg atgaccaact ttctcgag       238
```

<210> SEQ ID NO 53
<211> LENGTH: 70
<212> TYPE: PRT
<213> ORGANISM: Conus capitaneus

<400> SEQUENCE: 53

Gly Ser Met Met Ser Lys Leu Gly Val Leu Val Thr Ile Cys Leu Leu
1               5                   10                  15

Leu Phe Pro Leu Ala Ala Phe Pro Leu Asp Gly Asn Gln Pro Ala Asp
            20                  25                  30

His Pro Ala Lys Arg Thr Gln Asp Asp Ser Ser Ala Ala Leu Ile Asn
        35                  40                  45

Thr Trp Ile Asp His Ser His Ser Cys Cys Arg Asp Cys Gly Glu Asp
    50                  55                  60

Cys Val Gly Cys Cys Arg
65                  70

<210> SEQ ID NO 54
<211> LENGTH: 15
<212> TYPE: PRT
<213> ORGANISM: Conus capitaneus
<220> FEATURE:
<221> NAME/KEY: PEPTIDE
<222> LOCATION: (1)..(15)
<223> OTHER INFORMATION: Xaa at residue 8 is Glu or gamma-carboxy Glu

<400> SEQUENCE: 54

Ser Cys Cys Arg Asp Cys Gly Xaa Asp Cys Val Gly Cys Cys Arg
1               5                   10                  15

<210> SEQ ID NO 55
<211> LENGTH: 323
<212> TYPE: DNA
<213> ORGANISM: Conus caracteristicus

<400> SEQUENCE: 55

```
caagagggat cgatagcagt tcatgatgtc taaactggga gtcttgttga ccatctgtct      60
gcttctgttt cccttactg ctcttccaat ggatggagat caacctgcag accaacctgc     120
agatcgtatg caggacgaca tttcatctga gcagtatccc ttgtttgata tgagaaaaag     180
gtgttgcggc cccggcggtt catgccccgt atatttcaga gacaattta tttgtggttg     240
ttgttaaatg acaacgtgtc gatgaccaac ttcattatca cgactacgcc aagtgtctaa     300
tgaataagta aaatgattgc agt                                             323
```

<210> SEQ ID NO 56
<211> LENGTH: 74
<212> TYPE: PRT

```
<213> ORGANISM: Conus caracteristicus

<400> SEQUENCE: 56

Met Met Ser Lys Leu Gly Val Leu Leu Thr Ile Cys Leu Leu Leu Phe
1               5                   10                  15

Pro Leu Thr Ala Leu Pro Met Asp Gly Asp Gln Pro Ala Asp Gln Pro
                20                  25                  30

Ala Asp Arg Met Gln Asp Asp Ile Ser Ser Glu Gln Tyr Pro Leu Phe
            35                  40                  45

Asp Met Arg Lys Arg Cys Cys Gly Pro Gly Ser Cys Pro Val Tyr
        50                  55                  60

Phe Arg Asp Asn Phe Ile Cys Gly Cys Cys
65                  70

<210> SEQ ID NO 57
<211> LENGTH: 21
<212> TYPE: PRT
<213> ORGANISM: Conus caracteristicus
<220> FEATURE:
<221> NAME/KEY: PEPTIDE
<222> LOCATION: (1)..(21)
<223> OTHER INFORMATION: Xaa at residue 4 and 9 is Pro or Hyp; Xaa at
      residue 11 is Tyr, 125I-Tyr, mono-iodo-Tyr, di-iodo-Tyr,
      O-sulpho-Tyr or O-phospho-Tyr

<400> SEQUENCE: 57

Cys Cys Gly Xaa Gly Gly Ser Cys Xaa Val Xaa Phe Arg Asp Asn Phe
1               5                   10                  15

Ile Cys Gly Cys Cys
                20

<210> SEQ ID NO 58
<211> LENGTH: 316
<212> TYPE: DNA
<213> ORGANISM: Conus caracteristicus

<400> SEQUENCE: 58
caagagggat cgatagcagt tcatgatgtc taaactggga gtcttgttga ccatctgtct      60
gcttctgttt cccccttactg ctcttccgat ggatggagat gaacctgcaa accgacctgt    120
cgagcgtatg caggacaaca tttcatctga gcagtatccc ttgtttgaga agagacgaga    180
ttgttgcact ccgccgaaga aatgcaaaga ccgacaatgc aaaccccaga gatgttgcgc    240
tggacgataa cgtgttgatg accaacttta tcacggctac gtcaagtgtt tagtgaataa    300
gtaaaatgat tgcagt                                                     316

<210> SEQ ID NO 59
<211> LENGTH: 75
<212> TYPE: PRT
<213> ORGANISM: Conus caracteristicus

<400> SEQUENCE: 59

Met Met Ser Lys Leu Gly Val Leu Leu Thr Ile Cys Leu Leu Leu Phe
1               5                   10                  15

Pro Leu Thr Ala Leu Pro Met Asp Gly Asp Glu Pro Ala Asn Arg Pro
                20                  25                  30

Val Glu Arg Met Gln Asp Asn Ile Ser Ser Glu Gln Tyr Pro Leu Phe
            35                  40                  45

Glu Lys Arg Arg Asp Cys Cys Thr Pro Pro Lys Lys Cys Lys Asp Arg
        50                  55                  60
```

```
Gln Cys Lys Pro Gln Arg Cys Cys Ala Gly Arg
 65                  70                  75
```

<210> SEQ ID NO 60
<211> LENGTH: 22
<212> TYPE: PRT
<213> ORGANISM: Conus caracteristicus
<220> FEATURE:
<221> NAME/KEY: PEPTIDE
<222> LOCATION: (1)..(22)
<223> OTHER INFORMATION: Xaa at residue 6, 7 and 17 is Pro or Hyp

<400> SEQUENCE: 60

```
Arg Asp Cys Cys Thr Xaa Xaa Lys Lys Cys Lys Asp Arg Gln Cys Lys
 1               5                  10                  15

Xaa Gln Arg Cys Cys Ala
            20
```

<210> SEQ ID NO 61
<211> LENGTH: 314
<212> TYPE: DNA
<213> ORGANISM: Conus caracteristicus

<400> SEQUENCE: 61

```
caagagggat cgatagcagt tcatgatgtc taaactggga gtcttgttga ccatctgtct      60
gcttctgttt ccccttactg ctcttccact ggatggagat caacctgcag atcaatctgc    120
agagcgacct gcagagcgta cgcaggacga cattcagcag catccgttat atgatccgaa    180
aagaaggtgt tgccgttatc catgccccga cagctgccac ggatcttgct gctataagtg    240
ataacatgtt gatggccagc tttgttatca cggccacgtc aagtgtctta atgaataagt    300
aaaacgattg cagt                                                      314
```

<210> SEQ ID NO 62
<211> LENGTH: 72
<212> TYPE: PRT
<213> ORGANISM: Conus caracteristicus

<400> SEQUENCE: 62

```
Met Met Ser Lys Leu Gly Val Leu Leu Thr Ile Cys Leu Leu Leu Phe
 1               5                  10                  15

Pro Leu Thr Ala Leu Pro Leu Asp Gly Asp Gln Pro Ala Asp Gln Ser
            20                  25                  30

Ala Glu Arg Pro Ala Glu Arg Thr Gln Asp Asp Ile Gln Gln His Pro
        35                  40                  45

Leu Tyr Asp Pro Lys Arg Arg Cys Cys Arg Tyr Pro Cys Pro Asp Ser
    50                  55                  60

Cys His Gly Ser Cys Cys Tyr Lys
 65                  70
```

<210> SEQ ID NO 63
<211> LENGTH: 18
<212> TYPE: PRT
<213> ORGANISM: Conus caracteristicus
<220> FEATURE:
<221> NAME/KEY: PEPTIDE
<222> LOCATION: (1)..(18)
<223> OTHER INFORMATION: Xaa at residue 6 and 8 is Pro or Hyp; Xaa at
      residue 5 and 17 is Tyr, 125I-Tyr, mono-iodo-Tyr, di-iodo-Tyr,
      O-sulpho-Tyr or O-phospho-Tyr

<400> SEQUENCE: 63

```
Arg Cys Cys Arg Xaa Xaa Cys Xaa Asp Ser Cys His Gly Ser Cys Cys
```

Xaa Lys

<210> SEQ ID NO 64
<211> LENGTH: 292
<212> TYPE: DNA
<213> ORGANISM: Conus caracteristicus

<400> SEQUENCE: 64

```
caagagggat cgatagcagt tcatgatgtc taaactggga gccttgttga ccatctgtct    60
acttctgttt tcccttactg ctgttccgct ggatggagat caacatgcag accaacctgc   120
acagcgtctg caggaccgca ttccaactga agatcatccc ttatttgatc caacaaacg    180
gtgttgcccg ccggtggcat gcaacatggg atgcaagcct tgttgtggat gaccagcttt   240
gttatcgcgg tcttcatgaa gtgtcttaat gaataagtaa aatgattgca gt           292
```

<210> SEQ ID NO 65
<211> LENGTH: 69
<212> TYPE: PRT
<213> ORGANISM: Conus caracteristicus

<400> SEQUENCE: 65

Met Met Ser Lys Leu Gly Ala Leu Leu Thr Ile Cys Leu Leu Leu Phe
1               5                   10                  15

Ser Leu Thr Ala Val Pro Leu Asp Gly Asp Gln His Ala Asp Gln Pro
            20                  25                  30

Ala Gln Arg Leu Gln Asp Arg Ile Pro Thr Glu Asp His Pro Leu Phe
        35                  40                  45

Asp Pro Asn Lys Arg Cys Cys Pro Pro Val Ala Cys Asn Met Gly Cys
    50                  55                  60

Lys Pro Cys Cys Gly
65

<210> SEQ ID NO 66
<211> LENGTH: 15
<212> TYPE: PRT
<213> ORGANISM: Conus caracteristicus
<220> FEATURE:
<221> NAME/KEY: PEPTIDE
<222> LOCATION: (1)..(15)
<223> OTHER INFORMATION: Xaa at residue 3, 4 and 13 is Pro or Hyp

<400> SEQUENCE: 66

Cys Cys Xaa Xaa Val Ala Cys Asn Met Gly Cys Lys Xaa Cys Cys
1               5                   10                  15

<210> SEQ ID NO 67
<211> LENGTH: 293
<212> TYPE: DNA
<213> ORGANISM: Conus caracteristicus

<400> SEQUENCE: 67

```
caagagggat cgatagcagt tcatgatgtc taaactggga gccttgttga ccatctgtct    60
acttctgttt tccctaactg ctgttccgct ggatggagat caacatgcag accaacctgc   120
agagcgtctg catgaccgcc ttccaactga aaatcatccc ttatatgatc ccgtcaaacg   180
gtgttgcgat gattcggaat gcgactattc ttgctggcct tgctgtatgt ttggataacc   240
tttgttatcg cggcctcatc aagtgtctaa tgaataagta aaacgattgc agt          293
```

```
<210> SEQ ID NO 68
<211> LENGTH: 71
<212> TYPE: PRT
<213> ORGANISM: Conus caracteristicus

<400> SEQUENCE: 68

Met Met Ser Lys Leu Gly Ala Leu Leu Thr Ile Cys Leu Leu Leu Phe
1               5                   10                  15

Ser Leu Thr Ala Val Pro Leu Asp Gly Asp Gln His Ala Asp Gln Pro
            20                  25                  30

Ala Glu Arg Leu His Asp Arg Leu Pro Thr Glu Asn His Pro Leu Tyr
        35                  40                  45

Asp Pro Val Lys Arg Cys Cys Asp Asp Ser Glu Cys Asp Tyr Ser Cys
    50                  55                  60

Trp Pro Cys Cys Met Phe Gly
65                  70

<210> SEQ ID NO 69
<211> LENGTH: 17
<212> TYPE: PRT
<213> ORGANISM: Conus caracteristicus
<220> FEATURE:
<221> NAME/KEY: PEPTIDE
<222> LOCATION: (1)..(17)
<223> OTHER INFORMATION: Xaa at residue 6 is Glu or gamma-carboxy Glu;
      Xaa at residue 13 is Pro or Hyp; Xaa at residue 12 is Trp or
      bromo-Trp; Xaa at residue 9 is Tyr, 125I-Tyr, mono-iodo-Tyr,
      di-iodo-Tyr, O-sulpho-Tyr or O-phospho-Tyr

<400> SEQUENCE: 69

Cys Cys Asp Asp Ser Xaa Cys Asp Xaa Ser Cys Xaa Xaa Cys Cys Met
1               5                   10                  15

Phe

<210> SEQ ID NO 70
<211> LENGTH: 232
<212> TYPE: DNA
<213> ORGANISM: Conus caracteristicus

<400> SEQUENCE: 70
ggatccatga tgtctaaact gggagtcttg ttgaccatct gtctgcttct gtttccccett      60 actgctgttc cgctggatgg agatcaacct gcagaccgac ctgcagagcg taagcaggac     120
gtttcatctg aacagcatcc cttctttgat cccgtcaaac ggtgttgccg ccggtgttac     180
atgggatgca tcccttgttg cttttaacgt gttgatgacc aactttctcg ag            232

<210> SEQ ID NO 71
<211> LENGTH: 68
<212> TYPE: PRT
<213> ORGANISM: Conus caracteristicus

<400> SEQUENCE: 71

Gly Ser Met Met Ser Lys Leu Gly Val Leu Leu Thr Ile Cys Leu Leu
1               5                   10                  15

Leu Phe Pro Leu Thr Ala Val Pro Leu Asp Gly Asp Gln Pro Ala Asp
            20                  25                  30

Arg Pro Ala Glu Arg Lys Gln Asp Val Ser Ser Glu Gln His Pro Phe
        35                  40                  45

Phe Asp Pro Val Lys Arg Cys Cys Arg Arg Cys Tyr Met Gly Cys Ile
    50                  55                  60

Pro Cys Cys Phe
```

<210> SEQ ID NO 72
<211> LENGTH: 14
<212> TYPE: PRT
<213> ORGANISM: Conus caracteristicus
<220> FEATURE:
<221> NAME/KEY: PEPTIDE
<222> LOCATION: (1)..(14)
<223> OTHER INFORMATION: Xaa at residue 11 is Pro or Hyp; Xaa at
      residue 6 is Tyr, 125I-Tyr, mono-iodo-Tyr, di-iodo-Tyr,
      O-sulpho-Tyr or O-phospho-Tyr

<400> SEQUENCE: 72

Cys Cys Arg Arg Cys Xaa Met Gly Cys Ile Xaa Cys Cys Phe
1               5                   10

<210> SEQ ID NO 73
<211> LENGTH: 323
<212> TYPE: DNA
<213> ORGANISM: Conus circumcisus

<400> SEQUENCE: 73
caagaaggat cgatagcagt tcatgatgtc taaactgggg gtattgttga ccatctgtct      60
gcttctgttt ccccttactg ctcttccaat ggatggagat caacctgcag accaacctgc    120
agatcgtatg caggacgaca tttcatctga gcagtatccc ttgtttgata agagacgaaa    180
gtgttgcggc aaagacgggc catgccccaa atatttcaaa gacaattta tttgtggttg     240 ttgttaaatg acaacgtgtc gatgaccaac ttcgttatca cgattcgcca agtgtcttaa    300
tgaataagta aaatgattgc agt                                            323

<210> SEQ ID NO 74
<211> LENGTH: 74
<212> TYPE: PRT
<213> ORGANISM: Conus circumcisus

<400> SEQUENCE: 74

Met Met Ser Lys Leu Gly Val Leu Leu Thr Ile Cys Leu Leu Leu Phe
1               5                   10                  15

Pro Leu Thr Ala Leu Pro Met Asp Gly Asp Gln Pro Ala Asp Gln Pro
            20                  25                  30

Ala Asp Arg Met Gln Asp Asp Ile Ser Ser Glu Gln Tyr Pro Leu Phe
        35                  40                  45

Asp Lys Arg Arg Lys Cys Cys Gly Lys Asp Gly Pro Cys Pro Lys Tyr
    50                  55                  60

Phe Lys Asp Asn Phe Ile Cys Gly Cys Cys
65                  70

<210> SEQ ID NO 75
<211> LENGTH: 23
<212> TYPE: PRT
<213> ORGANISM: Conus circumcisus
<220> FEATURE:
<221> NAME/KEY: PEPTIDE
<222> LOCATION: (1)..(23)
<223> OTHER INFORMATION: Xaa at residue 9 and 11 is Pro or Hyp; Xaa at
      residue 13 is Tyr, 125I-Tyr, mono-iodo-Tyr, di-iodo-Tyr,
      O-sulpho-Tyr or O-phospho-Tyr

<400> SEQUENCE: 75

Arg Lys Cys Cys Gly Lys Asp Gly Xaa Cys Xaa Lys Xaa Phe Lys Asp
1               5                   10                  15

```
Asn Phe Ile Cys Gly Cys Cys
            20
```

<210> SEQ ID NO 76
<211> LENGTH: 293
<212> TYPE: DNA
<213> ORGANISM: Conus dalli

<400> SEQUENCE: 76

```
caagagggat cgatagcagt tcatgatgtc taaactggga gccttgttga ccatctgtct     60
acttctgttt tccctaactg ctgttccgct ggatggagat caacatgcag accaacctgc    120
agagcgtctg caggaccgcc ttccaactga aaatcatccc ttatatgatc ccgtcaaacg    180
gtgttgcgat gattcggaat gcgactattc ttgctggcct tgctgtattt tatcataacc    240
tttgttatcg cggcctcatc aagtgtcaaa tgaataagta aaatgattgc agt           293
```

<210> SEQ ID NO 77
<211> LENGTH: 71
<212> TYPE: PRT
<213> ORGANISM: Conus dalli

<400> SEQUENCE: 77

```
Met Met Ser Lys Leu Gly Ala Leu Leu Thr Ile Cys Leu Leu Leu Phe
1               5                  10                  15

Ser Leu Thr Ala Val Pro Leu Asp Gly Asp Gln His Ala Asp Gln Pro
            20                  25                  30

Ala Glu Arg Leu Gln Asp Arg Leu Pro Thr Glu Asn His Pro Leu Tyr
        35                  40                  45

Asp Pro Val Lys Arg Cys Cys Asp Asp Ser Glu Cys Asp Tyr Ser Cys
    50                  55                  60

Trp Pro Cys Cys Ile Leu Ser
65                  70
```

<210> SEQ ID NO 78
<211> LENGTH: 18
<212> TYPE: PRT
<213> ORGANISM: Conus dalli
<220> FEATURE:
<221> NAME/KEY: PEPTIDE
<222> LOCATION: (1)..(18)
<223> OTHER INFORMATION: Xaa at residue 6 is Glu or gamma-carboxy Glu;
      Xaa at residue 13 is Pro or Hyp; Xaa at residue 12 is Trp or
      bromo-Trp; Xaa at residue 9 is Tyr, 125I-Tyr, mono-iodo-Tyr,
      di-iodo-Tyr, O-sulpho-Tyr or O-phospho-Tyr

<400> SEQUENCE: 78

```
Cys Cys Asp Asp Ser Xaa Cys Asp Xaa Ser Cys Xaa Xaa Cys Cys Ile
1               5                  10                  15

Leu Ser
```

<210> SEQ ID NO 79
<211> LENGTH: 299
<212> TYPE: DNA
<213> ORGANISM: Conus dalli

<400> SEQUENCE: 79

```
caagagggat cgatagcagt tcatgatgtc taaactggga gtcttgttga ccatttgtct     60
acttctgttt ccccttactg ctgttccact ggatggagat cagcctgcag accgacctgc    120
agagcgtatg caggacggca tttcatctga acatcatcca ttttttgatt ccgtcaaaaa    180
gaaacaacag tgttgcccgc cggtggcatg caacatggga tgcgagcctt gttgtggatg    240
```
accagctttg ttatcgcggc tcatgaagtg tcctaatgaa aagtaaaac gattgcagt    299

<210> SEQ ID NO 80
<211> LENGTH: 72
<212> TYPE: PRT
<213> ORGANISM: Conus dalli

<400> SEQUENCE: 80

Met Met Ser Lys Leu Gly Val Leu Leu Thr Ile Cys Leu Leu Leu Phe
1               5                   10                  15

Pro Leu Thr Ala Val Pro Leu Asp Gly Asp Gln Pro Ala Asp Arg Pro
            20                  25                  30

Ala Glu Arg Met Gln Asp Gly Ile Ser Ser Glu His His Pro Phe Phe
        35                  40                  45

Asp Ser Val Lys Lys Gln Gln Cys Cys Pro Pro Val Ala Cys Asn
    50                  55                  60

Met Gly Cys Glu Pro Cys Cys Gly
65                  70

<210> SEQ ID NO 81
<211> LENGTH: 17
<212> TYPE: PRT
<213> ORGANISM: Conus dalli
<220> FEATURE:
<221> NAME/KEY: PEPTIDE
<222> LOCATION: (1)..(17)
<223> OTHER INFORMATION: Xaa at residue 1 is Gln or pyro-Glu; Xaa at
      residue 14 is Glu or gamma-carboxy Glu; Xaa at residue 5, 6 and
      15 is Pro or Hyp

<400> SEQUENCE: 81

Xaa Gln Cys Cys Xaa Xaa Val Ala Cys Asn Met Gly Cys Xaa Xaa Cys
1               5                   10                  15

Cys

<210> SEQ ID NO 82
<211> LENGTH: 290
<212> TYPE: DNA
<213> ORGANISM: Conus dalli

<400> SEQUENCE: 82
caagaaggat cgatagcagt tcatgatgtc taaactggga gtcttgttga tcatatgtct    60
atttctgttt cccttactg ctgttcagct caatggagat cagcctgcag accaatctgc    120
agagcgtatg caggacaaaa tttcatctga acatcatccc ttttttgatc cgtcaaacg    180 ttgttgcaac gcgggttttt gccgcttcgg atgcacgcct tgttgttggt gaccagcttt    240
gttatcgcgg cctcatcaag tgtctaatga ataagtaaaa tgattgcagt               290

<210> SEQ ID NO 83
<211> LENGTH: 69
<212> TYPE: PRT
<213> ORGANISM: Conus dalli

<400> SEQUENCE: 83

Met Met Ser Lys Leu Gly Val Leu Leu Ile Ile Cys Leu Phe Leu Phe
1               5                   10                  15

Pro Leu Thr Ala Val Gln Leu Asn Gly Asp Gln Pro Ala Asp Gln Ser
            20                  25                  30

Ala Glu Arg Met Gln Asp Lys Ile Ser Ser Glu His His Pro Phe Phe
        35                  40                  45

```
Asp Pro Val Lys Arg Cys Cys Asn Ala Gly Phe Cys Arg Phe Gly Cys
    50                  55                  60

Thr Pro Cys Cys Trp
65

<210> SEQ ID NO 84
<211> LENGTH: 16
<212> TYPE: PRT
<213> ORGANISM: Conus dalli
<220> FEATURE:
<221> NAME/KEY: PEPTIDE
<222> LOCATION: (1)..(16)
<223> OTHER INFORMATION: Xaa at residue 13 is Pro or Hyp; Xaa at
      residue 16 is Trp or bromo-Trp

<400> SEQUENCE: 84

Cys Cys Asn Ala Gly Phe Cys Arg Phe Gly Cys Thr Xaa Cys Cys Xaa
1               5                   10                  15

<210> SEQ ID NO 85
<211> LENGTH: 288
<212> TYPE: DNA
<213> ORGANISM: Conus distans

<400> SEQUENCE: 85
caagagggat cgatagcagt tcatgatgtc taaactggga gtcttgctga ccatctttct    60
gcttctgttt cccttactg ctgttccgct ggatggagat caacccgcag acggacttgc   120
agagcgcatg caggacgaca gttcagctgc actgattaga gactggcttc ttcaaacccg   180
acagtgttgt gtgcatccat gcccatgcac gccttgctgt agatgaccag ctttgtcatc   240
gcggctacgt caagtatcta atgaataagt aagtaaaacg attgcagt               288

<210> SEQ ID NO 86
<211> LENGTH: 67
<212> TYPE: PRT
<213> ORGANISM: Conus distans

<400> SEQUENCE: 86

Met Met Ser Lys Leu Gly Val Leu Leu Thr Ile Phe Leu Leu Leu Phe
1               5                   10                  15

Pro Leu Thr Ala Val Pro Leu Asp Gly Asp Gln Pro Ala Asp Gly Leu
                20                  25                  30

Ala Glu Arg Met Gln Asp Asp Ser Ser Ala Ala Leu Ile Arg Asp Trp
            35                  40                  45

Leu Leu Gln Thr Arg Gln Cys Cys Val His Pro Cys Pro Cys Thr Pro
        50                  55                  60

Cys Cys Arg
65

<210> SEQ ID NO 87
<211> LENGTH: 14
<212> TYPE: PRT
<213> ORGANISM: Conus distans
<220> FEATURE:
<221> NAME/KEY: PEPTIDE
<222> LOCATION: (1)..(14)
<223> OTHER INFORMATION: Xaa at residue 1 is Gln or pyro-Glu; Xaa at
      residue 6, 8 and 11 is Pro or Hyp

<400> SEQUENCE: 87

Xaa Cys Cys Val His Xaa Cys Xaa Cys Thr Xaa Cys Cys Arg
1               5                   10
```

<210> SEQ ID NO 88
<211> LENGTH: 303
<212> TYPE: DNA
<213> ORGANISM: Conus ermineus

<400> SEQUENCE: 88

| | | | | | |
|---|---|---|---|---|---|
| acctcaagag | ggatcgatcg | cagttcatga | tgtctaaact | gggagccttg | ttgaccatct | 60 |
| gtctgcttct | gtttcccatt | actgctcttc | tgatggatgg | agatcagcct | gcagaccgac | 120 |
| ctgcagagcg | tacggaggat | gacatttcat | ctgactacat | tccctgttgc | agttggccat | 180 |
| gcccccgata | ctccaacggt | aaacttgttt | gtttttgttg | ccttggatga | taatgtgttg | 240 |
| atgaccaact | ttgttatcac | ggctacgtca | agtgtctact | gaataagtaa | aatgattgca | 300 |
| gta | | | | | | 303 |

<210> SEQ ID NO 89
<211> LENGTH: 67
<212> TYPE: PRT
<213> ORGANISM: Conus ermineus

<400> SEQUENCE: 89

Met Met Ser Lys Leu Gly Ala Leu Leu Thr Ile Cys Leu Leu Leu Phe
1               5                   10                  15

Pro Ile Thr Ala Leu Leu Met Asp Gly Asp Gln Pro Ala Asp Arg Pro
            20                  25                  30

Ala Glu Arg Thr Glu Asp Asp Ile Ser Ser Asp Tyr Ile Pro Cys Cys
        35                  40                  45

Ser Trp Pro Cys Pro Arg Tyr Ser Asn Gly Lys Leu Val Cys Phe Cys
    50                  55                  60

Cys Leu Gly
65

<210> SEQ ID NO 90
<211> LENGTH: 20
<212> TYPE: PRT
<213> ORGANISM: Conus ermineus
<220> FEATURE:
<221> NAME/KEY: PEPTIDE
<222> LOCATION: (1)..(20)
<223> OTHER INFORMATION: Xaa at residue 5 and 7 is Pro or Hyp; Xaa at
      residue 4 is Trp or bromo-Trp; Xaa at residue 9 is Tyr, 125I-Tyr,
      mono-iodo-Tyr, di-iodo-Tyr, O-sulpho-Tyr or O-phospho-Tyr

<400> SEQUENCE: 90

Cys Cys Ser Xaa Xaa Cys Xaa Arg Xaa Ser Asn Gly Lys Leu Val Cys
1               5                   10                  15

Phe Cys Cys Leu
            20

<210> SEQ ID NO 91
<211> LENGTH: 241
<212> TYPE: DNA
<213> ORGANISM: Conus generalis

<400> SEQUENCE: 91

| | | | | | |
|---|---|---|---|---|---|
| ggatccatga | tgtctaaact | gggagtcttg | ttgaccatct | gtctggttct | gtttcccctt | 60 |
| actgctcttc | cactggatgg | agaacaacct | gtagaccgac | atgccgagca | tatgcaggat | 120 |
| gacaattcag | ctgcacagaa | ccctggggtt | attgccatca | gacagtgttg | cacgttctgc | 180 |
| aactttggat | gccaaccttg | ttgcctcacc | tgataacgtg | ttgatgacca | actttctcga | 240 |

```
g                                                                    241

<210> SEQ ID NO 92
<211> LENGTH: 70
<212> TYPE: PRT
<213> ORGANISM: Conus generalis

<400> SEQUENCE: 92

Gly Ser Met Met Ser Lys Leu Gly Val Leu Leu Thr Ile Cys Leu Val
1               5                   10                  15

Leu Phe Pro Leu Thr Ala Leu Pro Leu Asp Gly Glu Gln Pro Val Asp
            20                  25                  30

Arg His Ala Glu His Met Gln Asp Asp Asn Ser Ala Ala Gln Asn Pro
        35                  40                  45

Trp Val Ile Ala Ile Arg Gln Cys Cys Thr Phe Cys Asn Phe Gly Cys
    50                  55                  60

Gln Pro Cys Cys Leu Thr
65                  70

<210> SEQ ID NO 93
<211> LENGTH: 16
<212> TYPE: PRT
<213> ORGANISM: Conus generalis
<220> FEATURE:
<221> NAME/KEY: PEPTIDE
<222> LOCATION: (1)..(16)
<223> OTHER INFORMATION: Xaa at residue 1 is Gln or pyro-Glu; Xaa at
      residue 12 is Pro or Hyp

<400> SEQUENCE: 93

Xaa Cys Cys Thr Phe Cys Asn Phe Gly Cys Gln Xaa Cys Cys Leu Thr
1               5                   10                  15

<210> SEQ ID NO 94
<211> LENGTH: 241
<212> TYPE: DNA
<213> ORGANISM: Conus generalis

<400> SEQUENCE: 94
ggatccatga tgtctaaact gggagtcttg ttgaccatct gtctggttct gtttcccctt    60
actgctcttc cactggatgg agaacaacct gtagaccgac atgccgagca tatgcaggat   120
gacaattcag ctgcacagaa ccctgggtt attgccatca gacagtgttg cacgttctgc    180
aactttggat gccagccttg ttgcgtcccc tgataacgtg ttgatgacca actttctcga   240
g                                                                    241

<210> SEQ ID NO 95
<211> LENGTH: 70
<212> TYPE: PRT
<213> ORGANISM: Conus generalis

<400> SEQUENCE: 95

Gly Ser Met Met Ser Lys Leu Gly Val Leu Leu Thr Ile Cys Leu Val
1               5                   10                  15

Leu Phe Pro Leu Thr Ala Leu Pro Leu Asp Gly Glu Gln Pro Val Asp
            20                  25                  30

Arg His Ala Glu His Met Gln Asp Asp Asn Ser Ala Ala Gln Asn Pro
        35                  40                  45

Trp Val Ile Ala Ile Arg Gln Cys Cys Thr Phe Cys Asn Phe Gly Cys
    50                  55                  60
```

Gln Pro Cys Cys Val Pro
65              70

<210> SEQ ID NO 96
<211> LENGTH: 16
<212> TYPE: PRT
<213> ORGANISM: Conus generalis
<220> FEATURE:
<221> NAME/KEY: PEPTIDE
<222> LOCATION: (1)..(16)
<223> OTHER INFORMATION: Xaa at residue 1 is Gln or pyro-Glu; Xaa at
      residue 12 and 16 is Pro or Hyp

<400> SEQUENCE: 96

Xaa Cys Cys Thr Phe Cys Asn Phe Gly Cys Gln Xaa Cys Cys Val Xaa
1               5                   10                  15

<210> SEQ ID NO 97
<211> LENGTH: 862
<212> TYPE: DNA
<213> ORGANISM: Conus geographus

<400> SEQUENCE: 97
gtcgactcta gaggatccga caacaaagag tcaaccccac tgccacgtca agagcgaagc     60
gccacagcta agacaagagg gatcgatagc agttcatgat gtctaaactg ggagtcttgt    120
tgaccatctg tctgcttctg tttcccctta ctgctcttcc gatggatgga gatgaacctg    180
caaaccgacc tgtcgagcgt atgcaggaca catttcatc tgagcagtat cccttgtttg     240
agaagagacg agattgttgc actccgccga agaaatgcaa agaccgacaa tgcaaacccc    300
agagatgttg cgctggacga taacgtgttg atgaccaact ttatcacggc tacgtcaagt    360
gtttagtgaa taagtaaaat gattgcagtc ttgctcagat ttgcttttgt gttttggtct    420
aaagatcaat gaccaaaccg ttgttttgat gcggattgtc atatatttct cgattccaat    480
ccaacactag atgatttaat cacgatagat taattttcta tcaatgcctt gattttttcgt    540 ctgtcatatc agttttgttt atatttattt tttcgtcact gtctacacaa acgcatgcat    600
gcacgcatgc acgcacacac gcacgcacgc tcgcacaaac atgcgcgcgc acgcacacac    660
acacacacac acacaaacac acacacaagc aatcacacaa ttattgacat tatttattta    720
ttcattgatg tatttgttat tcgtttgctt gttttttagaa tagtttgagg ccgtcttttt    780 ggattttattt gaactgcttt attgtatacg agtacttcgt gctttgaaac actgctgaaa    840
ataaaacaaa cactgacgta gc                                              862

<210> SEQ ID NO 98
<211> LENGTH: 75
<212> TYPE: PRT
<213> ORGANISM: Conus geographus

<400> SEQUENCE: 98

Met Met Ser Lys Leu Gly Val Leu Leu Thr Ile Cys Leu Leu Leu Phe
1               5                   10                  15

Pro Leu Thr Ala Leu Pro Met Asp Gly Asp Glu Pro Ala Asn Arg Pro
            20                  25                  30

Val Glu Arg Met Gln Asp Asn Ile Ser Ser Glu Gln Tyr Pro Leu Phe
        35                  40                  45

Glu Lys Arg Arg Asp Cys Cys Thr Pro Pro Lys Lys Cys Lys Asp Arg
    50                  55                  60

Gln Cys Lys Pro Gln Arg Cys Cys Ala Gly Arg

<210> SEQ ID NO 99
<211> LENGTH: 22
<212> TYPE: PRT
<213> ORGANISM: Conus geographus
<220> FEATURE:
<221> NAME/KEY: PEPTIDE
<222> LOCATION: (1)..(22)
<223> OTHER INFORMATION: Xaa at residue 6, 7 and 17 is Pro or Hyp

<400> SEQUENCE: 99

Arg Asp Cys Cys Thr Xaa Xaa Lys Lys Cys Lys Asp Arg Gln Cys Lys
1               5                   10                  15

Xaa Gln Arg Cys Cys Ala
            20

<210> SEQ ID NO 100
<211> LENGTH: 860
<212> TYPE: DNA
<213> ORGANISM: Conus geographus

<400> SEQUENCE: 100
ggccagacga caacaaagag tcaaccccac tgccacgtca agagcgaagc gccacagcta      60
agacaagagg gatcgatagc agttcatgat gtctaaactg ggagtcttgt tgaccatctg    120
tctgcttctg tttcccctta ctgctcttcc gatggatgga gatgaacctg caaccgacc    180 tgtcgagcgt atgcaggaca acatttcatc tgagcagtat cccttgtttg agaagagacg    240
agattgttgc actccgccga ggaaatgcaa agaccgacga tgcaaaccca tgaaatgttg    300
cgctggacga taacgtgttg atgaccaact ttatcacggc tagctcagtg tttagtgaat    360
aagtaaaatg attgcagtct tgctcagatt gcttttgtgt tttggtctaa gatcaatgac    420 caaccgttg ttttgatgcg gattgtcata tatttctcga ttccaatcca acactagatg    480
atttaatcac gatagattaa ttttctatca atgccttgat ttttcgtctg tcatatcagt    540
tttgtttata tttattttt cgtcactgtc tacacaaacg catgcatgca cgcatgcacg    600
cacacacgca cgcacgctcg cacaaacatg cgcgcgcacg cacacacaca cacacacaca    660
aacacacaca cgaagcaatc acacaattag ttgacattat ttatttattc attgatgtat    720
ttgttattcg tttgcttgtt tttagaatag tttgaggccg tcttttggga tttatttgaa    780
ctgctttatt gtatacgagt acttcgtgct ttgaaacact gctgaaaata aaacaaacac    840
tgacgtagca aaaaaaaaaa                                                860

<210> SEQ ID NO 101
<211> LENGTH: 75
<212> TYPE: PRT
<213> ORGANISM: Conus geographus

<400> SEQUENCE: 101

Met Met Ser Lys Leu Gly Val Leu Leu Thr Ile Cys Leu Leu Leu Phe
1               5                   10                  15

Pro Leu Thr Ala Leu Pro Met Asp Gly Asp Glu Pro Ala Asn Arg Pro
            20                  25                  30

Val Glu Arg Met Gln Asp Asn Ile Ser Ser Glu Gln Tyr Pro Leu Phe
        35                  40                  45

Glu Lys Arg Arg Asp Cys Cys Thr Pro Pro Arg Lys Cys Lys Asp Arg
    50                  55                  60

Arg Cys Lys Pro Met Lys Cys Cys Ala Gly Arg

```
<210> SEQ ID NO 102
<211> LENGTH: 22
<212> TYPE: PRT
<213> ORGANISM: Conus geographus
<220> FEATURE:
<221> NAME/KEY: PEPTIDE
<222> LOCATION: (1)..(22)
<223> OTHER INFORMATION: Xaa at residue 6, 7 and 17 is Pro or Hyp

<400> SEQUENCE: 102

Arg Asp Cys Cys Thr Xaa Xaa Arg Lys Cys Lys Asp Arg Arg Cys Lys
1               5                   10                  15

Xaa Met Lys Cys Cys Ala
            20

<210> SEQ ID NO 103
<211> LENGTH: 22
<212> TYPE: PRT
<213> ORGANISM: Conus geographus
<220> FEATURE:
<221> NAME/KEY: PEPTIDE
<222> LOCATION: (1)..(22)
<223> OTHER INFORMATION: Xaa at residue 6, 7 and 17 is Pro or Hyp

<400> SEQUENCE: 103

Arg Asp Cys Cys Thr Xaa Xaa Lys Lys Cys Lys Asp Arg Arg Cys Lys
1               5                   10                  15

Xaa Leu Lys Cys Cys Ala
            20

<210> SEQ ID NO 104
<211> LENGTH: 321
<212> TYPE: DNA
<213> ORGANISM: Conus gloriamaris

<400> SEQUENCE: 104
ctcactatag gaattcgagc tcggtacacg ggatcgatag cagttcatga tgtctaaact      60
gggagccttg ttgaccatct gtctacttct gttttcccta actgctgttc cgctggatgg    120
agatcaacat gcagaccaac ctgcagagcg tctgcatgac cgccttccaa ctgaaaatca    180
tcccttatat gatcccgtca acggtgttg cgatgattcg gaatgcgact attcttgctg     240
gccttgctgt atgtttggat aacctttgtt atcgcggcct cgataagtgt ctaatgaata    300
agtaaaacga ttgcagtagg c                                              321

<210> SEQ ID NO 105
<211> LENGTH: 71
<212> TYPE: PRT
<213> ORGANISM: Conus gloriamaris

<400> SEQUENCE: 105

Met Met Ser Lys Leu Gly Ala Leu Leu Thr Ile Cys Leu Leu Leu Phe
1               5                   10                  15

Ser Leu Thr Ala Val Pro Leu Asp Gly Asp Gln His Ala Asp Gln Pro
            20                  25                  30

Ala Glu Arg Leu His Asp Arg Leu Pro Thr Glu Asn His Pro Leu Tyr
        35                  40                  45

Asp Pro Val Lys Arg Cys Cys Asp Asp Ser Glu Cys Asp Tyr Ser Cys
    50                  55                  60

Trp Pro Cys Cys Met Phe Gly
```

-continued

<210> SEQ ID NO 106
<211> LENGTH: 17
<212> TYPE: PRT
<213> ORGANISM: Conus gloriamaris
<220> FEATURE:
<221> NAME/KEY: PEPTIDE
<222> LOCATION: (1)..(17)
<223> OTHER INFORMATION: Xaa at residue is 6 Glu or gamma-carboxy Glu;
      Xaa at residue 13 is Pro or Hyp; Xaa at residue 12 is Trp or
      bromo-Trp; Xaa at residue 9 is Tyr, 125I-Tyr, mono-iodo-Tyr,
      di-iodo-Tyr, O-sulpho-Tyr or O-phospho-Tyr

<400> SEQUENCE: 106

Cys Cys Asp Asp Ser Xaa Cys Asp Xaa Ser Cys Xaa Xaa Cys Cys Met
1               5                   10                  15

Phe

<210> SEQ ID NO 107
<211> LENGTH: 257
<212> TYPE: DNA
<213> ORGANISM: Conus gloriamaris

<400> SEQUENCE: 107
gttcatgatg tctaaactgg gagtcttgtt gatcatctgt ctacttctgt ttccccttac      60
tgctgttccg ctggatggag atcaacctgc agaccgatat gcagagcgta tgcaggacga    120
catttcatct gaacatcatc ccatgtttga tgccgtcaga gggtgttgcc atctgttggc    180
atgccgcttc ggatgctcgc cttgttgttg gtgatcagct ttgttatcgc ggcctcatca    240
agtgactcta atgcaaa                                                   257

<210> SEQ ID NO 108
<211> LENGTH: 69
<212> TYPE: PRT
<213> ORGANISM: Conus gloriamaris

<400> SEQUENCE: 108

Met Met Ser Lys Leu Gly Val Leu Leu Ile Ile Cys Leu Leu Leu Phe
1               5                   10                  15

Pro Leu Thr Ala Val Pro Leu Asp Gly Asp Gln Pro Ala Asp Arg Tyr
                20                  25                  30

Ala Glu Arg Met Gln Asp Asp Ile Ser Ser Glu His His Pro Met Phe
            35                  40                  45

Asp Ala Val Arg Gly Cys Cys His Leu Leu Ala Cys Arg Phe Gly Cys
        50                  55                  60

Ser Pro Cys Cys Trp
65

<210> SEQ ID NO 109
<211> LENGTH: 17
<212> TYPE: PRT
<213> ORGANISM: Conus gloriamaris
<220> FEATURE:
<221> NAME/KEY: PEPTIDE
<222> LOCATION: (1)..(17)
<223> OTHER INFORMATION: Xaa at residue 14 is Pro or Hyp; Xaa at
      residue 17 is Trp or bromo-Trp

<400> SEQUENCE: 109

Gly Cys Cys His Leu Leu Ala Cys Arg Phe Gly Cys Ser Xaa Cys Cys
1               5                   10                  15

Xaa

<210> SEQ ID NO 110
<211> LENGTH: 471
<212> TYPE: DNA
<213> ORGANISM: Conus gloriamaris

<400> SEQUENCE: 110

```
gagacgacaa ggaacagtca accccacagc cacgccaaga gcagacagcc acagctacgt      60
gaagaagggt ggagagaggt tcgtgatgtt gaaaatggga gtggtgctat tcatcttcct     120
ggtactgttt cccctggcaa cgctccagct ggatgcagat caacctgtag aacgatatgc     180
ggagaacaaa cagctcctca acccagatga aggagggaa atcatattgc atgctctggg     240
gacgcgatgc tgttcttggg atgtgtgcga ccacccgagt tgtacttgct gcggcggtta     300
gcgccgaaca tccatggcgc tgtgctgggc ggttttatcc aacaacgaca gcgtttgttg     360
atttcatgta tcattgcgcc cacgtctctt gtctaagaat gacgaacatg attgcactct     420
ggttcagatt tcgtgttctt ttctgacaat aaatgacaaa actccaaaaa a              471
```

<210> SEQ ID NO 111
<211> LENGTH: 71
<212> TYPE: PRT
<213> ORGANISM: Conus gloriamaris

<400> SEQUENCE: 111

Met Leu Lys Met Gly Val Val Leu Phe Ile Phe Leu Val Leu Phe Pro
1               5                   10                  15

Leu Ala Thr Leu Gln Leu Asp Ala Asp Gln Pro Val Glu Arg Tyr Ala
            20                  25                  30

Glu Asn Lys Gln Leu Leu Asn Pro Asp Glu Arg Arg Glu Ile Ile Leu
        35                  40                  45

His Ala Leu Gly Thr Arg Cys Cys Ser Trp Asp Val Cys Asp His Pro
    50                  55                  60

Ser Cys Thr Cys Cys Gly Gly
65                  70

<210> SEQ ID NO 112
<211> LENGTH: 16
<212> TYPE: PRT
<213> ORGANISM: Conus gloriamaris
<220> FEATURE:
<221> NAME/KEY: PEPTIDE
<222> LOCATION: (1)..(16)
<223> OTHER INFORMATION: Xaa at residue 10 is Pro or Hyp; Xaa at
      residue 4 is Trp or bromo-Trp

<400> SEQUENCE: 112

Cys Cys Ser Xaa Asp Val Cys Asp His Xaa Ser Cys Thr Cys Cys Gly
1               5                   10                  15

<210> SEQ ID NO 113
<211> LENGTH: 304
<212> TYPE: DNA
<213> ORGANISM: Conus laterculatus

<400> SEQUENCE: 113

```
cgacctcaag aaggatcgat agcagttcat gatgtctaaa ctgggagtct tgttgaccat      60
ctgtctgctt ctgtttcccc ttactgctct tccgatggat ggagatcaac tgcagaccg     120
acctgcagag cgtatgcagg acgtttcatc tgaacagcat cccttgtatg atcccgtcaa     180
```

-continued

```
acggtgttgc gactggccat gcagcggatg catcccttgt tgctaatagt aacaacgtgt      240
tgataaccaa ctttcttacc acgactacgt caagtgtcta atgaataagt aaaatgattg      300
cagt                                                                   304
```

<210> SEQ ID NO 114
<211> LENGTH: 65
<212> TYPE: PRT
<213> ORGANISM: Conus laterculatus

<400> SEQUENCE: 114

```
Met Met Ser Lys Leu Gly Val Leu Leu Thr Ile Cys Leu Leu Leu Phe
 1               5                  10                  15

Pro Leu Thr Ala Leu Pro Met Asp Gly Asp Gln Pro Ala Asp Arg Pro
            20                  25                  30

Ala Glu Arg Met Gln Asp Val Ser Ser Glu Gln His Pro Leu Tyr Asp
        35                  40                  45

Pro Val Lys Arg Cys Cys Asp Trp Pro Cys Ser Gly Cys Ile Pro Cys
    50                  55                  60

Cys
65
```

<210> SEQ ID NO 115
<211> LENGTH: 13
<212> TYPE: PRT
<213> ORGANISM: Conus laterculatus
<220> FEATURE:
<221> NAME/KEY: PEPTIDE
<222> LOCATION: (1)..(13)
<223> OTHER INFORMATION: Xaa at residue 5 and 11 is Pro or Hyp; Xaa at
      residue 4 is Trp or bromo-Trp

<400> SEQUENCE: 115

```
Cys Cys Asp Xaa Xaa Cys Ser Gly Cys Ile Xaa Cys Cys
 1               5                  10
```

<210> SEQ ID NO 116
<211> LENGTH: 313
<212> TYPE: DNA
<213> ORGANISM: Conus laterculatus

<400> SEQUENCE: 116

```
cgacctcaag aaggatcgat agcagttcat gatgtctaaa ctgggagtct tgttgaccat       60
ctgtctgctt ctgtttcccc ttactgctct ggatggagat caacctgcag accgacttgc     120
agagcgtatg caggacgaca tttcatctga gcagcatccc tttgaaaaga gacgagactg     180
ttgcacacct ccgaagaaat gcagagaccg acaatgcaaa cctgcacgtt gttgcggagg     240
ataacgtgtt gatgaccaac tttgttatca cggctacgtc aagtgtctag tgaataagta     300
aaacgattgc agt                                                        313
```

<210> SEQ ID NO 117
<211> LENGTH: 71
<212> TYPE: PRT
<213> ORGANISM: Conus laterculatus

<400> SEQUENCE: 117

```
Met Met Ser Lys Leu Gly Val Leu Leu Thr Ile Cys Leu Leu Leu Phe
 1               5                  10                  15

Pro Leu Thr Ala Leu Asp Gly Asp Gln Pro Ala Asp Arg Leu Ala Glu
            20                  25                  30
```

```
Arg Met Gln Asp Asp Ile Ser Ser Glu Gln His Pro Phe Glu Lys Arg
            35                  40                  45

Arg Asp Cys Cys Thr Pro Pro Lys Lys Cys Arg Asp Arg Gln Cys Lys
        50                  55                  60

Pro Ala Arg Cys Cys Gly Gly
65                  70

<210> SEQ ID NO 118
<211> LENGTH: 22
<212> TYPE: PRT
<213> ORGANISM: Conus laterculatus
<220> FEATURE:
<221> NAME/KEY: PEPTIDE
<222> LOCATION: (1)..(22)
<223> OTHER INFORMATION: Xaa at residue 6, 17 and 17 is Pro or Hyp

<400> SEQUENCE: 118

Arg Asp Cys Cys Thr Xaa Xaa Lys Lys Cys Arg Asp Arg Gln Cys Lys
1               5                   10                  15

Xaa Ala Arg Cys Cys Gly
                20

<210> SEQ ID NO 119
<211> LENGTH: 314
<212> TYPE: DNA
<213> ORGANISM: Conus laterculatus

<400> SEQUENCE: 119
gggatcgata gcagttcatg atgtctaaac tgggagtctt gttgaccatc tgtctgcttc      60
tgtttcccct tactgctctt ccgatggatg gagatcaact tgcacgccga tctgcagagc     120
gtatgcagga caacatttca tctgagcagc atcacctctt gaaaagaga cgaccaccat      180 gttgcaccta tgacgggagt tgcctaaaag aatcatgcat gcgtaaagct tgttgcggat     240
gataacgtgt tgatgaccaa ctttgttatc acggctactc aagtgtctaa tgaataagta     300
aaatgattgc agta                                                       314

<210> SEQ ID NO 120
<211> LENGTH: 74
<212> TYPE: PRT
<213> ORGANISM: Conus laterculatus

<400> SEQUENCE: 120

Met Met Ser Lys Leu Gly Val Leu Leu Thr Ile Cys Leu Leu Leu Phe
1               5                   10                  15

Pro Leu Thr Ala Leu Pro Met Asp Gly Asp Gln Leu Ala Arg Arg Ser
                20                  25                  30

Ala Glu Arg Met Gln Asp Asn Ile Ser Ser Glu Gln His His Leu Phe
            35                  40                  45

Glu Lys Arg Arg Pro Pro Cys Cys Thr Tyr Asp Gly Ser Cys Leu Lys
        50                  55                  60

Glu Ser Cys Met Arg Lys Ala Cys Cys Gly
65                  70

<210> SEQ ID NO 121
<211> LENGTH: 22
<212> TYPE: PRT
<213> ORGANISM: Conus laterculatus
<220> FEATURE:
<221> NAME/KEY: PEPTIDE
<222> LOCATION: (1)..(22)
<223> OTHER INFORMATION: Xaa at residue 14 is Glu or gamma-carboxy Glu;
```

Xaa at residue 2 and 3 is Pro or Hyp; Xaa at residue 7 is Tyr,
        125I-Tyr, mono-iodo-Tyr, di-iodo-Tyr, O-sulpho-Tyr or O-phospho-Tyr

<400> SEQUENCE: 121

Arg Xaa Xaa Cys Cys Thr Xaa Asp Gly Ser Cys Leu Lys Xaa Ser Cys
1               5                   10                  15

Met Arg Lys Ala Cys Cys
            20

<210> SEQ ID NO 122
<211> LENGTH: 314
<212> TYPE: DNA
<213> ORGANISM: Conus laterculatus

<400> SEQUENCE: 122
gggatcgata gcagttcatg atgtctaaac tgggagtctt gttgaccacc tgtctgcttc      60
tgtttcccct tactgctctt ccgatggatg gagatcaact tgcacgccga cctgcagagc    120
gtatgcagga caacatttca tctgagcagc atccttcttt gaaaggaga cgaccaccat     180 gttgcaccta tgacgggagt tgcctaaaag aatcatgcaa gcgtaaagct tgttgcggat    240
aataacgtgt tgatgaccaa ctttgttatc acggctactc aagtgtctaa tgaataagta    300
aaatgattgc agta                                                      314

<210> SEQ ID NO 123
<211> LENGTH: 74
<212> TYPE: PRT
<213> ORGANISM: Conus laterculatus

<400> SEQUENCE: 123

Met Met Ser Lys Leu Gly Val Leu Leu Thr Thr Cys Leu Leu Leu Phe
1               5                   10                  15

Pro Leu Thr Ala Leu Pro Met Asp Gly Asp Gln Leu Ala Arg Arg Pro
            20                  25                  30

Ala Glu Arg Met Gln Asp Asn Ile Ser Ser Glu Gln His Pro Phe Phe
        35                  40                  45

Glu Arg Arg Arg Pro Pro Cys Cys Thr Tyr Asp Gly Ser Cys Leu Lys
    50                  55                  60

Glu Ser Cys Lys Arg Lys Ala Cys Cys Gly
65                  70

<210> SEQ ID NO 124
<211> LENGTH: 22
<212> TYPE: PRT
<213> ORGANISM: Conus laterculatus
<220> FEATURE:
<221> NAME/KEY: PEPTIDE
<222> LOCATION: (1)..(22)
<223> OTHER INFORMATION: Xaa at residue 14 is Glu or gamma-carboxy Glu;
        Xaa at residue 2 and 3 is Pro or Hyp; Xaa at residue7  is Tyr,
        125I-Tyr, mono-iodo-Tyr, di-iodo-Tyr, O-sulpho-Tyr or O-phospho-Tyr

<400> SEQUENCE: 124

Arg Xaa Xaa Cys Cys Thr Xaa Asp Gly Ser Cys Leu Lys Xaa Ser Cys
1               5                   10                  15

Lys Arg Lys Ala Cys Cys
            20

<210> SEQ ID NO 125
<211> LENGTH: 247
<212> TYPE: DNA
<213> ORGANISM: Conus leopardus -continued

<400> SEQUENCE: 125

```
ggatccatga tgtctaaact gggagtcttg ttgaccgtct gtctgcttct gtttcccctt      60
actgctcttc ggctggttgg agatcaacct gcagagcgac ctgcaaagcg tacgcaggac     120
gacattccag atggacagca tccgttaaat gataggcaga taaactgttg cccgtggcca     180
tgccctagta catgccgcca tcaatgctgc cattaatgat aacgtgttga tgaccaactt     240
tctcgag                                                               247
```

<210> SEQ ID NO 126
<211> LENGTH: 71
<212> TYPE: PRT
<213> ORGANISM: Conus leopardus

<400> SEQUENCE: 126

```
Gly Ser Met Met Ser Lys Leu Gly Val Leu Leu Thr Val Cys Leu Leu
1               5                   10                  15

Leu Phe Pro Leu Thr Ala Leu Arg Leu Val Gly Asp Gln Pro Ala Glu
            20                  25                  30

Arg Pro Ala Lys Arg Thr Gln Asp Asp Ile Pro Asp Gly Gln His Pro
        35                  40                  45

Leu Asn Asp Arg Gln Ile Asn Cys Cys Pro Trp Pro Cys Pro Ser Thr
    50                  55                  60

Cys Arg His Gln Cys Cys His
65                  70
```

<210> SEQ ID NO 127
<211> LENGTH: 19
<212> TYPE: PRT
<213> ORGANISM: Conus leopardus
<220> FEATURE:
<221> NAME/KEY: PEPTIDE
<222> LOCATION: (1)..(19)
<223> OTHER INFORMATION: Xaa at residue 1 is Gln or pyro-Glu; Xaa at
      residue 6, 8 and 10 is Pro or Hyp; Xaa at residue 7 is Trp or
      bromo-Trp

<400> SEQUENCE: 127

```
Xaa Ile Asn Cys Cys Xaa Xaa Xaa Cys Xaa Ser Thr Cys Arg His Gln
1               5                   10                  15

Cys Cys His
```

<210> SEQ ID NO 128
<211> LENGTH: 244
<212> TYPE: DNA
<213> ORGANISM: Conus lividus

<400> SEQUENCE: 128

```
ggatccatga tgtctaaact gggagtcttg ttgaccgtct gtctgcttct gtttcccctt      60
actgctcttc ggctggttag agatcaacct gcagagcgac ctgcaaagcg tacgcaggac     120
gacattccaa atggacagga tccgttaatt gataggcaga taaattgttg cccttggcca     180
tgccctgatt catgccacta tcaatgctgc cactgataac gtgttgatga ccaactttct     240
cgag                                                                  244
```

<210> SEQ ID NO 129
<211> LENGTH: 71
<212> TYPE: PRT
<213> ORGANISM: Conus lividus -continued

<400> SEQUENCE: 129

Gly Ser Met Met Ser Lys Leu Gly Val Leu Leu Thr Val Cys Leu Leu
1               5                   10                  15

Leu Phe Pro Leu Thr Ala Leu Arg Leu Val Arg Asp Gln Pro Ala Glu
            20                  25                  30

Arg Pro Ala Lys Arg Thr Gln Asp Asp Ile Pro Asn Gly Gln Asp Pro
        35                  40                  45

Leu Ile Asp Arg Gln Ile Asn Cys Cys Pro Trp Pro Cys Pro Asp Ser
    50                  55                  60

Cys His Tyr Gln Cys His
65                  70

<210> SEQ ID NO 130
<211> LENGTH: 19
<212> TYPE: PRT
<213> ORGANISM: Conus lividus
<220> FEATURE:
<221> NAME/KEY: PEPTIDE
<222> LOCATION: (1)..(19)
<223> OTHER INFORMATION: Xaa at residue 1 is Gln or pyro-Glu; Xaa at
      residue 6, 8 and 10 is Pro or Hyp; Xaa at residue 7 is Trp or
      bromo-Trp; Xaa at residue 15 is Tyr, 125I-Tyr, mono-iodo-Tyr,
      di-iodo-Tyr, O-sulpho-Tyr or O-phospho-Tyr

<400> SEQUENCE: 130

Xaa Ile Asn Cys Cys Xaa Xaa Xaa Cys Xaa Asp Ser Cys His Xaa Gln
1               5                   10                  15

Cys Cys His

<210> SEQ ID NO 131
<211> LENGTH: 275
<212> TYPE: DNA
<213> ORGANISM: Conus lynceus

<400> SEQUENCE: 131
aaggatcgat agcagttcat gatgtctaaa ctgggagtct tgttgaccat ctgtctgctt      60
ctgtttcccc ttactgctct tccgatggat ggagatcaat ctgcagaccg acttgcagag     120
cgtatgcagg acaacatttc atctgagcag catcccttct ttgaaaagag aggacgagac     180
tgttgcacac ctccgaggaa atgcagagac cgagcctgca aacctcaacg ttgttgcgga     240
ggataagctg ttgatgacca actttgttat acggc                                275

<210> SEQ ID NO 132
<211> LENGTH: 75
<212> TYPE: PRT
<213> ORGANISM: Conus lynceus

<400> SEQUENCE: 132

Met Met Ser Lys Leu Gly Val Leu Leu Thr Ile Cys Leu Leu Leu Phe
1               5                   10                  15

Pro Leu Thr Ala Leu Pro Met Asp Gly Asp Gln Ser Ala Asp Arg Leu
            20                  25                  30

Ala Glu Arg Met Gln Asp Asn Ile Ser Ser Glu Gln His Pro Phe Phe
        35                  40                  45

Glu Lys Arg Gly Arg Asp Cys Cys Thr Pro Pro Arg Lys Cys Arg Asp
    50                  55                  60

Arg Ala Cys Lys Pro Gln Arg Cys Cys Gly Gly
65                  70                  75

-continued

```
<210> SEQ ID NO 133
<211> LENGTH: 23
<212> TYPE: PRT
<213> ORGANISM: Conus lynceus
<220> FEATURE:
<221> NAME/KEY: PEPTIDE
<222> LOCATION: (1)..(23)
<223> OTHER INFORMATION: Xaa at residue 7, 8 and 18 is Pro or Hyp

<400> SEQUENCE: 133

Gly Arg Asp Cys Cys Thr Xaa Xaa Arg Lys Cys Arg Asp Arg Ala Cys
1               5                   10                  15

Lys Xaa Gln Arg Cys Cys Gly
            20
```

```
<210> SEQ ID NO 134
<211> LENGTH: 803
<212> TYPE: DNA
<213> ORGANISM: Conus magus

<400> SEQUENCE: 134
caagagggat cgatagcagt tcatgatgtc taaactggga gtcttgttga ccatctgtct    60
gcttctgttt cccttactg ctcttccgat ggatggagat gaacctgcaa accgacctgt   120
cgagcgtatg caggacaaca tttcatctga gcagtatccc ttgtttgaga agagacgaga   180
ttgttgcact ccgccgaaga aatgcaaaga ccgacaatgc aaaccccaga gatgttgcgc   240
tggacgataa cgtgttgatg accaacttta tcacggctac gtcaagtgtt tagtgaataa   300
gtaaaatgat tgcagtcttg ctcagatttg cttttgtgtt ttggtctaaa gatcaatgac   360
caaaccgttg ttttgatgcg gattgtcata tatttctcga ttccaatcca acactagatg   420
atttaatcac gatagattaa ttttctatca atgccttgat ttttcgtctg tcatatcagt   480
tttgtttata tttattttt cgtcactgtc tacacaaacg catgcatgca cgcatgcacg   540
cacacacgca cgcacgctcg cacaaacatg cgcgcgcacg cacacacaca cacacacaca   600
caaacacaca cacgaagcaa tcacacaatt agttgacatt atttatttat tcattgatgt   660
atttgttatt cgtttgcttg tttttagaat agtttgaggc cgtcttttg gatttatttg    720
aactgcttta ttgtatacga gtacttcgtg cggggaaaca ctgctgaaaa taaaacaaac   780
actgacgtag caaaaaaaaa aaa                                           803
```

```
<210> SEQ ID NO 135
<211> LENGTH: 75
<212> TYPE: PRT
<213> ORGANISM: Conus magus

<400> SEQUENCE: 135

Met Met Ser Lys Leu Gly Val Leu Leu Thr Ile Cys Leu Leu Leu Phe
1               5                   10                  15

Pro Leu Thr Ala Leu Pro Met Asp Gly Asp Glu Pro Ala Asn Arg Pro
            20                  25                  30

Val Glu Arg Met Gln Asp Asn Ile Ser Ser Gln Tyr Pro Leu Phe
        35                  40                  45

Glu Lys Arg Arg Asp Cys Cys Thr Pro Pro Lys Lys Cys Lys Asp Arg
    50                  55                  60

Gln Cys Lys Pro Gln Arg Cys Cys Ala Gly Arg
65                  70                  75
```

```
<210> SEQ ID NO 136
<211> LENGTH: 22
```

```
<212> TYPE: PRT
<213> ORGANISM: Conus magus
<220> FEATURE:
<221> NAME/KEY: PEPTIDE
<222> LOCATION: (1)..(22)
<223> OTHER INFORMATION: Xaa at residue 6 and 7 is Pro or Hyp

<400> SEQUENCE: 136

Arg Asp Cys Cys Thr Xaa Xaa Lys Lys Cys Lys Asp Arg Gln Cys Lys
1               5                   10                  15

Xaa Gln Arg Cys Cys Ala
            20

<210> SEQ ID NO 137
<211> LENGTH: 656
<212> TYPE: DNA
<213> ORGANISM: Conus magus

<400> SEQUENCE: 137
caagagggat cgatagcagt tcatgatgtc taaactggga gtcttgttga ccatctgtct      60
gcttctgttt ccccttactg ctcttccaat ggatggagat caacctgcag accaacctgc    120
agatcgtatg caggacgaca tttcatctga gcagtatccc ttgtttgata tgagaaaaag    180
gtgttgcggc cccggcggtt catgccccgt atatttcaga acaattttta tttgtggttg    240
ttgttaaatg acaacgtgtc gatgaccaac ttcattatca cgactacgcc aagtgtctaa    300
tgaataaata aaatgattgc agtctcgctc agatttgctt ttgtattttg gtctaaagat    360
caatgaccaa accgttgttt ggtgtggat tttcatatat ttctcgagtc ctatccaaca     420
ctagatgatt taatcacgat agatctgatt tttttatcaa aggcttggtt tttcgtctgt   480
cacatcagtt ttgtttatat ttaattttc gtcactgatt acacacacgc atgaacgcac    540
agagtactaa cacatacaca cacacacaca cacacacaca cacacacaca cacacacaca    600
cacacacaca cacgcgcgcg cgcggcgcca tctagtagcg ccgcgacgac acacac        656

<210> SEQ ID NO 138
<211> LENGTH: 74
<212> TYPE: PRT
<213> ORGANISM: Conus magus

<400> SEQUENCE: 138

Met Met Ser Lys Leu Gly Val Leu Leu Thr Ile Cys Leu Leu Leu Phe
1               5                   10                  15

Pro Leu Thr Ala Leu Pro Met Asp Gly Asp Gln Pro Ala Asp Gln Pro
            20                  25                  30

Ala Asp Arg Met Gln Asp Ile Ser Ser Glu Gln Tyr Pro Leu Phe
        35                  40                  45

Asp Met Arg Lys Arg Cys Cys Gly Pro Gly Gly Ser Cys Pro Val Tyr
    50                  55                  60

Phe Arg Asp Asn Phe Ile Cys Gly Cys Cys
65                  70

<210> SEQ ID NO 139
<211> LENGTH: 21
<212> TYPE: PRT
<213> ORGANISM: Conus magus
<220> FEATURE:
<221> NAME/KEY: PEPTIDE
<222> LOCATION: (1)..(21)
<223> OTHER INFORMATION: Xaa at residue 4 and 9 is Pro or Hyp; Xaa at
      residue is 11 Tyr, 125I-Tyr, mono-iodo-Tyr, di-iodo-Tyr,
      O-sulpho-Tyr or O-phospho-Tyr
```

<400> SEQUENCE: 139

Cys Cys Gly Xaa Gly Gly Ser Cys Xaa Val Xaa Phe Arg Asp Asn Phe
1               5                   10                  15

Ile Cys Gly Cys Cys
            20

<210> SEQ ID NO 140
<211> LENGTH: 594
<212> TYPE: DNA
<213> ORGANISM: Conus magus

<400> SEQUENCE: 140
caagagggat cgatagcagt tcatgatgtc taaactggga gtcttgttga ccatctgttt      60
gcttctgttt cccccttactg ctcttccgag ggatggagat caatctgtag accgacctgc   120
agagcgtatg caggacgaca tttcatctga gctgcatccc ttgtcaatca gaaaaagaat    180
gtgttgcggc gagagtgcgc catgccccag ctatttcaga acagtcaga tttgtcattg     240 ttgttaaatg acaacgtgtc gatgaccacc ttcgttatca cgactaatga taagtaaaat   300
gattgcagtc tcgctcagat ttgcttttgt attttggtct aaagatcaat gaccaaaccg  360
ttgttttgat gtggatttc atatatttct cgagtcctat ccaacactag atgatttaat    420
cacgatagat ctgatttttt tatcaaagcc ttggttttc gtctgtcaca tcagttttgt    480
ttatatttaa ttttcgtca ctgattacac acacgcatga acgcacagac gtactaacac   540
atacacacac acacacacac acacacacac acacacacac acacacacac acac         594

<210> SEQ ID NO 141
<211> LENGTH: 74
<212> TYPE: PRT
<213> ORGANISM: Conus magus

<400> SEQUENCE: 141

Met Met Ser Lys Leu Gly Val Leu Leu Thr Ile Cys Leu Leu Leu Phe
1               5                   10                  15

Pro Leu Thr Ala Leu Pro Arg Asp Gly Asp Gln Ser Val Asp Arg Pro
            20                  25                  30

Ala Glu Arg Met Gln Asp Asp Ile Ser Ser Glu Leu His Pro Leu Ser
        35                  40                  45

Ile Arg Lys Arg Met Cys Cys Gly Glu Ser Ala Pro Cys Pro Ser Tyr
    50                  55                  60

Phe Arg Asn Ser Gln Ile Cys His Cys Cys
65                  70

<210> SEQ ID NO 142
<211> LENGTH: 22
<212> TYPE: PRT
<213> ORGANISM: Conus magus
<220> FEATURE:
<221> NAME/KEY: PEPTIDE
<222> LOCATION: (1)..(22)
<223> OTHER INFORMATION: Xaa at residue 5 is Glu or gamma-carboxy Glu;
      Xaa at residue 8 and 10 is Pro or Hyp; Xaa at residue 12 is Tyr,
      125I-Tyr, mono-iodo-Tyr, di-iodo-Tyr, O-sulpho-Tyr or
      O-phospho-Tyr

<400> SEQUENCE: 142

Met Cys Cys Gly Xaa Ser Ala Xaa Cys Xaa Ser Xaa Phe Arg Asn Ser
1               5                   10                  15

Gln Ile Cys His Cys Cys

-continued

<210> SEQ ID NO 143
<211> LENGTH: 501
<212> TYPE: DNA
<213> ORGANISM: Conus magus

<400> SEQUENCE: 143

```
caagagggat cgatagcagt tcatgatgtc taaactggga gtcttgttga ccatctgtct      60
gcttctgttt ccccttactg ctcttccaat ggatggagat caacctgcag accaacctgc     120
agatcgtatg caggacgaca tttcatctga gcagtatccc ttgtttgata agagacaaaa     180
gtgttgcggc cccggcggtt catgccccgt atatttcaca gacaatttta tttgtggttg     240
ttgttaaatg acaacgtgtc gatgaccaac ttcattatca cgactacgcc aagtgtctaa     300
tgaataaata aaatgattgc agtctcgctc agatttgctt ttgtatttgg tctaaagatc     360
aatgaccaaa ccgttgtttt ggtgctggat tttcatatat ttctcgattc ctatccaaca     420
ctagatgatt taatcacgat agatctgatt ttttatcaa tgccttaatt ttttgctctg     480
tcatatcagt tttgttttata t                                              501
```

<210> SEQ ID NO 144
<211> LENGTH: 74
<212> TYPE: PRT
<213> ORGANISM: Conus magus

<400> SEQUENCE: 144

Met Met Ser Lys Leu Gly Val Leu Leu Thr Ile Cys Leu Leu Leu Phe
1               5                   10                  15

Pro Leu Thr Ala Leu Pro Met Asp Gly Asp Gln Pro Ala Asp Gln Pro
            20                  25                  30

Ala Asp Arg Met Gln Asp Asp Ile Ser Ser Glu Gln Tyr Pro Leu Phe
        35                  40                  45

Asp Lys Arg Gln Lys Cys Cys Gly Pro Gly Gly Ser Cys Pro Val Tyr
    50                  55                  60

Phe Thr Asp Asn Phe Ile Cys Gly Cys Cys
65                  70

<210> SEQ ID NO 145
<211> LENGTH: 23
<212> TYPE: PRT
<213> ORGANISM: Conus magus
<220> FEATURE:
<221> NAME/KEY: PEPTIDE
<222> LOCATION: (1)..(23)
<223> OTHER INFORMATION: Xaa at residue 1 is Gln or pyro-Glu; Xaa at
      residue 6 and 11 is Pro or Hyp; Xaa at residue 13 is Tyr,
      125I-Tyr, mono-iodo-Tyr, di-iodo-Tyr, O-sulpho-Tyr or
      O-phospho-Tyr

<400> SEQUENCE: 145

Xaa Lys Cys Cys Gly Xaa Gly Gly Ser Cys Xaa Val Xaa Phe Thr Asp
1               5                   10                  15

Asn Phe Ile Cys Gly Cys Cys
            20

<210> SEQ ID NO 146
<211> LENGTH: 454
<212> TYPE: DNA
<213> ORGANISM: Conus magus

<400> SEQUENCE: 146

```
caagagggat cgatagcagt tcatgatgtc taaactggga gtcttgttga ccatctgtct        60
gcttctgttt cccctactg ctcttccaat ggatggagat caacctgcag accaacctgc       120
agatcgtatg caggacgaca tttcatctga gcagtatccc ttgtttgata agagacaaaa       180
gtgttgcggc cccggcggtt catgccccgt atatttcaga gacaatttta tttgtggttg       240
ttgttaaatg acaacgtgtc gatgaccatc ttcattatca cgactacgcc aagtgtctaa       300
tgaataaata aaatgattgc agtctcgctc agatttgctt ttgtattttg gtctaaagat       360
caatgaccaa accgttgttt tggtgtggat tttcatatat ttctcgattc ctatccaaca       420
ctagatgatt taatcacgat agatctgatt tttt                                    454
```

<210> SEQ ID NO 147
<211> LENGTH: 74
<212> TYPE: PRT
<213> ORGANISM: Conus magus

<400> SEQUENCE: 147

```
Met Met Ser Lys Leu Gly Val Leu Leu Thr Ile Cys Leu Leu Leu Phe
1               5                   10                  15

Pro Leu Thr Ala Leu Pro Met Asp Gly Asp Gln Pro Ala Asp Gln Pro
            20                  25                  30

Ala Asp Arg Met Gln Asp Asp Ile Ser Ser Glu Gln Tyr Pro Leu Phe
        35                  40                  45

Asp Lys Arg Gln Lys Cys Cys Gly Pro Gly Gly Ser Cys Pro Val Tyr
    50                  55                  60

Phe Arg Asp Asn Phe Ile Cys Gly Cys Cys
65                  70
```

<210> SEQ ID NO 148
<211> LENGTH: 23
<212> TYPE: PRT
<213> ORGANISM: Conus magus
<220> FEATURE:
<221> NAME/KEY: PEPTIDE
<222> LOCATION: (1)..(23)
<223> OTHER INFORMATION: Xaa at residue 1 is Gln or pyro-Glu; Xaa at
      residue 6 and 11 is Pro or Hyp; Xaa at residue 13 is Tyr,
      125I-Tyr, mono-iodo-Tyr, di-iodo-Tyr, O-sulpho-Tyr or
      O-phospho-Tyr

<400> SEQUENCE: 148

```
Xaa Lys Cys Cys Gly Xaa Gly Gly Ser Cys Xaa Val Xaa Phe Arg Asp
1               5                   10                  15

Asn Phe Ile Cys Gly Cys Cys
            20
```

<210> SEQ ID NO 149
<211> LENGTH: 22
<212> TYPE: PRT
<213> ORGANISM: Conus magus
<220> FEATURE:
<221> NAME/KEY: PEPTIDE
<222> LOCATION: (1)..(22)
<223> OTHER INFORMATION: Xaa at residue 1 is Gln or pyro-Glu; Xaa at
      residue 10 and 20 is Pro or Hyp; Xaa at residue 12 is Tyr,
      125I-Tyr, mono-iodo-Tyr, di-iodo-Tyr, O-sulpho-Tyr or
      O-phospho-Tyr

<400> SEQUENCE: 149

```
Xaa Lys Cys Cys Ser Gly Gly Ser Cys Xaa Leu Xaa Phe Arg Asp Arg
1               5                   10                  15
```

-continued

```
Leu Ile Cys Xaa Cys Cys
            20

<210> SEQ ID NO 150
<211> LENGTH: 19
<212> TYPE: PRT
<213> ORGANISM: Conus marmoreus
<220> FEATURE:
<221> NAME/KEY: PEPTIDE
<222> LOCATION: (1)..(19)
<223> OTHER INFORMATION: Xaa at residue 16 is Pro or Hyp

<400> SEQUENCE: 150

Ser Lys Gln Cys Cys His Leu Ala Ala Cys Arg Phe Gly Cys Thr Xaa
1               5                   10                  15

Cys Cys Asn

<210> SEQ ID NO 151
<211> LENGTH: 321
<212> TYPE: DNA
<213> ORGANISM: Conus marmoreus

<400> SEQUENCE: 151
caagaaggat cgatagcagt tcatgatgtc taaactggga gtcttgttga ccatctgtct    60
gcttctgttt cccgttactg ctcttccgat ggatggtgat caacctgcag accgacttgt   120
agagcgtatg caggacaaca tttcatctga gcagcatccc ttctttgaaa agagaagagg   180
aggctgttgc acacctccga ggaaatgcaa agaccgagcc tgcaaacctg cacgttgctg   240
cggcccagga taacgtgttg atgaccaact ttgttatcac ggctacgtca agtgtctagt   300
gaataagtaa aacgattgca g                                            321

<210> SEQ ID NO 152
<211> LENGTH: 76
<212> TYPE: PRT
<213> ORGANISM: Conus marmoreus

<400> SEQUENCE: 152

Met Met Ser Lys Leu Gly Val Leu Leu Thr Ile Cys Leu Leu Leu Phe
1               5                   10                  15

Pro Val Thr Ala Leu Pro Met Asp Gly Asp Gln Pro Ala Asp Arg Leu
            20                  25                  30

Val Glu Arg Met Gln Asp Asn Ile Ser Ser Glu Gln His Pro Phe Phe
        35                  40                  45

Glu Lys Arg Arg Gly Gly Cys Cys Thr Pro Arg Lys Cys Lys Asp
    50                  55                  60

Arg Ala Cys Lys Pro Ala Arg Cys Cys Gly Pro Gly
65                  70                  75

<210> SEQ ID NO 153
<211> LENGTH: 24
<212> TYPE: PRT
<213> ORGANISM: Conus marmoreus
<220> FEATURE:
<221> NAME/KEY: PEPTIDE
<222> LOCATION: (1)..(24)
<223> OTHER INFORMATION: Xaa at residue 3, 8, 18 and 24 is Pro or Hyp

<400> SEQUENCE: 153

Arg Gly Gly Cys Cys Thr Xaa Xaa Arg Lys Cys Lys Asp Arg Ala Cys
1               5                   10                  15

Lys Xaa Ala Arg Cys Cys Gly Xaa
```

-continued

<210> SEQ ID NO 154
<211> LENGTH: 296
<212> TYPE: DNA
<213> ORGANISM: Conus marmoreus

<400> SEQUENCE: 154

```
gagctcggta ccccgacctc aagagggatc gatagcagtt catgatgtct aaactgggaa      60
tcttgttgac catctgtcta cttctatttc cccttactgc tgttccgctg gatggagatc     120
aacctgcaga ccgacctgca gagcgtatgc aggacgacat ttcatctgaa catcatccct     180
tttttgatcc cgtcaaacgg tgttgcaggt tatcatgcgg cctgggatgc cacccttgtt     240
gtggatgacc agctttgtta tcgcggcctc atcaagtgtc taatgaataa gtaaaa         296
```

<210> SEQ ID NO 155
<211> LENGTH: 68
<212> TYPE: PRT
<213> ORGANISM: Conus marmoreus

<400> SEQUENCE: 155

Met Met Ser Lys Leu Gly Ile Leu Leu Thr Ile Cys Leu Leu Leu Phe
1               5                   10                  15

Pro Leu Thr Ala Val Pro Leu Asp Gly Asp Gln Pro Ala Asp Arg Pro
                20                  25                  30

Ala Glu Arg Met Gln Asp Asp Ile Ser Ser Glu His His Pro Phe Phe
            35                  40                  45

Asp Pro Val Lys Arg Cys Cys Arg Leu Ser Cys Gly Leu Gly Cys His
        50                  55                  60

Pro Cys Cys Gly
65

<210> SEQ ID NO 156
<211> LENGTH: 14
<212> TYPE: PRT
<213> ORGANISM: Conus marmoreus
<220> FEATURE:
<221> NAME/KEY: PEPTIDE
<222> LOCATION: (1)..(14)
<223> OTHER INFORMATION: Xaa at residue 12 is Pro or Hyp

<400> SEQUENCE: 156

Cys Cys Arg Leu Ser Cys Gly Leu Gly Cys His Xaa Cys Cys
1               5                   10

<210> SEQ ID NO 157
<211> LENGTH: 355
<212> TYPE: DNA
<213> ORGANISM: Conus marmoreus

<400> SEQUENCE: 157

```
ggcctacacc aagcttgcat gcctgcaggt cgactctaga ggatccccga tcgatagcag      60
ttcatgatgt ctagactggg agtcttgttg accatctgtc tacttctgtt tccccttact     120
gctgttccgc tggatggaga tcaacctgcg gaccgacctg cagagcgcct gcaggacgac     180
atttcatctg aacatcatcc ccattttgat tccggcagag agtgttgcgg ttcgttcgca     240
tgccgctttg gatgcgtgcc ttgttgtgta tgaccagctt tgttatcacg gcctcatcga     300
gtgtctaatg aataagtaaa acgattgcag taggcgggta ccgagctcga attcc          355
```

```
<210> SEQ ID NO 158
<211> LENGTH: 69
<212> TYPE: PRT
<213> ORGANISM: Conus marmoreus

<400> SEQUENCE: 158

Met Met Ser Arg Leu Gly Val Leu Leu Thr Ile Cys Leu Leu Leu Phe
1               5                   10                  15

Pro Leu Thr Ala Val Pro Leu Asp Gly Asp Gln Pro Ala Asp Arg Pro
            20                  25                  30

Ala Glu Arg Leu Gln Asp Asp Ile Ser Ser Glu His His Pro His Phe
        35                  40                  45

Asp Ser Gly Arg Glu Cys Cys Gly Ser Phe Ala Cys Arg Phe Gly Cys
    50                  55                  60

Val Pro Cys Cys Val
65

<210> SEQ ID NO 159
<211> LENGTH: 17
<212> TYPE: PRT
<213> ORGANISM: Conus marmoreus
<220> FEATURE:
<221> NAME/KEY: PEPTIDE
<222> LOCATION: (1)..(17)
<223> OTHER INFORMATION: Xaa at residue 1 is Glu or gamma-carboxy Glu;
      Xaa at residue 14 is Pro or Hyp

<400> SEQUENCE: 159

Xaa Cys Cys Gly Ser Phe Ala Cys Arg Phe Gly Cys Val Xaa Cys Cys
1               5                   10                  15

Val

<210> SEQ ID NO 160
<211> LENGTH: 295
<212> TYPE: DNA
<213> ORGANISM: Conus marmoreus

<400> SEQUENCE: 160
cgacctcaag agggatcgat agcagttcat gatgtctaaa ctgggagtct tgttgaccat     60
ctgtctactt ctatttcccc ttactgctgt tccgctggat ggagaccaac ctgcagaccg    120
acctgcagag cgtatgcagg acgacatttc atctgaacgt catcctttt ttgatcgcag     180 caaacagtgt tgccatctgc cggcatgccg cttcggatgt acgccttgtt gttggtgatc    240
agctttgtta tcgcgtcctc atcaagtgtc taatgaataa gtaaaatgat tgcag         295

<210> SEQ ID NO 161
<211> LENGTH: 67
<212> TYPE: PRT
<213> ORGANISM: Conus marmoreus

<400> SEQUENCE: 161

Met Met Ser Lys Leu Gly Val Leu Leu Thr Ile Cys Leu Leu Leu Phe
1               5                   10                  15

Pro Leu Thr Ala Val Pro Leu Asp Gly Asp Gln Pro Ala Asp Arg Pro
            20                  25                  30

Ala Glu Arg Met Gln Asp Asp Ile Ser Ser His Pro Phe Asp Arg
        35                  40                  45

Ser Lys Gln Cys Cys His Leu Pro Ala Cys Arg Phe Gly Cys Thr Pro
    50                  55                  60

Cys Cys Trp
```

```
<210> SEQ ID NO 162
<211> LENGTH: 19
<212> TYPE: PRT
<213> ORGANISM: Conus marmoreus
<220> FEATURE:
<221> NAME/KEY: PEPTIDE
<222> LOCATION: (1)..(19)
<223> OTHER INFORMATION: Xaa at residue 8 and 16 is Pro or Hyp; Xaa at
      residue 19 is Trp or bromo-Trp

<400> SEQUENCE: 162

Ser Lys Gln Cys Cys His Leu Xaa Ala Cys Arg Phe Gly Cys Thr Xaa
1               5                   10                  15

Cys Cys Xaa

<210> SEQ ID NO 163
<211> LENGTH: 235
<212> TYPE: DNA
<213> ORGANISM: Conus marmoreus

<400> SEQUENCE: 163
ggatccatga tgtctaaact gggagtcttg ttgaccatct gtctgcttct gtttcccctt      60
actgctcttc cgctggatgg agatcaacct gcagaccaac gtgcagagcg tacgcaggcc     120
gagaagcatt ccttgcctga tccgagaatg ggctgttgcc cgtttccatg caaaaccagt     180
tgcactactt tgtgttgcgg gtgatgataa cgtgttgatg accaactttc tcgag          235

<210> SEQ ID NO 164
<211> LENGTH: 67
<212> TYPE: PRT
<213> ORGANISM: Conus marmoreus

<400> SEQUENCE: 164

Gly Ser Met Met Ser Lys Leu Gly Val Leu Leu Thr Ile Cys Leu Leu
1               5                   10                  15

Leu Phe Pro Leu Thr Ala Leu Pro Leu Asp Gly Asp Gln Pro Ala Asp
            20                  25                  30

Gln Arg Ala Glu Arg Thr Gln Ala Glu Lys His Ser Leu Pro Asp Pro
        35                  40                  45

Arg Met Gly Cys Cys Pro Phe Pro Cys Lys Ser Cys Thr Thr Leu
    50                  55                  60

Cys Cys Gly
65

<210> SEQ ID NO 165
<211> LENGTH: 17
<212> TYPE: PRT
<213> ORGANISM: Conus marmoreus
<220> FEATURE:
<221> NAME/KEY: PEPTIDE
<222> LOCATION: (1)..(17)
<223> OTHER INFORMATION: Xaa at residue 5 and 7 is Pro or Hyp

<400> SEQUENCE: 165

Met Gly Cys Cys Xaa Phe Xaa Cys Lys Thr Ser Cys Thr Thr Leu Cys
1               5                   10                  15

Cys

<210> SEQ ID NO 166
<211> LENGTH: 16
```

```
<212> TYPE: PRT
<213> ORGANISM: Conus marmoreus
<220> FEATURE:
<221> NAME/KEY: PEPTIDE
<222> LOCATION: (1)..(16)
<223> OTHER INFORMATION: Xaa at residue 4 and 6 is Trp or bromo-Trp

<400> SEQUENCE: 166

Cys Cys His Xaa Asn Xaa Cys Asp His Leu Cys Ser Cys Cys Gly Ser
1               5                   10                  15

<210> SEQ ID NO 167
<211> LENGTH: 357
<212> TYPE: DNA
<213> ORGANISM: Conus marmoreus

<400> SEQUENCE: 167
gccaagcttg catgcctgca ggatgactct agaggatccc cacctcaaga gggatcgata      60
gcagttcatg atgtctaaac tgggagtctt gttgaccatc tgtctacttc tgtttgccct    120
tactgctgtt ccgctggatg gagatcaacc tgcagaccga cctgcagaac gtatgcagga    180
cgacatttca tctgaacgtc atcccatgtt tgatgccgtc agagattgtt gcccgttgcc    240
ggcatgcccc tttggatgca acccttgttg tggatgacca gctttgttat cgggaccctca   300 tcaagtgtct aatgaataag taaaaaacga ttcgagtggg taccgagctc gaattcc       357

<210> SEQ ID NO 168
<211> LENGTH: 67
<212> TYPE: PRT
<213> ORGANISM: Conus marmoreus

<400> SEQUENCE: 168

Met Met Ser Lys Leu Gly Val Leu Leu Thr Ile Cys Leu Leu Leu Phe
1               5                   10                  15

Ala Leu Thr Ala Val Pro Leu Asp Gly Asp Gln Pro Ala Asp Arg Pro
            20                  25                  30

Ala Glu Arg Met Gln Asp Asp Ile Ser Ser His Pro Met Phe Asp Ala
        35                  40                  45

Val Arg Asp Cys Cys Pro Leu Pro Ala Cys Pro Phe Gly Cys Asn Pro
    50                  55                  60

Cys Cys Gly
65

<210> SEQ ID NO 169
<211> LENGTH: 16
<212> TYPE: PRT
<213> ORGANISM: Conus marmoreus
<220> FEATURE:
<221> NAME/KEY: PEPTIDE
<222> LOCATION: (1)..(16)
<223> OTHER INFORMATION: Xaa at residue 4, 6, 9 and 14 is Pro or Hyp

<400> SEQUENCE: 169

Asp Cys Cys Xaa Leu Xaa Ala Cys Xaa Phe Gly Cys Asn Xaa Cys Cys
1               5                   10                  15

<210> SEQ ID NO 170
<211> LENGTH: 16
<212> TYPE: PRT
<213> ORGANISM: Conus marmoreus
<220> FEATURE:
<221> NAME/KEY: PEPTIDE
<222> LOCATION: (1)..(16)
<223> OTHER INFORMATION: Xaa at residue 4 and 13 is Pro or Hyp
```

<400> SEQUENCE: 170

Cys Cys Ala Xaa Ser Ala Cys Arg Leu Gly Cys Arg Xaa Cys Cys Arg
1               5                   10                  15

<210> SEQ ID NO 171
<211> LENGTH: 16
<212> TYPE: PRT
<213> ORGANISM: Conus marmoreus
<220> FEATURE:
<221> NAME/KEY: PEPTIDE
<222> LOCATION: (1)..(16)
<223> OTHER INFORMATION: Xaa at residue 4 and 13 is Pro or Hyp

<400> SEQUENCE: 171

Cys Cys Ala Xaa Ser Ala Cys Arg Leu Gly Cys Arg Xaa Cys Cys Arg
1               5                   10                  15

<210> SEQ ID NO 172
<211> LENGTH: 16
<212> TYPE: PRT
<213> ORGANISM: Conus marmoreus
<220> FEATURE:
<221> NAME/KEY: PEPTIDE
<222> LOCATION: (1)..(16)
<223> OTHER INFORMATION: Xaa at residue 4 and 13 is Pro or Hyp

<400> SEQUENCE: 172

Cys Cys Ala Xaa Ser Ala Cys Arg Leu Gly Cys Arg Xaa Cys Cys Arg
1               5                   10                  15

<210> SEQ ID NO 173
<211> LENGTH: 17
<212> TYPE: PRT
<213> ORGANISM: Conus marmoreus
<220> FEATURE:
<221> NAME/KEY: PEPTIDE
<222> LOCATION: (1)..(17)
<223> OTHER INFORMATION: Xaa at residue 14 is Pro or Hyp

<400> SEQUENCE: 173

Gly Cys Cys Gly Ser Phe Ala Cys Arg Phe Gly Cys Val Xaa Cys Cys
1               5                   10                  15

Val

<210> SEQ ID NO 174
<211> LENGTH: 244
<212> TYPE: DNA
<213> ORGANISM: Conus nobilis

<400> SEQUENCE: 174
ggatccatga tgtctaaact gggagtcttg ttgaccatct gtctacttct gtttcccctt      60
actgctcttc cgctggatga agatcaaccg gtacaccgac ctgcagagcg tatgcaggac     120
atttcatctg atcaacatct cttctttgat ctcatcaaac ggtgctgcga gttgccatgc 180
gggccaggct tttgcgtccc ttgttgctga catcaataac gtgttgatga ccaactttct 240
cgag 244

<210> SEQ ID NO 175
<211> LENGTH: 69
<212> TYPE: PRT
<213> ORGANISM: Conus nobilis

<400> SEQUENCE: 175

Gly Ser Met Met Ser Lys Leu Gly Val Leu Leu Thr Ile Cys Leu Leu
1               5                   10                  15

Leu Phe Pro Leu Thr Ala Leu Pro Leu Asp Glu Asp Gln Pro Val His
            20                  25                  30

Arg Pro Ala Glu Arg Met Gln Asp Ile Ser Ser Asp Gln His Leu Phe
        35                  40                  45

Phe Asp Leu Ile Lys Arg Cys Cys Glu Leu Pro Cys Gly Pro Gly Phe
    50                  55                  60

Cys Val Pro Cys Cys
65

<210> SEQ ID NO 176
<211> LENGTH: 15
<212> TYPE: PRT
<213> ORGANISM: Conus nobilis
<220> FEATURE:
<221> NAME/KEY: PEPTIDE
<222> LOCATION: (1)..(15)
<223> OTHER INFORMATION: Xaa at residue 3 is Glu or gamma-carboxy Glu;
      Xaa at residue 5, 8 and 13 is Pro or Hyp

<400> SEQUENCE: 176

Cys Cys Xaa Leu Xaa Cys Gly Xaa Gly Phe Cys Val Xaa Cys Cys
1               5                   10                  15

<210> SEQ ID NO 177
<211> LENGTH: 262
<212> TYPE: DNA
<213> ORGANISM: Conus nobilis

<400> SEQUENCE: 177
ggatccatga tgtctaaact gggagtcttg ttgaccatct gtctacttct gtttcccctt      60
actgcttttc cgatggatgg agatcaacct gcagaccaac ctgcagatcg tatgcaggac     120
gacatttcat ctgagcagta tcccttgttt gataagagac aaaagtgttg cactgggaag     180 aagggtcat gctccggcaa agcatgcaaa atctcaaat gttgctctgg acgataacgt      240
gttgatgacc aactttctcg ag                                              262

<210> SEQ ID NO 178
<211> LENGTH: 78
<212> TYPE: PRT
<213> ORGANISM: Conus nobilis

<400> SEQUENCE: 178

Gly Ser Met Met Ser Lys Leu Gly Val Leu Leu Thr Ile Cys Leu Leu
1               5                   10                  15

Leu Phe Pro Leu Thr Ala Phe Pro Met Asp Gly Asp Gln Pro Ala Asp
            20                  25                  30

Gln Pro Ala Asp Arg Met Gln Asp Ile Ser Ser Glu Gln Tyr Pro
        35                  40                  45

Leu Phe Asp Lys Arg Gln Lys Cys Cys Thr Gly Lys Lys Gly Ser Cys
    50                  55                  60

Ser Gly Lys Ala Cys Lys Asn Leu Lys Cys Cys Ser Gly Arg
65                  70                  75

<210> SEQ ID NO 179
<211> LENGTH: 23
<212> TYPE: PRT
<213> ORGANISM: Conus nobilis
<220> FEATURE:
<221> NAME/KEY: PEPTIDE

```
<222> LOCATION: (1)..(23)
<223> OTHER INFORMATION: Xaa at residue 1 is Gln or pyro-Glu

<400> SEQUENCE: 179

Xaa Lys Cys Cys Thr Gly Lys Lys Gly Ser Cys Ser Gly Lys Ala Cys
1               5                   10                  15

Lys Asn Leu Lys Cys Cys Ser
            20

<210> SEQ ID NO 180
<211> LENGTH: 238
<212> TYPE: DNA
<213> ORGANISM: Conus pulicarius

<400> SEQUENCE: 180
ggatccatga tgtctaaact gggagttttg ttgaccatct gtctgcttct gtttcccctt     60
actgctgttc cgctggatgg agatcaacct gcagaccgac ctgcagagcg tatgcaggac    120
attgcaactg aacagcatcc cttctttgat cccgtcaaac ggtgttgcaa cagctgttac    180
atgggatgca tcccttgttg cttctagtaa taacgtgttg atgaccaact ttctcgag     238

<210> SEQ ID NO 181
<211> LENGTH: 68
<212> TYPE: PRT
<213> ORGANISM: Conus pulicarius

<400> SEQUENCE: 181

Gly Ser Met Met Ser Lys Leu Gly Val Leu Leu Thr Ile Cys Leu Leu
1               5                   10                  15

Leu Phe Pro Leu Thr Ala Val Pro Leu Asp Gly Asp Gln Pro Ala Asp
            20                  25                  30

Arg Pro Ala Glu Arg Met Gln Asp Ile Ala Thr Glu Gln His Pro Phe
        35                  40                  45

Phe Asp Pro Val Lys Arg Cys Cys Asn Ser Cys Tyr Met Gly Cys Ile
    50                  55                  60

Pro Cys Cys Phe
65

<210> SEQ ID NO 182
<211> LENGTH: 14
<212> TYPE: PRT
<213> ORGANISM: Conus pulicarius
<220> FEATURE:
<221> NAME/KEY: PEPTIDE
<222> LOCATION: (1)..(14)
<223> OTHER INFORMATION: Xaa at residue 11 is Pro or Hyp; Xaa at
      residue 5 is Tyr, 125I-Tyr, mono-iodo-Tyr, di-iodo-Tyr,
      O-sulpho-Tyr or O-phospho-Tyr

<400> SEQUENCE: 182

Cys Cys Asn Ser Cys Xaa Met Gly Cys Ile Xaa Cys Cys Phe
1               5                   10

<210> SEQ ID NO 183
<211> LENGTH: 238
<212> TYPE: DNA
<213> ORGANISM: Conus quercinus

<400> SEQUENCE: 183
ggatccatga tgtctaaact gggagtcttg ttgaccatct gtctgcttct gtttcccctt     60
acagctcttc agctggatgg agatcaacct gcagaccgac ctgcagagcg tacgcaggac    120
```

```
attgcatctg aacagtatcg aaagtttgat cagagacaga ggtgttgcca gtggccatgc    180
cccggtagtt gcagatgctg ccgtactggt taacgtgttg atgaccaact ttctcgag     238
```

<210> SEQ ID NO 184
<211> LENGTH: 70
<212> TYPE: PRT
<213> ORGANISM: Conus quercinus

<400> SEQUENCE: 184

Gly Ser Met Met Ser Lys Leu Gly Val Leu Leu Thr Ile Cys Leu Leu
1               5                   10                  15

Leu Phe Pro Leu Thr Ala Leu Gln Leu Asp Gly Asp Gln Pro Ala Asp
            20                  25                  30

Arg Pro Ala Glu Arg Thr Gln Asp Ile Ala Ser Glu Gln Tyr Arg Lys
        35                  40                  45

Phe Asp Gln Arg Gln Arg Cys Cys Gln Trp Pro Cys Pro Gly Ser Cys
    50                  55                  60

Arg Cys Cys Arg Thr Gly
65                  70

<210> SEQ ID NO 185
<211> LENGTH: 17
<212> TYPE: PRT
<213> ORGANISM: Conus quercinus
<220> FEATURE:
<221> NAME/KEY: PEPTIDE
<222> LOCATION: (1)..(17)
<223> OTHER INFORMATION: Xaa at residue 1 is Gln or pyro-Glu; Xaa at
      residue 7 and 9 is Pro or Hyp; Xaa at residue 6 is Trp or
      bromo-Trp

<400> SEQUENCE: 185

Xaa Arg Cys Cys Gln Xaa Xaa Cys Xaa Gly Ser Cys Arg Cys Cys Arg
1               5                   10                  15

Thr

<210> SEQ ID NO 186
<211> LENGTH: 15
<212> TYPE: PRT
<213> ORGANISM: Conus quercinus
<220> FEATURE:
<221> NAME/KEY: PEPTIDE
<222> LOCATION: (1)..(15)
<223> OTHER INFORMATION: Xaa at residue 11 and 14 is Pro or Hyp

<400> SEQUENCE: 186

Cys Cys Ser Gln Asp Cys Leu Val Cys Ile Xaa Cys Cys Xaa Asn
1               5                   10                  15

<210> SEQ ID NO 187
<211> LENGTH: 15
<212> TYPE: PRT
<213> ORGANISM: Conus quercinus
<220> FEATURE:
<221> NAME/KEY: PEPTIDE
<222> LOCATION: (1)..(15)
<223> OTHER INFORMATION: Xaa at residue 11 14 is Pro or Hyp; Xaa at
      residue 7 is Trp or bromo-Trp

<400> SEQUENCE: 187

Cys Cys Ser Arg His Cys Xaa Val Cys Ile Xaa Cys Cys Xaa Asn
1               5                   10                  15

<210> SEQ ID NO 188

```
<211> LENGTH: 323
<212> TYPE: DNA
<213> ORGANISM: Conus radiatus

<400> SEQUENCE: 188
tcaagaagga tcgatagcag ttcatgatgt ctaaactggg agtcttgttg accatctgtc    60
tgcttctgtt tccccttact gctcttccga tggatggaga tcaacctgta gaccgacttg   120
cagagcgtat gcaggacaac atttcatctg agcagcatac cttctttgaa aagagactac   180
catcgtgttg ctcccttaac ttgcggcttt gcccagtacc agcatgcaaa cgtaacccct   240
gttgcacagg ataacgtgtt gatgaccaac tttgttatca cggctacgtc aagtgtctag   300
tgaataagta aaacgattgc agt                                           323

<210> SEQ ID NO 189
<211> LENGTH: 76
<212> TYPE: PRT
<213> ORGANISM: Conus radiatus

<400> SEQUENCE: 189

Met Met Ser Lys Leu Gly Val Leu Leu Thr Ile Cys Leu Leu Leu Phe
1               5                   10                  15

Pro Leu Thr Ala Leu Pro Met Asp Gly Asp Gln Pro Val Asp Arg Leu
            20                  25                  30

Ala Glu Arg Met Gln Asp Asn Ile Ser Ser Glu Gln His Thr Phe Phe
        35                  40                  45

Glu Lys Arg Leu Pro Ser Cys Cys Ser Leu Asn Leu Arg Leu Cys Pro
    50                  55                  60

Val Pro Ala Cys Lys Arg Asn Pro Cys Cys Thr Gly
65                  70                  75

<210> SEQ ID NO 190
<211> LENGTH: 24
<212> TYPE: PRT
<213> ORGANISM: Conus radiatus
<220> FEATURE:
<221> NAME/KEY: PEPTIDE
<222> LOCATION: (1)..(24)
<223> OTHER INFORMATION: Xaa at residue 2, 13, 15 and 21 is Pro or Hyp

<400> SEQUENCE: 190

Leu Xaa Ser Cys Cys Ser Leu Asn Leu Arg Leu Cys Xaa Val Xaa Ala
1               5                   10                  15

Cys Lys Arg Asn Xaa Cys Cys Thr
            20

<210> SEQ ID NO 191
<211> LENGTH: 336
<212> TYPE: DNA
<213> ORGANISM: Conus radiatus

<400> SEQUENCE: 191
aggtcgactc tagaggatcc ccaaggatcg atagcagttc atgatgtcta aactgggagt    60
cttgttgacc atctgtctgc ttctgtttcc ccttactgct cttccgatgg atggagatca   120
acctgcagac cgacttgcag agcgtatgca ggacgacatt tcatctgagc agcatcccct   180
ctttaaaaag agacaacaaa gatgttgcac cgttaagagg atttgtccag taccagcatg   240
cagaagtaaa ccttgttgca atcataacg tattgatgac caactttgtt atcacggcta   300
cgtcaagtgt ctagtgaata agtaaaatga ttgcag                             336
```

```
<210> SEQ ID NO 192
<211> LENGTH: 75
<212> TYPE: PRT
<213> ORGANISM: Conus radiatus

<400> SEQUENCE: 192
```

Met Met Ser Lys Leu Gly Val Leu Leu Thr Ile Cys Leu Leu Leu Phe
1               5                   10                  15

Pro Leu Thr Ala Leu Pro Met Asp Gly Asp Gln Pro Ala Asp Arg Leu
            20                  25                  30

Ala Glu Arg Met Gln Asp Asp Ile Ser Ser Glu Gln His Pro Phe Phe
        35                  40                  45

Lys Lys Arg Gln Gln Arg Cys Cys Thr Val Lys Arg Ile Cys Pro Val
    50                  55                  60

Pro Ala Cys Arg Ser Lys Pro Cys Cys Lys Ser
65                  70                  75

```
<210> SEQ ID NO 193
<211> LENGTH: 24
<212> TYPE: PRT
<213> ORGANISM: Conus radiatus
<220> FEATURE:
<221> NAME/KEY: PEPTIDE
<222> LOCATION: (1)..(24)
<223> OTHER INFORMATION: Xaa at residue 1 is Gln or pyro-Glu; Xaa at
      residue 12, 14 and 20 is Pro or Hyp

<400> SEQUENCE: 193
```

Xaa Gln Arg Cys Cys Thr Val Lys Arg Ile Cys Xaa Val Xaa Ala Cys
1               5                   10                  15

Arg Ser Lys Xaa Cys Cys Lys Ser
            20

```
<210> SEQ ID NO 194
<211> LENGTH: 326
<212> TYPE: DNA
<213> ORGANISM: Conus radiatus

<400> SEQUENCE: 194
```

| | |
|---|---|
| acctcaagaa ggatcgatag cagttcatga tgtctaaact gggagtcttg ttgaccatct | 60 |
| gtctgcttct gtttcccgtt actgctcttc cgatggatgg tgatcaacct gcagaccgac | 120 |
| ttgtagagcg tatgcaggac aacatttcat ctgagcagca tcccttcttt gaaaagagaa | 180 |
| gaggaggctg ttgcacacct ccgaggaaat gcaaagaccg agcctgcaaa cctgcacgtt | 240 |
| gctgcggccc aggataacgt gttgatgacc aactttgtta tcacggctac gtcaagtgtc | 300 |
| tagtgaataa gtaaaacgat tgcagt | 326 |

```
<210> SEQ ID NO 195
<211> LENGTH: 76
<212> TYPE: PRT
<213> ORGANISM: Conus radiatus

<400> SEQUENCE: 195
```

Met Met Ser Lys Leu Gly Val Leu Leu Thr Ile Cys Leu Leu Leu Phe
1               5                   10                  15

Pro Val Thr Ala Leu Pro Met Asp Gly Asp Gln Pro Ala Asp Arg Leu
            20                  25                  30

Val Glu Arg Met Gln Asp Asn Ile Ser Ser Glu Gln His Pro Phe Phe
        35                  40                  45

```
Glu Lys Arg Arg Gly Gly Cys Cys Thr Pro Arg Lys Cys Lys Asp
 50                  55                  60
Arg Ala Cys Lys Pro Ala Arg Cys Cys Gly Pro Gly
 65                  70                  75
```

<210> SEQ ID NO 196
<211> LENGTH: 24
<212> TYPE: PRT
<213> ORGANISM: Conus radiatus
<220> FEATURE:
<221> NAME/KEY: PEPTIDE
<222> LOCATION: (1)..(24)
<223> OTHER INFORMATION: Xaa at residue 7, 8, 18 and 24 is Pro or Hyp

<400> SEQUENCE: 196

```
Arg Gly Gly Cys Cys Thr Xaa Xaa Arg Lys Cys Lys Asp Arg Ala Cys
 1               5                  10                  15
Lys Xaa Ala Arg Cys Cys Gly Xaa
             20
```

<210> SEQ ID NO 197
<211> LENGTH: 238
<212> TYPE: DNA
<213> ORGANISM: Conus rattus

<400> SEQUENCE: 197

```
ggatccatga tgtctaaact gggagtcttg gtgaccatct gcctgcttct gttccctctt      60
gctgcttttc cactggatgg agatcaacct gcagaccacc ctgcaaagcg tacgcaagat     120
gacagttcag ctgccctgat caatgcctgg cttgatgaat cccagacttg ctgcagtaac     180
tgcggtgaag attgtgatgg ttgttgccag taacgtgttg atgaccaact ttctcgag      238
```

<210> SEQ ID NO 198
<211> LENGTH: 70
<212> TYPE: PRT
<213> ORGANISM: Conus rattus

<400> SEQUENCE: 198

```
Gly Ser Met Met Ser Lys Leu Gly Val Leu Val Thr Ile Cys Leu Leu
 1               5                  10                  15
Leu Phe Pro Leu Ala Ala Phe Pro Leu Asp Gly Asp Gln Pro Ala Asp
             20                  25                  30
His Pro Ala Lys Arg Thr Gln Asp Asp Ser Ser Ala Ala Leu Ile Asn
         35                  40                  45
Ala Trp Leu Asp Glu Ser Gln Thr Cys Cys Ser Asn Cys Gly Glu Asp
     50                  55                  60
Cys Asp Gly Cys Cys Gln
 65                  70
```

<210> SEQ ID NO 199
<211> LENGTH: 16
<212> TYPE: PRT
<213> ORGANISM: Conus rattus
<220> FEATURE:
<221> NAME/KEY: PEPTIDE
<222> LOCATION: (1)..(16)
<223> OTHER INFORMATION: Xaa at residue 1 is Gln or pyro-Glu; Xaa at
      residue 9 is Glu or gamma-carboxy Glu

<400> SEQUENCE: 199

```
Xaa Thr Cys Cys Ser Asn Cys Gly Xaa Asp Cys Asp Gly Cys Cys Gln
 1               5                  10                  15
```

```
<210> SEQ ID NO 200
<211> LENGTH: 327
<212> TYPE: DNA
<213> ORGANISM: Conus stercusmuscarum

<400> SEQUENCE: 200
gacctcaaga gggatcgata gcagttcgtg atgtctaaac tgggagtctt gttgaccatc      60
tgtctgcttc tgtttcctct tactgctctt ccgatggatg gagatcaacc tgcagaccaa     120
cctgcagatc gtatgcagga cgacatttca tctgagcagt atcccttgtt tgataagaga     180
caaaagtgtt gcactgggaa gaagggtca tgctccggca agcatgcaa aaatctcaaa      240 tgttgctctg gacgataacg tgttgatgac caactttgtt atcacggcta cgtcaagtgt     300
ctaatgaata agtaaaacga ttgcagt                                         327

<210> SEQ ID NO 201
<211> LENGTH: 75
<212> TYPE: PRT
<213> ORGANISM: Conus stercusmuscarum

<400> SEQUENCE: 201

Met Ser Lys Leu Gly Val Leu Leu Thr Ile Cys Leu Leu Phe Pro
1               5                   10                  15

Leu Thr Ala Leu Pro Met Asp Gly Asp Gln Pro Ala Asp Gln Pro Ala
            20                  25                  30

Asp Arg Met Gln Asp Asp Ile Ser Ser Glu Gln Tyr Pro Leu Phe Asp
        35                  40                  45

Lys Arg Gln Lys Cys Cys Thr Gly Lys Lys Gly Ser Cys Ser Gly Lys
    50                  55                  60

Ala Cys Lys Asn Leu Lys Cys Cys Ser Gly Arg
65                  70                  75

<210> SEQ ID NO 202
<211> LENGTH: 23
<212> TYPE: PRT
<213> ORGANISM: Conus stercusmuscarum
<220> FEATURE:
<221> NAME/KEY: PEPTIDE
<222> LOCATION: (1)..(23)
<223> OTHER INFORMATION: Xaa at residue 1 is Gln or pyro-Glu

<400> SEQUENCE: 202

Xaa Lys Cys Cys Thr Gly Lys Lys Gly Ser Cys Ser Gly Lys Ala Cys
1               5                   10                  15

Lys Asn Leu Lys Cys Cys Ser
            20

<210> SEQ ID NO 203
<211> LENGTH: 316
<212> TYPE: DNA
<213> ORGANISM: Conus stercusmuscarum

<400> SEQUENCE: 203
gatcgatagc agttcgtgat gtctaaactg ggagtcttgt tgaccatctg tctgcttctg      60
tttcccctta ctgctcttcc gatggatgga gatcaacctg cagaccaacc tgcagatcgt     120
atgcagaacg acatttcatc tgagcagtat cccttgtttg ataagagaca aaagtgttgc     180
ggccccggcg cgtcatgccc cagatatttc aaagacaatt ttatttgtgg ttgttgttaa     240
atgacaacgt gtcgatgacc aacttcgtta tcacgacttc gccaagtgtc taatgaataa     300
```
gtaaaacgat tgcagt                                                    316

<210> SEQ ID NO 204
<211> LENGTH: 73
<212> TYPE: PRT
<213> ORGANISM: Conus stercusmuscarum

<400> SEQUENCE: 204

Met Ser Lys Leu Gly Val Leu Leu Thr Ile Cys Leu Leu Phe Pro
1               5                   10                  15

Leu Thr Ala Leu Pro Met Asp Gly Asp Gln Pro Ala Asp Gln Pro Ala
            20                  25                  30

Asp Arg Met Gln Asn Asp Ile Ser Ser Glu Gln Tyr Pro Leu Phe Asp
        35                  40                  45

Lys Arg Gln Lys Cys Cys Gly Pro Gly Ala Ser Cys Pro Arg Tyr Phe
    50                  55                  60

Lys Asp Asn Phe Ile Cys Gly Cys Cys
65                  70

<210> SEQ ID NO 205
<211> LENGTH: 23
<212> TYPE: PRT
<213> ORGANISM: Conus stercusmuscarum
<220> FEATURE:
<221> NAME/KEY: PEPTIDE
<222> LOCATION: (1)..(23)
<223> OTHER INFORMATION: Xaa at residue 1 is Gln or pyro-Glu; Xaa at
      residue 6 and 11 is Pro or Hyp; Xaa at residue 13 is Tyr,
      125I-Tyr, mono-iodo-Tyr, di-iodo-Tyr, O-sulpho-Tyr or
      O-phospho-Tyr

<400> SEQUENCE: 205

Xaa Lys Cys Cys Gly Xaa Gly Ala Ser Cys Xaa Arg Xaa Phe Lys Asp
1               5                   10                  15

Asn Phe Ile Cys Gly Cys Cys
            20

<210> SEQ ID NO 206
<211> LENGTH: 331
<212> TYPE: DNA
<213> ORGANISM: Conus striatus

<400> SEQUENCE: 206
cgacctttca agagggatcg atagcagttc gcgatgtcta aactgggggt attgttgacc     60
atctgtctgc ttctgtttcc ccttactgct cttccgatgg atgaagatca acctgcagac    120
caacttgaag atcgtatgca ggacgacatt tcatctgagc agtatccctc gtttgttagg    180
agacaaaagt gttgcggcga aggctcgtca tgccccaaat atttcaaaaa caatttatt    240 tgtggttgtt gttaaatgac aacgtgtcga tgaccaactt cgttatcacg actacgccaa    300
gtgtcttgtc taatgataat aaaatgattc c                                   331

<210> SEQ ID NO 207
<211> LENGTH: 73
<212> TYPE: PRT
<213> ORGANISM: Conus striatus

<400> SEQUENCE: 207

Met Ser Lys Leu Gly Val Leu Leu Thr Ile Cys Leu Leu Phe Pro
1               5                   10                  15

Leu Thr Ala Leu Pro Met Asp Glu Asp Gln Pro Ala Asp Gln Leu Glu
            20                  25                  30

```
Asp Arg Met Gln Asp Asp Ile Ser Ser Glu Gln Tyr Pro Ser Phe Val
        35                  40                  45

Arg Arg Gln Lys Cys Cys Gly Glu Gly Ser Ser Cys Pro Lys Tyr Phe
    50                  55                  60

Lys Asn Asn Phe Ile Cys Gly Cys Cys
65                  70
```

<210> SEQ ID NO 208
<211> LENGTH: 23
<212> TYPE: PRT
<213> ORGANISM: Conus striatus
<220> FEATURE:
<221> NAME/KEY: PEPTIDE
<222> LOCATION: (1)..(23)
<223> OTHER INFORMATION: Xaa at residue 1 is Gln or pyro-Glu; Xaa at
      residue 6 is Glu or gamma-carboxy Glu; Xaa at residue 11 is Pro or
      Hyp; Xaa at residue 13 is Tyr, 125I-Tyr, mono-iodo-Tyr,
      di-iodo-Tyr, O-sulpho-Tyr or O-phospho-Tyr

<400> SEQUENCE: 208

```
Xaa Lys Cys Cys Gly Xaa Gly Ser Ser Cys Xaa Lys Xaa Phe Lys Asn
1               5                   10                  15

Asn Phe Ile Cys Gly Cys Cys
            20
```

<210> SEQ ID NO 209
<211> LENGTH: 256
<212> TYPE: DNA
<213> ORGANISM: Conus striatus

<400> SEQUENCE: 209

```
ggatccatga tgtctaaact gggagtcttg ttgaccgtct gtctgcttct gtttcccctt     60
actgctcttc cgctggatgg agatcaacct gcagaccgac ctgcagagcg tatgcaggac    120
gacatttcat ctgacgagca tcccttgttt gataagagac aaaactgttg caatgggga    180 tgctccagca atggtgcag agatcacgca cgttgttgcg gtcgatgata acgtgttgat    240 gaccaactt ctcgag                                                     256
```

<210> SEQ ID NO 210
<211> LENGTH: 75
<212> TYPE: PRT
<213> ORGANISM: Conus striatus

<400> SEQUENCE: 210

```
Gly Ser Met Met Ser Lys Leu Gly Val Leu Leu Thr Val Cys Leu Leu
1               5                   10                  15

Leu Phe Pro Leu Thr Ala Leu Pro Leu Asp Gly Asp Gln Pro Ala Asp
            20                  25                  30

Arg Pro Ala Glu Arg Met Gln Asp Asp Ile Ser Ser Asp Glu His Pro
        35                  40                  45

Leu Phe Asp Lys Arg Gln Asn Cys Cys Asn Gly Gly Cys Ser Ser Lys
    50                  55                  60

Trp Cys Arg Asp His Ala Arg Cys Cys Gly Arg
65                  70                  75
```

<210> SEQ ID NO 211
<211> LENGTH: 20
<212> TYPE: PRT
<213> ORGANISM: Conus striatus
<220> FEATURE:
<221> NAME/KEY: PEPTIDE
<222> LOCATION: (1)..(20)
<223> OTHER INFORMATION: Xaa at residue 1 is Gln or pyro-Glu; Xaa at
      residue 12 is Trp or bromo-Trp

<400> SEQUENCE: 211

Xaa Asn Cys Cys Asn Gly Gly Cys Ser Ser Lys Xaa Cys Arg Asp His
1               5                   10                  15

Ala Arg Cys Cys
        20

<210> SEQ ID NO 212
<211> LENGTH: 235
<212> TYPE: DNA
<213> ORGANISM: Conus tessulatus

<400> SEQUENCE: 212
ggatccatga tgtctaaaact gggagtcttg ttgaccatgt gtctgcttct gtttcccctt    60
actgctgttc cgctggatgg agatcaacct gcagaccgac ctgcagagcg taggcaggac   120
attgcaactg acgatcatcc tttgtttgat cccgtcaaac ggtgctgcca caaatgctat   180
atgggatgca tcccttgttg catttagtaa cgtgttgatg accaactttc tcgag        235

<210> SEQ ID NO 213
<211> LENGTH: 68
<212> TYPE: PRT
<213> ORGANISM: Conus tessulatus

<400> SEQUENCE: 213

Gly Ser Met Met Ser Lys Leu Gly Val Leu Leu Thr Met Cys Leu Leu
1               5                   10                  15

Leu Phe Pro Leu Thr Ala Val Pro Leu Asp Gly Asp Gln Pro Ala Asp
            20                  25                  30

Arg Pro Ala Glu Arg Arg Gln Asp Ile Ala Thr Asp His Pro Leu
        35                  40                  45

Phe Asp Pro Val Lys Arg Cys Cys His Lys Cys Tyr Met Gly Cys Ile
    50                  55                  60

Pro Cys Cys Ile
65

<210> SEQ ID NO 214
<211> LENGTH: 14
<212> TYPE: PRT
<213> ORGANISM: Conus tessulatus
<220> FEATURE:
<221> NAME/KEY: PEPTIDE
<222> LOCATION: (1)..(14)
<223> OTHER INFORMATION: Xaa at residue 11 is Pro or Hyp; Xaa at
      residue 6 is Tyr, 125I-Tyr, mono-iodo-Tyr, di-iodo-Tyr,
      O-sulpho-Tyr or O-phospho-Tyr

<400> SEQUENCE: 214

Cys Cys His Lys Cys Xaa Met Gly Cys Ile Xaa Cys Cys Ile
1               5                   10

<210> SEQ ID NO 215
<211> LENGTH: 238
<212> TYPE: DNA
<213> ORGANISM: Conus tessulatus

<400> SEQUENCE: 215
ggatccatga tgtctaaaact gggagtcttg ttgaccatct gtgtgcttct gtttcccctt    60
actgctgttc cgctggatgg agatcaacct gcagaccaac ctgcagagcg tacgcagaac   120

```
gagcagcatc ccttgtatga tcagaaaaga aagtgttgcc ggccgccatg cgccatgagc    180
tgcggcatgg ctaggtgttg ctattaatga taacgtgttg atgaccaact ttctcgag     238
```

<210> SEQ ID NO 216
<211> LENGTH: 68
<212> TYPE: PRT
<213> ORGANISM: Conus tessulatus

<400> SEQUENCE: 216

Gly Ser Met Met Ser Lys Leu Gly Val Leu Leu Thr Ile Cys Val Leu
1               5                   10                  15

Leu Phe Pro Leu Thr Ala Val Pro Leu Asp Gly Asp Gln Pro Ala Asp
            20                  25                  30

Gln Pro Ala Glu Arg Thr Gln Asn Glu Gln His Pro Leu Tyr Asp Gln
        35                  40                  45

Lys Arg Lys Cys Cys Arg Pro Pro Cys Ala Met Ser Cys Gly Met Ala
    50                  55                  60

Arg Cys Cys Tyr
65

<210> SEQ ID NO 217
<211> LENGTH: 18
<212> TYPE: PRT
<213> ORGANISM: Conus tessulatus
<220> FEATURE:
<221> NAME/KEY: PEPTIDE
<222> LOCATION: (1)..(18)
<223> OTHER INFORMATION: Xaa at residue 5 and 6 is Pro or Hyp; Xaa at
      residue 18 is Tyr, 125I-Tyr, mono-iodo-Tyr, di-iodo-Tyr,
      O-sulpho-Tyr or O-phospho-Tyr

<400> SEQUENCE: 217

Lys Cys Cys Arg Xaa Xaa Cys Ala Met Ser Cys Gly Met Ala Arg Cys
1               5                   10                  15

Cys Xaa

<210> SEQ ID NO 218
<211> LENGTH: 564
<212> TYPE: DNA
<213> ORGANISM: Conus textile

<400> SEQUENCE: 218

```
gagtcaaccc actgtcacgc caagagcgga cgccacagct aaggcaagaa ggatcgatag    60
cagttcatga tgtctaaact gggagccttg ttgaccatct gtctacttct gttttccctt   120
actgctgttc cgctggatgg agatcaacat gcagaccaac ctgcacagcg tctgcaggac   180
cgcattccaa ctgaagatca tcccttattt gatcccaaca acggtgttg cccgccggtg    240 gcatgcaaca tgggatgcaa gccttgttgt ggatgaccag ctttgttatc gcggtctcat   300
gaagtgtcta atgaataagt aaaacgattg cagtttcgtt cagatttgct gttgtatttt   360
ggtctaaaga ttaatgacca aactgttctt ttgatccgga ttttcacgta tttctcgatt   420
cctattcaac actagataag ttaatcacga cagatctgat tttccatcaa tgccttgctt   480
tttggtctgt catataaatc ttgttttatat ttaatttctc gtcactttca acacgcacac   540
acacacacac acacacgcgc gcgc                                          564
```

<210> SEQ ID NO 219
<211> LENGTH: 69
<212> TYPE: PRT

<213> ORGANISM: Conus textile

<400> SEQUENCE: 219

```
Met Met Ser Lys Leu Gly Ala Leu Leu Thr Ile Cys Leu Leu Leu Phe
1               5                   10                  15

Ser Leu Thr Ala Val Pro Leu Asp Gly Asp Gln His Ala Asp Gln Pro
            20                  25                  30

Ala Gln Arg Leu Gln Asp Arg Ile Pro Thr Glu Asp His Pro Leu Phe
        35                  40                  45

Asp Pro Asn Lys Arg Cys Cys Pro Pro Val Ala Cys Asn Met Gly Cys
    50                  55                      60

Lys Pro Cys Cys Gly
65
```

<210> SEQ ID NO 220
<211> LENGTH: 16
<212> TYPE: PRT
<213> ORGANISM: Conus textile
<220> FEATURE:
<221> NAME/KEY: PEPTIDE
<222> LOCATION: (1)..(16)
<223> OTHER INFORMATION: Xaa at residue 3, 4 and 13 is Pro or Hyp

<400> SEQUENCE: 220

```
Cys Cys Xaa Xaa Val Ala Cys Asn Met Gly Cys Lys Xaa Cys Cys Gly
1               5                   10                  15
```

<210> SEQ ID NO 221
<211> LENGTH: 780
<212> TYPE: DNA
<213> ORGANISM: Conus textile

<400> SEQUENCE: 221

| | | | | | |
|---|---|---|---|---|---|
| ggatccagac | gacaaagaag | agtcaaccca | ctgccacgtc | aagagcagag | cccacagcta | 60 |
| agacaagaag | gatcgatagc | agttcatgat | gtttaaactg | ggagtcttgt | tgaccatctg | 120 |
| tctccttctg | ttttcccctta | atgctgttcc | gttggatgga | gatcaacctg | cagaccaacc | 180 |
| tgcagagcgt | ctgctggacg | acatttcatt | tgaaaataat | ccctttatg | atcccgccaa | 240 |
| acggtgttgc | aggacttgct | tcggttgcac | accttgttgt | ggatgaccag | cctcatcaag | 300 |
| tgtctaacga | ataagtaaag | cgattgcagt | ctcgttcaga | tttacttttg | tattctggtc | 360 |
| taaagattaa | tgaccaaact | cttctttga | tccggatgta | catatatttc | tcgattccta | 420 |
| tccaacgcta | gataagctaa | tcacgacaga | tctgatttc | tgtcaatgcc | ttgcttttg | 480 |
| gtctctcata | tcactcttgt | ttatatttaa | tttctcgtca | ctatatatat | atatacacac | 540 |
| acacacacac | ggaattccga | ttgtccagta | ccgttcttgg | gatcgaggta | ttgctgcgat | 600 |
| ggcttattct | gtactctttt | cttctgcgct | tgatagtgat | gtcttctact | cccatctgtg | 660 |
| ctaccctgg | cttgatcttt | gataggcgtg | tgcccttcac | tggttataaa | ccctctgat | 720 |
| cctactctct | ggacgcctcg | ggcccaac | ctccaaataa | agcgacatcc | aatgaaaaaa | 780 |

<210> SEQ ID NO 222
<211> LENGTH: 66
<212> TYPE: PRT
<213> ORGANISM: Conus textile

<400> SEQUENCE: 222

```
Met Met Phe Lys Leu Gly Val Leu Leu Thr Ile Cys Leu Leu Leu Phe
1               5                   10                  15
```

```
Ser Leu Asn Ala Val Pro Leu Asp Gly Asp Gln Pro Ala Asp Gln Pro
            20                  25                  30

Ala Glu Arg Leu Leu Asp Asp Ile Ser Phe Glu Asn Asn Pro Phe Tyr
        35                  40                  45

Asp Pro Ala Lys Arg Cys Cys Arg Thr Cys Phe Gly Cys Thr Pro Cys
    50                  55                  60

Cys Gly
65

<210> SEQ ID NO 223
<211> LENGTH: 12
<212> TYPE: PRT
<213> ORGANISM: Conus textile
<220> FEATURE:
<221> NAME/KEY: PEPTIDE
<222> LOCATION: (1)..(12)
<223> OTHER INFORMATION: Xaa at residue 10 is Pro or Hyp

<400> SEQUENCE: 223

Cys Cys Arg Thr Cys Phe Gly Cys Thr Xaa Cys Cys
1               5                   10

<210> SEQ ID NO 224
<211> LENGTH: 456
<212> TYPE: DNA
<213> ORGANISM: Conus textile

<400> SEQUENCE: 224
ggaacagtca accccacagc cacgccaaga gcagacagcc acagctacgt gaagaagggt      60
ggagagaggt tcatgatgtt gaaaatggga gtggtgctat tcatctttct ggtactgttt    120
cccctggcaa cgctccagct ggatgcagat caacctgtag aacgatatgc ggagaacaaa    180
cagctcctca acccagatga aggagggaa atcctattgc ctgctctgag gaagttctgc     240
tgtgattcga attggtgcca catttcggat tgtgagtgct gctacggtta gcgccgaaca    300
tccatggcac tgtgctgggc ggtttcatcc caacaacgac agcgtttgtt gatttcatgt    360
atcattgcgc ccacgtctct tgtctaagaa tgacgaacat gattgcactc tggttcagat    420
ttcgtgttct tttctgacaa taaatgacaa acctcc                              456

<210> SEQ ID NO 225
<211> LENGTH: 70
<212> TYPE: PRT
<213> ORGANISM: Conus textile

<400> SEQUENCE: 225

Met Met Leu Lys Met Gly Val Val Leu Phe Ile Phe Leu Val Leu Phe
1               5                   10                  15

Pro Leu Ala Thr Leu Gln Leu Asp Ala Asp Gln Pro Val Glu Arg Tyr
            20                  25                  30

Ala Glu Asn Lys Gln Leu Leu Asn Pro Asp Glu Arg Arg Glu Ile Leu
        35                  40                  45

Leu Pro Ala Leu Arg Lys Phe Cys Cys Asp Ser Asn Trp Cys His Asp
    50                  55                  60

Cys Glu Cys Cys Tyr Gly
65                  70

<210> SEQ ID NO 226
<211> LENGTH: 17
<212> TYPE: PRT
<213> ORGANISM: Conus textile
```

<220> FEATURE:
<221> NAME/KEY: PEPTIDE
<222> LOCATION: (1)..(17)
<223> OTHER INFORMATION: Xaa at residue 14 is Glu or gamma-carboxy Glu;
      Xaa at residue 7 is Trp or bromo-Trp; Xaa at residue 17 is Tyr,
      125I-Tyr, mono-iodo-Tyr, di-iodo-Tyr, O-sulpho-Tyr or
      O-phospho-Tyr

<400> SEQUENCE: 226

Phe Cys Cys Asp Ser Asn Xaa Cys His Ile Ser Asp Cys Xaa Cys Cys
1               5                   10                  15

Xaa

<210> SEQ ID NO 227
<211> LENGTH: 456
<212> TYPE: DNA
<213> ORGANISM: Conus textile
<220> FEATURE:
<221> NAME/KEY: misc_feature
<222> LOCATION: (1)..(456)
<223> OTHER INFORMATION: n may be any nucleotide

<400> SEQUENCE: 227
caaggaacag tcaaccccac agccacgcca agagcagaca gccacagcta cgtgaagaag      60
ggtggagaga ggttcgtgat gttgaaaatg ggagtggtgc tattcatctt cctggtactg    120
tttcccctgg caacgctcca gctggatgca gatcaacctg tagaacgata tgcggagaac    180
aaacagctcc tcagcccaga tgaaggagg gaaatcatat tgcatgctct ggggacgcga     240
tgctgttctt gggatgtgtg cgaccacccg agttgtactt gctgcggtta gcgccgaaca    300
tccatggcgc tgtgctgggc ggttttatcc caacaacgac agcgtttgtt gatttcatgt    360
atcattgcgc ccacgtctct tgtctaagaa tgacgaacat gattgcactc tggttcagat    420
ttcgtgttct tttctgacaa taaatgacaa acncc                               456

<210> SEQ ID NO 228
<211> LENGTH: 70
<212> TYPE: PRT
<213> ORGANISM: Conus textile

<400> SEQUENCE: 228

Met Leu Lys Met Gly Val Val Leu Phe Ile Phe Leu Val Leu Phe Pro
1               5                   10                  15

Leu Ala Thr Leu Gln Leu Asp Ala Asp Gln Pro Val Glu Arg Tyr Ala
            20                  25                  30

Glu Asn Lys Gln Leu Leu Ser Pro Asp Glu Arg Arg Glu Ile Ile Leu
        35                  40                  45

His Ala Leu Gly Thr Arg Cys Cys Ser Trp Asp Val Cys Asp His Pro
    50                  55                  60

Ser Cys Thr Cys Cys Gly
65              70

<210> SEQ ID NO 229
<211> LENGTH: 15
<212> TYPE: PRT
<213> ORGANISM: Conus textile
<220> FEATURE:
<221> NAME/KEY: PEPTIDE
<222> LOCATION: (1)..(15)
<223> OTHER INFORMATION: Xaa at residue 10 is Pro or Hyp; Xaa at
      residue 4 is Trp or bromo-Trp

<400> SEQUENCE: 229

```
Cys Cys Ser Xaa Asp Val Cys Asp His Xaa Ser Cys Thr Cys Cys
1               5                   10                  15
```

<210> SEQ ID NO 230
<211> LENGTH: 235
<212> TYPE: DNA
<213> ORGANISM: Conus textile

<400> SEQUENCE: 230

```
ggatccatga tgtctaaact gggagtcttg ttgaccatct gtctgcttct gtttcccctt      60
actgctcttc cgctggatgg agatcaaccc gcagaccaag ctgcagagcg tatgcaggcc     120
gagcagcatc ccttgtttga tcagaaaaga cggtgctgca agtttccatg ccccgatagt     180
tgcagatatt tgtgttgcgg gtgatgataa cgtgttgatg accaactttc tcgag         235
```

<210> SEQ ID NO 231
<211> LENGTH: 67
<212> TYPE: PRT
<213> ORGANISM: Conus textile

<400> SEQUENCE: 231

```
Gly Ser Met Met Ser Lys Leu Gly Val Leu Leu Thr Ile Cys Leu Leu
1               5                   10                  15

Leu Phe Pro Leu Thr Ala Leu Pro Leu Asp Gly Asp Gln Pro Ala Asp
            20                  25                  30

Gln Ala Ala Glu Arg Met Gln Ala Glu Gln His Pro Leu Phe Asp Gln
        35                  40                  45

Lys Arg Arg Cys Cys Lys Phe Pro Cys Pro Asp Ser Cys Arg Tyr Leu
    50                  55                  60

Cys Cys Gly
65
```

<210> SEQ ID NO 232
<211> LENGTH: 16
<212> TYPE: PRT
<213> ORGANISM: Conus textile
<220> FEATURE:
<221> NAME/KEY: PEPTIDE
<222> LOCATION: (1)..(16)
<223> OTHER INFORMATION: Xaa at residue 3 and 8 is Pro or Hyp; Xaa at
      residue 13 is Tyr, 125I-Tyr, mono-iodo-Tyr, di-iodo-Tyr,
      O-sulpho-Tyr or O-phospho-Tyr

<400> SEQUENCE: 232

```
Arg Cys Cys Lys Phe Xaa Cys Xaa Asp Ser Cys Arg Xaa Leu Cys Cys
1               5                   10                  15
```

<210> SEQ ID NO 233
<211> LENGTH: 321
<212> TYPE: DNA
<213> ORGANISM: Conus tulipa

<400> SEQUENCE: 233

```
cgacctcaag agggatcgat agcagttcat gtctaaactg ggagtcttgt tgacaatctg      60
tctgcttctg tttcccctta ctgctctgcc gatggatgga gatgaacctg cagaccgacc     120
tgcagagcgt atgcaggaca acatttcatc tgagcagcat cccttgtttg aggagagaca     180
cggatgttgc aaggggcccg aaggatgctc ctccagagaa tgcagacccc aacattgttg     240
cggtcgacga taacgtgttg agggccaact tgttatcac ggctacgtca agtgtttagt      300
gaataagtaa aatgattgca g                                                321
```

-continued

<210> SEQ ID NO 234
<211> LENGTH: 74
<212> TYPE: PRT
<213> ORGANISM: Conus tulipa

<400> SEQUENCE: 234

Met Ser Lys Leu Gly Val Leu Leu Thr Ile Cys Leu Leu Phe Pro
1               5                   10                  15

Leu Thr Ala Leu Pro Met Asp Gly Asp Glu Pro Ala Asp Arg Pro Ala
            20                  25                  30

Glu Arg Met Gln Asp Asn Ile Ser Ser Glu Gln His Pro Leu Phe Glu
        35                  40                  45

Glu Arg His Gly Cys Cys Lys Gly Pro Glu Gly Cys Ser Ser Arg Glu
    50                  55                  60

Cys Arg Pro Gln His Cys Cys Gly Arg Arg
65                  70

<210> SEQ ID NO 235
<211> LENGTH: 21
<212> TYPE: PRT
<213> ORGANISM: Conus tulipa
<220> FEATURE:
<221> NAME/KEY: PEPTIDE
<222> LOCATION: (1)..(21)
<223> OTHER INFORMATION: Xaa at residue 8 and 14 is Glu or gamma-carboxy
      Glu; Xaa at residue 7 and 17 is Pro or Hyp

<400> SEQUENCE: 235

His Gly Cys Cys Lys Gly Xaa Xaa Gly Cys Ser Ser Arg Xaa Cys Arg
1               5                   10                  15

Xaa Gln His Cys Cys
            20

<210> SEQ ID NO 236
<211> LENGTH: 287
<212> TYPE: DNA
<213> ORGANISM: Conus figulinus

<400> SEQUENCE: 236
caagaaggat cgatagcagt tcatgatgtc taaactggga gtcttgctga ccatctgtct      60
gcttctgatt ccccttactg ctctttcgct ggatggagat caacctgcag accgacctgc    120
agagcgtatg caggatggaa tttcatctga acagcatccc atgtttgatc ccgtcagacg    180
gtgttgcccg tggccatgca acataggatg cgtaccttgt tgttgatgac cagttttgtt    240
atcgcggcct catcaaatgt ctaatgaata agtaaaacga ttgcagt                  287

<210> SEQ ID NO 237
<211> LENGTH: 67
<212> TYPE: PRT
<213> ORGANISM: Conus figulinus

<400> SEQUENCE: 237

Met Met Ser Lys Leu Gly Val Leu Leu Thr Ile Cys Leu Leu Leu Ile
1               5                   10                  15

Pro Leu Thr Ala Leu Ser Leu Asp Gly Asp Gln Pro Ala Asp Arg Pro
            20                  25                  30

Ala Glu Arg Met Gln Asp Gly Ile Ser Ser Glu Gln His Pro Met Phe
        35                  40                  45

Asp Pro Val Arg Arg Cys Cys Pro Trp Pro Cys Asn Ile Gly Cys Val
    50                  55                  60

Pro Cys Cys
65

<210> SEQ ID NO 238
<211> LENGTH: 14
<212> TYPE: PRT
<213> ORGANISM: Conus figulinus
<220> FEATURE:
<221> NAME/KEY: PEPTIDE
<222> LOCATION: (1)..(14)
<223> OTHER INFORMATION: Xaa at residue 3, 5 and 12 is Pro or Hyp;
    Xaa at residue 4 is Trp or bromo-Trp

<400> SEQUENCE: 238

Cys Cys Xaa Xaa Xaa Cys Asn Ile Gly Cys Val Xaa Cys Cys
1               5                   10

<210> SEQ ID NO 239
<211> LENGTH: 283
<212> TYPE: DNA
<213> ORGANISM: Conus figulinus

<400> SEQUENCE: 239
caagagggat cgatagcagt tcatgatgtt taaactggga gtcctgttga ccatctgtat      60
gcttctgttt ccctttactg ctcttccgct ggatggagag caacctgcag accaacctgc     120
agagcgcatg cagtatgaca tgttacgtgc aatgaatccc tggtttgatc ccgtcaaaag     180
gtgctgctcg aagaactgcg cagtatgcat cccttgttgc ccgtaactga ccagcttgat     240
tatcgcggcc aaggctctaa tgaataagta aaacgattgc agt                       283

<210> SEQ ID NO 240
<211> LENGTH: 67
<212> TYPE: PRT
<213> ORGANISM: Conus figulinus

<400> SEQUENCE: 240

Met Met Phe Lys Leu Gly Val Leu Leu Thr Ile Cys Met Leu Leu Phe
1               5                   10                  15

Pro Phe Thr Ala Leu Pro Leu Asp Gly Glu Gln Pro Ala Asp Gln Pro
            20                  25                  30

Ala Glu Arg Met Gln Tyr Asp Met Leu Arg Ala Met Asn Pro Trp Phe
        35                  40                  45

Asp Pro Val Lys Arg Cys Cys Ser Lys Asn Cys Ala Val Cys Ile Pro
    50                  55                  60

Cys Cys Pro
65

<210> SEQ ID NO 241
<211> LENGTH: 14
<212> TYPE: PRT
<213> ORGANISM: Conus figulinus
<220> FEATURE:
<221> NAME/KEY: PEPTIDE
<222> LOCATION: (1)..(14)
<223> OTHER INFORMATION: Xaa at residue 11 and 14 is Pro or Hyp

<400> SEQUENCE: 241

Cys Cys Ser Lys Asn Cys Ala Val Cys Ile Xaa Cys Cys Xaa
1               5                   10

<210> SEQ ID NO 242
<211> LENGTH: 286

<212> TYPE: DNA
<213> ORGANISM: Conus figulinus

<400> SEQUENCE: 242
caagagggat cgatagcagt tcatgatgtc taaactgaga gtcttgttga ccttatgtct    60
gcttctgttt cccccttactg ctcttccgct gaatgaagat caacctgcag agcgtatgca   120
ggacgacaat tcatctgagc agcaccccctt gtatgaccac aaacgaaagt gttgccggtg   180
gccatgcccc gcaagatgcg gctcttgttg cctgtaataa cgtgttggcc aactttgtta   240
tcacggccac gtcaaatgtt taatgaataa gtaaaacgat tgcagt                  286

<210> SEQ ID NO 243
<211> LENGTH: 64
<212> TYPE: PRT
<213> ORGANISM: Conus figulinus

<400> SEQUENCE: 243

Met Met Ser Lys Leu Arg Val Leu Leu Thr Leu Cys Leu Leu Leu Phe
1               5                   10                  15

Pro Leu Thr Ala Leu Pro Leu Asn Glu Asp Gln Pro Ala Glu Arg Met
            20                  25                  30

Gln Asp Asp Asn Ser Ser Glu Gln His Pro Leu Tyr Asp His Lys Arg
        35                  40                  45

Lys Cys Cys Arg Trp Pro Cys Pro Ala Arg Cys Gly Ser Cys Cys Leu
    50                  55                  60

<210> SEQ ID NO 244
<211> LENGTH: 15
<212> TYPE: PRT
<213> ORGANISM: Conus figulinus
<220> FEATURE:
<221> NAME/KEY: PEPTIDE
<222> LOCATION: (1)..(15)
<223> OTHER INFORMATION: Xaa at residue 5 and 7 is Pro or Hyp; Xaa at
      residue 4 is Trp or bromo-Trp

<400> SEQUENCE: 244

Cys Cys Arg Xaa Xaa Cys Xaa Ala Arg Cys Gly Ser Cys Cys Leu
1               5                   10                  15

<210> SEQ ID NO 245
<211> LENGTH: 301
<212> TYPE: DNA
<213> ORGANISM: Conus figulinus

<400> SEQUENCE: 245
caagagggat cgatagcagt tcatgatgtc taaactggga gtcttgttga ccttatgtct    60
gcttctgttt cccctgactg ctcttccgct ggatgaagat caagctgcag accgacctgc   120
agagcgtatg cagggcatgt catctgaaca gcatcccttc tttgatcccg tcaaacggtg   180
ttgcgagttg tcacgctgcc ttggatgcgt cccttgttgc acatcttaat aacgtgtgga   240
tgaccaactg tgttatcacg gccacgtcaa gtgtctaatg aataagtaaa atgattgcag   300
t                                                                   301

<210> SEQ ID NO 246
<211> LENGTH: 68
<212> TYPE: PRT
<213> ORGANISM: Conus figulinus

<400> SEQUENCE: 246

Met Met Ser Lys Leu Gly Val Leu Leu Thr Leu Cys Leu Leu Leu Phe
1               5                   10                  15

Pro Leu Thr Ala Leu Pro Leu Asp Glu Asp Gln Ala Ala Asp Arg Pro
            20                  25                  30

Ala Glu Arg Met Gln Gly Met Ser Ser Glu Gln His Pro Phe Phe Asp
        35                  40                  45

Pro Val Lys Arg Cys Cys Glu Leu Ser Arg Cys Leu Gly Cys Val Pro
    50                  55                  60

Cys Cys Thr Ser
65

<210> SEQ ID NO 247
<211> LENGTH: 16
<212> TYPE: PRT
<213> ORGANISM: Conus figulinus
<220> FEATURE:
<221> NAME/KEY: PEPTIDE
<222> LOCATION: (1)..(16)
<223> OTHER INFORMATION: Xaa at residue 3 and 12 is Pro or Hyp

<400> SEQUENCE: 247

Cys Cys Xaa Leu Ser Arg Cys Leu Gly Cys Val Xaa Cys Cys Thr Ser
1               5                   10                  15

<210> SEQ ID NO 248
<211> LENGTH: 301
<212> TYPE: DNA
<213> ORGANISM: Conus figulinus

<400> SEQUENCE: 248
caagagggat cgatagcagt tcatgatgtc taaactggga gtcttgttga ccttatgtct      60
gcttctgttt ccctgactg ctcttccgct ggatgaagat caacctgcag accgacctgc     120
agagcgtatg cagggcatgt catctgaaca gcatcccttc tttgatcccg tcaaacggtg     180
ttgcgagttg tcaaaatgcc atggatgcgt cccttgttgc ataccttaat aacgtgcgga     240
tgaccaactg tgttatcacg gccacgtcaa gtgtctaatg aataagtaaa atgattgcag     300
t                                                                    301

<210> SEQ ID NO 249
<211> LENGTH: 68
<212> TYPE: PRT
<213> ORGANISM: Conus figulinus

<400> SEQUENCE: 249

Met Met Ser Lys Leu Gly Val Leu Leu Thr Leu Cys Leu Leu Leu Phe
1               5                   10                  15

Pro Leu Thr Ala Leu Pro Leu Asp Glu Asp Gln Pro Ala Asp Arg Pro
            20                  25                  30

Ala Glu Arg Met Gln Gly Met Ser Ser Glu Gln His Pro Phe Phe Asp
        35                  40                  45

Pro Val Lys Arg Cys Cys Glu Leu Ser Lys Cys His Gly Cys Val Pro
    50                  55                  60

Cys Cys Ile Pro
65

<210> SEQ ID NO 250
<211> LENGTH: 16
<212> TYPE: PRT
<213> ORGANISM: Conus figulinus
<220> FEATURE:

```
<221> NAME/KEY: PEPTIDE
<222> LOCATION: (1)..(16)
<223> OTHER INFORMATION: Xaa at residue 3 is Glu or gamma-carboxy Glu;
      Xaa at residue 12 and 16 is Pro or Hyp

<400> SEQUENCE: 250

Cys Cys Xaa Leu Ser Lys Cys His Gly Cys Val Xaa Cys Cys Ile Xaa
1               5                   10                  15

<210> SEQ ID NO 251
<211> LENGTH: 298
<212> TYPE: DNA
<213> ORGANISM: Conus quercinus

<400> SEQUENCE: 251
caagagggat cgatagcagt tcatgatgtc taaactcgga gtcttgttga ccatctgtct      60
ggttctgttt ccccttacag ctcttcagct ggatggagat caacctgcag accgacctgc    120
agagcgtacg caggacattt catctgaaca gtatcgaaag tttgatcaga gacagaggtg    180
ttgccggtgg ccatgccccg gtagttgcag atgctgccgt tatcgttaac gtgttggtga    240
ccagctttgt tatcacgacc acgccaagtg tctaacgaat aagtaaaatg attgcagt      298

<210> SEQ ID NO 252
<211> LENGTH: 68
<212> TYPE: PRT
<213> ORGANISM: Conus quercinus

<400> SEQUENCE: 252

Met Met Ser Lys Leu Gly Val Leu Leu Thr Ile Cys Leu Val Leu Phe
1               5                   10                  15

Pro Leu Thr Ala Leu Gln Leu Asp Gly Asp Gln Pro Ala Asp Arg Pro
            20                  25                  30

Ala Glu Arg Thr Gln Asp Ile Ser Ser Glu Gln Tyr Arg Lys Phe Asp
        35                  40                  45

Gln Arg Gln Arg Cys Cys Arg Trp Pro Cys Pro Gly Ser Cys Arg Cys
    50                  55                  60

Cys Arg Tyr Arg
65

<210> SEQ ID NO 253
<211> LENGTH: 18
<212> TYPE: PRT
<213> ORGANISM: Conus quercinus
<220> FEATURE:
<221> NAME/KEY: PEPTIDE
<222> LOCATION: (1)..(18)
<223> OTHER INFORMATION: Xaa at residue 1 is Gln or pyro-Glu; Xaa at
      residue 7 and 9 is Pro or Hyp; Xaa at residue 6 is Trp or
      bromo-Trp; Xaa at residue 17 is Tyr, 125I-Tyr, mono-iodo-Tyr,
      di-iodo-Tyr, O-sulpho-Tyr or O-phospho-Tyr

<400> SEQUENCE: 253

Xaa Arg Cys Cys Arg Xaa Xaa Cys Xaa Gly Ser Cys Arg Cys Cys Arg
1               5                   10                  15

Xaa Arg

<210> SEQ ID NO 254
<211> LENGTH: 313
<212> TYPE: DNA
<213> ORGANISM: Conus quercinus

<400> SEQUENCE: 254
```

```
caagagggat cgatagcagt tcatgatgtc taaactggga gtcttgttga ccatctgtct      60
gcttctgttt cccttactg ctcttccact ggatggagat caacctgcag atcaatctgc     120
agagcgacct gcagagcgta cgcaggacga cattcagcag catccgttat atgatccgaa     180
aagaaggtgt tgccgttatc catgccccga cagctgccac ggatcttgct gctataagtg     240
ataacatgtt gatggccagc tttgttatca cggccacgtc aagtgtctaa tgaataagta     300
aaacgattgc agt                                                        313
```

<210> SEQ ID NO 255
<211> LENGTH: 72
<212> TYPE: PRT
<213> ORGANISM: Conus quercinus

<400> SEQUENCE: 255

Met Met Ser Lys Leu Gly Val Leu Leu Thr Ile Cys Leu Leu Leu Phe
1               5                   10                  15

Pro Leu Thr Ala Leu Pro Leu Asp Gly Asp Gln Pro Ala Asp Gln Ser
            20                  25                  30

Ala Glu Arg Pro Ala Glu Arg Thr Gln Asp Asp Ile Gln Gln His Pro
        35                  40                  45

Leu Tyr Asp Pro Lys Arg Arg Cys Cys Arg Tyr Pro Cys Pro Asp Ser
    50                  55                  60

Cys His Gly Ser Cys Cys Tyr Lys
65                  70

<210> SEQ ID NO 256
<211> LENGTH: 18
<212> TYPE: PRT
<213> ORGANISM: Conus quercinus
<220> FEATURE:
<221> NAME/KEY: PEPTIDE
<222> LOCATION: (1)..(18)
<223> OTHER INFORMATION: Xaa at residue 6 and 8 is Pro or Hyp; Xaa at
      residue 5 and 17 is Tyr, 125I-Tyr, mono-iodo-Tyr, di-iodo-Tyr,
      O-sulpho-Tyr or O-phospho-Tyr

<400> SEQUENCE: 256

Arg Cys Cys Arg Xaa Xaa Cys Xaa Asp Ser Cys His Gly Ser Cys Cys
1               5                   10                  15

Xaa Lys

<210> SEQ ID NO 257
<211> LENGTH: 256
<212> TYPE: DNA
<213> ORGANISM: Conus wittigi

<400> SEQUENCE: 257

```
ggatccatga tgtctaaact ggagtcttg ttgaccatct gtctgcttct gtttcccatt      60
actgctcttc cggtgggtgg agatcagcct gcagaccgac ttgcagagcg tatgcaggac     120
gacacttcat ctgagcagca tccctttgaa aagagactac catcatgttg cgactttgag     180
aggctttgcg tagtaccagc atgcatacgt catcagtgtt gcacaggata acgtgttgat     240
gaccaacttt ctcgag                                                     256
```

<210> SEQ ID NO 258
<211> LENGTH: 74
<212> TYPE: PRT
<213> ORGANISM: Conus wittigi

<400> SEQUENCE: 258

```
Met Met Ser Lys Leu Gly Val Leu Leu Thr Ile Cys Leu Leu Leu Phe
1               5                   10                  15

Pro Ile Thr Ala Leu Pro Val Gly Gly Asp Gln Pro Ala Asp Arg Leu
            20                  25                  30

Ala Glu Arg Met Gln Asp Asp Thr Ser Ser Glu Gln His Pro Phe Glu
                35                  40                  45

Lys Arg Leu Pro Ser Cys Cys Asp Phe Glu Arg Leu Cys Val Val Pro
        50                  55                  60

Ala Cys Ile Arg His Gln Cys Cys Thr Gly
65                  70
```

<210> SEQ ID NO 259
<211> LENGTH: 23
<212> TYPE: PRT
<213> ORGANISM: Conus wittigi
<220> FEATURE:
<221> NAME/KEY: PEPTIDE
<222> LOCATION: (1)..(23)
<223> OTHER INFORMATION: Xaa at residue 8 is Glu or gamma-carboxy Glu;
      Xaa at residue 2 and 14 is Pro or Hyp

<400> SEQUENCE: 259

```
Leu Xaa Ser Cys Cys Asp Phe Xaa Arg Leu Cys Val Val Xaa Ala Cys
1               5                   10                  15

Ile Arg His Gln Cys Cys Thr
                20
```

<210> SEQ ID NO 260
<211> LENGTH: 14
<212> TYPE: PRT
<213> ORGANISM: Conus betulinus
<220> FEATURE:
<221> NAME/KEY: PEPTIDE
<222> LOCATION: (1)..(14)
<223> OTHER INFORMATION: Xaa at residue 11 is Pro or Hyp; Xaa at
      residue 14 is Trp or bromo-Trp

<400> SEQUENCE: 260

```
Cys Cys Lys Gln Ser Cys Thr Thr Cys Met Xaa Cys Cys Xaa
1               5                   10
```

<210> SEQ ID NO 261
<211> LENGTH: 259
<212> TYPE: DNA
<213> ORGANISM: Conus tulipa
<220> FEATURE:
<221> NAME/KEY: misc_feature
<222> LOCATION: (1)..(259)
<223> OTHER INFORMATION: n may be any nucleotide

<400> SEQUENCE: 261

```
ggatccatga tgtctaaact gggagtcttg ttgacaatct gtctgcttct gtttcccctt      60
actgctctgc cgatggatgg agatgaacct gcagaccgac ctgcagagcg tatgcaggac     120
aacatttcat ctgagcagca tcccttgttt gaggagagac acggatgttg cgaggggccg     180
aagggatgct cctccagaga atgcagaccc caacattgtt gcggtcgacg ataacgtgtt     240
gatgaccaac tntctcgag                                                  259
```

<210> SEQ ID NO 262
<211> LENGTH: 75
<212> TYPE: PRT
<213> ORGANISM: Conus tulipa -continued

<400> SEQUENCE: 262

Met Met Ser Lys Leu Gly Val Leu Leu Thr Ile Cys Leu Leu Leu Phe
1               5                   10                  15

Pro Leu Thr Ala Leu Pro Met Asp Gly Asp Glu Pro Ala Asp Arg Pro
            20                  25                  30

Ala Glu Arg Met Gln Asp Asn Ile Ser Ser Glu Gln His Pro Leu Phe
        35                  40                  45

Glu Glu Arg His Gly Cys Cys Glu Gly Pro Lys Gly Cys Ser Ser Arg
    50                  55                  60

Glu Cys Arg Pro Gln His Cys Cys Gly Arg Arg
65                  70                  75

<210> SEQ ID NO 263
<211> LENGTH: 21
<212> TYPE: PRT
<213> ORGANISM: Conus tulipa
<220> FEATURE:
<221> NAME/KEY: PEPTIDE
<222> LOCATION: (1)..(21)
<223> OTHER INFORMATION: Xaa at residue 5 and 14 is Glu or gamma-carboxy
      Glu; Xaa at residue 7 and 17 is Pro or Hyp

<400> SEQUENCE: 263

His Gly Cys Cys Xaa Gly Xaa Lys Gly Cys Ser Ser Arg Xaa Cys Arg
1               5                   10                  15

Xaa Gln His Cys Cys
            20

<210> SEQ ID NO 264
<211> LENGTH: 262
<212> TYPE: DNA
<213> ORGANISM: Conus aurisiacus
<220> FEATURE:
<221> NAME/KEY: misc_feature
<222> LOCATION: (1)..(262)
<223> OTHER INFORMATION: n may be any nucleotide

<400> SEQUENCE: 264
ggatccatga tgtctaaact gggagtcttg ttgaccatct gtctacttct gtttccccett      60 actgcttttc cgatggatgg agatcaacct gcagaccaac ctgcagatcg tatgcaggac     120
gacatttcat ctgagcagta tcccttgttt gataagagac aaaagtgttg cactgggagg     180 aagggtcat gctccggcaa agcatgcaaa aatctcaaat gttgctctgg acgataacgt      240
gttgatgacc aactttctcg an                                              262

<210> SEQ ID NO 265
<211> LENGTH: 76
<212> TYPE: PRT
<213> ORGANISM: Conus aurisiacus

<400> SEQUENCE: 265

Met Met Ser Lys Leu Gly Val Leu Leu Thr Ile Cys Leu Leu Leu Phe
1               5                   10                  15

Pro Leu Thr Ala Phe Pro Met Asp Gly Asp Gln Pro Ala Asp Gln Pro
            20                  25                  30

Ala Asp Arg Met Gln Asp Ile Ser Ser Glu Gln Tyr Pro Leu Phe
        35                  40                  45

Asp Lys Arg Gln Lys Cys Cys Thr Gly Arg Lys Gly Ser Cys Ser Gly
    50                  55                  60

Lys Ala Cys Lys Asn Leu Lys Cys Cys Ser Gly Arg

<210> SEQ ID NO 266
<211> LENGTH: 23
<212> TYPE: PRT
<213> ORGANISM: Conus aurisiacus
<220> FEATURE:
<221> NAME/KEY: PEPTIDE
<222> LOCATION: (1)..(23)
<223> OTHER INFORMATION: Xaa at residue 1 is Gln or pyro-Glu

<400> SEQUENCE: 266

Xaa Lys Cys Cys Thr Gly Arg Lys Gly Ser Cys Ser Gly Lys Ala Cys
1               5                   10                  15

Lys Asn Leu Lys Cys Cys Ser
            20

<210> SEQ ID NO 267
<211> LENGTH: 239
<212> TYPE: DNA
<213> ORGANISM: Conus betulinus

<400> SEQUENCE: 267
ggatccatga tgtctaaact gggagtcttg ttgaccatct gtctgcttct gtttcccctt     60
actgctgttc cgttggatgg agatcaacct gcagaccaac ctgcagagcg tatgcagaac    120
gagcagcatc cctcgtttga tcagaaaaga aggtgctgcc ggtggccatg ccccagtata    180
tgcggcatgg ctaggtgttg cttcgtcatg ataacgtgtt gatgaccaac tttctcgag    239

<210> SEQ ID NO 268
<211> LENGTH: 71
<212> TYPE: PRT
<213> ORGANISM: Conus betulinus

<400> SEQUENCE: 268

Met Met Ser Lys Leu Gly Val Leu Leu Thr Ile Cys Leu Leu Leu Phe
1               5                   10                  15

Pro Leu Thr Ala Val Pro Leu Asp Gly Asp Gln Pro Ala Asp Gln Pro
            20                  25                  30

Ala Glu Arg Met Gln Asn Glu Gln His Pro Ser Phe Asp Gln Lys Arg
        35                  40                  45

Arg Cys C

-continued

<210> SEQ ID NO 270
<211> LENGTH: 226
<212> TYPE: DNA
<213> ORGANISM: Conus betulinus
<220> FEATURE:
<221> NAME/KEY: misc_feature
<222> LOCATION: (1)..(226)
<223> OTHER INFORMATION: n may be any nucleotide

<400> SEQUENCE: 270

```
ggatccatga tgtctaaact gggagtcttg ttgatcatct gtctgcttct gtttcccctt     60
actgctgttc cgctggatgg agatcagcct gcagagcgta cgcagatcga gcagcatccc    120
ttgtttgacc agaaaagaag gtgttgccgg tggccatgcc ccagtagatg cggcatggct    180
aggtgttgct tcgtcatgat aacgtgttga tgancgacct ctcnag                   226
```

<210> SEQ ID NO 271
<211> LENGTH: 67
<212> TYPE: PRT
<213> ORGANISM: Conus betulinus

<400> SEQUENCE: 271

```
Met Met Ser Lys Leu Gly Val Leu Leu Ile Ile Cys Leu Leu Leu Phe
1               5                   10                  15

Pro Leu Thr Ala Val Pro Leu Asp Gly Asp Gln Pro Ala Glu Arg Thr
            20                  25                  30

Gln Ile Glu Gln His Pro Leu Phe Asp Gln Lys Arg Arg Cys Cys Arg
        35                  40                  45

Trp Pro Cys Pro Ser Arg Cys Gly Met Ala Arg Cys Cys Phe Val Met
    50                  55                  60

Ile Thr Cys
65
```

<210> SEQ ID NO 272
<211> LENGTH: 23
<212> TYPE: PRT
<213> ORGANISM: Conus betulinus
<220> FEATURE:
<221> NAME/KEY: PEPTIDE
<222> LOCATION: (1)..(23)
<223> OTHER INFORMATION: Xaa at residue 6 and 8 is Pro or Hyp; Xaa at residue 5 is Trp or bromo-Trp

<400> SEQUENCE: 272

```
Arg Cys Cys Arg Xaa Xaa Cys Xaa Ser Arg Cys Gly Met Ala Arg Cys
1               5                   10                  15

Cys Phe Val Met Ile Thr Cys
            20
```

<210> SEQ ID NO 273
<211> LENGTH: 262
<212> TYPE: DNA
<213> ORGANISM: Conus parius

<400> SEQUENCE: 273

```
ggatccatga tgtctaaact gggagtcttg ttgaccatct gtctgcttct gtttcccctt     60
actgctcttc cgatggatgg tgatcaacct gcagaccgac ttgtagagcg tatgcaggac    120
aacatttcat ctgagcagca tcccttcttt gaaaagagaa gaggaggctg ttgcacacct    180
ccgaagaaat gcaaagaccg agcctgcaaa cctgcacgtt gctgcggccc aggataacgt    240
gttgatgacc aactttctcg cc                                             262
```

<210> SEQ ID NO 274
<211> LENGTH: 76
<212> TYPE: PRT
<213> ORGANISM: Conus parius

<400> SEQUENCE: 274

Met Met Ser Lys Leu Gly Val Leu Leu Thr Ile Cys Leu Leu Leu Phe
1               5                   10                  15

Pro Leu Thr Ala Leu Pro Met Asp Gly Asp Gln Pro Ala Asp Arg Leu
            20                  25                  30

Val Glu Arg Met Gln Asp Asn Ile Ser Ser Glu Gln His Pro Phe Phe
        35                  40                  45

Glu Lys Arg Arg Gly Gly Cys Cys Thr Pro Lys Lys Cys Lys Asp
    50                  55                  60

Arg Ala Cys Lys Pro Ala Arg Cys Cys Gly Pro Gly
65                  70                  75

<210> SEQ ID NO 275
<211> LENGTH: 24
<212> TYPE: PRT
<213> ORGANISM: Conus parius
<220> FEATURE:
<221> NAME/KEY: PEPTIDE
<222> LOCATION: (1)..(24)
<223> OTHER INFORMATION: Xaa at residue 7, 8, 18 and 24 is Pro or Hyp

<400> SEQUENCE: 275

Arg Gly Gly Cys Cys Thr Xaa Xaa Lys Lys Cys Lys Asp Arg Ala Cys
1               5                   10                  15

Lys Xaa Ala Arg Cys Cys Gly Xaa
            20

<210> SEQ ID NO 276
<211> LENGTH: 259
<212> TYPE: DNA
<213> ORGANISM: Conus parius

<400> SEQUENCE: 276
ggatccatga tgtctaaaact gggagtcttg ttgaccatct gtctgcttct gtttcccctt      60
actgctcttc cgatggatgg tgatcaacct gcagaccgac ttgtagagcg tatgcaggac     120
aacatttcat ctgagcagca tccttctttt gaaaagagaa gaggctgttg cacacctccg     180
aggaaatgca agaccgagc ctgcaaacct gcacgttgtt gcggcccagg ataacgtgtt      240
gatgaccaac tttctcgag                                                  259

<210> SEQ ID NO 277
<211> LENGTH: 75
<212> TYPE: PRT
<213> ORGANISM: Conus parius

<400> SEQUENCE: 277

Met Met Ser Lys Leu Gly Val Leu Leu Thr Ile Cys Leu Leu Leu Phe
1               5                   10                  15

Pro Leu Thr Ala Leu Pro Met Asp Gly Asp Gln Pro Ala Asp Arg Leu
            20                  25                  30

Val Glu Arg Met Gln Asp Asn Ile Ser Ser Glu Gln His Pro Phe Phe
        35                  40                  45

Glu Lys Arg Arg Gly Cys Cys Thr Pro Pro Arg Lys Cys Lys Asp Arg
    50                  55                  60

Ala Cys Lys Pro Ala Arg Cys Cys Gly Pro Gly
65              70              75

<210> SEQ ID NO 278
<211> LENGTH: 23
<212> TYPE: PRT
<213> ORGANISM: Conus parius
<220> FEATURE:
<221> NAME/KEY: PEPTIDE
<222> LOCATION: (1)..(23)
<223> OTHER INFORMATION: Xaa at residue 6, 7, 17 and 23 is Pro or Hyp

<400> SEQUENCE: 278

Arg Gly Cys Cys Thr Xaa Xaa Arg Lys Cys Lys Asp Arg Ala Cys Lys
1               5                   10                  15

Xaa Ala Arg Cys Cys Gly Xaa
            20

<210> SEQ ID NO 279
<211> LENGTH: 241
<212> TYPE: DNA
<213> ORGANISM: Conus coronatus

<400> SEQUENCE: 279
ggatccatga tgtctaaact gggagtcttg ttgaccatct gtctgcttct gtttccaatt    60
actgcccttc cgctggatga agatcaacct gcagaccgac ctgcagagcg tatgcaggac   120
attgcaactg aacagcatcc cttgtttgat cccgtcaaac ggtgctgcga ttggccatgc   180
atcccaggat gcaccccttg ttgcttgcct tgataacgtg ttgatgacca actttctcga   240
g                                                                   241

<210> SEQ ID NO 280
<211> LENGTH: 68
<212> TYPE: PRT
<213> ORGANISM: Conus coronatus

<400> SEQUENCE: 280

Met Met Ser Lys Leu Gly Val Leu Leu Thr Ile Cys Leu Leu Leu Phe
1               5                   10                  15

Pro Ile Thr Ala Leu Pro Leu Asp Glu Asp Gln Pro Ala Asp Arg Pro
            20                  25                  30

Ala Glu Arg Met Gln Asp Ile Ala Thr Glu Gln His Pro Leu Phe Asp
        35                  40                  45

Pro Val Lys Arg Cys Cys Asp Trp Pro Cys Ile Pro Gly Cys Thr Pro
    50                  55                  60

Cys Cys Leu Pro
65

<210> SEQ ID NO 281
<211> LENGTH: 16
<212> TYPE: PRT
<213> ORGANISM: Conus coronatus
<220> FEATURE:
<221> NAME/KEY: PEPTIDE
<222> LOCATION: (1)..(16)
<223> OTHER INFORMATION: Xaa at residue 5, 8, 12 and 16 is Pro or Hyp;
      Xaa at residue 4 is Trp or bromo-Trp

<400> SEQUENCE: 281

Cys Cys Asp Xaa Xaa Cys Ile Xaa Gly Cys Thr Xaa Cys Cys Leu Xaa
1               5                   10                  15

<210> SEQ ID NO 282
<211> LENGTH: 244
<212> TYPE: DNA
<213> ORGANISM: Conus musicus

<400> SEQUENCE: 282

```
ggatccatga tgtctaaact gggagtcctg ttgaccatct gtctgcttct gtttcctctt      60
tctgctcttc cgatggatga agatcaactt gcagacctac ctgcagagcg tatgcgggac     120
actgcaactg tagatcatcc ctcctatgat cctgacaaag cgtgctgcga gcagagctgt     180
acaacatgct ttccgtgctg ctagccttga acacagtaac gtgttgatga ccaactttct     240
cgag                                                                  244
```

<210> SEQ ID NO 283
<211> LENGTH: 65
<212> TYPE: PRT
<213> ORGANISM: Conus musicus

<400> SEQUENCE: 283

Met Met Ser Lys Leu Gly Val Leu Leu Thr Ile Cys Leu Leu Phe
1               5                   10                  15

Pro Leu Ser Ala Leu Pro Met Asp Glu Asp Gln Leu Ala Asp Leu Pro
            20                  25                  30

Ala Glu Arg Met Arg Asp Thr Ala Thr Val Asp His Pro Ser Tyr Asp
        35                  40                  45

Pro Asp Lys Ala Cys Cys Glu Gln Ser Cys Thr Thr Cys Phe Pro Cys
    50                  55                  60

Cys
65

<210> SEQ ID NO 284
<211> LENGTH: 14
<212> TYPE: PRT
<213> ORGANISM: Conus musicus
<220> FEATURE:
<221> NAME/KEY: PEPTIDE
<222> LOCATION: (1)..(14)
<223> OTHER INFORMATION: Xaa at residue4  is Glu or gamma-carboxy Glu;
      Xaa at residue 12 is Pro or Hyp

<400> SEQUENCE: 284

Ala Cys Cys Xaa Gln Ser Cys Thr Thr Cys Phe Xaa Cys Cys
1               5                   10

<210> SEQ ID NO 285
<211> LENGTH: 14
<212> TYPE: PRT
<213> ORGANISM: Conus betulinus
<220> FEATURE:
<221> NAME/KEY: PEPTIDE
<222> LOCATION: (1)..(14)
<223> OTHER INFORMATION: Xaa at residue 4 is Glu or gamma-carboxy Glu;
      Xaa at residue 12 is Pro or Hyp

<400> SEQUENCE: 285

Ala Cys Cys Xaa Gln Ser Cys Thr Thr Cys Met Xaa Cys Cys
1               5                   10

<210> SEQ ID NO 286
<211> LENGTH: 14
<212> TYPE: PRT
<213> ORGANISM: Conus betulinus
<220> FEATURE:
<221> NAME/KEY: PEPTIDE

```
<222> LOCATION: (1)..(14)
<223> OTHER INFORMATION: Xaa at residue 3 is Glu or gamma-carboxy Glu;
      Xaa at residue 11 is Pro or Hyp; Xaa at residue 14 is Trp or
      bromo-Trp

<400> SEQUENCE: 286

Cys Cys Xaa Gln Ser Cys Thr Thr Cys Met Xaa Cys Cys Xaa
1               5                   10

<210> SEQ ID NO 287
<211> LENGTH: 235
<212> TYPE: DNA
<213> ORGANISM: Conus pennaceus

<400> SEQUENCE: 287
ggatccatga tgtctaaact gggagtcttg ttgaccatct gtctgcttct gtttcccctt    60
actgctcttc cgctggatgg agatcaacct gcataccaag ctgcagagcg tatgcaggcc   120
gagcatcatc ccttgtttga tcagaaaaga cggtgctgca agtttccatg ccccgatagt   180
tgcaaatatt tgtgttgcgg gtgatgataa catgttgatg accaactttc ttgag        235

<210> SEQ ID NO 288
<211> LENGTH: 65
<212> TYPE: PRT
<213> ORGANISM: Conus pennaceus

<400> SEQUENCE: 288

Met Met Ser Lys Leu Gly Val Leu Leu Thr Ile Cys Leu Leu Leu Phe
1               5                   10                  15

Pro Leu Thr Ala Leu Pro Leu Asp Gly Asp Gln Pro Ala Tyr Gln Ala
            20                  25                  30

Ala Glu Arg Met Gln Ala Glu His His Pro Leu Phe Asp Gln Lys Arg
        35                  40                  45

Arg Cys Cys Lys Phe Pro Cys Pro Asp Ser Cys Lys Tyr Leu Cys Cys
    50                  55                  60

Gly
65

<210> SEQ ID NO 289
<211> LENGTH: 16
<212> TYPE: PRT
<213> ORGANISM: Conus pennaceus
<220> FEATURE:
<221> NAME/KEY: PEPTIDE
<222> LOCATION: (1)..(16)
<223> OTHER INFORMATION: Xaa at residue 6 and 8 is Pro or Hyp; Xaa at
      residue 13 is Tyr, 125I-Tyr, mono-iodo-Tyr, di-iodo-Tyr,
      O-sulpho-Tyr or O-phospho-Tyr

<400> SEQUENCE: 289

Arg Cys Cys Lys Phe Xaa Cys Xaa Asp Ser Cys Lys Xaa Leu Cys Cys
1               5                   10                  15

<210> SEQ ID NO 290
<211> LENGTH: 241
<212> TYPE: DNA
<213> ORGANISM: Conus pulicarius

<400> SEQUENCE: 290
ggatccatga tgtctaaact gggagtcttg ttgaccatct gtctgcttct gtttcccctt    60
actgctcttc cgatggatgg tgatcaactt gcagaccgac ttgtagagcg tatgcaggac   120
aacatttcat ctgagcagca tcccttcttt gatcccgtca acggtgttg cgtcagctgt   180
```

-continued

```
tacatgggat gcatcccttg ttgcttctag taataacgtg ttgatgacca actttctcga    240
g                                                                   241
```

<210> SEQ ID NO 291
<211> LENGTH: 67
<212> TYPE: PRT
<213> ORGANISM: Conus pulicarius

<400> SEQUENCE: 291

Met Met Ser Lys Leu Gly Val Leu Leu Thr Ile Cys Leu Leu Phe
1               5                   10                  15

Pro Leu Thr Ala Leu Pro Met Asp Gly Asp Gln Leu Ala Asp Arg Leu
            20                  25                  30

Val Glu Arg Met Gln Asp Asn Ile Ser Ser Glu Gln His Pro Phe Phe
        35                  40                  45

Asp Pro Val Lys Arg Cys Cys Val Ser Cys Tyr Met Gly Cys Ile Pro
    50                  55                  60

Cys Cys Phe
65

<210> SEQ ID NO 292
<211> LENGTH: 14
<212> TYPE: PRT
<213> ORGANISM: Conus pulicarius
<220> FEATURE:
<221> NAME/KEY: PEPTIDE
<222> LOCATION: (1)..(14)
<223> OTHER INFORMATION: Xaa at residue 11 is Pro or Hyp; Xaa at
      residue 6 is Tyr, 125I-Tyr, mono-iodo-Tyr, di-iodo-Tyr,
      O-sulpho-Tyr or O-phospho-Tyr

<400> SEQUENCE: 292

Cys Cys Val Ser Cys Xaa Met Gly Cys Ile Xaa Cys Cys Phe
1               5                   10

<210> SEQ ID NO 293
<211> LENGTH: 244
<212> TYPE: DNA
<213> ORGANISM: Conus pulicarius

<400> SEQUENCE: 293

```
ggatccatga tgtctaaaact gggagtcttg ttgaccgtct gtctgcttct gtgtcccctt    60
actgctcttc cactggatga agatcaactt gcagaccgac tgcagagcg tatgcaggat    120 gacacttcag ctgcacagat tttcgggttt gatcccgtca aacggtgctg caaattgcta    180
tgctactcgg gatgcactcc ttgttgccat atttgataac gtgttgatga ccaactttct    240
cgag                                                                244
```

<210> SEQ ID NO 294
<211> LENGTH: 67
<212> TYPE: PRT
<213> ORGANISM: Conus pulicarius

<400> SEQUENCE: 294

Met Met Ser Lys Leu Gly Val Leu Leu Thr Val Cys Leu Leu Cys
1               5                   10                  15

Pro Leu Thr Ala Leu Pro Leu Asp Glu Asp Gln Leu Ala Asp Arg Pro
            20                  25                  30

Ala Glu Arg Met Gln Asp Asp Thr Ser Ala Ala Gln Ile Phe Gly Phe
        35                  40                  45

```
Asp Pro Val Lys Arg Cys Cys Lys Leu Leu Cys Gly Cys Thr Pro Cys
    50                  55                  60

Cys His Ile
65
```

<210> SEQ ID NO 295
<211> LENGTH: 16
<212> TYPE: PRT
<213> ORGANISM: Conus pulicarius
<220> FEATURE:
<221> NAME/KEY: PEPTIDE
<222> LOCATION: (1)..(16)
<223> OTHER INFORMATION: Xaa at residue 12 is Pro or Hyp; Xaa at
      residue 7 is Tyr, 125I-Tyr, mono-iodo-Tyr, di-iodo-Tyr,
      O-sulpho-Tyr or O-phospho-Tyr

<400> SEQUENCE: 295

```
Cys Cys Lys Leu Leu Cys Xaa Ser Gly Cys Thr Xaa Cys Cys His Ile
1               5                   10                  15
```

<210> SEQ ID NO 296
<211> LENGTH: 259
<212> TYPE: DNA
<213> ORGANISM: Conus rattus

<400> SEQUENCE: 296

```
ggatccatga tgtctaaact gggagtcttg ttgaccatct gtctgcttgt gtttccgctt    60
actgctcttc cgatggatgg tgatcaacct gcagaccgac ttgtagagcg tatacaggac   120
aacatttcat ctgagcagca tcccttcttt gaaaagagaa gaggctgttg cgcacctccg   180
aggaaatgca agaccgagc ctgcaaacct gcacgttgct gcggcccagg ataacgtgtt   240
gatgaccaac tttctcgag                                                259
```

<210> SEQ ID NO 297
<211> LENGTH: 75
<212> TYPE: PRT
<213> ORGANISM: Conus rattus

<400> SEQUENCE: 297

```
Met Met Ser Lys Leu Gly Val Leu Leu Thr Ile Cys Leu Leu Val Phe
1               5                   10                  15

Pro Leu Thr Ala Leu Pro Met Asp Gly Asp Gln Pro Ala Asp Arg Leu
            20                  25                  30

Val Glu Arg Ile Gln Asp Asn Ile Ser Ser Glu Gln His Pro Phe Phe
        35                  40                  45

Glu Lys Arg Arg Gly Cys Cys Ala Pro Pro Arg Lys Cys Lys Asp Arg
    50                  55                  60

Ala Cys Lys Pro Ala Arg Cys Cys Gly Pro Gly
65                  70                  75
```

<210> SEQ ID NO 298
<211> LENGTH: 23
<212> TYPE: PRT
<213> ORGANISM: Conus rattus
<220> FEATURE:
<221> NAME/KEY: PEPTIDE
<222> LOCATION: (1)..(23)
<223> OTHER INFORMATION: Xaa at residue 6, 7, 17 and 23 is Pro or Hyp

<400> SEQUENCE: 298

```
Arg Gly Cys Cys Ala Xaa Xaa Arg Lys Cys Lys Asp Arg Ala Cys Lys
1               5                   10                  15
```

```
Xaa Ala Arg Cys Cys Gly Xaa
            20
```

<210> SEQ ID NO 299
<211> LENGTH: 262
<212> TYPE: DNA
<213> ORGANISM: Conus stercusmuscarum

<400> SEQUENCE: 299

```
ggatccatga tgtctaaact gggagtcttg ttgacaatct gtctgcttct gtttcccctt      60
attgctcttc cgctggatgg agatcaacct gcagaccgac ctgcagagcg tatgcaggac     120
gacatttcat ctgagaagca tcccttgttt gataagagac aacggtgttg caatgggcgg     180
aggggatgct ccagcagatg gtgcagagat cactcacgtt gttgcggtcg acgataacgt     240
gttgatgacc aactttctcg ag                                              262
```

<210> SEQ ID NO 300
<211> LENGTH: 76
<212> TYPE: PRT
<213> ORGANISM: Conus stercusmuscarum

<400> SEQUENCE: 300

```
Met Met Ser Lys Leu Gly Val Leu Leu Thr Ile Cys Leu Leu Leu Phe
1               5                   10                  15

Pro Leu Ile Ala Leu Pro Leu Asp Gly Asp Gln Pro Ala Asp Arg Pro
            20                  25                  30

Ala Glu Arg Met Gln Asp Asp Ile Ser Ser Glu Lys His Pro Leu Phe
        35                  40                  45

Asp Lys Arg Gln Arg Cys Cys Asn Gly Arg Arg Gly Cys Ser Ser Arg
    50                  55                  60

Trp Cys Arg Asp His Ser Arg Cys Cys Gly Arg Arg
65                  70                  75
```

<210> SEQ ID NO 301
<211> LENGTH: 22
<212> TYPE: PRT
<213> ORGANISM: Conus stercusmuscarum
<220> FEATURE:
<221> NAME/KEY: PEPTIDE
<222> LOCATION: (1)..(22)
<223> OTHER INFORMATION: Xaa at residue 1 is Gln or pyro-Glu; Xaa at
      residue 14 is Trp or bromo-Trp

<400> SEQUENCE: 301

```
Xaa Arg Cys Cys Asn Gly Arg Arg Gly Cys Ser Ser Arg Xaa Cys Arg
1               5                   10                  15

Asp His Ser Arg Cys Cys
            20
```

<210> SEQ ID NO 302
<211> LENGTH: 241
<212> TYPE: DNA
<213> ORGANISM: Conus ebraceus

<400> SEQUENCE: 302

```
ggatccatga tgtctaaact gggagtcttg ttgaccatct gtctgcttct gtttcccctt      60
actgctcttc cactggatga aggtcaacct gcagacctac ctgcagagcg tatgcaggac     120
attgcaactg aacagcatcc cttgtttgat cctgtcaaac ggtgttgcga gcagccatgc     180
tacatgggat gcatcccttg ttgcttctaa taataacgtg ttgatgacca actttctcga     240
``` g                                                                                          241

<210> SEQ ID NO 303
<211> LENGTH: 67
<212> TYPE: PRT
<213> ORGANISM: Conus ebraceus

<400> SEQUENCE: 303

Met Met Ser Lys Leu Gly Val Leu Leu Thr Ile Cys Leu Leu Leu Phe
1               5                   10                  15

Pro Leu Thr Ala Leu Pro Leu Asp Glu Gly Gln Pro Ala Asp Leu Pro
            20                  25                  30

Ala Glu Arg Met Gln Asp Ile Ala Thr Glu Gln His Pro Leu Phe Asp
        35                  40                  45

Pro Val Lys Arg Cys Cys Glu Gln Pro Cys Tyr Met Gly Cys Ile Pro
    50                  55                  60

Cys Cys Phe
65

<210> SEQ ID NO 304
<211> LENGTH: 15
<212> TYPE: PRT
<213> ORGANISM: Conus ebraceus
<220> FEATURE:
<221> NAME/KEY: PEPTIDE
<222> LOCATION: (1)..(15)
<223> OTHER INFORMATION: Xaa at residue 3 is Glu or gamma-carboxy Glu;
      Xaa at residue 5 and 12 is Pro or Hyp; Xaa at residue 7 is Tyr,
      125I-Tyr, mono-iodo-Tyr, di-iodo-Tyr, O-sulpho-Tyr or
      O-phospho-Tyr

<400> SEQUENCE: 304

Cys Cys Xaa Gln Xaa Cys Xaa Met Gly Cys Ile Xaa Cys Cys Phe
1               5                   10                  15

<210> SEQ ID NO 305
<211> LENGTH: 241
<212> TYPE: DNA
<213> ORGANISM: Conus ebraceus

<400> SEQUENCE: 305
ggatccatga tgtctaaact gggagtcttg ttgaccatct gtctgcttct gtttcccctt      60
actgctcttc cactggatga agatcaacct gcagacctac ctgcagagcg tatgcaggac     120
attgcaactg aacagcatcc cttgtttgat cctgtcaaac ggtgctgcgc gcagccatgc     180
tacatgggat gcatcccttg ttgcttctaa taataacgtg ttgatgacca actttctcga     240
g                                                                    241

<210> SEQ ID NO 306
<211> LENGTH: 67
<212> TYPE: PRT
<213> ORGANISM: Conus ebraceus

<400> SEQUENCE: 306

Met Met Ser Lys Leu Gly Val Leu Leu Thr Ile Cys Leu Leu Leu Phe
1               5                   10                  15

Pro Leu Thr Ala Leu Pro Leu Asp Glu Asp Gln Pro Ala Asp Leu Pro
            20                  25                  30

Ala Glu Arg Met Gln Asp Ile Ala Thr Glu Gln His Pro Leu Phe Asp
        35                  40                  45

```
Pro Val Lys Arg Cys Cys Ala Gln Pro Cys Tyr Met Gly Cys Ile Pro
    50                  55                  60

Cys Cys Phe
65
```

<210> SEQ ID NO 307
<211> LENGTH: 15
<212> TYPE: PRT
<213> ORGANISM: Conus ebraceus
<220> FEATURE:
<221> NAME/KEY: PEPTIDE
<222> LOCATION: (1)..(15)
<223> OTHER INFORMATION: Xaa at residue 5 and 12 is Pro or Hyp; Xaa at
      residue 7 is Tyr, 125I-Tyr, mono-iodo-Tyr, di-iodo-Tyr,
      O-sulpho-Tyr or O-phospho-Tyr

<400> SEQUENCE: 307

```
Cys Cys Ala Gln Xaa Cys Xaa Met Gly Cys Ile Xaa Cys Cys Phe
1               5                   10                  15
```

<210> SEQ ID NO 308
<211> LENGTH: 238
<212> TYPE: DNA
<213> ORGANISM: Conus flavidus

<400> SEQUENCE: 308

```
ggatccatga tgtctaaact gggagtcttg ttgaccatct gtctgcttct gtttcccctt      60
actgctgttc cgttggatgg agatcaacct gcagaccagc ctgcagagcg tatgcagaac     120
gagcagcatc ccttgtttga tcagaaaaga aggtgctgcc ggtggccatg ccccagtata     180
tgcggcatgg ctaggtgttg ctcgtcatga taacgtgttg atgaccaact ttctcgag      238
```

<210> SEQ ID NO 309
<211> LENGTH: 67
<212> TYPE: PRT
<213> ORGANISM: Conus flavidus

<400> SEQUENCE: 309

```
Met Met Ser Lys Leu Gly Val Leu Leu Thr Ile Cys Leu Leu Leu Phe
1               5                   10                  15

Pro Leu Thr Ala Val Pro Leu Asp Gly Asp Gln Pro Ala Asp Gln Pro
            20                  25                  30

Ala Glu Arg Met Gln Asn Glu Gln His Pro Leu Phe Asp Gln Lys Arg
        35                  40                  45

Arg Cys Cys Arg Trp Pro Cys Pro Ser Ile Cys Gly Met Ala Arg Cys
    50                  55                  60

Cys Ser Ser
65
```

<210> SEQ ID NO 310
<211> LENGTH: 19
<212> TYPE: PRT
<213> ORGANISM: Conus flavidus
<220> FEATURE:
<221> NAME/KEY: PEPTIDE
<222> LOCATION: (1)..(19)
<223> OTHER INFORMATION: Xaa at residue 6 and 8 is Pro or Hyp; Xaa at
      residue 5 is Trp or bromo-Trp

<400> SEQUENCE: 310

```
Arg Cys Cys Arg Xaa Xaa Cys Xaa Ser Ile Cys Gly Met Ala Arg Cys
1               5                   10                  15

Cys Ser Ser
```

<210> SEQ ID NO 311
<211> LENGTH: 245
<212> TYPE: DNA
<213> ORGANISM: Conus miliaris
<220> FEATURE:
<221> NAME/KEY: misc_feature
<222> LOCATION: (1)..(245)
<223> OTHER INFORMATION: n may be any nucleotide

<400> SEQUENCE: 311

```
ggatccatga tgtctaaact gggagtcttg ttgaccatct gtctgcttct gtttccaatt    60
actgcccttc cactggatga agatcaacct gcagaccgac ctgcagagcg tatgcaggac   120
attgcaactg aacagcatcc cttgtttgat cccgtcaaac ggtgttgcga ttggccatgc   180
agcgcaggat gctaccttg ttgcttccct taataacgtg ttgatgacca actnangnaa    240
aaaaa                                                                245
```

<210> SEQ ID NO 312
<211> LENGTH: 68
<212> TYPE: PRT
<213> ORGANISM: Conus miliaris

<400> SEQUENCE: 312

```
Met Met Ser Lys Leu Gly Val Leu Leu Thr Ile Cys Leu Leu Leu Phe
1               5                   10                  15

Pro Ile Thr Ala Leu Pro Leu Asp Glu Asp Gln Pro Ala Asp Arg Pro
            20                  25                  30

Ala Glu Arg Met Gln Asp Ile Ala Thr Glu Gln His Pro Leu Phe Asp
        35                  40                  45

Pro Val Lys Arg Cys Cys Asp Trp Pro Cys Ser Ala Gly Cys Tyr Pro
    50                  55                  60

Cys Cys Phe Pro
65
```

<210> SEQ ID NO 313
<211> LENGTH: 16
<212> TYPE: PRT
<213> ORGANISM: Conus miliaris
<220> FEATURE:
<221> NAME/KEY: PEPTIDE
<222> LOCATION: (1)..(16)
<223> OTHER INFORMATION: Xaa at residue 5, 12 and 16 is Pro or Hyp;
      Xaa at residue 4 is Trp or bromo-Trp; Xaa at residue 11 is Tyr,
      125I-Tyr, mono-iodo-Tyr, di-iodo-Tyr, O-sulpho-Tyr or
      O-phospho-Tyr

<400> SEQUENCE: 313

```
Cys Cys Asp Xaa Xaa Cys Ser Ala Gly Cys Xaa Xaa Cys Cys Phe Xaa
1               5                   10                  15
```

<210> SEQ ID NO 314
<211> LENGTH: 230
<212> TYPE: DNA
<213> ORGANISM: Conus miliaris
<220> FEATURE:
<221> NAME/KEY: misc_feature
<222> LOCATION: (1)..(230)
<223> OTHER INFORMATION: n may be any nucleotide

<400> SEQUENCE: 314

```
ggatccatga tgtctaaact gggagtggtg ccattcgtct ttctggtcct gtttcccctg    60
gcaacactcc aactggatgc agatcaacct gcagaccgac ctgcgcgtaa aagggcatt   120
```

```
gcaactaaac ggcatcccctt gtctgatcct gtcagagggt gttgccctcc aatgtgcaca      180
ccatgcttcc cttgctgttt tcgttaataa cgtgttgatg natgatgnan                  230
```

<210> SEQ ID NO 315
<211> LENGTH: 66
<212> TYPE: PRT
<213> ORGANISM: Conus miliaris

<400> SEQUENCE: 315

```
Met Met Ser Lys Leu Gly Val Val Pro Phe Val Phe Leu Val Leu Phe
1               5                   10                  15

Pro Leu Ala Thr Leu Gln Leu Asp Ala Asp Gln Pro Ala Asp Arg Pro
            20                  25                  30

Ala Arg Lys Lys Gly Ile Ala Thr Lys Arg His Pro Leu Ser Asp Pro
        35                  40                  45

Val Arg Gly Cys Cys Pro Pro Met Cys Thr Pro Cys Phe Pro Cys Cys
    50                  55                  60

Phe Arg
65
```

<210> SEQ ID NO 316
<211> LENGTH: 16
<212> TYPE: PRT
<213> ORGANISM: Conus miliaris
<220> FEATURE:
<221> NAME/KEY: PEPTIDE
<222> LOCATION: (1)..(16)
<223> OTHER INFORMATION: Xaa at residue 4, 9 and 12 is Pro or Hyp;
      Xaa at residue 5 is Tyr, 125I-Tyr, mono-iodo-Tyr, di-iodo-Tyr,
      O-sulpho-Tyr or O-phospho-Tyr

<400> SEQUENCE: 316

```
Gly Cys Cys Xaa Xaa Met Cys Thr Xaa Cys Phe Xaa Cys Cys Phe Arg
1               5                   10                  15
```

<210> SEQ ID NO 317
<211> LENGTH: 295
<212> TYPE: DNA
<213> ORGANISM: Conus ammiralis

<400> SEQUENCE: 317

```
caagagggat cgatagcagt tcatgatgtc taaactggga gtcttgttga ccatctgtct      60
gcttctgttt ccccttactg ctcttccgct ggatggagat caacctgcag accaagctgc    120
agagcgtatg caggccgagc agcatcccctt gtttgatcag aaaagacggt gttgcaggtt    180
tccatgcccc gatacttgca gacatttgtg ttgcgggtga tgataacgtg ctgatgaccc    240
actttgtcat cacggctacg tcaagtgtct aatgaataag taaatgatt gcagt          295
```

<210> SEQ ID NO 318
<211> LENGTH: 65
<212> TYPE: PRT
<213> ORGANISM: Conus ammiralis

<400> SEQUENCE: 318

```
Met Met Ser Lys Leu Gly Val Leu Leu Thr Ile Cys Leu Leu Leu Phe
1               5                   10                  15

Pro Leu Thr Ala Leu Pro Leu Asp Gly Asp Gln Pro Ala Asp Gln Ala
            20                  25                  30

Ala Glu Arg Met Gln Ala Glu Gln His Pro Leu Phe Asp Gln Lys Arg
        35                  40                  45
```

Arg Cys Cys Arg Phe Pro Cys Pro Asp Thr Cys Arg His Leu Cys Cys
    50              55              60
Gly
65

<210> SEQ ID NO 319
<211> LENGTH: 16
<212> TYPE: PRT
<213> ORGANISM: Conus ammiralis
<220> FEATURE:
<221> NAME/KEY: PEPTIDE
<222> LOCATION: (1)..(16)
<223> OTHER INFORMATION: Xaa at residue 6 and 8 is Pro or Hyp

<400> SEQUENCE: 319

Arg Cys Cys Arg Phe Xaa Cys Xaa Asp Thr Cys Arg His Leu Cys Cys
1               5                   10                  15

<210> SEQ ID NO 320
<211> LENGTH: 267
<212> TYPE: DNA
<213> ORGANISM: Conus ammiralis

<400> SEQUENCE: 320
caagagggat cgatagcagt tcatgatgtt taaactggga gtcttgctga ccatctgtct       60
acttctgttt tcccttaatg ctgttccgct ggatggagat caacctgcag accaacctgc      120
agagcgtctg ctggacgaca tttcatctga aataatccc tttatgatc ccgccaaacg        180 gtgttgcatg acttgcttcg gttgcacacc ttgttgtgga tgaccagcct catcaagtgt      240
ctaacgaata agtaaaacga ttgcagt                                          267

<210> SEQ ID NO 321
<211> LENGTH: 66
<212> TYPE: PRT
<213> ORGANISM: Conus ammiralis

<400> SEQUENCE: 321

Met Met Phe Lys Leu Gly Val Leu Leu Thr Ile Cys Leu Leu Leu Phe
1               5                   10                  15

Ser Leu Asn Ala Val Pro Leu Asp Gly Asp Gln Pro Ala Asp Gln Pro
            20                  25                  30

Ala Glu Arg Leu Leu Asp Asp Ile Ser Ser Glu Asn Asn Pro Phe Tyr
        35                  40                  45

Asp Pro Ala Lys Arg Cys Cys Met Thr Cys Phe Gly Cys Thr Pro Cys
    50              55                  60

Cys Gly
65

<210> SEQ ID NO 322
<211> LENGTH: 12
<212> TYPE: PRT
<213> ORGANISM: Conus ammiralis
<220> FEATURE:
<221> NAME/KEY: PEPTIDE
<222> LOCATION: (1)..(12)
<223> OTHER INFORMATION: Xaa at residue 10 is Pro or Hyp

<400> SEQUENCE: 322

Cys Cys Met Thr Cys Phe Gly Cys Thr Xaa Cys Cys
1               5                   10

```
<210> SEQ ID NO 323
<211> LENGTH: 294
<212> TYPE: DNA
<213> ORGANISM: Conus ammiralis

<400> SEQUENCE: 323
caagaaggat cgatagcagt tcatgatgtc taaactggga gccttgttga ccatctgtct    60
acttctgttt tcccttactg ctgttccgct ggatggagat caacatgcag accaacctgc   120
agagcgtctg caggaccgcc ttccaactga aaatcatccc ttatatgatc ccgtcaaacg   180
gtgttgcgat gattcggaat gcgactattc ttgctggcct tgctgtattt tttcataacc   240
tttgttatcg cggcctcatc ctagtgtcaa atgaataagt aaaacgattg cagt          294

<210> SEQ ID NO 324
<211> LENGTH: 71
<212> TYPE: PRT
<213> ORGANISM: Conus ammiralis

<400> SEQUENCE: 324

Met Met Ser Lys Leu Gly Ala Leu Leu Thr Ile Cys Leu Leu Leu Phe
1               5                   10                  15

Ser Leu Thr Ala Val Pro Leu Asp Gly Asp Gln His Ala Asp Gln Pro
            20                  25                  30

Ala Glu Arg Leu Gln Asp Arg Leu Pro Thr Glu Asn His Pro Leu Tyr
        35                  40                  45

Asp Pro Val Lys Arg Cys Cys Asp Ser Glu Cys Asp Tyr Ser Cys
    50                  55                  60

Trp Pro Cys Cys Ile Phe Ser
65                  70

<210> SEQ ID NO 325
<211> LENGTH: 18
<212> TYPE: PRT
<213> ORGANISM: Conus ammiralis
<220> FEATURE:
<221> NAME/KEY: PEPTIDE
<222> LOCATION: (1)..(18)
<223> OTHER INFORMATION: Xaa at residue 6 is Glu or gamma-carboxy Glu;
      Xaa at residue 13 is Pro or Hyp; Xaa at residue 12 is Trp or
      bromo-Trp; Xaa at residue 9 is Tyr, 125I-Tyr, mono-iodo-Tyr,
      di-iodo-Tyr, O-sulpho-Tyr or O-phospho-Tyr

<400> SEQUENCE: 325

Cys Cys Asp Asp Ser Xaa Cys Asp Xaa Ser Cys Xaa Xaa Cys Cys Ile
1               5                   10                  15

Phe Ser

<210> SEQ ID NO 326
<211> LENGTH: 284
<212> TYPE: DNA
<213> ORGANISM: Conus ammiralis

<400> SEQUENCE: 326
caagagggat cgatagcagt tcatgatgtt taaactcgga gtcttgctga ccatctgtct    60
acttctgttt tccctaattg ctgttccgct ggatggagat caacatgcag accaacctgc   120
agagcgtctg caggaccgcc ttccaactga aaatcatccc ttatatgatc ccgtcaaacg   180
gtgttgcagg ttgttatgcc tcagttgcaa cccttgttgt ggatgaccag ctttgttatc   240
acggcctcat caagtgtcta atgaataagt aaaacgattg cagt                    284
```

```
<210> SEQ ID NO 327
<211> LENGTH: 67
<212> TYPE: PRT
<213> ORGANISM: Conus ammiralis

<400> SEQUENCE: 327

Met Met Phe Lys Leu Gly Val Leu Leu Thr Ile Cys Leu Leu Leu Phe
1               5                   10                  15

Ser Leu Ile Ala Val Pro Leu Asp Gly Asp Gln His Ala Asp Gln Pro
            20                  25                  30

Ala Glu Arg Leu Gln Asp Arg Leu Pro Thr Glu Asn His Pro Leu Tyr
        35                  40                  45

Asp Pro Val Lys Arg Cys Cys Arg Leu Leu Cys Leu Ser Cys Asn Pro
    50                  55                  60

Cys Cys Gly
65

<210> SEQ ID NO 328
<211> LENGTH: 13
<212> TYPE: PRT
<213> ORGANISM: Conus ammiralis
<220> FEATURE:
<221> NAME/KEY: PEPTIDE
<222> LOCATION: (1)..(13)
<223> OTHER INFORMATION: Xaa at residue 11 is Pro or Hyp

<400> SEQUENCE: 328

Cys Cys Arg Leu Leu Cys Leu Ser Cys Asn Xaa Cys Cys
1               5                   10

<210> SEQ ID NO 329
<211> LENGTH: 289
<212> TYPE: DNA
<213> ORGANISM: Conus ammiralis

<400> SEQUENCE: 329
caagaaggat cgatagcagt tcatgatgtc taaactggga gccttgttga ccatctgtct    60
acttctgttt tcccttactg ctgttccgct ggatggagat caacatgcag accaacctgc   120
agagcgtctg caggaccgca ttccaactga agatcatccc ttatttgatc ccaacaaacg   180
gtgttgcgat gattcggaat gcggctattc atgctggcct tgctgttatg gataagcttt   240
gttatcgcgg cctcatccag tgtcaacgaa taagtaaaac gattgcagt               289

<210> SEQ ID NO 330
<211> LENGTH: 70
<212> TYPE: PRT
<213> ORGANISM: Conus ammiralis

<400> SEQUENCE: 330

Met Met Ser Lys Leu Gly Ala Leu Leu Thr Ile Cys Leu Leu Leu Phe
1               5                   10                  15

Ser Leu Thr Ala Val Pro Leu Asp Gly Asp Gln His Ala Asp Gln Pro
            20                  25                  30

Ala Glu Arg Leu Gln Asp Arg Ile Pro Thr Glu Asp His Pro Leu Phe
        35                  40                  45

Asp Pro Asn Lys Arg Cys Cys Asp Asp Ser Glu Cys Gly Tyr Ser Cys
    50                  55                  60

Trp Pro Cys Cys Tyr Gly
65                  70
```

<210> SEQ ID NO 331
<211> LENGTH: 16
<212> TYPE: PRT
<213> ORGANISM: Conus ammiralis
<220> FEATURE:
<221> NAME/KEY: PEPTIDE
<222> LOCATION: (1)..(16)
<223> OTHER INFORMATION: Xaa at residue6  is Glu or gamma-carboxy Glu;
    Xaa at residue 13 is Pro or Hyp; Xaa at residue 12 is Trp or
    bromo-Trp; Xaa at residue 9 and 16 is Tyr, 125I-Tyr,
    mono-iodo-Tyr, di-iodo-Tyr, O-sulpho-Tyr or O-phospho-Tyr

<400> SEQUENCE: 331

Cys Cys Asp Asp Ser Xaa Cys Gly Xaa Ser Cys Xaa Xaa Cys Cys Xaa
1               5                   10                  15

<210> SEQ ID NO 332
<211> LENGTH: 272
<212> TYPE: DNA
<213> ORGANISM: Conus spurius

<400> SEQUENCE: 332
caagaaggat cgatagcagt tcatgatgtc taaactggga gtcttgctga ccatctgtct      60
gcttctgttt ccacgtactt ctcttccgct ggatggagat caacctgcag tccgatctgc     120
aaagcgtatg cattcatcta tacagcgtcg tttctttgat cccgtcaaac ggtgttgccc     180
tagatgcagc gagtgcaacc cttgttgtgg atgaccagct ttgtcatcgc ggcctcatta     240
agtgtctaat gaataagtaa aatgattgca gt                                   272

<210> SEQ ID NO 333
<211> LENGTH: 63
<212> TYPE: PRT
<213> ORGANISM: Conus spurius

<400> SEQUENCE: 333

Met Met Ser Lys Leu Gly Val Leu Leu Thr Ile Cys Leu Leu Leu Phe
1               5                   10                  15

Pro Arg Thr Ser Leu Pro Leu Asp Gly Asp Gln Pro Ala Val Arg Ser
            20                  25                  30

Ala Lys Arg Met His Ser Ser Ile Gln Arg Arg Phe Phe Asp Pro Val
        35                  40                  45

Lys Arg Cys Cys Pro Arg Cys Ser Glu Cys Asn Pro Cys Cys Gly
    50                  55                  60

<210> SEQ ID NO 334
<211> LENGTH: 12
<212> TYPE: PRT
<213> ORGANISM: Conus spurius
<220> FEATURE:
<221> NAME/KEY: PEPTIDE
<222> LOCATION: (1)..(12)
<223> OTHER INFORMATION: Xaa at residue 7 is Glu or gamma-carboxy Glu;
    Xaa at residue 3 and 10 is Pro or Hyp

<400> SEQUENCE: 334

Cys Cys Xaa Arg Cys Ser Xaa Cys Asn Xaa Cys Cys
1               5                   10

<210> SEQ ID NO 335
<211> LENGTH: 293
<212> TYPE: DNA
<213> ORGANISM: Conus omaria

<400> SEQUENCE: 335

```
caagagggat cgatagcagt tcatgatgtc taaactggga gtctcgttga ccatctgtct      60
acttctattt tcccttactg ctgttccgct tgatggagat caacatgcag accaacctgc    120
agagcgtctg cagggcgaca ttttatctga aaagcatccc ttatttaatc ccgtcaaacg    180
gtgttgcgat gaggaagaat gcagcagtgc atgctggcct tgttgttggg ggtgatcagc    240
tttgttatcg cggcctcatc aagtgtctaa tgaataagta aatgattgc agt            293
```

<210> SEQ ID NO 336
<211> LENGTH: 70
<212> TYPE: PRT
<213> ORGANISM: Conus omaria

<400> SEQUENCE: 336

```
Met Met Ser Lys Leu Gly Val Ser Leu Thr Ile Cys Leu Leu Leu Phe
1               5                   10                  15

Ser Leu Thr Ala Val Pro Leu Asp Gly Asp Gln His Ala Asp Gln Pro
            20                  25                  30

Ala Glu Arg Leu Gln Gly Asp Ile Leu Ser Glu Lys His Pro Leu Phe
        35                  40                  45

Asn Pro Val Lys Arg Cys Cys Asp Glu Glu Glu Cys Ser Ser Ala Cys
    50                  55                  60

Trp Pro Cys Cys Trp Gly
65                  70
```

<210> SEQ ID NO 337
<211> LENGTH: 16
<212> TYPE: PRT
<213> ORGANISM: Conus omaria
<220> FEATURE:
<221> NAME/KEY: PEPTIDE
<222> LOCATION: (1)..(16)
<223> OTHER INFORMATION: Xaa at residue 4, 5 and 6 is Glu or
      gamma-carboxy Glu; Xaa at residue 13 is Pro or Hyp; Xaa at
      residue 12 and 16 is Trp or bromo-Trp

<400> SEQUENCE: 337

```
Cys Cys Asp Xaa Xaa Xaa Cys Ser Ser Ala Cys Xaa Xaa Cys Cys Xaa
1               5                   10                  15
```

<210> SEQ ID NO 338
<211> LENGTH: 293
<212> TYPE: DNA
<213> ORGANISM: Conus omaria

<400> SEQUENCE: 338

```
caagaaggat cgatagcagt tcatgatgtc taaactggga gtcttgttga tcatctgtct      60
acttctgtgt cccttactg ctgttctgga ggatggagat caacctgcag accgacctgc    120
agagcgtatg caggacgaca tttcaactga gcatcatccc ttttatgatc ccgtcaaacg    180
gtgttgcaag tacgggtgga catgcttgct aggatgcact ccttgtgatt gttgaccagt    240
tttgttatcg cggcctcgtc aagtgtctaa tgaataagta aacgattgc agt            293
```

<210> SEQ ID NO 339
<211> LENGTH: 70
<212> TYPE: PRT
<213> ORGANISM: Conus omaria

<400> SEQUENCE: 339

```
Met Met Ser Lys Leu Gly Val Leu Leu Ile Ile Cys Leu Leu Leu Cys
1               5                   10                  15
```

```
Pro Leu Thr Ala Val Leu Glu Asp Gly Asp Gln Pro Ala Asp Arg Pro
         20                  25                  30

Ala Glu Arg Met Gln Asp Asp Ile Ser Thr Glu His His Pro Phe Tyr
         35                  40                  45

Asp Pro Val Lys Arg Cys Cys Lys Tyr Gly Trp Thr Cys Leu Leu Gly
         50                  55                  60

Cys Thr Pro Cys Asp Cys
 65              70

<210> SEQ ID NO 340
<211> LENGTH: 17
<212> TYPE: PRT
<213> ORGANISM: Conus omaria
<220> FEATURE:
<221> NAME/KEY: PEPTIDE
<222> LOCATION: (1)..(17)
<223> OTHER INFORMATION: Xaa at residue is 14 Pro or Hyp; Xaa at
      residue 6 is Trp or bromo-Trp; Xaa at residue 4 is Tyr,
      125I-Tyr, mono-iodo-Tyr, di-iodo-Tyr, O-sulpho-Tyr or
      O-phospho-Tyr

<400> SEQUENCE: 340

Cys Cys Lys Xaa Gly Xaa Thr Cys Leu Leu Gly Cys Thr Xaa Cys Asp
 1               5                  10                  15

Cys

<210> SEQ ID NO 341
<211> LENGTH: 290
<212> TYPE: DNA
<213> ORGANISM: Conus omaria

<400> SEQUENCE: 341
caagagggat cgatagcagt tcatgatgtc tatactggga gtcttgttga tcatctgtct      60
acttctgtgt ccccttactg ctgttctgga ggatggagat caacctgcag accgacctgc    120
agagcgtatg caggacggca tttcatctga acatcatccc ttttggatc ccgtcaaacg     180 gtgttgccat ctattggcat gccgctttgg atgctcgcct tgttgttggt gaccagcttt    240
gttatcgcgg cctcatcaag tgtctaatga ataagtaaaa cgattgcagt                290

<210> SEQ ID NO 342
<211> LENGTH: 69
<212> TYPE: PRT
<213> ORGANISM: Conus omaria

<400> SEQUENCE: 342

Met Met Ser Ile Leu Gly Val Leu Leu Ile Ile Cys Leu Leu Leu Cys
 1               5                  10                  15

Pro Leu Thr Ala Val Leu Glu Asp Gly Asp Gln Pro Ala Asp Arg Pro
         20                  25                  30

Ala Glu Arg Met Gln Asp Gly Ile Ser Ser Glu His His Pro Phe Leu
         35                  40                  45

Asp Pro Val Lys Arg Cys Cys His Leu Leu Ala Cys Arg Phe Gly Cys
         50                  55                  60

Ser Pro Cys Cys Trp
 65

<210> SEQ ID NO 343
<211> LENGTH: 16
<212> TYPE: PRT
<213> ORGANISM: Conus omaria
<220> FEATURE:
```

```
<221> NAME/KEY: PEPTIDE
<222> LOCATION: (1)..(16)
<223> OTHER INFORMATION: Xaa at residue 13 is Pro or Hyp; Xaa at
      residue 16 is Trp or bromo-Trp

<400> SEQUENCE: 343

Cys Cys His Leu Leu Ala Cys Arg Phe Gly Cys Ser Xaa Cys Cys Xaa
1               5                   10                  15

<210> SEQ ID NO 344
<211> LENGTH: 293
<212> TYPE: DNA
<213> ORGANISM: Conus omaria

<400> SEQUENCE: 344
caagaaggat cgatagcagt tcatgatgtc taaactggga gtcttgttga tcatctgtct    60
acttctttgt ccccttactg ctgttccgca ggatggagat caacctgcag accgacctgc   120
agagcgtatg cagggcggca tttcatctga acatcatccc ttttttgatc ccgtcaaacg   180
gtgttgcagg tacgggtgga catgctggct aggatgcact ccctgtggtt gttgaccagc   240
tttgttatcg cggcctcatc aagtgtctaa tgaataagta aaacgattgc agt          293

<210> SEQ ID NO 345
<211> LENGTH: 70
<212> TYPE: PRT
<213> ORGANISM: Conus omaria

<400> SEQUENCE: 345

Met Met Ser Lys Leu Gly Val Leu Leu Ile Ile Cys Leu Leu Leu Cys
1               5                   10                  15

Pro Leu Thr Ala Val Pro Gln Asp Gly Asp Gln Pro Ala Asp Arg Pro
            20                  25                  30

Ala Glu Arg Met Gln Gly Gly Ile Ser Ser Glu His His Pro Phe Phe
        35                  40                  45

Asp Pro Val Lys Arg Cys Cys Arg Tyr Gly Trp Thr Cys Trp Leu Gly
    50                  55                  60

Cys Thr Pro Cys Gly Cys
65                  70

<210> SEQ ID NO 346
<211> LENGTH: 17
<212> TYPE: PRT
<213> ORGANISM: Conus omaria
<220> FEATURE:
<221> NAME/KEY: PEPTIDE
<222> LOCATION: (1)..(17)
<223> OTHER INFORMATION: Xaa at residue 14 is Pro or Hyp; Xaa at
      residue 6 and 9 is Trp or bromo-Trp; Xaa at residue 4 is Tyr,
      125I-Tyr, mono-iodo-Tyr, di-iodo-Tyr, O-sulpho-Tyr or
      O-phospho-Tyr

<400> SEQUENCE: 346

Cys Cys Arg Xaa Gly Xaa Thr Cys Xaa Leu Gly Cys Thr Xaa Cys Gly
1               5                   10                  15

Cys

<210> SEQ ID NO 347
<211> LENGTH: 293
<212> TYPE: DNA
<213> ORGANISM: Conus episcopatus

<400> SEQUENCE: 347
```

```
caagaaggat cgatagcagt tcatgatgtc taaactggga gtcttgttga ccatctgtct    60
acttctgttt tcccttattg ctgttccgct tgatggagat caacatgcag accaacctgc   120
agagcgtctg cagggcgaca tttatctga aaagcatccc ttatttatgc ctgtcaaacg    180
gtgttgcgat gaggacgaat gcaacagttc atgctggcct tgttgttggg ggtgatcagc   240
tttgttatcg cggcctgatc aagtgtataa tgaataagta aaacgattgc agt          293
```

<210> SEQ ID NO 348
<211> LENGTH: 70
<212> TYPE: PRT
<213> ORGANISM: Conus episcopatus

<400> SEQUENCE: 348

```
Met Met Ser Lys Leu Gly Val Leu Leu Thr Ile Cys Leu Leu Leu Phe
1               5                   10                  15

Ser Leu Ile Ala Val Pro Leu Asp Gly Asp Gln His Ala Asp Gln Pro
            20                  25                  30

Ala Glu Arg Leu Gln Gly Asp Ile Leu Ser Glu Lys His Pro Leu Phe
        35                  40                  45

Met Pro Val Lys Arg Cys Cys Asp Glu Asp Glu Cys Asn Ser Ser Cys
    50                  55                  60

Trp Pro Cys Cys Trp Gly
65                  70
```

<210> SEQ ID NO 349
<211> LENGTH: 16
<212> TYPE: PRT
<213> ORGANISM: Conus episcopatus
<220> FEATURE:
<221> NAME/KEY: PEPTIDE
<222> LOCATION: (1)..(16)
<223> OTHER INFORMATION: Xaa at residue 4 and 6 is Glu or gamma-carboxy
      Glu; Xaa at residue 13 is Pro or Hyp; Xaa at residue 12 and 16 is
      Trp or bromo-Trp

<400> SEQUENCE: 349

```
Cys Cys Asp Xaa Asp Xaa Cys Asn Ser Ser Cys Xaa Xaa Cys Cys Xaa
1               5                   10                  15
```

<210> SEQ ID NO 350
<211> LENGTH: 293
<212> TYPE: DNA
<213> ORGANISM: Conus episcopatus

<400> SEQUENCE: 350

```
caagagggat cgatagcagt tcatgatgtc taaactggga gtcttgttga ccatctgtct    60
acttctgttt tcccttattg ctgttccgct tgatggagat caacatgcag accaacctgc   120
agagcgtctg cagggcgaca tttatctga aaagcatccc ttatttatgc ctgtcaaacg    180
gtgttgcgat gaggacgaat gcagcagttc atgctggcct tgttgttggg gatgagcagc   240
tttgttatcg cggcctcatc aagtgtctaa tgaataagta aaacgattgc agt          293
```

<210> SEQ ID NO 351
<211> LENGTH: 70
<212> TYPE: PRT
<213> ORGANISM: Conus episcopatus

<400> SEQUENCE: 351

```
Met Met Ser Lys Leu Gly Val Leu Leu Thr Ile Cys Leu Leu Leu Phe
1               5                   10                  15
```

```
Ser Leu Ile Ala Val Pro Leu Asp Gly Asp Gln His Ala Asp Gln Pro
        20                  25                  30

Ala Glu Arg Leu Gln Gly Asp Ile Leu Ser Glu Lys His Pro Leu Phe
            35                  40                  45

Met Pro Val Lys Arg Cys Cys Asp Glu Asp Glu Cys Ser Ser Ser Cys
        50                  55                  60

Trp Pro Cys Cys Trp Gly
65                  70

<210> SEQ ID NO 352
<211> LENGTH: 16
<212> TYPE: PRT
<213> ORGANISM: Conus episcopatus
<220> FEATURE:
<221> NAME/KEY: PEPTIDE
<222> LOCATION: (1)..(16)
<223> OTHER INFORMATION: Xaa at residue4 and 6  is Glu or gamma-carboxy
      Glu; Xaa at residue 13 is Pro or Hyp; Xaa at residue 12 and 16 is
      Trp or bromo-Trp

<400> SEQUENCE: 352

Cys Cys Asp Xaa Asp Xaa Cys Ser Ser Cys Xaa Xaa Cys Cys Xaa
1               5                   10                  15

<210> SEQ ID NO 353
<211> LENGTH: 290
<212> TYPE: DNA
<213> ORGANISM: Conus episcopatus

<400> SEQUENCE: 353
caagagggat cgatagcagt tcatgatgtc taaactggga gtcttgttga ccatctgtct      60
acttctgttt tcccttactg ctgttccgct tgatggagat caacatgcag accaacctgc     120
agagcgtctg cagggcgaca ttttatctga aaagcatccc ttatttaatc ccgtcaaacg     180
gtgttgcccg gcggcggcat gtgccatggg atgcaagcct tgttgtggat gagcagcttt     240
gttatcgtgg cctcatcaag tgtctaatga ataagtaaaa cgattgcagt                290

<210> SEQ ID NO 354
<211> LENGTH: 69
<212> TYPE: PRT
<213> ORGANISM: Conus episcopatus

<400> SEQUENCE: 354

Met Met Ser Lys Leu Gly Val Leu Leu Thr Ile Cys Leu Leu Leu Phe
1               5                   10                  15

Ser Leu Thr Ala Val Pro Leu Asp Gly Asp Gln His Ala Asp Gln Pro
            20                  25                  30

Ala Glu Arg Leu Gln Gly Asp Ile Leu Ser Glu Lys His Pro Leu Phe
        35                  40                  45

Asn Pro Val Lys Arg Cys Cys Pro Ala Ala Cys Ala Met Gly Cys
        50                  55                  60

Lys Pro Cys Cys Gly
65

<210> SEQ ID NO 355
<211> LENGTH: 15
<212> TYPE: PRT
<213> ORGANISM: Conus episcopatus
<220> FEATURE:
<221> NAME/KEY: PEPTIDE
<222> LOCATION: (1)..(15)
<223> OTHER INFORMATION: Xaa at residue 3 and 13 is Pro or Hyp
```

<400> SEQUENCE: 355

Cys Cys Xaa Ala Ala Ala Cys Ala Met Gly Cys Lys Xaa Cys Cys
1               5                   10                  15

<210> SEQ ID NO 356
<211> LENGTH: 295
<212> TYPE: DNA
<213> ORGANISM: Conus aulicus

<400> SEQUENCE: 356
caagagggat cgatagcagt tcatgatgtc taaactggga gtcttgttga ccatctgtct      60
gcttctgttt ccgttactg ctcttccgcc ggatggagat caacctgcag accgagctgc     120
agagcgtagg caggtcgagc agcatcccgt gtttgatcat gaaagagggt gttgctcgcc    180
accatgccac agtatttgcg ctgctttctg ttgcgggtga tgataacgtg ttgatgaccc    240
actttgtcat cacggctgcg tcaagtgtct aatgaataag taaatgatt gcagt          295

<210> SEQ ID NO 357
<211> LENGTH: 65
<212> TYPE: PRT
<213> ORGANISM: Conus aulicus

<400> SEQUENCE: 357

Met Met Ser Lys Leu Gly Val Leu Leu Thr Ile Cys Leu Leu Leu Phe
1               5                   10                  15

Ser Val Thr Ala Leu Pro Pro Asp Gly Asp Gln Pro Ala Asp Arg Ala
                20                  25                  30

Ala Glu Arg Arg Gln Val Glu Gln His Pro Val Phe Asp His Glu Arg
            35                  40                  45

Gly Cys Cys Ser Pro Pro Cys His Ser Ile Cys Ala Ala Phe Cys Cys
        50                  55                  60

Gly
65

<210> SEQ ID NO 358
<211> LENGTH: 16
<212> TYPE: PRT
<213> ORGANISM: Conus aulicus
<220> FEATURE:
<221> NAME/KEY: PEPTIDE
<222> LOCATION: (1)..(16)
<223> OTHER INFORMATION: Xaa at residue 5 and 6 is Pro or Hyp

<400> SEQUENCE: 358

Gly Cys Cys Ser Xaa Xaa Cys His Ser Ile Cys Ala Ala Phe Cys Cys
1               5                   10                  15

<210> SEQ ID NO 359
<211> LENGTH: 290
<212> TYPE: DNA
<213> ORGANISM: Conus aulicus

<400> SEQUENCE: 359
caagagggat cgatagcagt tcatgatgtc taaactggga gtcttgttga ccatctgtct      60
acttctgttt tcccttactg ctgttccgct tgatggagat caacatgcag accaacctgc    120
agagcgtctg cagggcgaca ttttatctga aaagcatccc ttatttaatc ccgtcaaacg    180
gtgttgccga ccggtggcat gtgccatggg atgcaagcct tgttgtggat gagcagcttt    240
gttatcgtgg cctcatcaag tgtctaatga ataagtaaaa tgattgcagt               290

<210> SEQ ID NO 360
<211> LENGTH: 69
<212> TYPE: PRT
<213> ORGANISM: Conus aulicus

<400> SEQUENCE: 360

Met Met Ser Lys Leu Gly Val Leu Leu Thr Ile Cys Leu Leu Leu Phe
1               5                   10                  15

Ser Leu Thr Ala Val Pro Leu Asp Gly Asp Gln His Ala Asp Gln Pro
            20                  25                  30

Ala Glu Arg Leu Gln Gly Asp Ile Leu Ser Glu Lys His Pro Leu Phe
        35                  40                  45

Asn Pro Val Lys Arg Cys Cys Arg Pro Val Ala Cys Ala Met Gly Cys
    50                  55                  60

Lys Pro Cys Cys Gly
65

<210> SEQ ID NO 361
<211> LENGTH: 15
<212> TYPE: PRT
<213> ORGANISM: Conus aulicus
<220> FEATURE:
<221> NAME/KEY: PEPTIDE
<222> LOCATION: (1)..(15)
<223> OTHER INFORMATION: Xaa at residue 4 and 13 is Pro or Hyp

<400> SEQUENCE: 361

Cys Cys Arg Xaa Val Ala Cys Ala Met Gly Cys Lys Xaa Cys Cys
1               5                   10                  15

<210> SEQ ID NO 362
<211> LENGTH: 290
<212> TYPE: DNA
<213> ORGANISM: Conus aulicus

<400> SEQUENCE: 362
caagagggat cgatagcagt tcatgatgtc taaactggga gtcttgttga tcatctgtct      60
acttctgtct cccttactg ctgttccgct ggatggagat caacctgcag accgacctgc     120
agagcgtatg caggacgaca tttcatctga acatcaaccc atgtttgatg ccatcagaca     180
gtgttgcccg gcggtggcat gcgccatggg atgcgagcct tgttgtggat gaccagcttt     240
gttatcgcgg cctcatcaag tgtctaatga ataagtaaaa tgattgcagt                 290

<210> SEQ ID NO 363
<211> LENGTH: 69
<212> TYPE: PRT
<213> ORGANISM: Conus aulicus

<400> SEQUENCE: 363

Met Met Ser Lys Leu Gly Val Leu Leu Ile Ile Cys Leu Leu Leu Ser
1               5                   10                  15

Pro Leu Thr Ala Val Pro Leu Asp Gly Asp Gln Pro Ala Asp Arg Pro
            20                  25                  30

Ala Glu Arg Met Gln Asp Asp Ile Ser Ser Glu His Gln Pro Met Phe
        35                  40                  45

Asp Ala Ile Arg Gln Cys Cys Pro Ala Val Ala Cys Ala Met Gly Cys
    50                  55                  60

Glu Pro Cys Cys Gly
65

<210> SEQ ID NO 364
<211> LENGTH: 16
<212> TYPE: PRT
<213> ORGANISM: Conus aulicus
<220> FEATURE:
<221> NAME/KEY: PEPTIDE
<222> LOCATION: (1)..(16)
<223> OTHER INFORMATION: Xaa at residue 1 is Gln or pyro-Glu; Xaa at
residue 13 is Glu or gamma-carboxy Glu; Xaa at residue 4 and 14 is
Pro or Hyp

<400> SEQUENCE: 364

Xaa Cys Cys Xaa Ala Val Ala Cys Ala Met Gly Cys Xaa Xaa Cys Cys
1               5                   10                  15

<210> SEQ ID NO 365
<211> LENGTH: 293
<212> TYPE: DNA
<213> ORGANISM: Conus aureus

<400> SEQUENCE: 365
caagaaggat cgatagcagt tcatgatgtc taaactggga gccttgttga ccatctgtct    60
acttctgttt tccttactg ctgttccgct ggatggagat caacatgcag accaacatgc    120
agagcgtctg catgaccgcc ttccaactga aaatcatccc ttatatgatc ccgtcaaacg    180
gtgttgcgat gattcggaat gcgactattc ttgctggcct tgctgtattt ttggataacc    240
tttgttatcg cggcctcatc aagtgtcaaa tgaataagta aaacgattgc agt          293

<210> SEQ ID NO 366
<211> LENGTH: 71
<212> TYPE: PRT
<213> ORGANISM: Conus aureus

<400> SEQUENCE: 366

Met Met Ser Lys Leu Gly Ala Leu Leu Thr Ile Cys Leu Leu Leu Phe
1               5                   10                  15

Ser Leu Thr Ala Val Pro Leu Asp Gly Asp Gln His Ala Asp Gln His
                20                  25                  30

Ala Glu Arg Leu His Asp Arg Leu Pro Thr Glu Asn His Pro Leu Tyr
            35                  40                  45

Asp Pro Val Lys Arg Cys Cys Asp Asp Ser Glu Cys Asp Tyr Ser Cys
        50                  55                  60

Trp Pro Cys Cys Ile Phe Gly
65                  70

<210> SEQ ID NO 367
<211> LENGTH: 17
<212> TYPE: PRT
<213> ORGANISM: Conus aureus
<220> FEATURE:
<221> NAME/KEY: PEPTIDE
<222> LOCATION: (1)..(17)
<223> OTHER INFORMATION: Xaa at residue 6 is Glu or gamma-carboxy Glu;
Xaa at residue 13 is Pro or Hyp; Xaa at residue 12 is Trp or
bromo-Trp; Xaa at residue 9 is Tyr, 125I-Tyr, mono-iodo-Tyr,
di-iodo-Tyr, O-sulpho-Tyr or O-phospho-Tyr

<400> SEQUENCE: 367

Cys Cys Asp Asp Ser Xaa Cys Asp Xaa Ser Cys Xaa Xaa Cys Cys Ile
1               5                   10                  15

Phe

<210> SEQ ID NO 368
<211> LENGTH: 290
<212> TYPE: DNA
<213> ORGANISM: Conus aureus

<400> SEQUENCE: 368

| caagagggat cgatagcagt tcatgatgtc taaactggga gccttgttga ccatctgtct | 60 |
| acttctgttt tccctaactg ctgttccgct ggatggagat caacatgcag accaacctgc | 120 |
| agagcgtctg caggaccgca ttccaactga aaatcatccc ttatttgatc cgaacaaacg | 180 |
| gtgttgcaat gattgggaat gcgacgattc atgctggcct tgctgttatg gataaccttt | 240 |
| gttatcgcgg cctcatcaag tgtcaaatga ataagtaaaa cgattgcagt | 290 |

<210> SEQ ID NO 369
<211> LENGTH: 70
<212> TYPE: PRT
<213> ORGANISM: Conus aureus

<400> SEQUENCE: 369

Met Met Ser Lys Leu Gly Ala Leu Leu Thr Ile Cys Leu Leu Leu Phe
1               5                   10                  15

Ser Leu Thr Ala Val Pro Leu Asp Gly Asp Gln His Ala Asp Gln Pro
            20                  25                  30

Ala Glu Arg Leu Gln Asp Arg Ile Pro Thr Glu Asn His Pro Leu Phe
        35                  40                  45

Asp Pro Asn Lys Arg Cys Cys Asn Asp Trp Glu Cys Asp Ser Cys
    50                  55                  60

Trp Pro Cys Cys Tyr Gly
65                  70

<210> SEQ ID NO 370
<211> LENGTH: 16
<212> TYPE: PRT
<213> ORGANISM: Conus aureus
<220> FEATURE:
<221> NAME/KEY: PEPTIDE
<222> LOCATION: (1)..(16)
<223> OTHER INFORMATION: Xaa at residue 6 is Glu or gamma-carboxy Glu;
      Xaa at residue 13 is Pro or Hyp; Xaa at residue 5 and 12 is Trp or
      bromo-Trp; Xaa at residue 16 is Tyr, 125I-Tyr, mono-iodo-Tyr,
      di-iodo-Tyr, O-sulpho-Tyr or O-phospho-Tyr

<400> SEQUENCE: 370

Cys Cys Asn Asp Xaa Xaa Cys Asp Ser Cys Xaa Xaa Cys Cys Xaa
1               5                   10                  15

<210> SEQ ID NO 371
<211> LENGTH: 310
<212> TYPE: DNA
<213> ORGANISM: Conus consors

<400> SEQUENCE: 371

| caagagggat cgatagcagt tcatgatgtc taaactggga gtcttgttga ccatctgttt | 60 |
| gcttctgttt ccccttactg ctcttccaat ggatggagat caatctgtag accgacctgc | 120 |
| agagcgtatg caggacgaca tttcatctga gctgcatccc ttgttcaatc agaaaagaat | 180 |
| gtgttgcggc gaaggtgcgc catgccccag ctatttcaga acagtcaga tttgtcattg | 240 |
| ttgttaaatg acaacgtgtc gatgaccaac ttcgttatca cgactaatga ataagtaaaa | 300 |
| tgattgcagt | 310 |

<210> SEQ ID NO 372
<211> LENGTH: 74
<212> TYPE: PRT
<213> ORGANISM: Conus consors

<400> SEQUENCE: 372

Met Met Ser Lys Leu Gly Val Leu Leu Thr Ile Cys Leu Leu Leu Phe
1               5                   10                  15

Pro Leu Thr Ala Leu Pro Met Asp Gly Asp Gln Ser Val Asp Arg Pro
            20                  25                  30

Ala Glu Arg Met Gln Asp Asp Ile Ser Ser Glu Leu His Pro Leu Phe
        35                  40                  45

Asn Gln Lys Arg Met Cys Cys Gly Glu Gly Ala Pro Cys Pro Ser Tyr
    50                  55                  60

Phe Arg Asn Ser Gln Ile Cys His Cys Cys
65                  70

<210> SEQ ID NO 373
<211> LENGTH: 22
<212> TYPE: PRT
<213> ORGANISM: Conus consors
<220> FEATURE:
<221> NAME/KEY: PEPTIDE
<222> LOCATION: (1)..(22)
<223> OTHER INFORMATION: Xaa at residue 5 is Glu or gamma-carboxy Glu;
      Xaa at residue 8 and 10 is Pro or Hyp; Xaa at residue 12 is Tyr,
      125I-Tyr, mono-iodo-Tyr, di-iodo-Tyr, O-sulpho-Tyr or
      O-phospho-Tyr

<400> SEQUENCE: 373

Met Cys Cys Gly Xaa Gly Ala Xaa Cys Xaa Ser Xaa Phe Arg Asn Ser
1               5                   10                  15

Gln Ile Cys His Cys Cys
            20

<210> SEQ ID NO 374
<211> LENGTH: 315
<212> TYPE: DNA
<213> ORGANISM: Conus consors

<400> SEQUENCE: 374
taagagggat cgatagcagt tcatgatgtc taaactggga gtcttgttga ccatctgtct      60
gcttctgttt ccccttattg ctcttccaat ggatggagat caacctgcag accgacctgc    120
agagcgtatg caggacgaca tttcatctca gcagcatccc ttgtttgata agagaggccg    180
ctgttgcgat gtgccgaacg catgctccgg cagatggtgc agagatcacg cacaatgttg    240
cggatgacga taacgtgttg atgaccaact ttgtgatcac ggctacatca agtgaataag    300
taaaacgatt gcagt                                                     315

<210> SEQ ID NO 375
<211> LENGTH: 74
<212> TYPE: PRT
<213> ORGANISM: Conus consors

<400> SEQUENCE: 375

Met Met Ser Lys Leu Gly Val Leu Leu Thr Ile Cys Leu Leu Leu Phe
1               5                   10                  15

Pro Leu Ile Ala Leu Pro Met Asp Gly Asp Gln Pro Ala Asp Arg Pro
            20                  25                  30

Ala Glu Arg Met Gln Asp Asp Ile Ser Ser Gln Gln His Pro Leu Phe

Asp Lys Arg Gly Arg Cys Cys Asp Val Pro Asn Ala Cys Ser Gly Arg
        50                  55                  60

Trp Cys Arg Asp His Ala Gln Cys Cys Gly
65                  70

<210> SEQ ID NO 376
<211> LENGTH: 22
<212> TYPE: PRT
<213> ORGANISM: Conus consors
<220> FEATURE:
<221> NAME/KEY: PEPTIDE
<222> LOCATION: (1)..(22)
<223> OTHER INFORMATION: Xaa at residue 7 is Pro or Hyp; Xaa at
      residue 14 is Trp or bromo-Trp

<400> SEQUENCE: 376

Gly Arg Cys Cys Asp Val Xaa Asn Ala Cys Ser Gly Arg Xaa Cys Arg
1               5                   10                  15

Asp His Ala Gln Cys Cys
            20

<210> SEQ ID NO 377
<211> LENGTH: 322
<212> TYPE: DNA
<213> ORGANISM: Conus consors

<400> SEQUENCE: 377
caagagggat cgatagcagt tcatgatgtc taaactggga gtcttgttga ctgtctgttt      60
gcttctgttt cccctactg ctcttccgat ggatggagat caacctgcag accaacctgc     120
agagcgtatg caggacgaca tttcatctga gcagcatccc ttgtttgata agagacaaag     180
gtgttgcact gggaagaagg ggtcatgctc cggtaaagca tgcaaaagtc tcaaatgttg     240
ctctggacga taacgtgttg atgaccaact ttgttatcac ggctacgtca agtgtctagt     300
gaataagtaa aacgattgca gt                                             322

<210> SEQ ID NO 378
<211> LENGTH: 76
<212> TYPE: PRT
<213> ORGANISM: Conus consors

<400> SEQUENCE: 378

Met Met Ser Lys Leu Gly Val Leu Leu Thr Val Cys Leu Leu Leu Phe
1               5                   10                  15

Pro Leu Thr Ala Leu Pro Met Asp Gly Asp Gln Pro Ala Asp Gln Pro
            20                  25                  30

Ala Glu Arg Met Gln Asp Asp Ile Ser Ser Glu Gln His Pro Leu Phe
        35                  40                  45

Asp Lys Arg Gln Arg Cys Cys Thr Gly Lys Lys Gly Ser Cys Ser Gly
    50                  55                  60

Lys Ala Cys Lys Ser Leu Lys Cys Cys Ser Gly Arg
65                  70                  75

<210> SEQ ID NO 379
<211> LENGTH: 23
<212> TYPE: PRT
<213> ORGANISM: Conus consors
<220> FEATURE:
<221> NAME/KEY: PEPTIDE
<222> LOCATION: (1)..(23)
<223> OTHER INFORMATION: Xaa at residue 1 is Gln or pyro-Glu

<400> SEQUENCE: 379

Xaa Arg Cys Cys Thr Gly Lys Lys Gly Ser Cys Ser Gly Lys Ala Cys
1               5                   10                  15

Lys Ser Leu Lys Cys Cys Ser
            20

<210> SEQ ID NO 380
<211> LENGTH: 284
<212> TYPE: DNA
<213> ORGANISM: Conus emaciatus

<400> SEQUENCE: 380
caagagggat cgatagcagt tcatgatgtc taaactggga gtcttgctga ccatctgtct      60
gcttctgttt ccccttactg ttcttccgat ggatggagat caacctgcag acctacctgc    120
attgcgtgcg cagttctttg cacctgaaca tagtccccgg tttgaccccg tcaaacggtg    180
ctgctcgcgg gattgcagtg tttgcatccc ttgttgcccg tatggatcac cttgattatt    240
gcggccacgt caagtgtcta atgaataagt aaaatgattg cagt                     284

<210> SEQ ID NO 381
<211> LENGTH: 70
<212> TYPE: PRT
<213> ORGANISM: Conus emaciatus

<400> SEQUENCE: 381

Met Met Ser Lys Leu Gly Val Leu Leu Thr Ile Cys Leu Leu Leu Phe
1               5                   10                  15

Pro Leu Thr Val Leu Pro Met Asp Gly Asp Gln Pro Ala Asp Leu Pro
            20                  25                  30

Ala Leu Arg Ala Gln Phe Phe Ala Pro Glu His Ser Pro Arg Phe Asp
        35                  40                  45

Pro Val Lys Arg Cys Cys Ser Arg Asp Cys Ser Val Cys Ile Pro Cys
    50                  55                  60

Cys Pro Tyr Gly Ser Pro
65                  70

<210> SEQ ID NO 382
<211> LENGTH: 18
<212> TYPE: PRT
<213> ORGANISM: Conus emaciatus
<220> FEATURE:
<221> NAME/KEY: PEPTIDE
<222> LOCATION: (1)..(18)
<223> OTHER INFORMATION: Xaa at residue 11, 14 and 18 is Pro or Hyp;
      Xaa at residue 15 is Tyr, 125I-Tyr, mono-iodo-Tyr, di-iodo-Tyr,
      O-sulpho-Tyr or O-phospho-Tyr

<400> SEQUENCE: 382

Cys Cys Ser Arg Asp Cys Ser Val Cys Ile Xaa Cys Cys Xaa Xaa Gly
1               5                   10                  15

Ser Xaa

<210> SEQ ID NO 383
<211> LENGTH: 13
<212> TYPE: PRT
<213> ORGANISM: Conus aurisiacus

<400> SEQUENCE: 383

Cys Cys Lys Val Gln Cys Glu Ser Cys Thr Pro Cys Cys
1               5                   10

<210> SEQ ID NO 384
<211> LENGTH: 15
<212> TYPE: PRT
<213> ORGANISM: Conus atlanticus

<400> SEQUENCE: 384

Cys Cys Glu Leu Pro Cys Gly Pro Gly Phe Cys Val Pro Cys Cys
1               5                   10                  15

<210> SEQ ID NO 385
<211> LENGTH: 14
<212> TYPE: PRT
<213> ORGANISM: Conus arentus

<400> SEQUENCE: 385

Cys Cys Glu Arg Pro Cys Asn Ile Gly Cys Val Pro Cys Cys
1               5                   10

<210> SEQ ID NO 386
<211> LENGTH: 16
<212> TYPE: PRT
<213> ORGANISM: Conus bandus

<400> SEQUENCE: 386

Cys Cys Asn Trp Pro Cys Ser Met Gly Cys Ile Pro Cys Cys Tyr Tyr
1               5                   10                  15

<210> SEQ ID NO 387
<211> LENGTH: 15
<212> TYPE: PRT
<213> ORGANISM: Conus betulinus

<400> SEQUENCE: 387

Cys Cys Glu Leu Pro Cys His Gly Cys Val Pro Cys Cys Trp Pro
1               5                   10                  15

<210> SEQ ID NO 388
<211> LENGTH: 16
<212> TYPE: PRT
<213> ORGANISM: Conus betulinus

<400> SEQUENCE: 388

Cys Cys Gly Leu Pro Cys Asn Gly Cys Val Pro Cys Cys Trp Pro Ser
1               5                   10                  15

<210> SEQ ID NO 389
<211> LENGTH: 18
<212> TYPE: PRT
<213> ORGANISM: Conus betulinus

<400> SEQUENCE: 389

Cys Cys Ser Arg Asn Cys Ala Val Cys Ile Pro Cys Cys Pro Asn Trp
1               5                   10                  15

Pro Ala

<210> SEQ ID NO 390
<211> LENGTH: 14
<212> TYPE: PRT
<213> ORGANISM: Conus betulinus

<400> SEQUENCE: 390

Cys Cys Lys Gln Ser Cys Thr Thr Cys Met Pro Cys Cys Trp
1               5                   10

```
<210> SEQ ID NO 391
<211> LENGTH: 14
<212> TYPE: PRT
<213> ORGANISM: Conus betulinus
<220> FEATURE:
<221> NAME/KEY: PEPTIDE
<222> LOCATION: (1)..(14)
<223> OTHER INFORMATION: Xaa is Glu or gamma-carboxy Glu

<400> SEQUENCE: 391

Ala Cys Cys Xaa Gln Ser C

```
<213> ORGANISM: Conus textile

<400> SEQUENCE: 397

Cys Cys Pro Pro Val Ala Cys Asn Met Gly Cys Lys Pro Cys Cys Gly
1               5                   10                  15

<210> SEQ ID NO 398
<211> LENGTH: 19
<212> TYPE: PRT
<213> ORGANISM: Conus marmoreus
<220> FEATURE:
<221> NAME/KEY: PEPTIDE
<222> LOCATION: (1)..(19)
<223> OTHER INFORMATION: Xaa is Hyp

<400> SEQUENCE: 398

Ser Lys Gln Cys Cys His Leu Ala Ala Cys Arg Phe Gly Cys Thr Xaa
1               5                   10                  15

Cys Cys Asn

<210> SEQ ID NO 399
<211> LENGTH: 15
<212> TYPE: PRT
<213> ORGANISM: Conus capitaneus

<400> SEQUENCE: 399

Ser Cys Cys Arg Asp Cys Gly Glu Asp Cys Val Gly Cys Cys Arg
1               5                   10                  15

<210> SEQ ID NO 400
<211> LENGTH: 16
<212> TYPE: PRT
<213> ORGANISM: Conus coronatus

<400> SEQUENCE: 400

Cys Cys Asp Trp Pro Cys Ile Pro Gly Cys Thr Pro Cys Cys Leu Pro
1               5                   10                  15

<210> SEQ ID NO 401
<211> LENGTH: 18
<212> TYPE: PRT
<213> ORGANISM: Conus dalli

<400> SEQUENCE: 401

Cys Cys Asp Asp Ser Glu Cys Asp Tyr Ser Cys Trp Pro Cys Cys Ile
1               5                   10                  15

Leu Ser

<210> SEQ ID NO 402
<211> LENGTH: 17
<212> TYPE: PRT
<213> ORGANISM: Conus dalli

<400> SEQUENCE: 402

Glx Gln Cys Cys Pro Pro Val Ala Cys Asn Met Gly Cys Glu Pro Cys
1               5                   10                  15

Cys

<210> SEQ ID NO 403
<211> LENGTH: 16
<212> TYPE: PRT
<213> ORGANISM: Conus dalli

<400> SEQUENCE: 403
```

Cys Cys Asn Ala Gly Phe Cys Arg Phe Gly Cys Thr Pro Cys Cys Trp
1               5                   10                  15

<210> SEQ ID NO 404
<211> LENGTH: 14
<212> TYPE: PRT
<213> ORGANISM: Conus distans

<400> SEQUENCE: 404

Glx Cys Cys Val His Pro Cys Pro Cys Thr Pro Cys Cys Arg
1               5                   10

<210> SEQ ID NO 405
<211> LENGTH: 14
<212> TYPE: PRT
<213> ORGANISM: Conus figulinus

<400> SEQUENCE: 405

Cys Cys Pro Trp Pro Cys Asn Ile Gly Cys Val Pro Cys Cys
1               5                   10

<210> SEQ ID NO 406
<211> LENGTH: 14
<212> TYPE: PRT
<213> ORGANISM: Conus figulinus

<400> SEQUENCE: 406

Cys Cys Ser Lys Asn Cys Ala Val Cys Ile Pro Cys Cys Pro
1               5                   10

<210> SEQ ID NO 407
<211> LENGTH: 15
<212> TYPE: PRT
<213> ORGANISM: Conus figulinus

<400> SEQUENCE: 407

Cys Cys Arg Trp Pro Cys Pro Ala Arg Cys Gly Ser Cys Cys Leu
1               5                   10                  15

<210> SEQ ID NO 408
<211> LENGTH: 16
<212> TYPE: PRT
<213> ORGANISM: Conus figulinus

<400> SEQUENCE: 408

Cys Cys Glu Leu Ser Arg Cys Leu Gly Cys Val Pro Cys Cys Thr Ser
1               5                   10                  15

<210> SEQ ID NO 409
<211> LENGTH: 16
<212> TYPE: PRT
<213> ORGANISM: Conus figulinus

<400> SEQUENCE: 409

Cys Cys Glu Leu Ser Lys Cys His Gly Cys Val Pro Cys Cys Ile Pro
1               5                   10                  15

<210> SEQ ID NO 410
<211> LENGTH: 16
<212> TYPE: PRT
<213> ORGANISM: Conus generalis

<400> SEQUENCE: 410

Glx Cys Cys Thr Phe Cys Asn Phe Gly Cys Gln Pro Cys Cys Val Pro

<210> SEQ ID NO 411
<211> LENGTH: 16
<212> TYPE: PRT
<213> ORGANISM: Conus generalis

<400> SEQUENCE: 411

Glx Cys Cys Thr Phe Cys Asn Phe Gly Cys Gln Pro Cys Cys Leu Thr
1               5                   10                  15

<210> SEQ ID NO 412
<211> LENGTH: 16
<212> TYPE: PRT
<213> ORGANISM: Conus generalis

<400> SEQUENCE: 412

Glx Cys Cys Thr Phe Cys Asn Phe Gly Cys Gln Pro Cys Cys Val Pro
1               5                   10                  15

<210> SEQ ID NO 413
<211> LENGTH: 17
<212> TYPE: PRT
<213> ORGANISM: Conus gloriamaris

<400> SEQUENCE: 413

Cys Cys Asp Asp Ser Glu Cys Asp Tyr Ser Cys Trp Pro Cys Cys Met
1               5                   10                  15

Phe

<210> SEQ ID NO 414
<211> LENGTH: 17
<212> TYPE: PRT
<213> ORGANISM: Conus gloriamaris

<400> SEQUENCE: 414

Gly Cys Cys His Leu Leu Ala Cys Arg Phe Gly Cys Ser Pro Cys Cys
1               5                   10                  15

Trp

<210> SEQ ID NO 415
<211> LENGTH: 16
<212> TYPE: PRT
<213> ORGANISM: Conus gloriamaris

<400> SEQUENCE: 415

Cys Cys Ser Trp Asp Val Cys Asp His Pro Ser Cys Thr Cys Cys Gly
1               5                   10                  15

<210> SEQ ID NO 416
<211> LENGTH: 13
<212> TYPE: PRT
<213> ORGANISM: Conus laterculatus

<400> SEQUENCE: 416

Cys Cys Asp Trp Pro Cys Ser Gly Cys Ile Pro Cys Cys
1               5                   10

<210> SEQ ID NO 417
<211> LENGTH: 19
<212> TYPE: PRT
<213> ORGANISM: Conus leopardus

<400> SEQUENCE: 417

```
Glx Ile Asn Cys Cys Pro Trp Pro Cys Pro Ser Thr Cys Arg His Gln
1               5                   10                  15

Cys Cys His

<210> SEQ ID NO 418
<211> LENGTH: 19
<212> TYPE: PRT
<213> ORGANISM: Conus lividus

<400> SEQUENCE: 418

Glx Ile Asn Cys Cys Pro Trp Pro Cys Pro Asp Ser Cys His Tyr Gln
1               5                   10                  15

Cys Cys His

<210> SEQ ID NO 419
<211> LENGTH: 14
<212> TYPE: PRT
<213> ORGANISM: Conus marmoreus

<400> SEQUENCE: 419

Cys Cys Arg Leu Ser Cys Gly Leu Gly Cys His Pro Cys Cys
1               5                   10

<210> SEQ ID NO 420
<211> LENGTH: 17
<212> TYPE: PRT
<213> ORGANISM: Conus marmoreus

<400> SEQUENCE: 420

Glu Cys Cys Gly Ser Phe Ala Cys Arg Phe Gly Cys Val Pro Cys Cys
1               5                   10                  15

Val

<210> SEQ ID NO 421
<211> LENGTH: 19
<212> TYPE: PRT
<213> ORGANISM: Conus marmoreus

<400> SEQUENCE: 421

Ser Lys Gln Cys Cys His Leu Pro Ala Cys Arg Phe Gly Cys Thr Pro
1               5                   10                  15

Cys Cys Trp

<210> SEQ ID NO 422
<211> LENGTH: 17
<212> TYPE: PRT
<213> ORGANISM: Conus marmoreus

<400> SEQUENCE: 422

Met Gly Cys Cys Pro Phe Pro Cys Lys Thr Ser Cys Thr Thr Leu Cys
1               5                   10                  15

Cys

<210> SEQ ID NO 423
<211> LENGTH: 14
<212> TYPE: PRT
<213> ORGANISM: Conus musicus

<400> SEQUENCE: 423

Ala Cys Cys Glu Gln Ser Cys Thr Thr Cys Phe Pro Cys Cys
1               5                   10
```

<210> SEQ ID NO 424
<211> LENGTH: 15
<212> TYPE: PRT
<213> ORGANISM: Conus nobilis

<400> SEQUENCE: 424

Cys Cys Glu Leu Pro Cys Gly Pro Gly Phe Cys Val Pro Cys Cys
1               5                   10                  15

<210> SEQ ID NO 425
<211> LENGTH: 14
<212> TYPE: PRT
<213> ORGANISM: Conus pulicarius

<400> SEQUENCE: 425

Cys Cys Asn Ser Cys Tyr Met Gly Cys Ile Pro Cys Cys Phe
1               5                   10

<210> SEQ ID NO 426
<211> LENGTH: 17
<212> TYPE: PRT
<213> ORGANISM: Conus quercinus

<400> SEQUENCE: 426

Glx Arg Cys Cys Gln Trp Pro Cys Pro Gly Ser Cys Arg Cys Arg
1               5                   10                  15

Thr

<210> SEQ ID NO 427
<211> LENGTH: 18
<212> TYPE: PRT
<213> ORGANISM: Conus quercinus

<400> SEQUENCE: 427

Glx Arg Cys Cys Arg Trp Pro Cys Pro Gly Ser Cys Arg Cys Arg
1               5                   10                  15

Tyr Arg

<210> SEQ ID NO 428
<211> LENGTH: 18
<212> TYPE: PRT
<213> ORGANISM: Conus quercinus

<400> SEQUENCE: 428

Arg Cys Cys Arg Tyr Pro Cys Pro Asp Ser Cys His Gly Ser Cys Cys
1               5                   10                  15

Tyr Lys

<210> SEQ ID NO 429
<211> LENGTH: 15
<212> TYPE: PRT
<213> ORGANISM: Conus quercinus
<220> FEATURE:
<221> NAME/KEY: PEPTIDE
<222> LOCATION: (1)..(15)
<223> OTHER INFORMATION: Xaa is Hyp

<400> SEQUENCE: 429

Cys Cys Ser Gln Asp Cys Leu Val Cys Ile Xaa Cys Cys Pro Asn
1               5                   10                  15

<210> SEQ ID NO 430

```
<211> LENGTH: 15
<212> TYPE: PRT
<213> ORGANISM: Conus quercinus
<220> FEATURE:
<221> NAME/KEY: PEPTIDE
<222> LOCATION: (1)..(15)
<223> OTHER INFORMATION: Xaa is Hyp

<400> SEQUENCE: 430

Cys Cys Ser Arg His Cys Trp Val Cys Ile Xaa Cys Cys Pro Asn
1               5                   10                  15

<210> SEQ ID NO 431
<211> LENGTH: 16
<212> TYPE: PRT
<213> ORGANISM: Conus rattus

<400> SEQUENCE: 431

Glx Thr Cys Cys Ser Asn Cys Gly Glu Asp Cys Asp Gly Cys Cys Gln
1               5                   10                  15

<210> SEQ ID NO 432
<211> LENGTH: 20
<212> TYPE: PRT
<213> ORGANISM: Conus striatus

<400> SEQUENCE: 432

Glx Asn Cys Cys Asn Gly Gly Cys Ser Ser Lys Trp Cys Arg Asp His
1               5                   10                  15

Ala Arg Cys Cys
            20

<210> SEQ ID NO 433
<211> LENGTH: 12
<212> TYPE: PRT
<213> ORGANISM: Conus textile
<220> FEATURE:
<221> NAME/KEY: PEPTIDE
<222> LOCATION: (1)..(12)
<223> OTHER INFORMATION: Xaa is Hyp

<400> SEQUENCE: 433

Cys Cys Arg Thr Cys Phe Gly Cys Thr Xaa Cys Cys
1               5                   10

<210> SEQ ID NO 434
<211> LENGTH: 14
<212> TYPE: PRT
<213> ORGANISM: Conus tessulatus

<400> SEQUENCE: 434

Cys Cys His Lys Cys Tyr Met Gly Cys Ile Pro Cys Cys Ile
1               5                   10

<210> SEQ ID NO 435
<211> LENGTH: 18
<212> TYPE: PRT
<213> ORGANISM: Conus tessulatus

<400> SEQUENCE: 435

Lys Cys Cys Arg Pro Pro Cys Ala Met Ser Cys Gly Met Ala Arg Cys
1               5                   10                  15

Cys Tyr

<210> SEQ ID NO 436
```

<211> LENGTH: 23
<212> TYPE: PRT
<213> ORGANISM: Conus betulinus

<400> SEQUENCE: 436

Arg Cys Cys Arg Trp Pro Cys Pro Ser Ile Cys Gly Met Ala Arg Cys
1               5                   10                  15

Cys Phe Val Met Ile Thr Cys
            20

<210> SEQ ID NO 437
<211> LENGTH: 23
<212> TYPE: PRT
<213> ORGANISM: Conus betulinus

<400> SEQUENCE: 437

Arg Cys Cys Arg Trp Pro Cys Pro Ser Arg Cys Gly Met Ala Arg Cys
1               5                   10                  15

Cys Phe Val Met Ile Thr Cys
            20

<210> SEQ ID NO 438
<211> LENGTH: 15
<212> TYPE: PRT
<213> ORGANISM: Conus textile

<400> SEQUENCE: 438

Phe Cys Cys Asp Ser Asn Trp Cys His Asp Cys Glu Cys Cys Tyr
1               5                   10                  15

<210> SEQ ID NO 439
<211> LENGTH: 16
<212> TYPE: PRT
<213> ORGANISM: Conus marmoreus

<400> SEQUENCE: 439

Cys Cys His Trp Asn Trp Cys Asp His Leu Cys Ser Cys Cys Gly Ser
1               5                   10                  15

<210> SEQ ID NO 440
<211> LENGTH: 16
<212> TYPE: PRT
<213> ORGANISM: Conus marmoreus
<220> FEATURE:
<221> NAME/KEY: PEPTIDE
<222> LOCATION: (1)..(16)
<223> OTHER INFORMATION: Xaa is Hyp

<400> SEQUENCE: 440

Asp Cys Cys Xaa Leu Pro Ala Cys Pro Phe Gly Cys Asn Xaa Cys Cys
1               5                   10                  15

<210> SEQ ID NO 441
<211> LENGTH: 16
<212> TYPE: PRT
<213> ORGANISM: Conus marmoreus
<220> FEATURE:
<221> NAME/KEY: PEPTIDE
<222> LOCATION: (1)..(16)
<223> OTHER INFORMATION: Xaa is Hyp

<400> SEQUENCE: 441

Cys Cys Ala Pro Ser Ala Cys Arg Leu Gly Cys Arg Xaa Cys Cys Arg
1               5                   10                  15

```
<210> SEQ ID NO 442
<211> LENGTH: 16
<212> TYPE: PRT
<213> ORGANISM: Conus marmoreus
<220> FEATURE:
<221> NAME/KEY: PEPTIDE
<222> LOCATION: (1)..(16)
<223> OTHER INFORMATION: Xaa is Hyp

<400> SEQUENCE: 442

Cys Cys Ala Xaa Ser Ala Cys Arg Leu Gly Cys Arg Xaa Cys Cys Arg
1               5                   10                  15

<210> SEQ ID NO 443
<211> LENGTH: 16
<212> TYPE: PRT
<213> ORGANISM: Conus marmoreus

<400> SEQUENCE: 443

Cys Cys Ala Pro Ser Ala Cys Arg Leu Gly Cys Arg Pro Cys Cys Arg
1               5                   10                  15

<210> SEQ ID NO 444
<211> LENGTH: 17
<212> TYPE: PRT
<213> ORGANISM: Conus marmoreus
<220> FEATURE:
<221> NAME/KEY: PEPTIDE
<222> LOCATION: (1)..(17)
<223> OTHER INFORMATION: Xaa is Hyp

<400> SEQUENCE: 444

Gly Cys Cys Gly Ser Phe Ala Cys Arg Phe Gly Cys Val Xaa Cys Cys
1               5                   10                  15

Val

<210> SEQ ID NO 445
<211> LENGTH: 15
<212> TYPE: PRT
<213> ORGANISM: Conus textile

<400> SEQUENCE: 445

Cys Cys Ser Trp Asp Val Cys Asp His Pro Ser Cys Thr Cys Cys
1               5                   10                  15

<210> SEQ ID NO 446
<211> LENGTH: 16
<212> TYPE: PRT
<213> ORGANISM: Conus textile

<400> SEQUENCE: 446

Arg Cys Cys Lys Phe Pro Cys Pro Asp Ser Cys Arg Tyr Leu Cys Cys
1               5                   10                  15

<210> SEQ ID NO 447
<211> LENGTH: 17
<212> TYPE: PRT
<213> ORGANISM: Conus aureus

<400> SEQUENCE: 447

Cys Cys Asp Asp Ser Glu Cys Asp Tyr Ser Cys Trp Pro Cys Cys Ile
1               5                   10                  15

Phe

<210> SEQ ID NO 448
```

```
<211> LENGTH: 16
<212> TYPE: PRT
<213> ORGANISM: Conus aureus

<400> SEQUENCE: 448

Cys Cys Asn Asp Trp Glu Cys Asp Asp Ser Cys Trp Pro Cys Cys Tyr
1               5                   10                  15

<210> SEQ ID NO 449
<211> LENGTH: 16
<212> TYPE: PRT
<213> ORGANISM: Conus ammiralis

<400> SEQUENCE: 449

Arg Cys Cys Arg Phe Pro Cys Pro Asp Thr Cys Arg His Leu Cys Cys
1               5                   10                  15

<210> SEQ ID NO 450
<211> LENGTH: 12
<212> TYPE: PRT
<213> ORGANISM: Conus ammiralis

<400> SEQUENCE: 450

Cys Cys Met Thr Cys Phe Gly Cys Thr Pro Cys Cys
1               5                   10

<210> SEQ ID NO 451
<211> LENGTH: 18
<212> TYPE: PRT
<213> ORGANISM: Conus ammiralis

<400> SEQUENCE: 451

Cys Cys Asp Asp Ser Glu Cys Asp Tyr Ser Cys Trp Pro Cys Cys Ile
1               5                   10                  15

Phe Ser

<210> SEQ ID NO 452
<211> LENGTH: 13
<212> TYPE: PRT
<213> ORGANISM: Conus ammiralis

<400> SEQUENCE: 452

Cys Cys Arg Leu Leu Cys Leu Ser Cys Asn Pro Cys Cys
1               5                   10

<210> SEQ ID NO 453
<211> LENGTH: 16
<212> TYPE: PRT
<213> ORGANISM: Conus ammiralis

<400> SEQUENCE: 453

Cys Cys Asp Asp Ser Glu Cys Gly Tyr Ser Cys Trp Pro Cys Cys Tyr
1               5                   10                  15

<210> SEQ ID NO 454
<211> LENGTH: 16
<212> TYPE: PRT
<213> ORGANISM: Conus aulicus

<400> SEQUENCE: 454

Gly Cys Cys Ser Pro Pro Cys His Ser Ile Cys Ala Ala Phe Cys Cys
1               5                   10                  15

<210> SEQ ID NO 455
```

<211> LENGTH: 15
<212> TYPE: PRT
<213> ORGANISM: Conus aulicus

<400> SEQUENCE: 455

Cys Cys Arg Pro Val Ala Cys Ala Met Gly Cys Lys Pro Cys Cys
1               5                   10                  15

<210> SEQ ID NO 456
<211> LENGTH: 16
<212> TYPE: PRT
<213> ORGANISM: Conus aulicus

<400> SEQUENCE: 456

Glx Cys Cys Pro Ala Val Ala Cys Ala Met Gly Cys Glu Pro Cys Cys
1               5                   10                  15

<210> SEQ ID NO 457
<211> LENGTH: 18
<212> TYPE: PRT
<213> ORGANISM: Conus emaciatus

<400> SEQUENCE: 457

Cys Cys Ser Arg Asp Cys Ser Val Cys Ile Pro Cys Cys Pro Tyr Gly
1               5                   10                  15

Ser Pro

<210> SEQ ID NO 458
<211> LENGTH: 16
<212> TYPE: PRT
<213> ORGANISM: Conus episcopatus

<400> SEQUENCE: 458

Cys Cys Asp Glu Asp Glu Cys Asn Ser Ser Cys Trp Pro Cys Cys Trp
1               5                   10                  15

<210> SEQ ID NO 459
<211> LENGTH: 16
<212> TYPE: PRT
<213> ORGANISM: Conus episcopatus

<400> SEQUENCE: 459

Cys Cys Asp Glu Asp Glu Cys Ser Ser Ser Cys Trp Pro Cys Cys Trp
1               5                   10                  15

<210> SEQ ID NO 460
<211> LENGTH: 15
<212> TYPE: PRT
<213> ORGANISM: Conus episcopatus

<400> SEQUENCE: 460

Cys Cys Pro Ala Ala Cys Ala Met Gly Cys Lys Pro Cys Cys
1               5                   10                  15

<210> SEQ ID NO 461
<211> LENGTH: 16
<212> TYPE: PRT
<213> ORGANISM: Conus omaria

<400> SEQUENCE: 461

Cys Cys Asp Glu Glu Glu Cys Ser Ser Ala Cys Trp Pro Cys Cys Trp
1               5                   10                  15

<210> SEQ ID NO 462

```
<211> LENGTH: 16
<212> TYPE: PRT
<213> ORGANISM: Conus omaria

<400> SEQUENCE: 462

Cys Cys His Leu Leu Ala Cys Arg Phe Gly Cys Ser Pro Cys Cys Trp
1               5                   10                  15

<210> SEQ ID NO 463
<211> LENGTH: 12
<212> TYPE: PRT
<213> ORGANISM: Conus spurius

<400> SEQUENCE: 463

Cys Cys Pro Arg Cys Ser Glu Cys Asn Pro Cys Cys
1               5                   10

<210> SEQ ID NO 464
<211> LENGTH: 16
<212> TYPE: PRT
<213> ORGANISM: Conus pennaceus

<400> SEQUENCE: 464

Arg Cys Cys Lys Phe Pro Cys Pro Asp Ser Cys Lys Tyr Leu Cys Cys
1               5                   10                  15

<210> SEQ ID NO 465
<211> LENGTH: 19
<212> TYPE: PRT
<213> ORGANISM: Conus flavidus

<400> SEQUENCE: 465

Arg Cys Cys Arg Trp Pro Cys Pro Ser Ile Cys Gly Met Ala Arg Cys
1               5                   10                  15

Cys Ser Ser

<210> SEQ ID NO 466
<211> LENGTH: 14
<212> TYPE: PRT
<213> ORGANISM: Conus pulicarius

<400> SEQUENCE: 466

Cys Cys Lys Leu Leu Cys Gly Cys Thr Pro Cys Cys His Ile
1               5                   10

<210> SEQ ID NO 467
<211> LENGTH: 15
<212> TYPE: PRT
<213> ORGANISM: Conus ebraceus

<400> SEQUENCE: 467

Cys Cys Glu Gln Pro Cys Tyr Met Gly Cys Ile Pro Cys Cys Phe
1               5                   10                  15

<210> SEQ ID NO 468
<211> LENGTH: 15
<212> TYPE: PRT
<213> ORGANISM: Conus ebraceus

<400> SEQUENCE: 468

Cys Cys Ala Gln Pro Cys Tyr Met Gly Cys Ile Pro Cys Cys Phe
1               5                   10                  15

<210> SEQ ID NO 469
```

```
<211> LENGTH: 14
<212> TYPE: PRT
<213> ORGANISM: Conus pulicarius

<400> SEQUENCE: 469

Cys Cys Val Ser Cys Tyr Met Gly Cys Ile Pro Cys Cys Phe
1               5                   10

<210> SEQ ID NO 470
<211> LENGTH: 16
<212> TYPE: PRT
<213> ORGANISM: Conus miliaris

<400> SEQUENCE: 470

Cys Cys Asp Trp Pro Cys Ser Ala Gly Cys Tyr Pro Cys Cys Phe Pro
1               5                   10                  15

<210> SEQ ID NO 471
<211> LENGTH: 16
<212> TYPE: PRT
<213> ORGANISM: Conus miliaris

<400> SEQUENCE: 471

Gly Cys Cys Pro Pro Met Cys Thr Pro Cys Phe Pro Cys Cys Phe Arg
1               5                   10                  15

<210> SEQ ID NO 472
<211> LENGTH: 23
<212> TYPE: PRT
<213> ORGANISM: Conus rattus

<400> SEQUENCE: 472

Arg Gly Cys Cys Ala Pro Pro Arg Lys Cys Lys Asp Arg Ala Cys Lys
1               5                   10                  15

Pro Ala Arg Cys Cys Gly Pro
            20

<210> SEQ ID NO 473
<211> LENGTH: 22
<212> TYPE: PRT
<213> ORGANISM: Conus stercusmuscarum

<400> SEQUENCE: 473

Glx Arg Cys Cys Asn Gly Arg Arg Gly Cys Ser Ser Arg Trp Cys Arg
1               5                   10                  15

Asp His Ser Arg Cys Cys
            20

<210> SEQ ID NO 474
<211> LENGTH: 22
<212> TYPE: PRT
<213> ORGANISM: Conus consors

<400> SEQUENCE: 474

Gly Arg Cys Cys Asp Val Pro Asn Ala Cys Ser Gly Arg Trp Cys Arg
1               5                   10                  15

Asp His Ala Gln Cys Cys
            20

<210> SEQ ID NO 475
<211> LENGTH: 23
<212> TYPE: PRT
<213> ORGANISM: Conus consors
```

<400> SEQUENCE: 475

Glx Arg Cys Cys Thr Gly Lys Lys Gly Ser Cys Ser Gly Lys Ala Cys
1               5                   10                  15

Lys Ser Leu Lys Cys Cys Ser
            20

<210> SEQ ID NO 476
<211> LENGTH: 22
<212> TYPE: PRT
<213> ORGANISM: Conus aurisiacus

<400> SEQUENCE: 476

Met Cys Cys Gly Glu Gly Arg Lys Cys Pro Ser Tyr Phe Arg Asn Ser
1               5                   10                  15

Gln Ile Cys His Cys Cys
            20

<210> SEQ ID NO 477
<211> LENGTH: 19
<212> TYPE: PRT
<213> ORGANISM: Conus aurisiacus

<400> SEQUENCE: 477

Cys Cys Arg Trp Pro Cys Pro Arg Gln Ile Asp Gly Glu Tyr Cys Gly
1               5                   10                  15

Cys Cys Leu

<210> SEQ ID NO 478
<211> LENGTH: 22
<212> TYPE: PRT
<213> ORGANISM: Conus bullatus

<400> SEQUENCE: 478

Arg Cys Cys Gly Glu Gly Leu Thr Cys Pro Arg Tyr Trp Lys Asn Ser
1               5                   10                  15

Gln Ile Cys Ala Cys Cys
            20

<210> SEQ ID NO 479
<211> LENGTH: 21
<212> TYPE: PRT
<213> ORGANISM: Conus caracteristicus

<400> SEQUENCE: 479

Cys Cys Gly Pro Gly Gly Ser Cys Pro Val Tyr Phe Arg Asp Asn Phe
1               5                   10                  15

Ile Cys Gly Cys Cys
            20

<210> SEQ ID NO 480
<211> LENGTH: 23
<212> TYPE: PRT
<213> ORGANISM: Conus circumcisus

<400> SEQUENCE: 480

Arg Lys Cys Cys Gly Lys Asp Gly Pro Cys Pro Lys Tyr Phe Lys Asp
1               5                   10                  15

Asn Phe Ile Cys Gly Cys Cys
            20

<210> SEQ ID NO 481

<211> LENGTH: 20
<212> TYPE: PRT
<213> ORGANISM: Conus ermineus

<400> SEQUENCE: 481

Cys Cys Ser Trp Pro Cys Pro Arg Tyr Ser Asn Gly Lys Leu Val Cys
1               5                   10                  15

Phe Cys Cys Leu
            20

<210> SEQ ID NO 482
<211> LENGTH: 21
<212> TYPE: PRT
<213> ORGANISM: Conus magus

<400> SEQUENCE: 482

Cys Cys Gly Pro Gly Gly Ser Cys Pro Val Tyr Phe Arg Asp Asn Phe
1               5                   10                  15

Ile Cys Gly Cys Cys
            20

<210> SEQ ID NO 483
<211> LENGTH: 22
<212> TYPE: PRT
<213> ORGANISM: Conus magus

<400> SEQUENCE: 483

Met Cys Cys Gly Glu Ser Ala Pro Cys Pro Ser Tyr Phe Arg Asn Ser
1               5                   10                  15

Gln Ile Cys His Cys Cys
            20

<210> SEQ ID NO 484
<211> LENGTH: 22
<212> TYPE: PRT
<213> ORGANISM: Conus magus

<400> SEQUENCE: 484

Glx Lys Cys Cys Gly Pro Gly Gly Ser Cys Pro Val Tyr Phe Thr Asp
1               5                   10                  15

Asn Phe Ile Cys Gly Cys
            20

<210> SEQ ID NO 485
<211> LENGTH: 23
<212> TYPE: PRT
<213> ORGANISM: Conus magus

<400> SEQUENCE: 485

Glx Lys Cys Cys Gly Pro Gly Gly Ser Cys Pro Val Tyr Phe Arg Asp
1               5                   10                  15

Asn Phe Ile Cys Gly Cys Cys
            20

<210> SEQ ID NO 486
<211> LENGTH: 23
<212> TYPE: PRT
<213> ORGANISM: Conus striatus

<400> SEQUENCE: 486

Glx Lys Cys Cys Gly Glu Gly Ser Ser Cys Pro Lys Tyr Phe Lys Asn
1               5                   10                  15

-continued

Asn Phe Ile Cys Gly Cys Cys
            20

<210> SEQ ID NO 487
<211> LENGTH: 22
<212> TYPE: PRT
<213> ORGANISM: Conus magus

<400> SEQUENCE: 487

Glx Lys Cys Cys Ser Gly Gly Ser Cys Pro Leu Tyr Phe Arg Asp Arg
1               5                   10                  15

Leu Ile Cys Pro Cys Cys
            20

<210> SEQ ID NO 488
<211> LENGTH: 23
<212> TYPE: PRT
<213> ORGANISM: Conus stercusmuscarum

<400> SEQUENCE: 488

Glx Lys Cys Cys Gly Pro Gly Ala Ser Cys Pro Arg Tyr Phe Lys Asp
1               5                   10                  15

Asn Phe Ile Cys Gly Cys Cys
            20

<210> SEQ ID NO 489
<211> LENGTH: 22
<212> TYPE: PRT
<213> ORGANISM: Conus consors

<400> SEQUENCE: 489

Met Cys Cys Gly Glu Gly Ala Pro Cys Pro Ser Tyr Phe Arg Asn Ser
1               5                   10                  15

Gln Ile Cys His Cys Cys
            20

<210> SEQ ID NO 490
<211> LENGTH: 23
<212> TYPE: PRT
<213> ORGANISM: Conus aurisiacus

<400> SEQUENCE: 490

Glx Lys Cys Cys Thr Gly Lys Lys Gly Ser Cys Ser Gly Lys Ala Cys
1               5                   10                  15

Lys Asn Leu Lys Cys Cys Ser
            20

<210> SEQ ID NO 491
<211> LENGTH: 23
<212> TYPE: PRT
<213> ORGANISM: Conus aurisiacus

<400> SEQUENCE: 491

Glx Lys Cys Cys Thr Gly Arg Lys Gly Ser Cys Ser Gly Lys Ala Cys
1               5                   10                  15

Lys Asn Leu Lys Cys Cys Ser
            20

<210> SEQ ID NO 492
<211> LENGTH: 23
<212> TYPE: PRT
<213> ORGANISM: Conus bullatus

<400> SEQUENCE: 492

Val Thr Asp Arg Cys Cys Lys Gly Lys Arg Glu Cys Gly Arg Trp Cys
1               5                   10                  15

Arg Asp His Ser Arg Cys Cys
            20

<210> SEQ ID NO 493
<211> LENGTH: 23
<212> TYPE: PRT
<213> ORGANISM: Conus bullatus

<400> SEQUENCE: 493

Val Gly Asp Arg Cys Cys Lys Gly Lys Arg Gly Cys Gly Arg Trp Cys
1               5                   10                  15

Arg Asp His Ser Arg Cys Cys
            20

<210> SEQ ID NO 494
<211> LENGTH: 24
<212> TYPE: PRT
<213> ORGANISM: Conus bullatus

<400> SEQUENCE: 494

Val Gly Glu Arg Cys Cys Lys Asn Gly Lys Arg Gly Cys Gly Arg Trp
1               5                   10                  15

Cys Arg Asp His Ser Arg Cys Cys
            20

<210> SEQ ID NO 495
<211> LENGTH: 26
<212> TYPE: PRT
<213> ORGANISM: Conus bullatus

<400> SEQUENCE: 495

Ile Val Asp Arg Cys Cys Asn Lys Gly Asn Gly Lys Arg Gly Cys Ser
1               5                   10                  15

Arg Trp Cys Arg Asp His Ser Arg Cys Cys
            20                  25

<210> SEQ ID NO 496
<211> LENGTH: 25
<212> TYPE: PRT
<213> ORGANISM: Conus bullatus

<400> SEQUENCE: 496

Val Gly Cys Cys Arg Pro Lys Pro Asn Gly Gln Met Met Cys Asp Arg
1               5                   10                  15

Trp Cys Glu Lys Asn Ser Arg Cys Cys
            20                  25

<210> SEQ ID NO 497
<211> LENGTH: 22
<212> TYPE: PRT
<213> ORGANISM: Conus caracteristicus

<400> SEQUENCE: 497

Arg Asp Cys Cys Thr Pro Pro Lys Cys Lys Asp Arg Gln Cys Lys
1               5                   10                  15

Pro Gln Arg Cys Cys Ala
            20

<210> SEQ ID NO 498
<211> LENGTH: 23
<212> TYPE: PRT
<213> ORGANISM: Conus lynceus

<400> SEQUENCE: 498

Gly Arg Asp Cys Cys Thr Pro Pro Arg Lys Cys Arg Asp Arg Ala Cys
1               5                   10                  15

Lys Pro Gln Arg Cys Cys Gly
            20

<210> SEQ ID NO 499
<211> LENGTH: 22
<212> TYPE: PRT
<213> ORGANISM: Conus lynceus

<400> SEQUENCE: 499

Glx Arg Leu Cys Cys Gly Phe Pro Lys Ser Cys Arg Ser Arg Gln Cys
1               5                   10                  15

Lys Pro His Arg Cys Cys
            20

<210> SEQ ID NO 500
<211> LENGTH: 22
<212> TYPE: PRT
<213> ORGANISM: Conus laterculatus

<400> SEQUENCE: 500

Arg Asp Cys Cys Thr Pro Pro Lys Lys Cys Arg Asp Arg Gln Cys Lys
1               5                   10                  15

Pro Ala Arg Cys Cys Gly
            20

<210> SEQ ID NO 501
<211> LENGTH: 22
<212> TYPE: PRT
<213> ORGANISM: Conus laterculatus

<400> SEQUENCE: 501

Arg Pro Pro Cys Cys Thr Tyr Asp Gly Ser Cys Leu Lys Glu Ser Cys
1               5                   10                  15

Met Arg Lys Ala Cys Cys
            20

<210> SEQ ID NO 502
<211> LENGTH: 22
<212> TYPE: PRT
<213> ORGANISM: Conus laterculatus

<400> SEQUENCE: 502

Arg Pro Pro Cys Cys Thr Tyr Asp Gly Ser Cys Leu Lys Glu Ser Cys
1               5                   10                  15

Lys Arg Lys Ala Cys Cys
            20

<210> SEQ ID NO 503
<211> LENGTH: 22
<212> TYPE: PRT
<213> ORGANISM: Conus geographus
<220> FEATURE:
<221> NAME/KEY: PEPTIDE
<222> LOCATION: (1)..(22)
<223> OTHER INFORMATION: Xaa is Hyp

```
<400> SEQUENCE: 503

Arg Asp Cys Cys Thr Xaa Xaa Lys Lys Cys Lys Asp Arg Gln Cys Lys
1               5                   10                  15

Xaa Gln Arg Cys Cys Ala
            20

<210> SEQ ID NO 504
<211> LENGTH: 22
<212> TYPE: PRT
<213> ORGANISM: Conus geographus
<220> FEATURE:
<221> NAME/KEY: PEPTIDE
<222> LOCATION: (1)..(22)
<223> OTHER INFORMATION: Xaa is Hyp

<400> SEQUENCE: 504

Arg Asp Cys Cys Thr Xaa Xaa Arg Lys Cys Lys Asp Arg Arg Cys Lys
1               5                   10                  15

Xaa Met Lys Cys Cys Ala
            20

<210> SEQ ID NO 505
<211> LENGTH: 22
<212> TYPE: PRT
<213> ORGANISM: Conus geographus
<220> FEATURE:
<221> NAME/KEY: PEPTIDE
<222> LOCATION: (1)..(22)
<223> OTHER INFORMATION: Xaa is Hyp

<400> SEQUENCE: 505

Arg Asp Cys Cys Thr Xaa Xaa Lys Lys Cys Lys Asp Arg Arg Cys Lys
1               5                   10                  15
Xaa Leu Lys Cys Cys Ala
            20

<210> SEQ ID NO 506
<211> LENGTH: 22
<212> TYPE: PRT
<213> ORGANISM: Conus purpurascens
<220> FEATURE:
<221> NAME/KEY: PEPTIDE
<222> LOCATION: (1)..(22)
<223> OTHER INFORMATION: Xaa is Hyp

<400> SEQUENCE: 506

Glx Arg Leu Cys Cys Gly Phe Xaa Lys Ser Cys Arg Ser Arg Gln Cys
1               5                   10                  15

Lys Xaa His Arg Cys Cys
            20

<210> SEQ ID NO 507
<211> LENGTH: 22
<212> TYPE: PRT
<213> ORGANISM: Conus magus

<400> SEQUENCE: 507

Arg Asp Cys Cys Thr Pro Pro Lys Lys Cys Lys Asp Arg Gln Cys Lys
1               5                   10                  15

Pro Gln Arg Cys Cys Ala
            20

<210> SEQ ID NO 508
<211> LENGTH: 24
```

```
<212> TYPE: PRT
<213> ORGANISM: Conus marmoreus

<400> SEQUENCE: 508

Arg Gly Gly Cys Cys Thr Pro Pro Arg Lys Cys Lys Asp Arg Ala Cys
1               5                   10                  15

Lys Pro Ala Arg Cys Cys Gly Pro
            20

<210> SEQ ID NO 509
<211> LENGTH: 23
<212> TYPE: PRT
<213> ORGANISM: Conus nobilis

<400> SEQUENCE: 509

Glx Lys Cys Cys Thr Gly Lys Lys Gly Ser Cys Ser Gly Lys Ala Cys
1               5                   10                  15

Lys Asn Leu Lys Cys Cys Ser
            20

<210> SEQ ID NO 510
<211> LENGTH: 24
<212> TYPE: PRT
<213> ORGANISM: Conus parius

<400> SEQUENCE: 510

Arg Gly Gly Cys Cys Thr Pro Pro Lys Lys Cys Lys Asp Arg Ala Cys
1               5                   10                  15

Lys Pro Ala Arg Cys Cys Gly Pro
            20

<210> SEQ ID NO 511
<211> LENGTH: 23
<212> TYPE: PRT
<213> ORGANISM: Conus parius

<400> SEQUENCE: 511

Arg Gly Cys Cys Thr Pro Pro Arg Lys Cys Lys Asp Arg Ala Cys Lys
1               5                   10                  15

Pro Ala Arg Cys Cys Gly Pro
            20

<210> SEQ ID NO 512
<211> LENGTH: 24
<212> TYPE: PRT
<213> ORGANISM: Conus radiatus
<220> FEATURE:
<221> NAME/KEY: PEPTIDE
<222> LOCATION: (1)..(24)
<223> OTHER INFORMATION: Xaa is Hyp

<400> SEQUENCE: 512

Leu Xaa Ser Cys Cys Ser Leu Asn Leu Arg Leu Cys Xaa Val Xaa Ala
1               5                   10                  15

Cys Lys Arg Asn Xaa Cys Cys Thr
            20

<210> SEQ ID NO 513
<211> LENGTH: 24
<212> TYPE: PRT
<213> ORGANISM: Conus radiatus
<220> FEATURE:
<221> NAME/KEY: PEPTIDE
<222> LOCATION: (1)..(24)
```

<223> OTHER INFORMATION: Xaa is Hyp

<400> SEQUENCE: 513

Glx Gln Arg Cys Cys Thr Val Lys Arg Ile Cys Xaa Val Xaa Ala Cys
1               5                   10                  15

Arg Ser Lys Xaa Cys Cys Lys Ser
            20

<210> SEQ ID NO 514
<211> LENGTH: 24
<212> TYPE: PRT
<213> ORGANISM: Conus radiatus

<400> SEQUENCE: 514

Arg Gly Gly Cys Cys Thr Pro Pro Arg Lys Cys Lys Asp Arg Ala Cys
1               5                   10                  15

Lys Pro Ala Arg Cys Cys Gly Pro
            20

<210> SEQ ID NO 515
<211> LENGTH: 23
<212> TYPE: PRT
<213> ORGANISM: Conus stercusmuscarum

<400> SEQUENCE: 515

Glx Lys Cys Cys Thr Gly Lys Lys Gly Ser Cys Ser Gly Lys Ala Cys
1               5                   10                  15

Lys Asn Leu Lys Cys Cys Ser
            20

<210> SEQ ID NO 516
<211> LENGTH: 21
<212> TYPE: PRT
<213> ORGANISM: Conus tulipa
<220> FEATURE:
<221> NAME/KEY: PEPTIDE
<222> LOCATION: (1)..(21)
<223> OTHER INFORMATION: Xaa is Hyp

<400> SEQUENCE: 516

His Gly Cys Cys Lys Gly Xaa Glu Gly Cys Ser Ser Arg Glu Cys Arg
1               5                   10                  15

Xaa Gln His Cys Cys
            20

<210> SEQ ID NO 517
<211> LENGTH: 21
<212> TYPE: PRT
<213> ORGANISM: Conus tulipa

<400> SEQUENCE: 517

His Gly Cys Cys Glu Gly Pro Lys Gly Cys Ser Ser Arg Glu Cys Arg
1               5                   10                  15

Pro Gln His Cys Cys
            20

<210> SEQ ID NO 518
<211> LENGTH: 23
<212> TYPE: PRT
<213> ORGANISM: Conus wittigi

<400> SEQUENCE: 518

Leu Pro Ser Cys Cys Asp Phe Glu Arg Leu Cys Val Val Pro Ala Cys

-continued

```
                1               5              10              15
Ile Arg His Gln Cys Cys Thr
                20

<210> SEQ ID NO 519
<211> LENGTH: 17
<212> TYPE: PRT
<213> ORGANISM: Conus omaria

<400> SEQUENCE: 519

Cys Cys Lys Tyr Gly Trp Thr Cys Leu Leu Gly Cys Thr Pro Cys Asp
1               5                   10                  15

Cys

<210> SEQ ID NO 520
<211> LENGTH: 17
<212> TYPE: PRT
<213> ORGANISM: Conus omaria

<400> SEQUENCE: 520

Cys Cys Arg Tyr Gly Trp Thr Cys Trp Leu Gly Cys Thr Pro Cys Gly
1               5                   10                  15

Cys
```

MU-CONOPEPTIDES

CROSS-REFERENCE TO RELATED APPLICATIONS

The present application claims benefit under 35 USC §119(e) to U.S. provisional patent applications Ser. No. 60/219,619 filed on Jul. 21, 2000, Ser. No. 60/245,157 filed on Nov. 3, 2000, Ser. No. 60/264,319 filed on Jan. 29, 2001 and Ser. No. 60/277,270 filed on Mar. 21, 2001. Each of these applications is incorporated herein by reference.

This invention was made with Government support under Grant No. PO1 GM48677 awarded by the National Institute of General Medical Sciences, National Institutes of Health, Bethesda, Md. The United States Government has certain rights in the invention.

BACKGROUND OF THE INVENTION

The present invention is to $\mu$-conopeptides, derivatives or pharmaceutically acceptable salts thereof. The present invention is further directed to the use of this peptide, derivatives thereof and pharmaceutically acceptable salts thereof for the treatment of disorders associated with voltage-gated sodium channels. Thus, the $\mu$-conopeptides or derivatives are useful as neuromuscular blocking agents, local anesthetic agents, analgesic agents and neuroprotective agents. The $\mu$-conopeptides are also useful for treating neuromuscular disorders. The invention is further directed to nucleic acid sequences encoding the $\mu$-conopeptides and encoding propeptides, as well as the propeptides.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Conus is a genus of predatory marine gastropods (snails) which envenomate their prey. Venomous cone snails use a highly developed projectile apparatus to deliver their cocktail of toxic conotoxins into their prey. In fish-eating species such as *Conus magus* the cone detects the presence of the fish using chemosensors in its siphon and when close enough extends its proboscis and fires a hollow harpoon-like tooth containing venom into the fish. This immobilizes the fish and enables the cone snail to wind it into its mouth via an attached filament. Prey capture is accomplished through a sophisticated arsenal of peptides which target specific ion channel and receptor subtypes. Each Conus species venom appears to contain a unique set of 50–200 peptides. The composition of the venom differs greatly between species and between individual snails within each species, each optimally evolved to paralyse it's prey. The active components of the venom are small peptides toxins, typically 10–40 amino acid residues in length and are typically highly constrained peptides due to their high density of disulphide bonds.

The venoms consist of a large number of different peptide components that when separated exhibit a range of biological activities: when injected into mice they elicit a range of physiological responses from shaking to depression. The paralytic components of the venom that have been the focus of recent investigation are the $\alpha$-, $\omega$- and $\mu$-conotoxins. All of these conotoxins act by preventing neuronal communication, but each targets a different aspect of the process to achieve this. The $\alpha$-conotoxins target nicotinic ligand gated channels, the $\mu$-conotoxins target the voltage-gated sodium channels and the $\omega$-conotoxins target the voltage-gated calcium channels (Olivera et al., 1985; Olivera et al., 1990). For example a linkage has been established between $\alpha$-, $\alpha$A- & $\psi$-conotoxins and the nicotinic ligand-gated ion channel; $\omega$-conotoxins and the voltage-gated calcium channel; $\mu$-conotoxins and the voltage-gated sodium channel; $\delta$-conotoxins and the voltage-gated sodium channel; $\nu$-conotoxins and the voltage-gated potassium channel; conantokins and the ligand-gated glutamate (NMDA) channel.

However, the structure and function of only a small minority of these peptides have been determined to date. For peptides where function has been determined, three classes of targets have been elucidated: voltage-gated ion channels; ligand-gated ion channels, and G-protein-linked receptors.

Conus peptides which target voltage-gated ion channels include those that delay the inactivation of sodium channels, as well as blockers specific for sodium channels, calcium channels and potassium channels. Peptides that target ligand-gated ion channels include antagonists of NMDA and serotonin receptors, as well as competitive and noncompetitive nicotinic receptor antagonists. Peptides which act on G-protein receptors include neurotensin and vasopressin receptor agonists. The unprecedented pharmaceutical selectivity of conotoxins is at least in part defined by a specific disulfide bond frameworks combined with hypervariable amino acids within disulfide loops (for a review see McIntosh et al., 1998).

There are drugs used in the treatment of pain, which are known in the literature and to the skilled artisan. See, for example, Merck Manual, 16th Ed. (1992). However, there is a demand for more active analgesic agents with diminished side effects and toxicity and which are non-addictive. The ideal analgesic would reduce the awareness of pain, produce analgesia over a wide range of pain types, act satisfactorily whether given orally or parenterally, produce minimal or no side effects, be free from tendency to produce tolerance and drug dependence.

Due to the high potency and exquisite selectivity of the conopeptides, several are in various stages of clinical development for treatment of human disorders. For example, two Conus peptides are being developed for the treatment of pain. The most advanced is $\omega$-conotoxin MVIIA (ziconotide), an N-type calcium channel blocker (see Heading, C., 1999; U.S. Pat. No. 5,859,186). $\omega$-Conotoxin MVIIA, isolated from *Conus magus*, is approximately 1000 times more potent than morphine, yet does not produce the tolerance or addictive properties of opiates. $\omega$-Conotoxin MVIIA has completed Phase III (final stages) of human clinical trials and has been approved as a therapeutic agent. $\omega$-Conotoxin MVIIA is introduced into human patients by means of an implantable, programmable pump with a catheter threaded into the intrathecal space. Preclinical testing for use in post-surgical pain is being carried out on another Conus peptide, contulakin-G, isolated from *Conus geographus* (Craig et al. 1999). Contulakin-G is a 16 amino acid O-linked glycopeptide whose C-terminus resembles neurotensin. It is an agonist of neurotensin receptors, but appears significantly more potent than neurotensin in inhibiting pain in in vivo assays.

In view of a large number of biologically active substances in Conus species it is desirable to further characterize them and to identify peptides capable of treating disorders involving voltage gated ion channels, such as stroke and pain. Surprisingly, and in accordance with this invention, Applicants have discovered novel conotoxins that can be useful for the treatment of disorders involving voltage gated

SUMMARY OF THE INVENTION

The present invention is to µ-conopeptides, derivatives or pharmaceutically acceptable salts thereof. The present invention is further directed to the use of this peptide, derivatives thereof and pharmaceutically acceptable salts thereof for the treatment of disorders associated with voltage-gated sodium channels. Thus, the µ-conopeptides or derivatives are useful as neuromuscular blocking agents, local anesthetic agents, analgesic agents and neuroprotective agents. The µ-conopeptides are also useful for treating neuromuscular disorders. The invention is further directed to nucleic acid sequences encoding the µ-conopeptides and encoding propeptides, as well as the propeptides.

More specifically, the present invention is directed to µ-conopeptides, having the amino acid sequences set forth in Tables 1 and 2 below.

The present invention is also directed to derivatives or pharmaceutically acceptable salts of the µ-conopeptides or the derivatives. Examples of derivatives include peptides in which the Arg residues may be substituted by Lys, ornithine, homoargine, nor-Lys, N-methyl-Lys, N,N-dimethyl-Lys, N,N,N-trimethyl-Lys or any synthetic basic amino acid; the Lys residues may be substituted by Arg, ornithine, homoargine, nor-Lys, or any synthetic basic amino acid; the Tyr residues may be substituted with meta-Tyr, ortho-Tyr, nor-Tyr, mono-halo-Tyr, di-halo-Tyr, O-sulpho-Tyr, O-phospho-Tyr, nitro-Tyr or any synthetic hydroxy containing amino acid; the Ser residues may be substituted with Thr or any synthetic hydroxylated amino acid; the Thr residues may be substituted with Ser or any synthetic hydroxylated amino acid; the Phe residues may be substituted with any synthetic aromatic amino acid; the Trp residues may be substituted with Trp (D), neo-Trp, halo-Trp (D or L) or any aromatic synthetic amino acid; and the Asn, Ser, Thr or Hyp residues may be glycosylated. The halogen may be iodo, chloro, fluoro or bromo; preferably iodo for halogen substituted-Tyr and bromo for halogen-substituted Trp. The Tyr residues may also be substituted with the 3-hydroxyl or 2-hydroxyl isomers (meta-Tyr or ortho-Tyr, respectively) and corresponding O-sulpho- and O-phospho-derivatives. The acidic amino acid residues may be substituted with any synthetic acidic amino acid, e.g., tetrazolyl derivatives of Gly and Ala. The aliphatic amino acids may be substituted by synthetic derivatives bearing non-natural aliphatic branched or linear side chains $C_nH_{2n+2}$ up to and including n=8. The Met residues may be substituted by norleucine (Nle). The Cys residues may be in D or L configuration and may optionally be substituted with homocysteine (D or L).

Examples of synthetic aromatic amino acid include, but are not limited to, nitro-Phe, 4-substituted-Phe wherein the substituent is $C_1$-$C_3$ alkyl, carboxyl, hyrdroxymethyl, sulphomethyl, halo, phenyl, —CHO, —CN, —$SO_3H$ and —NHAc. Examples of synthetic hydroxy containing amino acid, include, but are not limited to, such as 4-hydroxymethyl-Phe, 4-hydroxyphenyl-Gly, 2,6-dimethyl-Tyr and 5-amino-Tyr. Examples of synthetic basic amino acids include, but are not limited to, N-1-(2-pyrazolinyl)-Arg, 2-(4-piperinyl)-Gly, 2-(4-piperinyl)-Ala, 2-[3-(2S) pyrrolininyl)-Gly and 2-[3-(2S)pyrrolininyl)-Ala. These and other synthetic basic amino acids, synthetic hydroxy containing amino acids or synthetic aromatic amino acids are described in Building Block Index, Version 3.0(1999 Catalog, pages 4–47 for hydroxy containing amino acids and aromatic amino acids and pages 66–87 for basic amino acids incorporated herein by reference, by and available from RSP Amino Acid Analogues, Inc., Worcester, Mass. Examples of synthetic acid amino acids include those derivatives bearing acidic functionality, including carboxyl, phosphate, sulfonate and synthetic tetrazolyl derivatives such as described by Ornstein et al. (1993) and in U.S. Pat. No. 5,331,001, each incorporated herein by reference.

Optionally, in the µ-conopeptides of the present invention, the Asn residues may be modified to contain an N-glycan and the Ser, Thr and Hyp residues may be modified to contain an O-glycan (e.g., g-N, g-S, g-T and g-Hyp). In accordance with the present invention, a glycan shall mean any N-, S- or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The gylcan may also include similar polyhydroxy groups, such as D-penicillamine 2,5 and halogenated derivatives thereof or polypropylene glycol derivatives. The glycosidic linkage is beta and 1–4 or 1–3, preferably 1–3. The linkage between the glycan and the amino acid may be alpha or beta, preferably alpha and is 1-.

Core O-glycans have been described by Van de Steen et al. (1998), incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and connectivities) are defined for each core glycan. Suitable glycans and glycan analogs are described further in U.S. Ser. No. 09/420, 797 filed Oct. 19, 1999 and in PCT Application No. PCT/US99/24380 filed Oct. 19, 1999 (PCT Published Application No. WO 00/23092), each incorporated herein by reference. A preferred glycan is Gal(β1→3)GalNAc(α1→).

Optionally, in the µ-conopeptides described above, pairs of Cys residues may be replaced pairwise with isoteric lactam or ester-thioether replacements, such as Ser/(Glu or Asp), Lys/(Glu or Asp), Cys/(Glu or Asp) or Cys/Ala combinations. Sequential coupling by known methods (Barnay et al., 2000; Hruby et al., 1994; Bitan et al., 1997) allows replacement of native Cys bridges with lactam bridges. Thioether analogs may be readily synthesized using halo-Ala residues commercially available from RSP Amino Acid Analogues.

The present invention is further directed to derivatives of the above peptides and peptide derivatives which are acylic permutations in which the cyclic permutants retain the native bridging pattern of native toxin. See, for example, Craik et al. (2001).

The present invention is further directed to a method of treating disorders associated with voltage gated ion channel disorders in a subject comprising administering to the subject an effective amount of the pharmaceutical composition comprising a therapeutically effective amount of a µ-conopeptide described herein or a pharmaceutically acceptable salt or solvate thereof. The present invention is also directed to a pharmaceutical composition comprising a therapeutically effective amount of a μ-conopeptide described herein or a pharmaceutically acceptable salt or solvate thereof and a pharmaceutically acceptable carrier.

More specifically, the present invention is further directed to uses of these peptides or nucleic acids as described herein as neuromuscular blocking agents, local anesthetic agents, analgesic agents and neuroprotective agents. The μ-conopeptides are also useful for treating neuromuscular disorders.

The present invention is directed to the use of μ-conopeptides as a local anesthetic for treating pain. The μ-conopeptides have long lasting anesthetic activity and are particularly useful for spinal anesthesia, either administered acutely for post-operative pain or via an intrathecal pump for severe chronic pain situations. The μ-conopeptides are also useful as analgesics in chronic and neuropathic pain states, such as trigeminal neuralgia, diabetic neuropathy, post-herpetic neuralgia, neuroma pain and phantom limb pain. The μ-conopeptides are also useful for treating burn pain and as ocular anesthetics.

The present invention is directed to the use of μ-conopeptides as neuroprotectants. The μ-conopeptides are useful for the treatment and alleviation of epilepsy and as a general anticonvulsant agent. The μ-conopeptides are also useful for treating neurodegenerative diseases, such as Amyotrophic Lateral Sclerosis (ALS). The μ-conopeptides are further useful as cerebroprotectants, such as for reducing neurotoxic injury associated with conditions of hypoxia, anoxia or ischemia which typically follows stroke, cerebrovascular accident, brain or spinal cord trauma, myocardial infarct, physical trauma, drowning, suffocation, perinatal asphyxia, or hypoglycemic events.

The present invention is directed to the use of μ-conopeptides as neuromuscular blockers and for treating neuromuscular disorders. As such, the μ-conopeptides are useful for providing relaxation of muscle, for treating benign essential blepharospasm and other forms of focal dystonia and for anti-wrinkle use.

More specifically, the present invention is also directed to nucleic acids which encode μ-conopeptides of the present invention or which encodes precursor peptides for these μ-conopeptides, as well as the precursor peptide. The nucleic acid sequences encoding the precursor peptides of other μ-conopeptides of the present invention are set forth in Table 1. Table 1 also sets forth the amino acid sequences of these precursor peptides.

The present invention is further directed to the use of selectively radioiodinated or radiotritiated μ-conopeptides for characterizing pore occlusion sites on different sodium channel subtypes or for use in screening assays.

The present invention is also directed to the use of μ-conopeptides for screening small molecule libraries to identify small molecules that are selective blocking agents at specific sodium channel subtypes expressed in mammalian systems. In one embodiment, the blocking activity of a small molecule at a particular sodium channel subtype is compared to the blocking activity of a μ-conopeptide at the same sodium channel subtype. In a second embodiment, the ability of a small molecule to displace a μ-conopeptide from a sodium channel subtype is determined. In a third emdiment, the binding affinity of a small molecule for a sodium channel subtype is compared to the binding affinity of a μ-conopeptide for the same sodium channel subtype.

DETAILED DESCRIPTION OF THE PREFERRED EMBODIMENT

The present invention is to μ-conopeptides, derivatives or pharmaceutically acceptable salts thereof. The present invention is further directed to the use of this peptide, derivatives thereof and pharmaceutically acceptable salts thereof for the treatment of disorders associated with voltage-gated sodium channels. Thus, the μ-conopeptides or derivatives are useful as neuromuscular blocking agents, local anesthetic agents, analgesic agents and neuroprotective agents. The μ-conopeptides are also useful for treating neuromuscular disorders. The invention is further directed to nucleic acid sequences encoding the μ-conopeptides and encoding propeptides, as well as the propeptides.

The present invention, in another aspect, relates to a pharmaceutical composition comprising an effective amount of an μ-conopeptides, a mutein thereof, an analog thereof, an active fragment thereof or pharmaceutically acceptable salts or solvates. Such a pharmaceutical composition has the capability of acting at voltage gated ion channels, and are thus useful for treating a disorder or disease of a living animal body, including a human, which disorder or disease is responsive to the partial or complete blockade of voltage gated ion channels of the central nervous system comprising the step of administering to such a living animal body, including a human, in need thereof a therapeutically effective amount of a pharmaceutical composition of the present invention.

The present invention is directed to the use of μ-conopeptides as neuromuscular blockers and for treating neuromuscular disorders. As such, the μ-conopeptides are useful for providing relaxation of muscle, for treating benign essential blepharospasm and other forms of focal dystonia and for anti-wrinkle use. Thus, in one aspect, the μ-conopeptides are useful as neurmuscular blocking agents in conjunction with surgery or for intubation of the trachea by conventional parenteral administration e.g., intramuscular or intravenous administration in solution. In a second aspect, the μ-conopeptides are useful as agents for treating neuromuscular disorders such as myofacial pain syndrome, chronic muscle spasm, dystonias and spasticity.

The primary factor detrimental to neurons in neurological disorders associated with deficient oxygen supply or mitochondrial dysfunction is insufficient ATP production relative to their requirement. As a large part of the energy consumed by brain cells is used for maintenance of the $Na^+$ gradient across the cellular membrane, reduction of energy demand by down-modulation of voltage-gated Na(+)-channels is one strategy for neuroprotection. In addition, preservation of the inward $Na^+$ gradient may be beneficial because it is an essential driving force for vital ion exchanges and transport mechanisms such as $Ca^{2+}$ homeostasis and neurotransmitter uptake. Thus, the μ-conopeptides of the present invention are useful as neuroprotectants.

Thus, the pharmaceutical compositions of the present invention are useful as neuroprotectants, especially cerebroprotectants, neuromuscular blockers, analgesics (both as a local anesthetic and for general analgesia use) or adjuvants to general anesthetics. A "neurological disorder or disease" is a disorder or disease of the nervous system including, but not limited to, global and focal ischemic and hemorrhagic stroke, head trauma, spinal cord injury, hypoxia-induced nerve cell damage as in cardiac arrest or neonatal distress or epilepsy. In addition, a "neurological disorder or disease" is a disease state and condition in which a neuroprotectant, anticonvulsant, analgesic and/or as an adjunct in general anesthesia may be indicated, useful, recommended or prescribed.

More specifically, the present invention is directed to the use of these compounds for reducing neurotoxic injury associated with conditions of hypoxia, anoxia or ischemia which typically follows stroke, cerebrovascular accident, brain or spinal cord trauma, myocardial infarct, physical trauma, drowning, suffocation, perinatal asphyxia, or hypoglycemic events. The present invention is further directed to the use of these compounds for treating pain, including acute and chronic pain, such migraine, nociceptive and neuropathic pain.

A "neuroprotectant" is a compound capable of preventing the neuronal death associated with a neurological disorder or disease. An "analgesic" is a compound capable of relieving pain by altering perception of nociceptive stimuli without producing anesthesia or loss it of consciousness. A "muscle relaxant" is a compound that reduces muscular tension. An "adjunct in general anesthesia" is a compound useful in conjunction with anesthetic agents in producing the loss of ability to perceive pain associated with the loss of consciousness.

The invention relates as well to methods useful for treatment of neurological disorders and diseases, including, but not limited to, global and focal ischemic and hemorrhagic stroke, head trauma, spinal cord injury, hypoxia-induced nerve cell damage such as in cardiac arrest or neonatal distress, epilepsy or other convulsive disorders without undesirable side effects.

Thus, in one embodiment, the invention provides a method of reducing/alleviating/ decreasing the perception of pain by a subject or for inducing analgesia in a subject comprising administering to the subject an effective amount of the pharmaceutical composition comprising a therapeutically effective amount of a $\mu$-conopeptide described herein or a pharmaceutically acceptable salt or solvate thereof. The pain may be acute, persistent, inflammatory or neuropathic pain. The $\mu$-conopeptides are useful as an analgesia for chronic and neuropathic pain states, such as trigeminal neuralgia, diabetic neuropathy, post-herpetic neuralgia, neuroma pain, phantom limb pain. These peptides are also useful for treating burn pain and as ocular anesthetics.

In a second embodiment, the invention provides a method of reducing/alleviating/decreasing the perception of pain by a subject or for inducing analgesia, particularly local analgesia, in a subject comprising administering to the subject an effective amount of the pharmaceutical composition comprising a therapeutically effective amount of a $\mu$-conopeptide described herein or a pharmaceutically acceptable salt or solvate thereof. These peptides are also useful for treating burn pain and as ocular anesthetics.

In a third embodiment, the invention provides a method of treating stroke, head or spinal cord trauma or injury, anoxia, hypoxia-induced nerve cell damage, ischemia, migraine, psychosis, anxiety, schizophrenia, inflammation, movement disorder, epilepsy, any other convulsive disorder or in the prevention of the degenerative changes connected with the same in a subject comprising administering to the subject an effective amount of the pharmaceutical composition comprising a therapeutically effective amount of a $\mu$-conopeptide described herein or a pharmaceutically acceptable salt or solvate thereof.

In a fourth embodiment, the invention provides a method for providing a neuromuscular block or for treating neuromuscular disorders, such as methods for providing relaxation of muscle, for treating benign essential blepharospasm and other forms of focal dystonia and for anti-wrinkle use. Thus, in one aspect, the $\mu$-conopeptides are useful as neuromuscular blocking agents in conjunction with surgery or for intubation of the trachea by conventional parenteral administration e.g., intramuscular or intravenous administration in solution. In a second aspect, the $\mu$-conopeptides are useful as agents for treating neuromuscular disorders such as myofacial pain syndrome, chronic muscle spasm, dystonias and spasticity.

The present invention is also directed to the use of $\mu$-conopeptides for screening small molecule libraries to identify small molecules that are selective blocking agents at specific sodium channel subtypes expressed in mammalian systems. In one embodiment, the blocking activity of a small molecule at a particular sodium channel subtype is compared to the blocking activity of a $\mu$-conopeptide at the same sodium channel subtype. In a second embodiment, the ability of a small molecule to displace a $\mu$-conopeptide from a sodium channel subtype is determined. In a third emdiment, the binding affinity of a small molecule for a sodium channel subtype is compared to the binding affinity of a $\mu$-conopeptide for the same sodium channel subtype.

The $\mu$-conopeptides described herein are sufficiently small to be chemically synthesized. General chemical syntheses for preparing the foregoing $\omega$-conotoxin peptides are described hereinafter. Various ones of the $\mu$-conopeptides can also be obtained by isolation and purification from specific Conus species using the technique described in U.S. Pat. No. 4,447,356 (Olivera et al., 1984); U.S. Pat. Nos. 5,514,774; 5,719,264; and 5,591,821, as well as in PCT published application WO 98/03189, the disclosures of which are incorporated herein by reference.

Although the $\mu$-conopeptides of the present invention can be obtained by purification from cone snails, because the amounts of $\mu$-conopeptides obtainable from individual snails are very small, the desired substantially pure $\mu$-conopeptides are best practically obtained in commercially valuable amounts by chemical synthesis using solid-phase strategy. For example, the yield from a single cone snail may be about 10 micrograms or less of $\mu$-conopeptides peptide. By "substantially pure" is meant that the peptide is present in the substantial absence of other biological molecules of the same type; it is preferably present in an amount of at least about 85% purity and preferably at least about 95% purity. Chemical synthesis of biologically active $\mu$-conopeptides peptides depends of course upon correct determination of the amino acid sequence.

The $\mu$-conopeptides can also be produced by recombinant DNA techniques well known in the art. Such techniques are described by Sambrook et al. (1989). A gene of interest (i.e., a gene that encodes a suitable $\mu$-conopeptides) can be inserted into a cloning site of a suitable expression vector by using standard techniques. These techniques are well known to those skilled in the art. The expression vector containing the gene of interest may then be used to transfect the desired cell line. Standard transfection techniques such as calcium phosphate co-precipitation, DEAE-dextran transfection or electroporation may be utilized. A wide variety of host/ expression vector combinations may be used to express a gene encoding a conotoxin peptide of interest. Such combinations are well known to a skilled artisan. The peptides produced in this manner are isolated, reduced if necessary, and oxidized to form the correct disulfide bonds.

One method of forming disulfide bonds in the $\mu$-conopeptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. No. 3,842,067 (1974) and U.S. Pat. No. 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, —NH—MBHA resin support, or —NH—MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):CH$_2$Cl$_2$ (1:1) or in DMF or CH$_2$Cl$_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the -amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

The peptides are also synthesized using an automatic synthesizer. Amino acids are sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodimide in N-methylpyrrolidinone (NMP) or by 2-(1H-benzotriazole-1-yl)-1,1,3,3-tetramethyluronium hexafluorophosphate (HBTU) and diethylisopropylethylamine (DIEA). The FMOC protecting group is removed by treatment with a 20% solution of piperidine in dimethylformamide(DMF). Resins are subsequently washed with DMF (twice), followed by methanol and NMP.

Muteins, analogs or active fragments, of the foregoing conotoxin peptides are also contemplated here. See, e.g., Hammerland et al. (1992). Derivative muteins, analogs or active fragments of the conotoxin peptides may be synthesized according to known techniques, including conservative amino acid substitutions, such as outlined in U.S. Pat. No. 5,545,723 (see particularly col. 2, line 50 —col. 3, line 8); U.S. Pat. No. 5,534,615 (see particularly col. 19, line 45—col. 22, line 33); and U.S. Pat. No. 5,364,769 (see particularly col. 4, line 55—col. 7, line 26), each herein incorporated by reference.

The μ-conopeptides of the present invention are also useful to reduce neurotoxic injury associated with conditions of hypoxia, anoxia or ischemia which typically follows stroke, cerebrovascular accident, brain or spinal chord trauma, myocardial infarct, physical trauma, drownings, suffocation, perinatal asphyxia, or hypoglycemic events. To reduce neurotoxic injury, an ω-conopeptide should be administered in a therapeutically effective amount to the patient within 24 hours of the onset of the hypoxic, anoxic or ischemic condition in order for the μ-conopeptide to effectively minimize the CNS damage which the patient will experience.

The μ-conopeptides of the present invention are further useful in controlling pain, e.g., as analgesic agents, and the treatment of migraine, acute pain or persistent pain. They can be used prophylactically or to relieve the symptoms associated with a migraine episode, or to treat acute or persistent pain. For these uses, an μ-conopeptide is administered in a therapeutically effective amount to overcome or to ease the pain.

The μ-conopeptides of the present invention are also useful as neuromuscular blockers and for treating neuromuscular disorders. They can be used for providing relaxation of muscle, for treating benign essential blepharospasm and other forms of focal dystonia and for anti-wrinkle use. Thus, in one aspect, the μ-conopeptides are used as neurmuscular blocking agents in conjunction with surgery or for intubation of the trachea by conventional parenteral administration e.g., intramuscular or intravenous administration in solution. In a second aspect, the μ-conopeptides are used as agents for treating neuromuscular disorders such as myofacial pain syndrome, chronic muscle spasm, dystonias and spasticity. For these uses, a μ-conopeptide is administered in a therapeutically effective amount to relax muscle or provide a neuromuscular block.

Pharmaceutical compositions containing a compound of the present invention as the active ingredient can be prepared according to conventional pharmaceutical compounding techniques. See, for example, *Remington's Pharmaceutical Sciences*, 18th Ed. (1990, Mack Publishing Co., Easton, Pa.). Typically, an antagonistic amount of active ingredient will be admixed with a pharmaceutically acceptable carrier. The carrier may take a wide variety of forms depending on the form of preparation desired for administration, e.g., intravenous, oral, parenteral or intrathecally. For examples of delivery methods see U.S. Pat. No. 5,844,077, incorporated herein by reference.

"Pharmaceutical composition" means physically discrete coherent portions suitable for medical administration. "Pharmaceutical composition in dosage unit form" means physically discrete coherent units suitable for medical administration, each containing a daily dose or a multiple (up to four times) or a sub-multiple (down to a fortieth) of a daily dose of the active compound in association with a carrier and/or enclosed within an envelope. Whether the composition contains a daily dose, or for example, a half, a third or a quarter of a daily dose, will depend on whether the pharmaceutical composition is to be administered once or, for example, twice, three times or four times a day, respectively.

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques.

Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alohatocopherol and the like; and the metal chelating agents such as citric acid, ethylenediamine tetraacetic acid (EDTA), sorbitol, tartaric acid, phosphoric acid and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, epidural, irrigation, intramuscular, release pumps, or infusion.

For example, administration of the active agent according to this invention may be achieved using any suitable delivery means, including:

(a) pump (see, e.g., Luer & Hatton (1993), Zimm et al. (1984) and Ettinger et al. (1978));

(b), microencapsulation (see, e.g., U.S. Pat. Nos. 4,352,883; 4,353,888; and 5,084,350);

(c) continuous release polymer implants (see, e.g., U.S. Pat. No. 4,883,666);

(d) macroencapsulation (see, e.g., U.S. Pat. Nos. 5,284,761, 5,158,881, 4,976,859 and 4,968,733 and published PCT patent applications WO92/19195, WO 95/05452);

(e) naked or unencapsulated cell grafts to the CNS (see, e.g., U.S. Pat. Nos. 5,082,670 and 5,618,531);

(f) injection, either subcutaneously, intravenously, intraarterially, intramuscularly, or to other suitable site; or (g) oral administration, in capsule, liquid, tablet, pill, or prolonged release formulation.

In one embodiment of this invention, an active agent is delivered directly into the CNS, preferably to the brain ventricles, brain parenchyma, the intrathecal space or other suitable CNS location, most preferably intrathecally.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

The active agents, which are peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the developed sequences and the known genetic code.

Exemplary methods for administering such muscle relaxant compounds (e.g., so as to achieve sterile or aseptic conditions) will be apparent to the skilled artisan. Certain methods suitable for administering compounds useful according to the present invention are set forth in Goodman and Gilman's *The Pharmacological Basis of Therapeutics*, 7th Ed. (1985). The administration to the patient can be intermittent; or at a gradual, continuous, constant or controlled rate. Administration can be to a warm-blooded animal (e.g. a mammal, such as a mouse, rat, cat, rabbit, dog, pig, cow or monkey); but advantageously is administered to a human being. Administration occurs after general anesthesia is administered. The frequency of administration normally is determined by an anesthesiologist, and typically varies from patient to patient.

The active agent is preferably administered in an therapeutically effective amount. By a "therapeutically effective amount" or simply "effective amount" of an active compound is meant a sufficient amount of the compound to treat the desired condition at a reasonable benefit/risk ratio applicable to any medical treatment. The actual amount administered, and the rate and time-course of administration, will depend on the nature and severity of the condition being treated. Prescription of treatment, e.g. decisions on dosage, timing, etc., is within the responsibility of general practitioners or spealists, and typically takes account of the disorder to be treated, the condition of the individual patient, the site of delivery, the method of administration and other factors known to practitioners. Examples of techniques and protocols can be found in *Remington's Parmaceutical Sciences.*

Dosage may be adjusted appropriately to achieve desired drug levels, locally or systemically. Typically the active agents of the present invention exhibit their effect at a dosage range from about 0.001 mg/kg to about 250 mg/kg, preferably from about 0.01 mg/kg to about 100 mg/kg of the active ingredient, more preferably from about 0.05 mg/kg to about 75 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved. In the event that the response in a subject is insufficient at such doses, even higher doses (or effective higher doses by a different, more localized delivery route) may be employed to the extent that patient tolerance permits. Continuous dosing over, for example 24 hours or multiple doses per day are contemplated to achieve appropriate systemic levels of compounds.

For the treatment of pain, if the route of administration is directly to the CNS, the dosage contemplated is from about 1 ng to about 100 mg per day, preferably from about 100 ng to about 10 mg per day, more preferably from about 1 µg to about 100 µg per day. If administered peripherally, the dosage contemplated is somewhat higher, from about 100 ng to about 1000 mg per day, preferably from about 10 µg to about 100 mg per day, more preferably from about 100 µg to about 10 mg per day. If the conopeptide is delivered by continuous infusion (e.g., by pump delivery, biodegradable polymer delivery or cell-based delivery), then a lower dosage is contemplated than for bolus delivery.

Advantageously, the compositions are formulated as dosage units, each unit being adapted to supply a fixed dose of active ingredients. Tablets, coated tablets, capsules, ampoules and suppositories are examples of dosage forms according to the invention.

It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian for use humans or animals.

The pharmaceutical compositions will generally contain from about 0.0001 to 99 wt. %, preferably about 0.001 to 50 wt. %, more preferably about 0.01 to 10 wt. % of the active ingredient by weight of the total composition. In addition to the active agent, the pharmaceutical compositions and medicaments can also contain other pharmaceutically active compounds. Examples of other pharmaceutically active compounds include, but are not limited to, analgesic agents, cytokines and therapeutic agents in all of the major areas of clinical medicine. When used with other pharmaceutically active compounds, the conopeptides of the present invention may be delivered in the form of drug cocktails. A cocktail is a mixture of any one of the compounds useful with this invention with another drug or agent. In this embodiment, a common administration vehicle (e.g., pill, tablet, implant, pump, injectable solution, etc.) would contain both the instant composition in combination supplementary potentiating agent. The individual drugs of the cocktail are each administered in therapeutically effective amounts. A therapeutically effective amount will be determined by the parameters described above; but, in any event, is that amount which establishes a level of the drugs in the area of body where the drugs are required for a period of time which is effective in attaining the desired effects.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel et al., 1992; Glover, 1985; Anand, 1992; Guthrie and Fink, 1991; Harlow and Lane, 1988; Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); Riott, *Essential Immunology*, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986).

EXAMPLES

The present invention is described by reference to the following Examples, which are offered by way of illustration and are not intended to limit the invention in any manner. Standard techniques well known in the art or the techniques specifically described below were utilized.

Example 1

Isolation of µ-Conopeptides

Crude venom was extracted from venom ducts (Cruz et al., 1976), and the components were purified as previously described (Cartier et al., 1996). The crude extract from venom ducts was purified by reverse phase liquid chromatography (RPLC) using a Vydac $C_{18}$ semi-preparative column (10×250 mm). Further purification of bioactive peaks was done on a Vydac $C_{18}$ analytical column (4.6×220 mm).

The effluents were monitored at 220 nm. Peaks were collected, and aliquots were assayed for activity. Throughout purification, HPLC fractions were assayed by means of intracerebral ventricular (i.c.v.) injection into mice (Clark et al., 1981).

The amino acid sequence of the purified peptides were determined by standard methods. The purified peptides were reduced and alkylated prior to sequencing by automated Edman degradation on an Applied Biosystems 477A Protein Sequencer with a 120A Analyzer (DNA/Peptide Facility, University of Utah) (Martinez et al., 1995; Shon et al., 1994).

In accordance with this method, the μ-conopeptides described as "isolated" in Table 1 were obtained. These μ-conopeptides, as well as the other μ-conopeptides and the μ-conopeptide precursors set forth in Table 1 are synthesized as described in U.S. Pat. No. 5,670,622.

Example 2
Isolation of DNA Encoding μ-Conopeptides

DNA coding for μ-conopeptides was isolated and cloned in accordance with conventional techniques using general procedures well known in the art, such as described in Olivera et al. (1996). Alternatively, cDNA libraries was prepared from Conus venom duct using conventional techniques. DNA from single clones was amplified by conventional techniques using primers which correspond approximately to the M13 universal priming site and the M13 reverse universal priming site. Clones having a size of approximately 300–500 nucleotides were sequenced and screened for similarity in sequence to known μ-conotoxins. The DNA sequences and encoded propeptide sequences are set forth in Table 1. DNA sequences coding for the mature toxin can also be prepared on the basis of the DNA sequences set forth in Table1. An alignment of the μ-conopeptides of the present invention is set forth in Table 2.

TABLE 1

DNA and Amino Acid Sequences of μ-Conopeptides and Precursors

Name: Ar3.1
Species: arenatus
Cloned: Yes

DNA Sequence:

CAAGAAGGATCGATAGCAGTTCATGATGTCTAAACTGGGAGTCTTCTTGACCATCTG (SEQ ID NO:1)

TATGCTTCTGTTTCCCCTTACTGCTCTTCCGCTGGATGGGGATCAACCTGCAGACCG

ACCTGCAGAGCGTATGCAGGACGACTTTATAACTGAGCATCATCCCCTGTTTGATCC

TGTCAAACGGTGTTGCGAGAGGCCATGCAACATAGGATGCGTACCTTGTTGTTAATG

ACCAGCTTTGTCATCGCGGCCTCATCAAGCGAATAAGTAAAACGATTGCAGT

Translation:

MMSKIGVFLTICMLLFPLTALPLDGDQPADRPAERMQDDFITEHHPLFDPVKRCCERPC (SEQ ID NO:2)

NIGCVPCC

Toxin Sequence:

Cys-Cys-Xaa1-Arg-Xaa3-Cys-Asn-Ile-Gly-Cys-Val-Xaa3-Cys-Cys-^ (SEQ ID NO:3)

Name: Ak3.1
Species: atlanticus
Cloned: Yes

DNA Sequence:

GGATCCATGATGTCTAAACTGGGAGTCTTGTTGACCATCTGTCTGCTTCTGTTTCCAC (SEQ ID NO:4)

TTACTGCTCTTCCGCTGGATGAAGATCAACCGGTACACCGACCTGCAGAGCGTATGC

AGGACATTTCATCTGATCAACATCTCTTCTTTGATCTCATCAAACGGTGCTGCGAGT

TGCCATGCGGGCCAGGCTTTTGCGTCCCTTGTTGCTGACATCAATAACGTGTTGATG

ACCAACTTTCTCGAG

Translation:

GSMMSKLGVLLTICLLLFPLTALPLDEDQPVHRPAERMQDISSDQHLFFDLIKRCCELPC (SEQ ID NO:5)

GPGFCVPCC

Toxin Sequence:

Cys-Cys-Xaa1-Leu-Xaa3-Cys-Gly-Xaa3-Gly-Phe-Cys-Val-Xaa3-Cys-Cys-^ (SEQ ID NO:6)

Name: A3.1
Species: aurisiacus
Cloned: Yes

TABLE 1-continued

DNA and Amino Acid Sequences of µ-Conopeptides and Precursors

DNA Sequence:

CAAGAGGGATCGATAGCAGTTCATGATGTCTAAACTGGGAGTCTTGTTGACCATCTG (SEQ ID NO:7)

TTTGCTTCTGTTTCCCCTTACTGCTCTTCCGATGGATGGAGATCAATCTGTAGACCGA

CCTGAAGAGCGTATGCAGGACGACATTTCATCTGAGCAGCATCCCTTGTTTAATCAG

AAAAGAATGTGTTGCGGCGAAGGCCGGAAATGCCCCAGCTATTTCAGAAACAGTCA

GATTTGTCATTGTTGTTAAATGACAACGTGTCGATGACCAACTTCGTTATCACGACT

AATGAATAAGTAAAACGATTGCAGT

Translation:

MMSKLGVLLTICLLLFPLTALPMDGDQSVDRPEERMQDDISSEQHPLFNQKRMCCGEG (SEQ ID NO:8)

RKCPSYFRNSQICHCC

Toxin Sequence:

Met-Cys-Cys-Gly-Xaa1-Gly-Arg-Lys-Cys-Xaa3-Ser-Xaa5-Phe-Arg-Asn-Ser-Gln-Ile-Cys-His- (SEQ ID NO:9)

Cys-Cys-^

Name: A3.2
Species: *aurisiacus*
Cloned: Yes

DNA Sequence:

GGATCCATGATGTCTAAACTGGGAGTCTTGTTGACCATCTGTTTGCTTCTGTTTCCCC (SEQ ID NO:10)

TTACTGCTCTTCCGATCGATGGAGATCAATCTGTAGACCGACCTGCAGAGCGTATGC

AGGATGACATTTCATCTGAGCAGCATCGCTTGTTCAATCAGAAAAGAAGGTGCTGC

CGGTGGCCATGCCCCCGACAAATCGACGGTGAATATTGTGGCTGTTGCCTTGGATGA

TAACCGTGTTGATGACCAACTTTCTCGAG

Translation:

GSMMSKLGVLLTICLLLFPLTALPIDGDQSVDRPAERMQDDISSEQHRLFNQKRRCCRW (SEQ ID NO:11)

PCPRQIDGEYCGCCLG

Toxin Sequence:

Cys-Cys-Arg-Xaa4-Xaa3-Cys-Xaa3-Arg-Gln-Ile-Asp-Gly-Xaa1-Xaa5-Cys-Gly-Cys-Cys-Leu-# (SEQ ID NO:12)

Name: A3.3
Species: *aurisiacus*
Cloned: Yes

DNA Sequence:

GGATCCATGATGTCTAAACTGGGAGTCTTGTTGACCATCTGTCTACTTCTGTTTCCCC (SEQ ID NO:13)

TTACTGCTTTTCCGATGGATGGAGATCAACCTGCAGACCAACCTGCAGATCGTATGC

AGGACGACATTTCATCTGAGCAGTATCCCTTGTTTGATAAGAGACAAAAGTGTTGCA

CTGGGAAGAAGGGGTCATGCTCCGGCAAAGCATGCAAAAATCTCAAATGTTGCTCT

GGACGATAACGTGTTGATGACCAACTTTCTCGAG

Translation:

GSMMSKLGVLLTICLLLFPLTAFPMDGDQPADQPADRMQDDISSEQYPLFDKRQKCCT (SEQ ID NO:14)

GKKGSCSGKACKNLKCCSGR

Toxin Sequence:

Xaa2-Lys-Cys-Cys-Thr-Gly-Lys-Lys-Gly-Ser-Cys-Ser-Gly-Lys-Ala-Cys-Lys-Asn-Leu-Lys- (SEQ ID NO:15)

TABLE 1-continued

DNA and Amino Acid Sequences of μ-Conopeptides and Precursors

Cys-Cys-Ser-#

Name: A3.4
Species: *aurisiacus*
Cloned: Yes

DNA Sequence:

GGATCCATGATGTCTAAACTGGGAGTCTTGCTGACCATCTGTCTGCTTCTGTTTCCAC (SEQ ID NO:16)

TTACTGCTGTTCCGCTGGATGGAGATCAACCTCTAGACCGACACGCGGAGCGTATGC

ATGATGGCATTTCACCTAAACGCCATCCCTGGTTTGATCCCGTCAAACGGTGTTGCA

AGGTGCAATGCGAGTCTTGCACCCCTTGTTGCTAACGTGTTGATGACCAACTTTCTC

GAG

Translation:

GSMMSKLGVLLTICLLLFPLTAVPLDGDQPLDRHAERMHDGISPKRHPWFDPVKRCCK (SEQ ID NO:17)

VQCESCTPCC

Toxin Sequence:

Cys-Cys-Lys-Val-Gln-Cys-Xaa1-Ser-Cys-Thr-Xaa3-Cys-Cys-^ (SEQ ID NO:18)

Name: Bn3.1
Species: *bandanus*
Cloned: Yes

DNA Sequence:

GGATCCATGATGTCTAAACTGGGAGTCTTGTTGACCATCTGTATGCTTCTGTTTCCCC (SEQ ID NO:19)

TCACTGCTCTTCCGATGGATGGAGATCAACCTGCAGACCGACCTGCAGAGCGTAGT

CAGGACGTTTCATCTGAACAGCATCCCTTGTTTGATCCCGTCAAACGGTGTTGCAAC

TGGCCATGCTCCATGGGATGCATCCCTTGTTGCTACTATTAATAACGTGTTGATGAC

CAACTTTCTCGAG

Translation:

GSMMSKLGVLLTICMLLFPLTALPMDGDQPADRPAERSQDVSSEQHPLFDPVKRCCNW (SEQ ID NO:20)

PCSMGCIPCCYY

Toxin Sequence:

Cys-Cys-Asn-Xaa4-Xaa3-Cys-Ser-Met-Gly-Cys-Ile-Xaa3-Cys-Cys-Xaa5-Xaa5-^ (SEQ ID NO:21)

Name: Bt3.1
Species: *betulinus*
Cloned: Yes

DNA Sequence:

CAAGAGGGATCGATAGCAGTTCATGATGTCTAAACTGGGAGTCTTGTTGACCTTCTG (SEQ ID NO:22)

TCTGCTTCTGTTTCCCCTGACTGCTCTTCCGCTGGATGAAGATCAACCTGCAGACCG

ACCTGCAGAGCGTATGCAGGACATTTCATCTGAACAGCATCCCTTGTTTGATCCCGT

CAAACGGTGTTGCGAATTGCCATGCCATGGATGCGTCCCTTGTTGCTGGCCTTAATA

ACGTGTGGATGACCAACTGTGTTATCACGGCCACGTCAAGTGTCTAATGAATAAGT

AAAATGATTGCAGT

Translation:

MMSKLGVLLTFCLLLFPLTALPLDEDQPADRPAERMQDISSEQHPLFDPVKRCCELPCH (SEQ ID NO:23)

GCVPCCWP

TABLE 1-continued

DNA and Amino Acid Sequences of µ-Conopeptides and Precursors

Toxin Sequence:

Cys-Cys-Xaa1-Leu-Xaa3-Cys-His-Gly-Cys-Val-Xaa3-Cys-Xaa3-^ (SEQ ID NO:24)

Name: Bt3.2
Species: *betulinus*
Cloned: Yes

DNA Sequence:

CAAGAGGGATCGATAGCAGTTCATGATGTCTAAACTGGGAGTCTTGTTGACCTTCTG (SEQ ID NO:25)

TCTGCTTCTGTTTCCCCTGACTGCTCTTCCGCTGGATGAAGATCAACCTGCAGACCG

ACATGCAGAGCGTATGCAGGACATTTCACCTGAACAGCATCCCTCGTTTGATCCCGT

CAAACGGTGTTGCGGGCTGCCATGCAATGGATGCGTCCCTTGTTGCTGGCCTTCATA

ACGTGTGGACGACCAACTTTGTTATCACGGCCACGTCAAGTGTCTGATGAATAAGTA

AAACGATTGCAGT

Translation:

MMSKLGVLLTFCLLLFPLTALPLDEDQPADRHAERMQDISPEQRPSFDPVKRCCGLPCN (SEQ ID NO:26)

GCVPCCWPS

Toxin Sequence:

Cys-Cys-Gly-Leu-Xaa3-Cys-Asn-Gly-Cys-Val-Xaa3-Cys-Cys-Xaa4-Xaa3-Ser-^ (SEQ ID NO:27)

--------------------------------

Name: Bt3.3
Species: *betulinus*
Cloned: Yes

DNA Sequence:

CAAGAGGGATCGATAGCAGTTCATGATGTTTAAACTGGGAGTCTTGTTGACCATCTA (SEQ ID NO:28)

TATGCTTCTGTTTCCCTTTACTGCTCTTCCGCTGGATGGAGATCAACCTGCAGACCAA

CCTCTAGAGCGCATGCAGTATGACATGTTACGTGCAGTGAATCCCTGGTTTGATCCC

GTCAAAAGGTGCTGCTCGAGGAACTGCGCAGTATGCATCCCTTGTTGCCCGAATTGG

CCAGCTTGATTATCGCGGCCAAGAGTCTAATGAATAAGTAAAACGATTGCAGT

Translation:

MMFKLGVLLTIYMLLFPFTALPLDGDQPADQPLERMQYDMLRAVNPWFDPVKRCCSR (SEQ ID NO:29)

NCAVCIPCCPNWPA

Toxin Sequence:

Cys-Cys-Ser-Arg-Asn-Cys-Ala-Val-Cys-Ile-Xaa3-Cys-Cys-Xaa3-Asn-Xaa4-Xaa3-Ala-^ (SEQ ID NO:30)

Name: Bu3.1
Species: *bullatus*
Cloned: Yes

DNA Sequence:

CAAGAAGGATCGATAGCAGTTCATGATGTCTAAACTGGGAGTCTTGTTGACCATCTG (SEQ ID NO:31)

TCTGCTTCTGTTTCCCCTTTTTGCTCTTCCGCAGGATGGAGATCAACCTGCAGACCGA

CCTGCAGAGCGTATGCAGGACGACATTTCATCTGAGCAGAATTCCTTGCTTGAGAA

GAGAGTTACTGACAGGTGCTGCAAAGGGAAGAGGGAATGCGGCAGATGGTGCAGA

GATCACTCGCGTTGTTGCGGTCGACGATAAGCTGTTGATGACCAGCTTTGTTATCAC

GGCTACATCAAGTGTCTAGTGAATAAGTAAAATGATTGCAGT

TABLE 1-continued

DNA and Amino Acid Sequences of μ-Conopeptides and Precursors

Translation:

MMSKLGVLLTICLLLFPLFALPQDGDQPADRPAERMQDDISSEQNSLLEKRVTDRCCKG (SEQ ID NO:32)

KRECGRWCRDHSRCCGRR

Toxin Sequence:

Val-Thr-Asp-Arg-Cys-Cys-Lys-Gly-Lys-Arg-Xaa1-Cys-Gly-Arg-Xaa4-Cys-Arg-Asp-His-Ser- (SEQ ID NO:33)

Arg-Cys-Cys-#

Name: Bu3.1A
Species: bullatus
Cloned: Yes

DNA Sequence:

CAAGAGGGATCGATAGCAGTTCATGATGTCTAAACTGGGAGTCTTGTTGACCATCTG (SEQ ID NO:34)

TCTGCTTCTGTTTCCCCTTTTTGCTCTTCGGCAGGATGGAGATCAACCTGCAGACCGA

CCTGCAGAGCGTATGCAGGATGACATTTCATCTGAGCAGAATCCCTTGCTTGAGAA

GAGAGTTGGTGACAGGTGCTGCAAAGGGAAGAGGGGGTGCGGCAGATGGTGCAGA

GATCACTCACGTTGTTGCGGTCGACGATAACGTGTTGATGACCAGCTTTGTTATCAC

GGCTACATCAAGTGTCTTAGTGATTAAGTAAAACGATTGCAGT

Translation:

MMSKLGVLLTICLLLFPLFALRQDGDQPADRPAERMQDDISSEQNPLLEKRVGDRCCK (SEQ ID NO:35)

GKRGCGRWCRDHSRCCGRR

Toxin Sequence:

Val-Gly-Asp-Arg-Cys-Cys-Lys-Gly-Lys-Arg-Gly-Cys-Gly-Arg-Xaa4-Cys-Arg-Asp-His-Ser- (SEQ ID NO:36)

Arg-Cys-Cys-#

Name: Bu3.2
Species: bullatus
Cloned: Yes

DNA Sequence:

CAAGAAGGATCGATAGCAGTTCATGATGTCTAAACTGGGAGTCTTGTTGACCATCTG (SEQ ID NO:37)

TCTGCTTCTGTTTCCCCTTTTTGCTCTTCCGCAGGATGGAGATCAACCTGCAGACCGA

CCTGCAGAGCGTATGCAGGACGACATTTCATCTGAGCAGAATCCCTTGCTTGAGAA

GAGAGTTGGTGAAAGGTGCTGCAAAAACGGGAAGAGGGGGTGCGGCAGATGGTGC

AGAGATCACTCACGTTGTTGCGGTCGACGATAACGTGTTGATGACCGAGGCTTTCGT

TATCACGGCTACATCAAGTGTCTAGTGAATAAGTAAAACGATTGCAGT

Translation:

MMSKLGVLLTICLLLFPLFALPQDGDQPADRPAERMQDDISSEQNPLLEKRVGERCCKN (SEQ ID NO:38)

GKRGCGRWCRDHSRCCGRR

Toxin Sequence:

Val-Gly-Xaa1-Arg-Cys-Cys-Lys-Asn-Gly-Lys-Arg-Gly-Cys-Gly-Arg-Xaa4-Cys-Arg-Asp-His-Ser- (SEQ ID NO:39)

Arg-Cys-Cys-#

Name: Bu3.3
Species: bullatus
Cloned: Yes

TABLE 1-continued

DNA and Amino Acid Sequences of μ-Conopeptides and Precursors

DNA Sequence:

CAAGAGGGATCGATAGCAGTTCATGATGTCTAAACTGGGAGTCTTGTTGACCATCTG (SEQ ID NO:40)

TCTGCTTCTGTTTCCCCTTTTTGCTCTTCCGCAGGACGGAGATCAACCTGCAGACCG

ACCTGCAGAGCGTATGCAGGACGACCTTTCATCTGAGCAGCATCCCTTGTTTGAGAA

GAGAATTGTTGACAGGTGCTGCAACAAAGGGAACGGGAAGAGGGGGTGCAGCAGA

TGGTGCAGAGATCACTCACGTTGTTGCGGTCGACGATGAACTGTTGATGACCGAGG

CTTTGGTTATCACGGCTACATCAAGTGTCTAGTGAATAAGTAAAACGATTGCAGT

Translation:

MMSKLGVLLTICLLLFPLFALPQDGDQPADRPAERMQDDLSSEQHPLFEKLRIVDRCCNK (SEQ ID NO:41)

GNGKRGCSRWCRDHSRCCGRR

Toxin Sequence:

Ile-Val-Asp-Arg-Cys-Cys-Asn-Lys-Gly-Asn-Gly-Lys-Arg-Gly-Cys-Ser-Arg-Xaa4-Cys-Arg- (SEQ ID NO:42)

Asp-His-Ser-Arg-Cys-Cys-#

Name: Bu3.4
Species: *bullatus*
Cloned: Yes

DNA Sequence:

CAAGAAGGATCGATAGCAGTTCATGATGTCTAAACTGGGAGTCTTGTTGACCATCTG (SEQ ID NO:43)

TCTGCTTCTGTTTCCCCTTTTTGCTCTTCCGCAGGATGGAGATCAACCTGCAGACCGA

CCTGCTGAGCGTATGCAGGACGACATTTCATCTGAGCGGAATCCCTTGTTTGAGAAG

AGCGTTGGTTTATATTGCTGCCGACCCAAACCCAACGGGCAGATGATGTGCGACAG

ATGGTGCGAAAAAAACTCACGTTGTTGCGGTCGACGATAATGTGTTGATGACCAGC

TTTGTTATCAAGGCTACATCAAGTATCTAGTGAATAAGTAAAACGATTGCAGT

Translation:

MMSKLGVLLTICLLLFPLFALPQDGDQPADRPAERMQDDISSERNPLFEKSVGLYCCRP (SEQ ID NO:44)

KPNGQMMCDRWCEKNSRCCGRR

Toxin Sequence:

Val-Gly-Leu-Xaa5-Cys-Cys-Arg-Xaa3-Lys-Xaa3-Asn-Gly-Gln-Met-Met-Cys-Asp-Arg-Xaa4- (SEQ ID NO:45)

Cys-Xaa1-Lys-Asn-Ser-Arg-Cys-Cys-#

------------------------------

Name: Bu3.5
Species: *bullatus*
Cloned: Yes

DNA Sequence:

CAAGAAGGATCGATAGCAGTTCATGATGTCTAAACTGGGAGTTTTGTTGACCATCTG (SEQ ID NO:46)

TCTGCTTCTGTTTCCCCTTACTGCTCTTCCGATGGATGGAGATCAATCTGTAGACCGA

CCTGCAGAACGTATGCAGGACGACCTTTCATCTGAGCAGCATCCCTTGTTTGTTCAG

AAAAGAAGGTGTTGCGGCGAAGGCTTGACATGCCCCAGATATTGGAAAAACAGTCA

GATTTGTGCTTGTTGTTAAATGACAACGTGTCGATGACCAACTTCGGTATCACGACT

ACGCCAAGTGTCTAATGAATAAGTAAAACGATTGCAGT

TABLE 1-continued

DNA and Amino Acid Sequences of μ-Conopeptides and Precursors

Translation:

MMSKLGVLLTICLLLFPLTALPMDGDQSVDRPAERMQDDLSSEQHPLFVQKRRCCGEG (SEQ ID NO:47)

LTCPRYWKINSQICACC

Toxin Sequence:

Arg-Cys-Cys-Gly-Xaa1-GIy-Leu-Thr-Cys-Xaa3-Arg-Xaa5-Xaa4-Lys-Asn-Ser-Gln-Ile-Cys-Ala- (SEQ ID NO:48)

Cys-Cys-^

Name: Bu3.5A
Species: *bullatus*
Cloned: Yes

DNA Sequence:

CAAGAGGGATCGATAGCAGTTCATGATGTCTAAACTGGGAGTCTTGTTGACCATCTG (SEQ ID NO:49)

TCTGCTTCTGTTTCCCCTTTTTGCTCTTCCGCAGGATGGAGATCAACCTGCAGACCGA

CCTGCTGAGCGTATGCAGGACGACATTTCATCTGAGCAGGATCCCTTGTTTGTTCAG

AAAAGAAGGTGTTGCGGCGAAGGCTTGACATGCCCCAGATATTGGAAAAACAGTCA

GATTTGTGCTTGTTGTTAAATGACAACGTGTGATGACCAACTTCGGTATCACGACTA

CGCCAAGTGTCTAATGAATAAGTAAAACGATTGCAGT

Translation:

MMSKLGVLLTICLLLFPLFALPQDGDQPADRPAERMQDDISSEQDPLFVQKRRCCGEGL (SEQ ID NO:50)

TCPRYWKNSQICACC

Toxin Sequence:

Arg-Cys-Cys-Gly-Xaa1-Gly-Leu-Thr-Cys-Xaa3-Arg-Xaa5-Xaa4-Lys-Asn-Ser-Gln-Ile-CyS-Ala- (SEQ ID NO:51)

Cys-Cys-^

Name: Cp3.1
Species: *capitaneus*
Cloned: Yes

DNA Sequence:

GGATCCATGATGTCTAAACTGGGAGTCTTGGTGACCATCTGCCTGCTTCTGTTTCCC (SEQ ID NO:52)

CTTGCTGCTTTTCCACTGGATGGAATCAACCTGCAGACCACCCTGCAAAGCGTACG

CAAGATGACAGTTCAGCTGCCCTGATCAATACCTGGATTGATCATTCCCATTCTTGC

TGCAGGGACTGCGGTGAAGATTGTGTTGGTTGTTGCCGGTAACGTGTTGATGACCAA

CTTTCTCGAG

Translation:

GSMMSKLGVLVTICLLLFPLAAFPLDGNQPADHPAKRTQDDSSAALINTWIDHSHSCCR (SEQ ID NO:53)

DCGEDCVGCCR

Toxin Sequence:

Ser-Cys-Cys-Arg-Asp-Cys-Gly-Xaa1-Asp-Cys-Val-Gly-Cys-Cys-Arg-^ (SEQ ID NO:54)

Name: Ca3.1
Species: *caracteristicus*
Cloned: Yes

DNA Sequence:

CAAGAGGGATCGATAGCAGTTCATGATGTCTAAACTGGGAGTCTTGTTGACCATCTG (SEQ ID NO:55)

TCTGCTTCTGTTTCCCCTTACTGCTCTTCCAATGGATGGAGATCAACCTGCAGACCA

TABLE 1-continued

DNA and Amino Acid Sequences of μ-Conopeptides and Precursors

ACCTGCAGATCGTATGCAGGACGACATTTCATCTGAGCAGTATCCCTTGTTTGATAT

GAGAAAAAGGTGTTGCGGCCCCGGCGGTTCATGCCCCGTATATTTCAGAGACAATT

TTATTTGTGGTTGTTGTTAAATGACAACGTGTCGATGACCAACTTCATTATCACGAC

TACGCCAAGTGTCTAATGAATAAGTAAAATGATTGCAGT

Translation:

MMSKLGVLLTICLLLFPLTALPMDGDQPADQPADRMQDDISSEQYPLFDMRKRCCGPG (SEQ ID NO:56)

GSCPVYFRDNTICGCC

Toxin Sequence:

Cys-Cys-Gly-Xaa3-Gly-Gly-Ser-Cys-Xaa3-Val-Xaa5-Phe-Arg-Asp-Asn-Phe-Ile-Cys-Gly-Cys- (SEQ ID NO:57)

Cys-^

Name: Ca3.2
Species: *caracteristicus*
Cloned: Yes

DNA Sequence:

CAAGAGGGATCGATAGCAGTTCATGATGTCTAAACTGGGAGTCTTGTTGACCATCTG (SEQ ID NO:58)

TCTGCTTCTGTTTCCCCTTACTGCTCTTCCGATGGATGGAGATGAACCTGCAAACCG

ACCTGTCGAGCGTATGCAGGACAACATTTCATCTGAGCAGTATCCCTTGTTTGAGAA

GAGACGAGATTGTTGCACTCCGCCGAAGAAATGCAAAGACCGACAATGCAAACCCC

AGAGATGTTGCGCTGGACGATAACGTGTTGATGACCAACTTTATCACGGCTACGTCA

AGTGTTTAGTGAATAAGTAAAATGATTGCAGT

Translation:

MMSKLGVLLTICLLLFPLTALPMDGDEPANPVERMQDNISSEQYPLFEKRRDCCTPPK (SEQ ID NO:59)

KCKDRQCKPQRCCAGR

Toxin Sequence:

Arg-Asp-Cys-Cys-Thr-Xaa3-Xaa3-Lys-Lys-Cys-Lys-Asp-Arg-Gln-Cys-Lys-Xaa3-Gln-Arg- (SEQ ID NO:60)

Cys-Cys-Ala-#

Name: Ca3.3
Species: *caracteristicus*
Cloned: Yes

DNA Sequence:

CAAGAGGGATCGATAGCAGTTCATGATGTCTAAACTGGGAGTCTTGTTGACCATCTG (SEQ ID NO:61)

TCTGCTTCTGTTTCCCCTTACTGCTCTTCCACTGGATGGAGATCAACCTGCAGATCAA

TCTGCAGAGCGACCTGCAGAGCGTACGCAGGACGACATTCAGCAGCATCCGTTATA

TGATCCGAAAAGAAGGTGTTGCCGTTATCCATGCCCCGACAGCTGCCACGGATCTTG

CTGCTATAAGTGATAACATGTTGATGGCCAGCTTTGTTATCACGGCCACGTCAAGTG

TCTTAATGAATAAGTAAAACGATTGCAGT

Translation:

MMSKLGVLLTICLLLFPLTALPLDGDQPADQSAERPAERTQDDIQQHPLYDPKRRCCRY (SEQ ID NO:62)

PCPDSCHGSCCYK

Toxin Sequence:

Arg-Cys-Cys-Arg-Xaa5-Xaa3-Cys-Xaa3-Asp-Ser-Cys-His-Gly-Ser-Cys-Cys-Xaa5-Lys-^ (SEQ ID NO:63)

TABLE 1-continued

DNA and Amino Acid Sequences of μ-Conopeptides and Precursors

Name: Ca3.4
Species: *caracteristicus*
Cloned: Yes

DNA Sequence:

CAAGAGGGATCGATAGCAGTTCATGATGTCTAAACTGGGAGCCTTGTTGACCATCT    (SEQ ID NO:64)

GTCTACTTCTGTTTTCCCTTACTGCTGTTCCGCTGGATGGAGATCAACATGCAGACC

AACCTGCACAGCGTCTGCAGGACCGCATTCCAACTGAAGATCATCCCTTATTTGATC

CCAACAAACGGTGTTGCCCGCCGGTGGCATGCAACATGGGATGCAAGCCTTGTTGT

GGATGACCAGCTTTGTTATCGCGGTCTTCATGAAGTGTCTTAATGAATAAGTAAAAT

GATTGCAGT

Translation:

MMSKLGALLTICLLLFSLTAVPLDGDQHADQPAQRLQDRIPTEDHPLFDPNKRCCPPVA    (SEQ ID NO:65)

CNMGCKPCCG

Toxin Sequence:

Cys-Cys-Xaa3-Xaa3-Val-Ala-Cys-Asn-Met-Gly-Cys-Lys-Xaa3-Cys-Cys-#    (SEQ ID NO:66)

Name: Ca3.5
Species: *caracteristicus*
Cloned: Yes

DNA Sequence:

CAAGAGGGATCGATAGCAGTTCATGATGTCTAAACTGGGAGCCTTGTTGACCATCT    (SEQ ID NO:67)

GTCTACTTCTGTTTTCCCTAACTGCTGTTCCGCTGGATGGAGATCAACATGCAGACC

AACCTGCAGAGCGTCTGCATGACCGCCTTCCAACTGAAAATCATCCCTTATATGATC

CCGTCAAACGGTGTTGCGATGATTCGGAATGCGACTATTCTTGCTGGCCTTGCTGTA

TGTTTGGATAACCTTTGTTATCGCGGCCTCATCAAGTGTCTAATGAATAAGTAAAAC

GATTGCAGT

Translation:

MMSKLGALLTICLLLFSLTAVPLDGDQHADQPAERLHDRLPTENHPLYDPVKRCCDDSE    (SEQ ID NO:68)

CDYSCWPCCMFG

Toxin Sequence:

Cys-Cys-Asp-Asp-Ser-Xaa1-Cys-Asp-Xaa5-Ser-Cys-Xaa4-Xaa3-Cys-Cys-Met-Phe-#    (SEQ ID NO:69)

Name: Ca3.6
Species: *caracteristicus*
Cloned: Yes

DNA Sequence:

GGATCCATGATGTCTAAACTGGGAGTCTTGTTGACCATCTGTCTGCTTCTGTTTCCCC    (SEQ ID NO:70)

TTACTGCTGTTCCGCTGGATGGAGATCAACCTGCAGACCGACCTGCAGAGCGTAAG

CAGGACGTTTCATCTGAACAGCATCCCTTCTTTGATCCCGTCAAACGGTGTTGCCGC

CGGTGTTACATGGGATGCATCCCTTGTTGCTTTTAACGTGTTGATGACCAACTTTCTC

GAG

Translation:

GSMMSKLGVLLTICLLLFPLTAVPLDGDQPADRPAERKQDVSSEQKPFFDPVKRCCRRC    (SEQ ID NO:71)

YMGCIPCCFID

TABLE 1-continued

DNA and Amino Acid Sequences of µ-Conopeptides and Precursors

Toxin Sequence:

Cys-Cys-Arg-Arg-Cys-Xaa5-Met-Gly-Cys-Ile-Xaa3-Cys-Cys-Phe-^ (SEQ ID NO:72)

Name: Cr3.1
Species: *circumcisus*
Cloned: Yes

DNA Sequence:

CAAGAAGGATCGATAGCAGTTCATGATGTCTAAACTGGGGGTATTGTTGACCATCT (SEQ ID NO:73)

GTCTGCTTCTGTTTCCCCTTACTGCTCTTCCAATGGATGGAGATCAACCTGCAGACC

AACCTGCAGATCGTATGCAGGACGACATTTCATCTGAGCAGTATCCCTTGTTTGATA

AGAGACGAAAGTGTTGCGGCAAAGACGGGCCATGCCCCAAATATTTCAAAGACAAT

TTTATTTGTGGTTGTTGTTAAATGACAACGTGTCGATGACCAACTTCGTTATCACGAT

TCGCCAAGTGTCTTAATGAATAAGTAAAATGATTGCAGT

Translation:

MMSKLGVLLTICLLLFPLTALPMDGDQPADQPADRMQDDISSEQYPLFDKRRKCCGKD (SEQ ID NO:74)

GPCPKYFKDKFICGCC

Toxin Sequence:

Arg-Lys-Cys-Cys-Gly-Lys-Asp-Gly-Xaa3-Cys-Xaa3-Lys-Xaa5-Phe-Lys-Asp-Asn-Phe-Ile-Cys- (SEQ ID NO:75)

Gly-Cys-Cys-^

Name: Da3.1
Species: *dalli*
Cloned: Yes

DNA Sequence:

CAAGAGGGATCGATAGCAGTTCATGATGTCTAAACTGGGAGCCTTGTTGACCATCT (SEQ ID NO:76)

GTCTACTTCTGTTTTCCCTAACTGCTGTTCCGCTGGATGGAGATCAACATGCAGACC

AACCTGCAGAGCGTCTGCAGGACCGCCTTCCAACTGAAAATCATCCCTTATATGATC

CCGTCAAACGGTGTTGCGATGATTCGGAATGCGACTATTCTTGCTGGCCTTGCTGTA

TTTTATCATAACCTTTGTTATCGCGGCCTCATCAAGTGTCAAATGAATAAGTAAAAT

GATTGCAGT

Translation:

MMSKLGALLTICLLLFSLTAVPLDGDQHADQPAERLQDRLPTENHPLYDPVKRCCDDSE (SEQ ID NO:77)

CDYSCWPCCILS

Toxin Sequence:

Cys-Cys-Asp-Asp-Ser-Xaa1-Cys-Asp-Xaa5-Ser-Cys-Xaa4-Xaa3-Cys-Cys-Ile-Leu-Ser-^ (SEQ ID NO:78)

Name: Da3.2
Species: *dalli*
Cloned: Yes

DNA Sequence:

CAAGAGGGATCGATAGCAGTTCATGATGTCTAAACTGGGAGTCTTGTTGACCATTTG (SEQ ID NO:79)

TCTACTTCTGTTTCCCCTTACTGCTGTTCCACTGGATGGAGATCAGCCTGCAGACCG

ACCTGCAGAGCGTATGCAGGACGGCATTTCATCTGAACATCATCCATTTTTTGATTC

CGTCAAAAAGAAACAACAGTGTTGCCCGCCGGTGGCATGCAACATGGGATGCGAGC

CTTGTTGTGGATGACCAGCTTTGTTATCGCGGCTCATGAAGTGTCCTAATGAATAAG

TABLE 1-continued

DNA and Amino Acid Sequences of µ-Conopeptides and Precursors

TAAAACGATTGCAGT

Translation:

MMSKLGVLLTICLLLFPLTAVPLDGDQPADRPAERMQDGISSEHHPFFDSVKKKQQCCP (SEQ ID NO:80)

PVACNMGCEPCCG

Toxin Sequence:

Xaa2-Gln-Cys-Cys-Xaa3-Xaa3-Val-Ala-Cys-Asn-Met-Gly-Cys-Xaa1-Xaa3-Cys-Cys-# (SEQ ID NO:81)

Name: Da3.3
Species: *dalli*
Cloned: Yes

DNA Sequence:

CAAGAAGGATCGATAGCAGTTCATGATGTCTAAACTGGGAGTCTTGTTGATCATATG (SEQ ID NO:82)

TCTATTTCTGTTTCCCCTTACTGCTGTTCAGCTCAATGGAGATCAGCCTGCAGACCAA

TCTGCAGAGCGTATGCAGGACAAAATTTCATCTGAACATCATCCCTTTTTTGATCCC

GTCAAACGTTGTTGCAACGCGGGGTTTTGCCGCTTCGGATGCACGCCTTGTTGTTGG

TGACCAGCTTTGTTATCGCGGCCTCATCAAGTGTCTAATGAATAAGTAAAATGATTG

CAGT

Translation:

MMSKLGVLLIICLFLFPLTAVQLNGDQPADQSAERMQDKISSEHHPFFDPYKRCCNAGF (SEQ ID NO:83)

CRFGCTPCCW

Toxin Sequence:

Cys-Cys-Asn-Ala-Gly-Phe-Cys-Arg-Phe-Gly-Cys-Thr-Xaa3-Cys-Cys-Xaa4-^ (SEQ ID NO:84)

Name: Di3.1
Species: *distans*
Cloned: Yes

DNA Sequence:

CAAGAGGGATCGATAGCAGTTCATGATGTCTAAACTGGGAGTCTTGCTGACCATCTT (SEQ ID NO:85)

TCTGCTTCTGTTTCCCCTTACTGCTGTTCCGCTGGATGGAGATCAACCCGCAGACGG

ACTTGCAGAGCGCATGCAGGACGACAGTTCAGCTGCACTGATTAGAGACTGGCTTC

TTCAAACCCGACAGTGTTGTGTGCATCCATGCCCATGCACGCCTTGCTGTAGATGAC

CAGCTTTGTCATCGCGGCTACGTCAAGTATCTAATGAATAAGTAAGTAAAACGATTG

CAGT

Translation:

MMSKLGVLLTIFLLLFPLTAVPLDGDQPADGLAERMQDDSSAALIRDWLLQTRQCCVH (SEQ ID NO:86)

PCPCTPCCR

Toxin Sequence:

Xaa2-Cys-Cys-Val-His-Xaa3-Cys-Xaa3-Cys-Thr-Xaa3-Cys-Cys-Arg-^ (SEQ ID NO:87)

Name: E6.1
Species: *ermineus*
Cloned: Yes

DNA Sequence:

ACCTCAAGAGGGATCGATCGCAGTTCATGATGTCTAAACTGGGAGCCTTGTTGACC (SEQ ID NO:88)

ATCTGTCTGCTTCTGTTTCCCATTACTGCTCTTCTGATGGATGGAGATCAGCCTGCAG

TABLE 1-continued

DNA and Amino Acid Sequences of µ-Conopeptides and Precursors

ACCGACCTGCAGAGCGTACGGAGGATGACATTTCATCTGACTACATTCCCTGTTGCA

GTTGGCCATGCCCCCGATACTCCAACGGTAAACTTGTTTGTTTTTGTTGCCTTGGATG

ATAATGTGTTGATGACCAACTTTGTTATCACGGCTACGTCAAGTGTCTACTGAATAA

GTAAAATGATTGCAGTA

Translation:

MMSKLGALLTICLLLFPITALLMDGDQPADRPAERTEDDISSDYIPCCSWPCPRYSNGKL (SEQ ID NO:89)

VCFCCLG

Toxin Sequence:

Cys-Cys-Ser-Xaa4-Xaa3-Cys-Xaa3-Arg-Xaa5-Ser-Asn-Gly-Lys-Leu-Val-Cys-Phe-Cys-Cys- (SEQ ID NO:90)

Leu-#

Name: Ge3.2
Species: *generalis*
Cloned: Yes

DNA Sequence:

GGATCCATGATGTCTAAACTGGGAGTCTTGTTGACCATCTGTCTGGTTCTGTTTCCCC (SEQ ID NO:91)

TTACTGCTCTTCCACTGGATGGAGAACAACCTGTAGACCGACATGCCGAGCATATGC

AGGATGACAATTCAGCTGCACAGAACCCCTGGGTTATTGCCATCAGACAGTGTTGC

ACGTTCTGCAACTTTGGATGCCAACCTTGTTGCCTCACCTGATAACGTGTTGATGAC

CAACTTTCTCGAG

Translation:

GSMMSKLGVLLTICLVLFPLTALPLDGEQPVDRHAEHMQDDNSAAQNPWVIAIRQCCT (SEQ ID NO:92)

FCNFGCQPCCLT

Toxin Sequence:

Xaa2-Cys-Cys-Thr-Phe-Cys-Asn-Phe-Gly-Cys-Gln-Xaa3-Cys-Cys-Leu-Thr-^ (SEQ ID NO:93)

Name: Ge3.3
Species: *generalis*
Cloned: Yes

DNA Sequence:

GGATCCATGATGTCTAAACTGGGAGTCTTGTTGACCATCTGTCTGGTTCTGTTTCCCC (SEQ ID NO:94)

TTACTGCTCTTCCACTGGATGGAGAACAACCTGTAGACCGACATGCCGAGCATATGC

AGGATGACAATTCAGCTGCACAGAACCCCTGGGTTATTGCCATCAGACAGTGTTGC

ACGTTCTGCAACTTTGGATGCCAGCCTTGTTGCGTCCCCTGATAACGTGTTGATGAC

CAACTTTCTCGAG

Translation:

GSMMSKLGVLLTICLVLFPLTALPLDGEQPVDRHAEHMQDDNSAAQNPWVIAIRQCCT (SEQ ID NO:95)

FCNFGCQPCCVP

Toxin Sequence:

Xaa2-Cys-Cys-Thr-Phe-Cys-Asn-Phe-Gly-Cys-Gln-Xaa3-Cys-Cys-Val-Xaa3-^ (SEQ ID NO:96)

Name: µ-GIIIA
Species: *geographus*
Cloned: Yes

TABLE 1-continued

DNA and Amino Acid Sequences of μ-Conopeptides and Precursors

DNA Sequence:

GTCGACTCTAGAGGATCCGACAACAAAGAGTCAACCCCACTGCCACGTCAAGAGCG (SEQ ID NO:97)

AAGCGCCACAGCTAAGACAAGAGGGATCGATAGCAGTTCATGATGTCTAAACTGGG

AGTCTTGTTGACCATCTGTCTGCTTCTGTTTCCCCTTACTGCTCTTCCGATGGATGGA

GATGAACCTGCAAACCGACCTGTCGAGCGTATGCAGGACAACATTTCATCTGAGCA

GTATCCCTTGTTTGAGAAGAGACGAGATTGTTGCACTCCGCCGAAGAAATGCAAAG

ACCGACAATGCAAACCCCAGAGATGTTGCGCTGGACGATAACGTGTTGATGACCAA

CTTTATCACGGCTACGTCAAGTGTTTAGTGAATAAGTAAAATGATTGCAGTCTTGCT

CAGATTTGCTTTTGTGTTTTGGTCTAAAGATCAATGACCAAACCGTTGTTTTGATGCG

GATTGTCATATATTTCTCGATTCCAATCCAACACTAGATGATTTAATCACGATAGAT

TAATTTTCTATCAATGCCTTGATTTTCGTCTGTCATATCAGTTTTGTTTATATTTATT

TTTTCGTCACTGTCTACACAAACGCATGCATGCACGCATGCACGCACACACGCACGC

ACGCTCGCACAAACATGCGCGCGCACGCACACACACACACACACACACACACAAACACA

CACACAAGCAATCACACAATTATTGACATTATTTATTTATTCATTGATGTATTTGTTA

TTCGTTTGCTTGTTTTTAGAATAGTTTGAGGCCGTCTTTTTGGATTTATTTGAACTGC

TTTATTGTATACGAGTACTTCGTGCTTTGAAACACTGCTGAAAATAAAACAAACACT

GACGTAGC

Translation:

MMSKLGVLLTICLLLFPLTALPMDGDEPANRPVERMQDNISSEQYPLFEKRRDCCTPPK (SEQ ID NO:98)

KCKDRQCRPQRCCAGR

Toxin Sequence:

Arg-Asp-Cys-Cys-Thr-Xaa3-Xaa3-Lys-Lys-Cys-Lys-Asp-Arg-Gln-Cys-Lys-Xaa3-Gln-Arg- (SEQ ID NO:99)

Cys-Cys-Ala-#

Name: μ-GIIIB
Species: geographus
Isolated: Yes
Cloned: Yes

DNA Sequence:

GGCCAGACGACAACAAAGAGTCAACCCCACTGCCACGTCAAGAGCGAAGCGCCAC (SEQ ID NO:100)

AGCTAAGACAAGAGGGATCGATAGCAGTTCATGATGTCTAAACTGGGAGTCTTGTT

GACCATCTGTCTGCTTCTGTTTCCCCTTACTGCTCTTCCGATGGATGGAGATGAACCT

GCAAACCGACCTGTCGAGCGTATGCAGGACAACATTTCATCTGAGCAGTATCCCTTG

TTTGAGAAGAGACGAGATTGTTGCACTCCGCCGAGGAAATGCAAAGACCGACGATG

CAAACCCATGAAATGTTGCGCTGGACGATAACGTGTTGATGACCAACTTTATCACG

GCTAGCTCAGTGTTTAGTGAATAAGTAAAATGATTGCAGTCTTGCTCAGATTGCTTT

TGTGTTTTGGTCTAAAGATCAATGACCAAACCGTTGTTTTGATGCGGATTGTCATATA

TTTCTCGATTCCAATCCAACACTAGATGATTTAATCACGATAGATTAATTTTCTATCA

ATGCCTTGATTTTCGTCTGTCATATCAGTTTTGTTTATATTTATTTTTTCGTCACTGT

CTACACAAACGCATGCATGCACGCATGCACGCACACACGCACGCACGCTCGCACAA

ACATGCGCGCACGCACACACACACACACACACACAAACACACACACGAAGCAATC

TABLE 1-continued

DNA and Amino Acid Sequences of μ-Conopeptides and Precursors

ACACAATTAGTTGACATTATTTATTTATTCATTGATGTATTTGTTATTCGTTTGCTTGT

TTTTAGAATAGTTTGAGGCCGTCTTTTTGGATTTATTTGAACTGCTTTATTGTATACG

AGTACTTCGTGCTTTGAAACACTGCTGAAAATAAAACAAACACTGACGTAGCAAAA

AAAAAAA

Translation:

MMSKLGVLLTICLLLFPLTALPMDGDEPANRPVERMQDNISSEQYPLFEKRRDCCTPPR (SEQ ID NO:101)

KCKDRRCKPMKCCAGR

Toxin Sequence:

Arg-Asp-Cys-Cys-Thr-Xaa3-Xaa3-Xaa3-Arg-Lys-Cys-Lys-Asp-Arg-Arg-Cys-Lys-Xaa3-Met-Lys- (SEQ ID NO:102)

Cys-Cys-Ala-#

Name: μ-GIIIC
Species: geographus
Isolated: Yes

Toxin Sequence:

Arg-Asp-Cys-Cys-Thr-Xaa3-Xaa3-Lys-Lys-Cys-Lys-Asp-Arg-Arg-Cys-Lys-Xaa3-Leu-Lys- (SEQ ID NO:103)

Cys-Cys-Ala-#

Name: Gm3.1
Species: gloriamaris
Cloned: Yes

DNA Sequence:

CTCACTATAGGAATTCGAGCTCGGTACACGGGATCGATAGCAGTTCATGATGTCTAA (SEQ ID NO:104)

ACTGGGAGCCTTGTTGACCATCTGTCTACTTCTGTTTTCCCTAACTGCTGTTCCGCTG

GATGGAGATCAACATGCAGACCAACCTGCAGAGCGTCTGCATGACCGCCTTCCAAC

TGAAAATCATCCCTTATATGATCCCGTCAAACGGTGTTGCGATGATTCGGAATGCGA

CTATTCTTGCTGGCCTTGCTGTATGTTTGGATAACCTTTGTTATCGCGGCCTCGATAA

GTGTCTAATGAATAAGTAAAACGATTGCAGTAGGC

Translation:

MMSKGALLTICLLLFSLTAVPLDGDQHADQPAHDQPAERLHDRLPTENHPLYDPVKRCCDDSE (SEQ ID NO:105)

CDYSCWPCCMFG

Toxin Sequence:

Cys-Cys-Asp-Asp-Ser-Xaa1-Cys-Asp-Xaa5-Ser-Cys-Xaa4-Xaa3-Cys-Cys-Met-Phe-# (SEQ ID NO:106)

Name: Gm3.2
Species: gloriamaris
Cloned: Yes

DNA Sequence:

GTTCATGATGTCTAAACTGGGAGTCTTGTTGATCATCTGTCTACTTCTGTTTCCCCTT (SEQ ID NO:107)

ACTGCTGTTCCGCTGGATGGAGATCAACCTGCAGACCGATATGCAGAGCGTATGCA

GGACGACATTTCATCTGAACATCATCCCATGTTTGATGCCGTCAGAGGGTGTTGCCA

TCTGTTGGCATGCCGCTTCGGATGCTCGCCTTGTTGTGGTGATCAGCTTTGTTATCG

CGGCCTCATCAAGTGACTCTAATGCAAA

Translation:

MMSKLGVLLIICLLLFPLTAVPLDGDQPADRYAERMQDDISSEHHPMFDAVRGCCHLLA (SEQ ID NO:108)

TABLE 1-continued

DNA and Amino Acid Sequences of μ-Conopeptides and Precursors

CRFGCSPCCW

Toxin Sequence:

Gly-Cys-Cys-His-Leu-Leu-Ala-Cys-Arg-Phe-Gly-Cys-Ser-Xaa3-Cys-Cys-Xaa4-^ (SEQ ID NO:109)

Name: Gm3.3
Species: *gloriamaris*
Cloned: Yes

DNA Sequence:

GAGACGACAAGGAACAGTCAACCCCACAGCCACGCCAAGAGCAGACAGCCACAGC (SEQ ID NO:110)

TACGTGAAGAAGGGTGGAGAGAGGTTCGTGATGTTGAAAATGGGAGTGGTGCTATT

CATCTTCCTGGTACTGTTTCCCCTGGCAACGCTCCAGCTGGATGCAGATCAACCTGT

AGAACGATATGCGGAGAACAAACAGCTCCTCAACCCAGATGAAAGGAGGGAAATC

ATATTGCATGCTCTGGGGACGCGATGCTGTTCTTGGGATGTGTGCGACCACCCGAGT

TGTACTTGCTGCGGCGGTTAGCGCCGAACATCCATGGCGCTGTGCTGGGCGGTTTTA

TCCAACAACGACAGCGTTTGTTGATTTCATGTATCATTGCGCCCACGTCTCTTGTCTA

AGAATGACGAACATGATTGCACTCTGGTTCAGATTTCGTGTTCTTTTCTGACAATAA

ATGACAAAACTCCAAAAAA

Translation:

MLKMGVVLFIFLVLFPLATLQLDADQPVERYAENKQLLNPDERREIILHALGTRCCSWD (SEQ ID NO:111)

VCDHPSCTCCGG

Toxin Sequence:

Cys-Cys-Ser-Xaa4-Asp-Val-Cys-Asp-His-Xaa3-Ser-Cys-Thr-Cys-Cys-Gly-# (SEQ ID NO:112)

Name: La3.1
Species: *laterculatus*
Cloned: Yes

DNA Sequence:

CGACCTCAAGAAGGATCGATAGCAGTTCATGATGTCTAAACTGGGAGTCTTGTTGA (SEQ ID NO:113)

CCATCTGTCTGCTTCTGTTTCCCCTTACTGCTCTTCCGATGGATGGAGATCAACCTGC

AGACCGACCTGCAGAGCGTATGCAGGACGTTTCATCTGAACAGCATCCCTTGTATG

ATCCCGTCAAACGGTGTTGCGACTGGCCATGCAGCGGATGCATCCCTTGTTGCTAAT

AGTAACAACGTGTTGATAACCAACTTTCTTACCACGACTACGTCAAGTGTCTAATGA

ATAAGTAAAATGATTGCAGT

Translation:

MMSKLGVLLTICLLLFPLTALPMDGDQPADRPAERMQDVSSEQHPLYDPVKRCCDWPC (SEQ ID NO:114)

SGCIPCC

Toxin Sequence:

Cys-Cys-Asp-Xaa4-Xaa3-Cys-Ser-Gly-Cys-Ile-Xaa3-Cys-Cys-^ (SEQ ID NO:115)

Name: La3.2
Species: *laterculatus*
Cloned: Yes

DNA Sequence:

CGACCTCAAGAAGGATCGATAGCAGTTCATGATGTCTAAACTGGGAGTCTTGTTGA (SEQ ID NO:116)

CCATCTGTCTGCTTCTGTTTCCCCTTACTGCTCTGGATGGAGATCAACCTGCAGACC

TABLE 1-continued

DNA and Amino Acid Sequences of μ-Conopeptides and Precursors

GACTTGCAGAGCGTATGCAGGACGACATTTCATCTGAGCAGCATCCCTTTGAAAAG

AGACGAGACTGTTGCACACCTCCGAAGAAATGCAGAGACCGACAATGCAAACCTGC

ACGTTGTTGCGGAGGATAACGTGTTGATGACCAACTTTGTTATCACGGCTACGTCAA

GTGTCTAGTGAATAAGTAAAACGATTGCAGT

Translation:

MMSKLGVLLTICLLLFPLTALDGDQPADRLAERMQDDISSEQHPFEKRRDCCTPPKKCR (SEQ ID NO:117)

DRQCKPARCCGG

Toxin Sequence:

Arg-Asp-Cys-Cys-Thr-Xaa3-Xaa3-Lys-Lys-Cys-Arg-Asp-Arg-Gln-Cys-Lys-Xaa3-Ala-Arg- (SEQ ID NO:118)

Cys-Cys-Gly-#

Name: La3.3
Species: laterculatus
Cloned: Yes

DNA Sequence:

GGGATCGATAGCAGTTCATGATGTCTAAACTGGGAGTCTTGTTGACCATCTGTCTGC (SEQ ID NO:119)

TTCTGTTTCCCCTTACTGCTCTTCCGATGGATGGAGATCAACTTGCACGCCGATCTGC

AGAGCGTATGCAGGACAACATTTCATCTGAGCAGCATCACCTCTTTGAAAAGAGAC

GACCACCATGTTGCACCTATGACGGGAGTTGCCTAAAAGAATCATGCATGCGTAAA

GCTTGTTGCGGATGATAACGTGTTGATGACCAACTTTGTTATCACGGCTACTCAAGT

GTCTAATGAATAAGTAAAATGATTGCAGTA

Translation:

MMSKLGVLLTICLLLFPLTALPMDGDQLARRSAERMQDNISSEQHHLFEKRRPPCCTYD (SEQ ID NO:120)

GSCLKESCMRKACCG

Toxin Sequence:

Arg-Xaa3-Xaa3-Cys-Cys-Thr-Xaa5-Asp-Gly-Ser-Cys-Leu-Lys-Xaa1-Ser-Cys-Met-Arg-Lys- (SEQ ID NO:121)

Ala-Cys-Cys-#

Name: La3.3A
Species: laterculatus
Cloned: Yes

DNA Sequence:

GGGATCGATAGCAGTTCATGATGTCTAAACTGGGAGTCTTGTTGACCACCTGTCTGC (SEQ ID NO:122)

TTCTGTTTCCCCTTACTGCTCTTCCGATGGATGGAGATCAACTTGCACGCCGACCTG

CAGAGCGTATGCAGGACAACATTTCATCTGAGCAGCATCCCTTCTTTGAAAGGAGA

CGACCACCATGTTGCACCTATGACGGGAGTTGCCTAAAAGAATCATGCAAGCGTAA

AGCTTGTTGCGGATAATAACGTGTTGATGACCAACTTTGTTATCACGGCTACTCAAG

TGTCTAATGAATAAGTAAAATGATTGCAGTA

Translation:

MMSKLGVLLTTCLLLFPLTALPMDGDQLARRPAERMQDNISSEQHPFFERRRPPCCTYD (SEQ ID NO:123)

GSCLKESCKRKACCG

Toxin Sequence:

Arg-Xaa3-Xaa3-Cys-Cys-Thr-Xaa5-Asp-Gly-Ser-Cys-Leu-Lys-Xaa1-Ser-Cys-Lys-Arg-Lys- (SEQ ID NO:124)

TABLE 1-continued

DNA and Amino Acid Sequences of μ-Conopeptides and Precursors

Ala-Cys-Cys-#

Name: Lp3.1
Species: *leopardus*
Cloned: Yes

DNA Sequence:

GGATCCATGATGTCTAAACTGGGAGTCTTGTTGACCGTCTGTCTGCTTCTGTTTCCCC (SEQ ID NO:125)

TTACTGCTCTTCGGCTGGTTGGAGATCAACCTGCAGAGCGACCTGCAAAGCGTACGC

AGGACGACATTCCAGATGGACAGCATCCGTTAAATGATAGGCAGATAAACTGTTGC

CCGTGGCCATGCCCTAGTACATGCCGCCATCAATGCTGCCATTAATGATAACGTGTT

GATGACCAACTTTCTCGAG

Translation:

GSMMSKLGVLLTVCLLLFPLTALRLVGDQPAERPAKRTQDDIPDGQHPLNDRQINCCP (SEQ ID NO:126)

WPCPSTCRHQCCH

Toxin Sequence:

Xaa2-Ile-Asn-Cys-Cys-Xaa3-Xaa4-Xaa3-Cys-Xaa3-Ser-Thr-Cys-Arg-His-Gln-Cys-Cys-His-^ (SEQ ID NO:127)

Name: Lv3.1
Species: *lividus*
Cloned: Yes

DNA Sequence:

GGATCCATGATGTCTAAACTGGGAGTCTTGTTGACCGTCTGTCTGCTTCTGTTTCCCC (SEQ ID NO:128)

TTACTGCTCTTCGGCTGGTTAGAGATCAACCTGCAGAGCGACCTGCAAAGCGTACGC

AGGACGACATTCCAAATGGACAGGATCCGTTAATTGATAGGCAGATAAATTGTTGC

CCTTGGCCATGCCCTGATTCATGCCACTATCAATGCTGCCACTGATAACGTGTTGAT

GACCAACTTTCTCGAG

Translation:

GSMMSKLGVLLTVCLLLFPLTALRLVRDQPAERPAKRTQDDIPNGQDPLIDRQTNCCPW (SEQ ID NO:129)

PCPDSCHYQCCH

Toxin Sequence:

Xaa2-Ile-Asn-Cys-Cys-Xaa3-Xaa4_Xaa3-Cys-Xaa3-Asp-Ser-Cys-His-Xaa5-Gln-Cys-Cys-His-^ (SEQ ID NO:130)

Name: L3.1
Species: *lynceus*
Cloned: Yes

DNA Sequence:

AAGGATCGATAGCAGTTCATGATGTCTAAACTGGGAGTCTTGTTGACCATCTGTCTG (SEQ ID NO:131)

CTTCTGTTTCCCCTTACTGCTCTTCCGATGGATGGAGATCAATCTGCAGACCGACTTG

CAGAGCGTATGCAGGACAACATTTCATCTGAGCAGCATCCCTTCTTTGAAAAGAGA

GGACGAGACTGTTGCACACCTCCGAGGAAATGCAGAGACCGAGCCTGCAAACCTCA

ACGTTGTTGCGGAGGATAAGCTGTTGATGACCAACTTTGTTATACGGC

Translation:

MMSKLGVLLTICLLLFPLTALPMDGDQSADRLAERMQDNISSEQHPFFEKRGRDCCTPP (SEQ ID NO:132)

RKCRDRACKPQRCCGG

TABLE 1-continued

DNA and Amino Acid Sequences of μ-Conopeptides and Precursors

Toxin Sequence:

Gly-Arg-Asp-Cys-Cys-Thr-Xaa3-Xaa3-Arg-Lys-Cys-Arg-Asp-Arg-Ala-Cys-Lys-Xaa3-GLn- (SEQ ID NO:133)

Arg-Cys-Cys-Gly-#

Name: M3.1
Species: *magus*
Cloned: Yes

DNA Sequence:

CAAGAGGGATCGATAGCAGTTCATGATGTCTAAACTGGGAGTCTTGTTGACCATCTG (SEQ ID NO:134)

TCTGCTTCTGTTTCCCCTTACTGCTCTTCCGATGGATGGAGATGAACCTGCAAACCG

ACCTGTCGAGCGTATGCAGGACAACATTTCATCTGAGCAGTATCCCTTGTTTGAGAA

GAGACGAGATTGTTGCACTCCGCCAAGAAATGCAAAGACCGACAATGCAAACCCC

AGAGATGTTGCGCTGGACGATAACGTGTTGATGACCAACTTTATCACGGCTACGTCA

AGTGTTTAGTGAATAAGTAAAATGATTGCAGTCTTGCTCAGATTTGCTTTTGTGTTTT

GGTCTAAAGATCAATGACCAAACCGTTGTTTTGATGCGGATTGTCATATATTTCTCG

ATTCCAATCCAACACTAGATGATTTAATCACGATAGATTAATTTTCTATCAATGCCT

TGATTTTTCGTCTGTCATATCAGTTTTGTTTATATTTATTTTTTCGTCACTGTCTACAC

AAACGCATGCATGCACGCATGCACGCACACACGCACGCACGCTCGCACAAACATGC

GCGCGCACGCACACACACACACACACAAACACACACACGAAGCAATCACAC

AATTAGTTGACATTATTTATTTATTCATTGATGTATTTGTTATTCGTTTGCTTGTTTTT

AGAATAGTTTGAGGCCGTCTTTTTGGATTTATTTGAACTGCTTTATTGTATACGAGTA

CTTCGTGCGGGAAACACTGCTGAAAATAAAACAAACACTGACGTAGCAAAAAAA

AAAAA

Translation:

MMSKLGVLLTICLLLFPLTALPMDGDEPANRPVERMQDNISSEQYPLFEKRRDCCTPPK (SEQ ID NO:135)

KCKDRQCKPQRCCAGR

Toxin Sequence:

Arg-Asp-Cys-Cys-Thr-Xaa3-Xaa3-Lys-Lys-Cys-Lys-Asp-Arg-Gln-Cys-Lys-Xaa3-Gln-Arg- (SEQ ID NO:136)

Cys-Cys-Ala-#

Name: M3.2
Species: *magus*
Cloned: Yes

DNA Sequence:

CAAGAGGGATCGATAGCAGTTCATGATGTCTAAACTGGGAGTCTTGTTGACCATCTG (SEQ ID NO:137)

TCTGCTTCTGTTTCCCCTTACTGCTCTTCCAATGGATGGAGATCAACCTGCAGACCA

ACCTGCAGATCGTATGCAGGACGACATTTCATCTGAGCAGTATCCCTTGTTTGATAT

GAGAAAAAGGTGTTGCGGCCCCGGCGGTTCATGCCCCGTATATTTCAGAGACAATT

TTATTTGTGGTTGTTGTTAAATGACAACGTGTCGATGACCAACTTCATTATCACGAC

TACGCCAAGTGTCTAATGAATAAATAAAATGATTGCAGTCTCGCTCAGATTTGCTTT

TGTATTTTGGTCTAAAGATCAATGACCAAACCGTTGTTTTGGTGTGGATTTTCATATA

TTTCTCGAGTCCTATCCAACACTAGATGATTTAATCACGATAGATCTGATTTTTTAT

CAAAGGCTTGGTTTTTCGTCTGTCACATCAGTTTTGTTTATATTTAATTTTTCGTCACT

TABLE 1-continued

DNA and Amino Acid Sequences of μ-Conopeptides and Precursors

GATTACACACACGCATGAACGCACAGAGTACTAACACATACACACACACACACA

CACACACACACACACACACACACACACACACACACACGCGCGCGCGGCG

CCATCTAGTAGCGCCGCGACGACACAC

Translation:

MMSKLGVLLTICLLLFPLTALPMDGDQPADQPADRMQDDISSEQYPLFDMRKRCCGPG (SEQ ID NO:138)

GSCPVYFRDNFICGCC

Toxin Sequence:

Cys-Cys-Gly-Xaa3-Gly-Gly-Ser-Cys-Xaa3-Val-Xaa5-Phe-Arg-Asp-Asn-Phe-Ile-Cys-Gly-Cys- (SEQ ID NO:139)

Cys-

Name: M3.3
Species: magus
Cloned: Yes

DNA Sequence:

CAAGAGGGATCGATAGCAGTTCATGATGTCTAAACTGGGAGTCTTGTTGACCATCTG (SEQ ID NO:140)

TTTGCTTCTGTTTCCCCTTACTGCTCTTCCGAGGGATGGAGATCAATCTGTAGACCGA

CCTGCAGAGCGTATGCAGGACGACATTTCATCTGAGCTGCATCCCTTGTCAATCAGA

AAAAGAATGTGTTGCGGCGAGAGTGCGCCATGCCCCAGCTATTTCAGAAACAGTCA

GATTTGTCATTGTTGTTAAATGACAACGTGTCGATGACCACCTTCGTTATCACGACT

AATGATAAGTAAAATGATTGCAGTCTCGCTCAGATTTGCTTTTGTATTTTGGTCTAA

AGATCAATGACCAAACCGTTGTTTTGATGTGGATTTTCATATATTTCTCGAGTCCTAT

CCAACACTAGATGATTTAATCACGATAGATCTGATTTTTTTATCAAAGCCTTGGTTTT

TCGTCTGTCACATCAGTTTTGTTTATATTTAATTTTTCGTCACTGATTACACACACGC

ATGAACGCACAGACGTACTAACACATACACACACACACACACACACACACAC

ACACACACACACACACACAC

Translation:

MMSKLGVLLTICLLLFPLTALPRDGDQSVDRPAERMQDDISSELHPLSIRKRMCCGESAP (SEQ ID NO:141)

CPSYFRNSQICHCC

Toxin Sequence:

Met-Cys-Cys-Gly-Xaa1-Ser-Ala-Xaa3-Cys-Xaa3-Ser-Xaa5-Phe-Arg-Asn-Ser-Gln-Ile-Cys-His- (SEQ ID NO:142)

Cys-Cys-

Name: M3.4
Species: magus
Cloned: Yes

DNA Sequence:

CAAGAGGGATCGATAGCAGTTCATGATGTCTAAACTGGGAGTCTTGTTGACCATCTG (SEQ ID NO:143)

TCTGCTTCTGTTTCCCCTTACTGCTCTTCCAATGGATGGAGATCAACCTGCAGACCA

ACCTGCAGATCGTATGCAGGACGACATTTCATCTGAGCAGTATCCCTTGTTTGATAA

GAGACAAAAGTGTTGCGGCCCCGGCGGTTCATGCCCCGTATATTTCACAGACAATTT

TATTTGTGGTTGTTGTTAAATGACAACGTGTCGATGACCAACTTCATTATCACGACT

ACGCCAAGTGTCTAATGAATAAATAAAATGATTGCAGTCTCGCTCAGATTTGCTTTT

GTATTTGGTCTAAAGATCAATGACCAAACCGTTGTTTTGGTGCTGGATTTTCATATA

TABLE 1-continued

DNA and Amino Acid Sequences of μ-Conopeptides and Precursors

TTTCTCGATTCCTATCCAACACTAGATGATTTAATCACGATAGATCTGATTTTTTTAT

CAATGCCTTAATTTTTTGCTCTGTCATATCAGTTTTGTTTATAT

Translation:

MMSKLGVLLTICLLLFPLTALPMDGDQPADQPADRMQDDISSEQYPLFDKRQKCCGPG (SEQ ID NO:144)

GSCPVYFTDNFICGCC

Toxin Sequence:

Xaa2-Lys-Cys-Cys-Gly-Xaa3-Gly-Gly-Ser-Cys-Xaa3-Val-Xaa5-Phe-Thr-Asp-Asn-Phe-Ile-Cys- (SEQ ID NO:145)

Gly-Cys-Cys-^

Name: M3.5
Species: *magus*
Cloned: Yes

DNA Sequence:

CAAGAGGGATCGATAGCAGTTCATGATGTCTAAACTGGGAGTCTTGTTGACCATCTG (SEQ ID NO:146)

TCTGCTTCTGTTTCCCCTTACTGCTCTTCCAATGGATGGAGATCAACCTGCAGACCA

ACCTGCAGATCGTATGCAGGACGACATTTCATCTGAGCAGTATCCCTTGTTTGATAA

GAGACAAAAGTGTTGCGGCCCCGGCGGTTCATGCCCCGTATATTTCAGAGACAATTT

TATTTGTGGTTGTTGTTAAATGACAACGTGTCGATGACCATCTTCATTATCACGACT

ACGCCAAGTGTCTAATGAATAAATAAAATGATTGCAGTCTCGCTCAGATTTGCTTTT

GTATTTTGGTCTAAAGATCAATGACCAAACCGTTGTTTTGGTGTGGATTTTCATATAT

TTCTCGATTCCTATCCAACACTAGATGATTTAATCACGATAGATCTGATTTTTT

Translation:

MMSKLGVLLTICLLLFPLTALPMDGDQPADQPADRMQDDISSEQYPLFDKRQKCCGPG (SEQ ID NO:147)

GSCPVYFRDNFICGCC

Toxin Sequence:

Xaa2-Lys-Cys-Cys-Gly-Xaa3-Gly-Gly-Ser-Cys-Xaa3-Val-Xaa5-Phe-Arg-Asp-Asn-Phe-Ile- (SEQ ID NO:148)

Cys-Gly-Cys-Cys-^

Name: U001
Species: *magus*
Isolated: No

Toxin Sequence:

Xaa2-Lys-Cys-Cys-Ser-Gly-Gly-Ser-Cys-Xaa3-Leu-Xaa5-Phe-Arg-Asp-Arg-Leu-Ile-Cys-Xaa3- (SEQ ID NO:149)

Cys-Cys-^

Name: Comatose/Death
Species: *marmoreus*
Isolated: Yes

Toxin Sequence:

Ser-Lys-Gln-Cys-Cys-His-Leu-Ala-Ala-Cys-Arg-Phe-Gly-Cys-Thr-Xaa3-Cys-Cys-Asn-^ (SEQ ID NO:150)

Name: Mr3.1
Species: *marmoreus*
Cloned: Yes

DNA Sequence:

CAAGAAGGATCGATAGCAGTTCATGATGTCTAAACTGGGAGTCTTGTTGACCATCTG (SEQ ID NO:151)

TCTGCTTCTGTTTCCCGTTACTGCTCTTCCGATGGATGGTGATCAACCTGCAGACCGA

TABLE 1-continued

DNA and Amino Acid Sequences of μ-Conopeptides and Precursors

CTTGTAGAGCGTATGCAGGACAACATTTCATCTGAGCAGCATCCCTTCTTTGAAAAG

AGAAGAGGAGGCTGTTGCACACCTCCGAGGAAATGCAAAGACCGAGCCTGCAAAC

CTGCACGTTGCTGCGGCCCAGGATAACGTGTTGATGACCAACTTTGTTATCACGGCT

ACGTCAAGTGTCTAGTGAATAAGTAAAACGATTGCAG

Translation:

MMSKLGVLLTICLLLFPVTALPMDGDQPADRLVERMQDNISSEQHPFFEKRRGGCCTPP (SEQ ID NO:152)

RKCKDRACKPARCCGPG

Toxin Sequence:

Arg-Gly-Gly-Cys-Cys-Thr-Xaa3-Xaa3-Arg-Lys-Cys-Lys-Asp-Arg-Ala-Cys-Lys-Xaa3-Ala-Arg- (SEQ ID NO:153)

Cys-Cys-Gly-Xaa3-#

Name: Mr3.2
Species: *marmoreus*
Cloned: Yes

DNA Sequence:

GAGCTCGGTACCCCGACCTCAAGAGGGATCGATAGCAGTTCATGATGTCTAAACTG (SEQ ID NO:154)

GGAATCTTGTTGACCATCTGTCTACTTCTATTTCCCCTTACTGCTGTTCCGCTGGATG

GAGATCAACCTGCAGACCGACCTGCAGAGCGTATGCAGGACGACATTTCATCTGAA

CATCATCCCTTTTTTGATCCCGTCAAACGGTGTTGCAGGTTATCATGCGGCCTGGGA

TGCCACCCTTGTTGTGGATGACCAGCTTTGTTATCGCGGCCTCATCAAGTGTCTAAT

GAATAAGTAAAA

Translation:

MMSKLGILLTICLLLFPLTAVPLDGDQPADRPAERMQDDISSEHHPFFDPVKRCCRLSCG (SEQ ID NO:155)

LGCHPCCG

Toxin Sequence:

Cys-Cys-Arg-Leu-Ser-Cys-Gly-Leu-Gly-Cys-His-Xaa3-Cys-Cys-# (SEQ ID NO:156)

Name: Mr3.3
Species: *marmoreus*
Cloned: Yes

DNA Sequence:

GGCCTACACCAAGCTTGCATGCCTGCAGGTCGACTCTAGAGGATCCCCGATCGATA (SEQ ID NO:157)

GCAGTTCATGATGTCTAGACTGGGAGTCTTGTTGACCATCTGTCTACTTCTGTTTCCC

CTTACTGCTGTTCCGCTGGATGGAGATCAACCTGCGGACCGACCTGCAGAGCGCCTG

CAGGACGACATTTCATCTGAACATCATCCCCATTTTGATTCCGGCAGAGAGTGTTGC

GGTTCGTTCGCATGCCGCTTTGGATGCGTGCCTTGTTGTGTATGACCAGCTTTGTTAT

CACGGCCTCATCGAGTGTCTAATGAATAAGTAAAACGATTGCAGTAGGCGGGTACC

GAGCTCGAATTCC

Translation:

MMSRLGVLLTICLLLFPLTAVPLDGDQPADRPAERLQDDISSEHHPHFDSGRECCGSFAC (SEQ ID NO:158)

RFGCVPCCV

Toxin Sequence:

Xaa1-Cys-Cys-Gly-Ser-Phe-Ala-Cys-Arg-Phe-Gly-Cys-Val-Xaa3-Cys-Cys-Val- (SEQ ID NO:159)

TABLE 1-continued

DNA and Amino Acid Sequences of µ-Conopeptides and Precursors

Name: Mr3.4
Species: *marmoreus*
Cloned: Yes

DNA Sequence:

CGACCTCAAGAGGGATCGATAGCAGTTCATGATGTCTAAACTGGGAGTCTTGTTGA (SEQ ID NO:160)

CCATCTGTCTACTTCTATTTCCCCTTACTGCTGTTCCGCTGGATGGAGACCAACCTGC

AGACCGACCTGCAGAGCGTATGCAGGACGACATTTCATCTGAACGTCATCCTTTTTT

TGATCGCAGCAAACAGTGTTGCCATCTGCCGGCATGCCGCTTCGGATGTACGCCTTG

TTGTTGGTGATCAGCTTTGTTATCGCGTCCTCATCAAGTGTCTAATGAATAAGTAAA

ATGATTGCAG

Translation:

MMSKLGVLLTICLLLFPLTAVPLDGDQPADRPAERMQDDISSERHPFFDRSKQCCHLPA (SEQ ID NO:161)

CRFGCTPCCW

Toxin Sequence:

Ser-Lys-Gln-Cys-Cys-His-Leu-Xaa3-Ala-Cys-Arg-Phe-Gly-Cys-Thr-Xaa3-Cys-Cys-Xaa4-^ (SEQ ID NO:162)

Name: Mr3.5
Species: *marmoreus*
Cloned: Yes

DNA Sequence:

GGATCCATGATGTCTAAACTGGGAGTCTTGTTGACCATCTGTCTGCTTCTGTTTCCCC (SEQ ID NO:163)

TTACTGCTCTTCCGCTGGATGGAGATCAACCTGCAGACCAACGTGCAGAGCGTACG

CAGGCCGAGAAGCATTCCTTGCCTGATCCGAGAATGGGCTGTTGCCCGTTTCCATGC

AAAACCAGTTGCACTACTTTGTGTTGCGGGTGATGATAACGTGTTGATGACCAACTT

TCTCGAG

Translation:

GSMMSKLGVLLTICLLLFPLTALPLDGDQPADQRAERTQAEKHSLPDPRMGCCPFPCKT (SEQ ID NO:164)

SCTTLCCG

Toxin Sequence:

Met-Gly-Cys-Cys-Xaa3-Phe-Xaa3-Cys-Lys-Thr-Ser-Cys-Thr-Thr-Leu-Cys-Cys-# (SEQ ID NO:165)

Name: U014
Species: *marmoreus*
Isolated: Yes

Toxin Sequence:

Cys-Cys-His-Xaa4-Asn-Xaa4-Cys-Asp-His-Leu-Cys-Ser-Cys-Ser-Cys-Cys-Gly-Ser-^ (SEQ ID NO:166)

Name: U017
Species: *marmoreus*
Cloned: Yes

DNA Sequence:

GCCAAGCTTGCATGCCTGCAGGATGACTCTAGAGGATCCCCACCTCAAGAGGGATC (SEQ ID NO:167)

GATAGCAGTTCATGATGTCTAAACTGGGAGTCTTGTTGACCATCTGTCTACTTCTGTT

TGCCCTTACTGCTGTTCCGCTGGATGGAGATCAACCTGCAGACCGACCTGCAGAACG

TATGCAGGACGACATTTCATCTGAACGTCATCCCATGTTTGATGCCGTCAGAGATTG

TTGCCCGTTGCCGGCATGCCCCTTTGGATGCAACCCTTGTTGTGGATGACCAGCTTT

TABLE 1-continued

DNA and Amino Acid Sequences of µ-Conopeptides and Precursors

GTTATCGGGACCTCATCAAGTGTCTAATGAATAAGTAAAAAACGATTCGAGTGGGT

ACCGAGCTCGAATTCC

Translation:

MMSKLGVLLTICLLLFALTAVPLDGDQPADRPAERMQDDISSERHPMFDAVRDCCPLP  (SEQ ID NO:168)

ACPFGCNPCCG

Toxin Sequence:

Asp-Cys-Cys-Xaa3-Leu-Xaa3-Ala-Cys-Xaa3-Phe-Gly-Cys-Asn-Xaa3-Cys-Cys-#  (SEQ ID NO:169)

Name: U019
Species: *marmoreus*
Isolated: Yes

Toxin Sequence:

Cys-Cys-Ala-Xaa3-Ser-Ala-Cys-Arg-Leu-Gly-Cys-Arg-Xaa3-Cys-Cys-Arg-^  (SEQ ID NO:170)

Name: U020
Species: *marmoreus*
Isolated: Yes

Toxin Sequence:

Cys-Cys-Ala-Xaa3-Ser-Ala-Cys-Arg-Leu-Gly-Cys-Arg-Xaa3-Cys-Cys-Arg-^  (SEQ ID NO:171)

Name: U022
Species: *marmoreus*
Isolated: Yes

Toxin Sequence:

Cys-Cys-Ala-Xaa3-Ser-Ala-Cys-Arg-Leu-Gly-Cys-Arg-Xaa3-Cys-Cys-Arg-^  (SEQ ID NO:172)

Name: U024
Species: *marmoreus*
Isolated: Yes

Toxin Sequence:

Gly-Cys-Cys-Gly-Ser-Phe-Ala-Cys-Arg-Phe-Gly-Cys-Val-Xaa3-Cys-Cys-Val-^  (SEQ ID NO:173)

Name: Nb3.1
Species: *nobilis*
Cloned: Yes

DNA Sequence:

GGATCCATGATGTCTAAACTGGGAGTCTTGTTGACCATCTGTCTACTTCTGTTTCCCC  (SEQ ID NO:174)

TTACTGCTCTTCCGCTGGATGAAGATCAACCGGTACACCGACCTGCAGAGCGTATGC

AGGACATTTCATCTGATCAACATCTCTTCTTTGATCTCATCAAACGGTGCTGCGAGT

TGCCATGCGGGCCAGGCTTTTGCGTCCCTTGTTGCTGACATCAATAACGTGTTGATG

ACCAACTTTCTCGAG

Translation:

GSMMSKLGVLLTICLLLFPLTALPLDEDQPVHRPAERMQDISSDQHLFFDLIKRCCELPC  (SEQ ID NO:175)

GPGFCVPCC

Toxin Sequence:

Cys-Cys-Xaa1-Leu-Xaa3-Cys-Gly-Xaa3-Gly-Phe-Cys-Val-Xaa3-Cys-Cys-^  (SEQ ID NO:176)

Name: Nb3.2
Species: *nobilis*
Cloned: Yes

TABLE 1-continued

DNA and Amino Acid Sequences of μ-Conopeptides and Precursors

DNA Sequence:

GGATCCATGATGTCTAAACTGGGAGTCTTGTTGACCATCTGTCTACTTGTGTTTCCCC (SEQ ID NO:177)

TTACTGCTTTTCCGATGGATGGAGATCAACCTGCAGACCAACCTGCAGATCGTATGC

AGGACGACATTTCATCTGAGCAGTATCCCTTGTTTGATAAGAGACAAAAGTGTTGCA

CTGGGAAGAAGGGGTCATGCTCCGGCAAAGCATGCAAAAATCTCAAATGTTGCTCT

GGACGATAACGTGTTGATGACCAACTTTCTCGAG

Translation:

GSMMSKLGVLLTICLLLFPLTAFPMDGDQPADQPADRMQDDISSEQYPLFDKRQKCCT (SEQ ID NO:178)

GKKGSCSGKACKNLKCCSGR

Toxin Sequence:

Xaa2-Lys-Cys-Cys-Thr-Gly-Lys-Lys-Gly-Ser-Cys-Ser-Gly-Lys-Ala-Cys-Lys-Asn-Leu-Lys- (SEQ ID NO:179)

Cys-Cys-Ser-#

Name: Pu3.1
Species: *pulicarius*
Cloned: Yes

DNA Sequence:

GGATCCATGATGTCTAAACTGGGAGTTTTGTTGACCATCTGTCTGCTTCTGTTTCCCC (SEQ ID NO:180)

TTACTGCTGTTCCGCTGGATGGAGATCAACCTGCAGACCGACCTGCAGAGCGTATGC

AGGACATTGCAACTGAACAGCATCCCTTCTTTGATCCCGTCAAACGGTGTTGCAACA

GCTGTTACATGGGATGCATCCCTTGTTGCTTCTAGTAATAACGTGTTGATGACCAAC

TTTCTCGAG

Translation:

GSMMSRLGVLLTICLLLFPLTAVPLDGDQPADRPAERMQDIATEQHPFFDPVKCCNSC (SEQ ID NO:181)

YMGCIPCCF

Toxin Sequence:

Cys-Cys-Asn-Ser-Cys-Xaa5-Met-Gly-Cys-Ile-Xaa3-Cys-Cys-Phe-^ (SEQ ID NO:182)

Name: Qc3.1
Species: *quercinus*
Cloned: Yes

DNA Sequence:

GGATCCATGATGTCTAAACTGGGAGTCTTGTTGACCATCTGTCTGCTTCTGTTTCCCC (SEQ ID NO:183)

TTACAGCTCTTCAGCTGGATGGAGATCAACCTGCAGACCGACCTGCAGAGCGTACG

CAGGACATTGCATCTGAACAGTATCGAAAGTTTGATCAGAGACAGAGGTGTTGCCA

GTGGCCATGCCCCGGTAGTTGCAGATGCTGCCGTACTGGTTAACGTGTTGATGACCA

ACTTTCTCGAG

Translation:

GSMMSKLGVLLTICLLLFPLTALQLDGDQPADRPAERTQDIASEQYRKFDQRQRCCQW (SEQ ID NO:184)

PCPGSCRCCRTG

Toxin Sequence:

Xaa2-Arg-Cys-Cys-Gln-Xaa4-Xaa3-Cys-Xaa3-Gly-Ser-Cys-Arg-Cys-Cys-Arg-Thr-# (SEQ ID NO:185)

TABLE 1-continued

DNA and Amino Acid Sequences of µ-Conopeptides and Precursors

Name: QcIIIA
Species: *quercinus*
Isolated: Yes

Toxin Sequence:

Cys-Cys-Ser-Gln-Asp-Cys-Leu-Val-Cys-Ile-Xaa3-Cys-Cys-Xaa3-Asn-# (SEQ ID NO:186)

Name: QcIIIB
Species: *quercinus*
Isolated: Yes

Toxin Sequence:

Cys-Cys-Ser-Arg-His-Cys-Xaa4-Val-Cys-Ile-Xaa3-Cys-Cys-Xaa3-Asn-# (SEQ ID NO:187)

Name: R3.1
Species: *radiatus*
Isolated: Yes
Cloned: Yes

DNA Sequence:

TCAAGAAGGATCGATAGCAGTTCATGATGTCTAAACTGGGAGTCTTGTTGACCATCT (SEQ ID NO:188)

GTCTGCTTCTGTTTCCCCTTACTGCTCTTCCGATGGATGGAGATCAACCTGTAGACCG

ACTTGCAGAGCGTATGCAGGACAACATTTCATCTGAGCAGCATACCTTCTTTGAAAA

GAGACTACCATCGTGTTGCTCCCTTAACTTGCGGCTTTGCCCAGTACCAGCATGCAA

ACGTAACCCTTGTTGCACAGGATAACGTGTTGATGACCAACTTTGTTATCACGGCTA

CGTCAAGTGTCTAGTGAATAAGTAAAACGATTGCAGT

Translation:

MMSKLGVLLTICLLLFPLTALPMDGDQPVDRLAERMQDNISSEQHTFFEKRLPSCCSLN (SEQ ID NO:189)

LRLCPVPACKRNPCCTG

Toxin Sequence:

Leu-Xaa3-Ser-Cys-Cys-Ser-Leu-Asn-Leu-Arg-Leu-Cys-Xaa3-Val-Xaa3-Ala-Cys-LyS-Arg-Asn- (SEQ ID NO:190)

Xaa3-Cys-Cys-Thr-#

Name: R3.2
Species: *radiatus*
Cloned: Yes

DNA Sequence:

AGGTCGACTCTAGAGGATCCCCAAGGATCGATAGCAGTTCATGATGTCTAAACTGG (SEQ ID NO:191)

GAGTCTTGTTGACCATCTGTCTGCTTCTGTTTCCCCTTACTGCTCTTCCGATGGATGG

AGATCAACCTGCAGACCGACTTGCAGAGCGTATGCAGGACGACATTTCATCTGAGC

AGCATCCCTTCTTTAAAAAGAGACAACAAAGATGTTGCACCGTTAAGAGGATTTGT

CCAGTACCAGCATGCAGAAGTAAACCTTGTTGCAAATCATAACGTATTGATGACCA

ACTTTGTTATCACGGCTACGTCAAGTGTCTAGTGAATAAGTAAAATGATTGCAG

Translation:

MMSKLGVLLTICLLLFPLTALPMDGDQPADRLAERMQDDISSEQHPFFKKRQQRCCTV (SEQ ID NO:192)

KRICPVPACRSKPCCKS

Toxin Sequence:

Xaa2-Gln-Arg-Cys-Cys-Thr-Val-Lys-Arg-Ile-Cys-Xaa3-Val-Xaa3-Ala-Cys-Arg-Ser-Lys-Xaa3- (SEQ ID NO:193)

Cys-Cys-Lys-Ser-#

TABLE 1-continued

DNA and Amino Acid Sequences of μ-Conopeptides and Precursors

Name: R3.3
Species: *radiatus*
Cloned: Yes

DNA Sequence:

ACCTCAAGAAGGATCGATAGCAGTTCATGATGTCTAAACTGGGAGTCTTGTTGACC (SEQ ID NO:194)

ATCTGTCTGCTTCTGTTTCCCGTTACTGCTCTTCCGATGGATGGTGATCAACCTGCAG

ACCGACTTGTAGAGCGTATGCAGGACAACATTTCATCTGAGCAGCATCCCTTCTTTG

AAAAGAGAAGAGGAGGCTGTTGCACACCTCCGAGGAAATGCAAAGACCGAGCCTG

CAAACCTGCACGTTGCTGCGGCCCAGGATAACGTGTTGATGACCAACTTTGTTATCA

CGGCTACGTCAAGTGTCTAGTGAATAAGTAAAACGATTGCAGT

Translation:

MMSKLGVLLTICLLLFPVTALPMDGDQPADRLVERMQDNISSEQHPFFEKRRGGCCTPP (SEQ ID NO:195)

RKCKDRACKPARCCGPG

Toxin Sequence:

Arg-Gly-Gly-Cys-Cys-Thr-Xaa3-Xaa3-Arg-Lys-Cys-Lys-Asp-Arg-Ala-Cys-Lys-Xaa3-Ala-Arg- (SEQ ID NO:196)

Cys-Cys-Gly-Xaa3-#

Name: Ra3.1
Species: *rattus*
Cloned: Yes

DNA Sequence:

GGATCCATGATGTCTAAACTGGGAGTCTTGGTGACCATCTGCCTGCTTCTGTTCCCT (SEQ ID NO:197)

CTTGCTGCTTTTCCACTGGATGGAGATCAACCTGCAGACCACCCTGCAAAGCGTACG

CAAGATGACAGTTCAGCTGCCCTGATCAATGCCTGGCTTGATGAATCCCAGACTTGC

TGCAGTAACTGCGGTGAAGATTGTGATGGTTGTTGCCAGTAACGTGTTGATGACCAA

CTTTCTCGAG

Translation:

GSMMSKLGVLVTICLLLFPLAAFPLDGDQPADHPAKRTQDDSSAALINAWLDESQTCCS (SEQ ID NO:198)

NCGEDCDGCCQ

Toxin Sequence:

Xaa2-Thr-Cys-Cys-Ser-Asn-Cys-Gly-Xaa1-Asp-Cys-Asp-Gly-Cys-Cys-Gln-^ (SEQ ID NO:199)

Name: Sm3.1
Species: *stercusmuscarum*
Cloned: Yes

DNA Sequence:

GACCTCAAGAGGGATCGATAGCAGTTCGTGATGTCTAAACTGGGAGTCTTGTTGAC (SEQ ID NO:200)

CATCTGTCTGCTTCTGTTTCCTCTTACTGCTCTTCCGATGGATGGAGATCAACCTGCA

GACCAACCTGCAGATCGTATGCAGGACGACATTTCATCTGAGCAGTATCCCTTGTTT

GATAAGAGACAAAAGTGTTGCACTGGGAAGAAGGGGTCATGCTCCGGCAAAGCAT

GCAAAAATCTCAAATGTTGCTCTGGACGATAACGTGTTGATGACCAACTTTGTTATC

ACGGCTACGTCAAGTGTCTAATGAATAAGTAAAACGATTGCAGT

Translation:

MSKLGVLLTICLLLFPLTALPMDGDQPADQPADRMQDDISSEQYPLFDRRQKCCTGKK (SEQ ID NO:201)

TABLE 1-continued

DNA and Amino Acid Sequences of μ-Conopeptides and Precursors

GSCSGKACKNLKCCSGR

Toxin Sequence:

Xaa2-Lys-Cys-Cys-Thr-Gly-Lys-Lys-Gly-Ser-Cys-Ser-Gly-Lys-Ala-Cys-Lys-Asn-Leu-Lys- (SEQ ID NO:202)

Cys-Cys-Ser-#

Name: U034
Species: *stercusmuscarum*
Isolated: Yes
Cloned: Yes

DNA Sequence:

GATCGATAGCAGTTCGTGATGTCTAAACTGGGAGTCTTGTTGACCATCTGTCTGCTT (SEQ ID NO:203)

CTGTTTCCCCTTACTGCTCTTCCGATGGATGGAGATCAACCTGCAGACCAACCTGCA

GATCGTATGCAGAACGACATTTCATCTGAGCAGTATCCCTTGTTTGATAAGAGACAA

AAGTGTTGCGGCCCCGGCGCGTCATGCCCCAGATATTTCAAAGACAATTTTATTTGT

GGTTGTTGTTAAATGACAACGTGTCGATGACCAACTTCGTTATCACGACTTCGCCAA

GTGTCTAATGAATAAGTAAAACGATTGCAGT

Translation:

MSKLGVLLTICLLLFPLTALPMDGDQPADQPADRMQNDISSEQYPLFDKRQKCCGPGAS (SEQ ID NO:204)

CPRYFKDNFICGCC

Toxin Sequence:

Xaa2-Lys-Cys-Cys-Gly-Xaa3-Gly-Ala-Ser-Cys-Xaa3-Arg-Xaa5-Phe-Lys-Asp-Asn-Phe-Ile- (SEQ ID NO:205)

Cys-Gly-Cys-Cys-^

Name: S3.1
Species: *striatus*
Cloned: Yes

DNA Sequence:

CGACCTTTCAAGAGGGATCGATAGCAGTTCGCGATGTCTAAACTGGGGGTATTGTTG (SEQ ID NO:206)

ACCATCTGTCTGCTTCTGTTTCCCCTTACTGCTCTTCCGATGGATGAAGATCAACCTG

CAGACCAACTTGAAGATCGTATGCAGGACGACATTTCATCTGAGCAGTATCCCTCGT

TTGTTAGGAGACAAAAGTGTTGCGGCGAAGGCTCGTCATGCCCCAAATATTTCAAA

AACAATTTTATTTGTGGTTGTTGTTAAATGACAACGTGTCGATGACCAACTTCGTTA

TCACGACTACGCCAAGTGTCTTGTCTAATGATAATAAAATGATTCC

Translation:

MSKLGVLLTICLLLFPLTALPMDEDQPADQLEDRMQDDISSEQYPSFVRRQKCCGEGSS (SEQ ID NO:207)

CPKYFKNNFICGCC

Toxin Sequence:

Xaa2-Lys-Cys-Cys-Gly-Xaa1-Gly-Ser-Ser-Cys-Xaa3-Lys-Xaa5-Phe-Lys-Asn-Asn-Phe-Ile-Cys- (SEQ ID NO:208)

Gly-Cys-Cys-^

Name: S3.2
Species: *striatus*
Cloned: Yes

DNA Sequence:

GGATCCATGATGTCTAAACTGGGAGTCTTGTTGACCGTCTGTCTGCTTCTGTTTCCCC (SEQ ID NO:209)

TABLE 1-continued

DNA and Amino Acid Sequences of μ-Conopeptides and Precursors

TTACTGCTCTTCCGCTGGATGGAGATCAACCTGCAGACCGACCTGCAGAGCGTATGC

AGGACGACATTTCATCTGACGAGCATCCCTTGTTTGATAAGAGACAAAACTGTTGCA

ATGGGGATGCTCCAGCAAATGGTGCAGAGATCACGCACGTTGTTGCGGTCGATGA

TAACGTGTTGATGACCAACTTTCTCGAG

Translation:

GSMMSKLGVLLTVCLLLFPLTALPLDGDQPADRPAERMQDDISSDEHPLFDKRQNCCN (SEQ ID NO:210)

GGCSSKWCRDHARCCGR

Toxin Sequence:

Xaa2-Asn-Cys-Cys-Asn-Gly-Gly-Cys-Ser-Ser-Lys-Xaa4-Cys-Arg-Asp-His-Als-Arg-Cys-Cys-# (SEQ ID NO:211)

Name: Ts3.1
Species: *tessulatus*
Cloned: Yes

DNA Sequence:

GGATCCATGATGTCTAAACTGGGAGTCTTGTTGACCATGTGTCTGCTTCTGTTTCCCC (SEQ ID NO:212)

TTACTGCTGTTCCGCTGGATGGAGATCAACCTGCAGACCGACCTGCAGAGCGTAGG

CAGGACATTGCAACTGACGATCATCCTTTGTTTGATCCCGTCAAACGGTGCTGCCAC

AAATGCTATATGGGATGCATCCCTTGTTGCATTTAGTAACGTGTTGATGACCAACTT

TCTCGAG

Translation:

GSMMSKLGVLLTMCLLLFPLTAVPLDGDQPADRPAERRQDIATDDHPLFDPVKRCCHK (SEQ ID NO:213)

CYMGCIPCCI

Toxin Sequence:

Cys-Cys-His-Lys-Cys-Xaa5-Met-Gly-Cys-Ile-Xaa3-Cys-Cys-Ile-^ (SEQ ID NO:214)

Name: Ts3.2
Species: *tessulatus*
Cloned: Yes

DNA Sequence:

GGATCCATGATGTCTAAACTGGGAGTCTTGTTGACCATCTGTGTGCTTCTGTTTCCCC (SEQ ID NO:215)

TTACTGCTGTTCCGCTGGATGGAGATCAACCTGCAGACCAACCTGCAGAGCGTACG

CAGAACGAGCAGCATCCCTTGTATGATCAGAAAAGAAAGTGTTGCCGGCCGCCATG

CGCCATGAGCTGCGGCATGGCTAGGTGTTGCTATTAATGATAACGTGTTGATGACCA

ACTTTCTCGAG

Translation:

GSMMSKLGVLLTICVLLFPLTAVPLDGDQPADQPAERTQNEQHPLYDQKRKCCRPPCA (SEQ ID NO:216)

MSCGMARCCY

Toxin Sequence:

Lys-Cys-Cys-Arg-Xaa3-Xaa3-Cys-Ala-Met-Ser-Cys-Gly-Met-Ala-Arg-Cys-Cys-Xaa5-^ (SEQ ID NO:217)

Name: Circling
Species: textile
Isolated: Yes
Cloned: Yes

TABLE 1-continued

DNA and Amino Acid Sequences of μ-Conopeptides and Precursors

DNA Sequence:

GAGTCAACCCACTGTCACGCCAAGAGCGGACGCCACAGCTAAGGCAAGAAGGATC (SEQ ID NO:218)

GATAGCAGTTCATGATGTCTAAACTGGGAGCCTTGTTGACCATCTGTCTACTTCTGT

TTTCCCTTACTGCTGTTCCGCTGGATGGAGATCAACATGCAGACCAACCTGCACAGC

GTCTGCAGGACCGCATTCCAACTGAAGATCATCCCTTATTTGATCCCAACAAACGGT

GTTGCCCGCCGGTGGCATGCAACATGGGATGCAAGCCTTGTTGTGGATGACCAGCTT

TGTTATCGCGGTCTCATGAAGTGTCTAATGAATAAGTAAAACGATTGCAGTTTCGTT

CAGATTTGCTGTTGTATTTTGGTCTAAAGATTAATGACCAAACTGTTCTTTTGATCCG

GATTTTCACGTATTTCTCGATTCCTATTCAACACTAGATAAGTTAATCACGACAGAT

CTGATTTTCCATCAATGCCTTGCTTTTTGGTCTGTCATATAAATCTTGTTTATATTTAA

TTTCTCGTCACTTTCAACACGCACACACACACACACACACGCGCGC

Translation:

MMSKLGALLTICLLLFSLTAVPLDGDQHADQPAQRLQDRIPTEDHPLFDPNKRCCPPVA (SEQ ID NO:219)

CNMGCKPCCG

Toxin Sequence:

Cys-Cys-Xaa3-Xaa3-Val-Ala-Cys-Asn-Met-Gly-Cys-Lys-Xaa3-Cys-Cys-Gly-^ (SEQ ID NO:220)

Name: Scratcher I
Species: textile
Cloned: Yes

DNA Sequence:

GGATCCAGACGACAAAGAAGAGTCAACCCACTGCCACGTCAAGAGCAGAGCCCAC (SEQ ID NO:221)

AGCTAAGACAAGAAGGATCGATAGCAGTTCATGATGTTTAAACTGGGAGTCTTGTT

GACCATCTGTCTCCTTCTGTTTTCCCTTAATGCTGTTCCGTTGGATGGAGATCAACCT

GCAGACCAACCTGCAGAGCGTCTGCTGGACGACATTTCATTTGAAAATAATCCCTTT

TATGATCCCGCCAAACGGTGTTGCAGGACTTGCTTCGGTTGCACACCTTGTTGTGGA

TGACCAGCCTCATCAAGTGTCTAACGAATAAGTAAAGCGATTGCAGTCTCGTTCAG

ATTTACTTTTGTATTCTGGTCTAAAGATTAATGACCAAACTCTTCTTTTGATCCGGAT

GTACATATATTTCTCGATTCCTATCCAACGCTAGATAAGCTAATCACGACAGATCTG

ATTTTCTGTCAATGCCTTGCTTTTTGGTCTCTCATATCACTCTTGTTTATATTTAATTT

CTCGTCACTATATATATATACACACACACACACACACGGAATTCCGATTGTCCAGTA

CCGTTCTTGGGATCGAGGTATTGCTGCGATGGCTTATTCTGTACTCTTTTCTTCTGCG

CTTGATAGTGATGTCTTCTACTCCCATCTGTGCTACCCCTGGCTTGATCTTTGATAGG

CGTGTGCCCTTCACTGGTTATAAACCCCTCTGATCCTACTCTCTGGACGCCTCGGGG

GCCCAACCTCCAAATAAAGCGACATCCAATGAAAAAA

Translation:

MMFKLGVLLTICLLLFSLNAVPLDGDQPADQPAERLLDDISFENNPFYDPAKRCCRTCF (SEQ ID NO:222)

GCTPCCG

Toxin Sequence:

Cys-Cys-Arg-Thr-Cys-Phe-Gly-Cys-Thr-Xaa3-Cys-Cys-# (SEQ ID NO:223)

TABLE 1-continued

DNA and Amino Acid Sequences of μ-Conopeptides and Precursors

Name: Tx3.1
Species: textile
Cloned: Yes

DNA Sequence:

GGAACAGTCAACCCCACAGCCACGCCAAGAGCAGACAGCCACAGCTACGTGAAGA (SEQ ID NO:224)

AGGGTGGAGAGAGGTTCATGATGTTGAAAATGGGAGTGGTGCTATTCATCTTTCTGG

TACTGTTTCCCCTGGCAACGCTCCAGCTGGATGCAGATCAACCTGTAGAACGATATG

CGGAGAACAAACAGCTCCTCAACCCAGATGAAAGGAGGGAAATCCTATTGCCTGCT

CTGAGGAAGTTCTGCTGTGATTCGAATTGGTGCCACATTTCGGATTGTGAGTGCTGC

TACGGTTAGCGCCGAACATCCATGGCACTGTGCTGGGCGGTTTCATCCCAACAACG

ACAGCGTTTGTTGATTTCATGTATCATTGCGCCCACGTCTCTTGTCTAAGAATGACG

AACATGATTGCACTCTGGTTCAGATTTCGTGTTCTTTTCTGACAATAAATGACAAAcC

TCC

Translation:

MMLKMGVVLFIFLVLFPLATLQLDADQPVERYAENKQLLNPDERREILLPALRKIFCCDS (SEQ ID NO:225)

NWCHISDCECCYG

Toxin Sequence:

Phe-Cys-Cys-Asp-Ser-Asn-Xaa4-Cys-His-Ile-Ser-Asp-Cys-Xaa1-Cys-Cys-Xaa5-# (SEQ ID NO:226)

Name: U031
Species: textile
Isolated: Yes
Cloned: Yes

DNA Sequence:

CAAGGAACAGTCAACCCCACAGCCACGCCAAGAGCAGACAGCCACAGCTACGTGA (SEQ ID NO:227)

AGAAGGGTGGAGAGAGGTTCGTGATGTTGAAAATGGGAGTGGTGCTATTCATCTTC

CTGGTACTGTTTCCCGTGGCAACGCTCCAGCTGGATGCAGATCAACCTGTAGAACGA

TATGCGGAGAACAAACAGCTCCTCAGCCCAGATGAAAGGAGGGAAATCATATTGCA

TGCTCTGGGGACGCGATGCTGTTCTTGGGATGTGTGCGACCACCCGAGTTGTACTTG

CTGCGGTTAGCGCCGAACATCCATGGCGCTGTGCTGGGCGGTTTTATCCCAACAACG

ACAGCGTTTGTTGATTTCATGTATCATTGCGCCCACGTCTCTTGTCTAAGAATGACG

AACATGATTGCACTCTGGTTCAGATTTCGTGTTCTTTTCTGACAATAATGACAAAA

CNCC

Translation:

MLKMGVVLFIFLVLFPLATLQLDADQPVERYAENKQLLSPDERRIILHALGTRCCSWD (SEQ ID NO:228)

VCDHPSCTCCG

Toxin Sequence:

Cys-Cys-Ser-Xaa4-Asp-Val-Cys-Asp-His-Xaa3-Ser-Cys-Thr-Cys-Cys-# (SEQ ID NO:229)

Name: U032
Species: textile
Isolated: Yes
Cloned: Yes

DNA Sequence:

GGATCCATGATGTCTAAACTGGGAGTCTTGTTGACCATCTGTCTGCTTCTGTTTCCCC (SEQ ID NO:230)

TABLE 1-continued

DNA and Amino Acid Sequences of μ-Conopeptides and Precursors

TTACTGCTCTTCCGCTGGATGGAGATCAACCCGCAGACCAAGCTGCAGAGCGTATG

CAGGCCGAGCAGCATCCCTTGTTTGATCAGAAAAGACGGTGCTGCAAGTTTCCATG

CCCCGATAGTTGCAGATATTTGTGTTGCGGGTGATGATAACGTGTTGATGACCAACT

TTCTCGAG

Translation:

GSMMSKLGVLLTICLLLFPLTALPLDGDQPADQAAERMQAEQHPLFDQKRRCCKFPCP (SEQ ID NO:231)

DSCRYLCCG

Toxin Sequence:

Arg-Cys-Cys-Lys-Phe-Xaa3-Cys-Xaa3-Asp-Ser-Cys-Arg-Xaa5-Leu-Cys-Cys-# (SEQ ID NO:232)

Name: T3.1
Species: *tulipa*
Cloned: Yes

DNA Sequence:

CGACCTCAAGAGGGATCGATAGCAGTTCATGTCTAAACTGGGAGTCTTGTTGACAA (SEQ ID NO:233)

TCTGTCTGCTTCTGTTTCCCCTTACTGCTCTGCCGATGGATGGAGATGAACCTGCAG

ACCGACCTGCAGAGCGTATGCAGGACAACATTTCATCTGAGCAGCATCCCTTGTTTG

AGGAGAGACACGGATGTTGCAAGGGGCCCGAAGGATGCTCCTCCAGAGAATGCAG

ACCCCAACATTGTTGCGGTCGACGATAACGTGTTGAGGGCCAACTTTGTTATCACGG

CTACGTCAAGTGTTTAGTGAATAAGTAAAATGATTGCAG

Translation:

MSKLGVLLTICLLLFPLTALPMDGDEPADRPAERMQDNISSEQHPLFEERHGCCKGPEG (SEQ ID NO:234)

CSSRECRPQHCCGRR

Toxin Sequence:

His-Gly-Cys-Cys-Lys-Gly-Xaa3-Xaa1-Gly-Cys-Ser-Ser-Arg-Xaa1-Cys-Arg-Xaa3-Gln-His- (SEQ ID NO:235)

Cys-Cys-#

Name: Fi3.1
Species: *figulinus*
Cloned: Yes

DNA Sequence:

CAAGAAGGATCGATAGCAGTTCATGATGTCTAAACTGGGAGTCTTGCTGACCATCT (SEQ ID NO:236)

GTCTGCTTCTGATTCCCCTTACTGCTCTTTCGCTGGATGGAGATCAACCTGCAGACC

GACCTGCAGAGCGTATGCAGGATGGAATTTCATCTGAACAGCATCCATGTTTGATC

CCGTCAGACGGTGTTGCCCGTGGCCATGCAACATAGGATGCGTACCTTGTTGTTGAT

GACCAGTTTTGTTATCGCGGCCTCATCAAATGTCTAATGAATAAGTAAAACGATTGC

AGT

Translation:

MMSKLGVLLTICLLLIPLTALSLDGDQPADRPAERMQDGISSEQHPMFDPVRRCCPWPC (SEQ ID NO:237)

NIGCVPCC

Toxin Sequence:

Cys-Cys-Xaa3-Xaa4-Xaa3-Cys-Asn-Ile-Gly-Cys-Val-Xaa3-Cys-Cys-^ (SEQ ID NO:238)

TABLE 1-continued

DNA and Amino Acid Sequences of μ-Conopeptides and Precursors

Name: Fi3.2
Species: *figulinus*
Cloned: Yes

DNA Sequence:

CAAGAGGGATCGATAGCAGTTCATGATGTTTAAACTGGGAGTCCTGTTGACCATCTG (SEQ ID NO:239)

TATGCTTCTGTTTCCCTTTACTGCTCTTCCGCTGGATGGAGAGCAACCTGCAGACCA

ACCTGCAGAGCGCATGCAGTATGACATGTTACGTGCAATGAATCCCTGGTTTGATCC

CGTCAAAAGGTGCTGCTCGAAGAACTGCGCAGTATGCATCCCTTGTTGCCCGTAACT

GACCAGCTTGATTATCGCGGCCAAGGCTCTAATGAATAAGTAAAACGATTGCAGT

Translation:

MMFKLGVLLTICMLLFPFTALPLDGEQPA QPAERMQYDMLRAMNPWFDPVRRCCSK (SEQ ID NO:240)

NCAVCIPCCP

Toxin Sequence:

Cys-Cys-Ser-Lys-Asn-Cys-Ala-Val-Cys-Ile-Xaa3-Cys-Cys-Xaa3-^ (SEQ ID NO:241)

Name: Fi3.3
Species: *figulinus*
Cloned: Yes

DNA Sequence:

CAAGAGGGATCGATAGCAGTTCATGATGTCTAAACTGAGAGTCTTGTTGACCTTATG (SEQ ID NO:242)

TCTGCTTCTGTTTCCCCTTACTGCTCTTCCGCTGAATGAAGATCAACCTGCAGAGCGT

ATGCAGGACGACAATTCATCTGAGCAGCACCCCTTGTATGACCACAAACGAAAGTG

TTGCCGGTGGCCATGCCCCGCAAGATGCGGCTCTTGTTGCCTGTAATAACGTGTTGG

CCAACTTTGTTATCACGGCCACGTCAAATGTTTAATGAATAAGTAAAACGATTGCAG

T

Translation:

MMSKLRVLLTLCLLLFPLTALPLNEDQPAERMQDDNSSEQHPLYDHKRKCCRWPCPAR (SEQ ID NO:243)

CGSCCL

Toxin Sequence:

Cys-Cys-Arg-Xaa4-Xaa3-Cys-Xaa3-Ala-Arg-Cys-Gly-Ser-Cys-Cys-Leu-^ (SEQ ID NO:244)

Name: Fi3.4
Species: *figulinus*
Cloned: Yes

DNA Sequence:

CAAGAGGGATCGATAGCAGTTCATGATGTCTAAACTGGGAGTCTTGTTGACCTTATG (SEQ ID NO:245)

TCTGCTTCTGTTTCCCCTGACTGCTCTTCCGCTGGATGAAGATCAAGCTGCAGACCG

ACCTGCAGAGCGTATGCAGGGCATGTCATCTGAACAGCATCCCTTCTTTGATCCCGT

CAAACGGTGTTGCGAGTTGTCACGCTGCCTTGGATGCGTCCCTTGTTGCACATCTTA

ATAACGTGTGGATGACCAACTGTGTTATCACGGCCACGTCAAGTGTCTAATGAATA

AGTAAAATGATTGCAGT

Translation:

MMSKLGVLLTLCLLLFPLTALPLDEDQAADRPAERMQGMSSEQHPFFDPVKRCCELSR (SEQ ID NO:246)

CLGCVPCCTS

TABLE 1-continued

DNA and Amino Acid Sequences of μ-Conopeptides and Precursors

Toxin Sequence:

Cys-Cys-Xaa1-Leu-Ser-Arg-Cys-Leu-Gly-Cys-Val-Xaa3-Cys-Cys-Thr-Ser-^ (SEQ ID NO:247)

Name: Fi3.5
Species: *figulinus*
Cloned: Yes

DNA Sequence:

CAAGAGGGATCGATAGCAGTTCATGATGTCTAAACTGGGAGTCTTGTTGACCTTATG (SEQ ID NO:248)

TCTGCTTCTGTTTCCCCTGACTGCTCTTCCGCTGGATGAAGATCAACCTGCAGACCG

ACCTGCAGAGCGTATGCAGGGCATGTCATCTGAACAGCATCCCTTCTTTGATCCCGT

CAAACGGTGTTGCGAGTTGTCAAAATGCCATGGATGCGTCCCTTGTTGCATACCTTA

ATAACGTGCGGATGACCAACTGTGTTATCACGGCCACGTCAAGTGTCTAATGAATA

AGTAAAATGATTGCAGT

Translation:

MMSKLGVLLTLCLLLFPLTALPLDEDQPADRPAERMQGMSSEQHPFFDPVKRCCELSK (SEQ ID NO:249)

CHGCVPCCIP

Toxin Sequence:

Cys-Cys-Xaa1-Leu-Ser-Lys-Cys-His-Gly-Cys-Val-Xaa3-Cys-Cys-Ile-Xaa3-^ (SEQ ID NO:250)

Name: Qc3.2
Species: *quercinus*
Cloned: Yes

DNA Sequence:

CAAGAGGGATCGATAGCAGTTCATGATGTCTAAACTCGGAGTCTTGTTGACCATCTG (SEQ ID NO:251)

TCTGGTTCTGTTTCCCCTTACAGCTCTTCAGCTGGATGGAGATCAACCTGCAGACCG

ACCTGCAGAGCGTACGCAGGACATTTCATCTGAACAGTATCGAAAGTTTGATCAGA

GACAGAGGTGTTGCCGGTGGCCATGCCCCGGTAGTTGCAGATGCTGCCGTTATCGTT

AACGTGTTGGTGACCAGCTTTGTTATCACGACCACGCCAAGTGTCTAACGAATAAGT

AAAATGATTGCAGT

Translation:

MMSKLGVLLTICLVLFPLTALQLDGDQPADRPAERTQDISSEQYRKFDQRQRCCRWPCP (SEQ ID NO:252)

GSCRCCRYR

Toxin Sequence:

Xaa2-Arg-Cys-Cys-Arg-Xaa4-Xaa3-Cys-Xaa3-Gly-Ser-Cys-Arg-Cys-Cys-Arg-Xaa5-Arg-^ (SEQ ID NO:253)

Name: Qc3.3
Species: *quercinus*
Cloned: Yes

DNA Sequence:

CAAGAGGGATCGATAGCAGTTCATGATGTCTAAACTGGGAGTCTTGTTGACCATCTG (SEQ ID NO:254)

TCTGCTTCTGTTTCCCCTTACTGCTCTTCCACTGGATGGAGATCAACCTGCAGATCAA

TCTGCAGAGCGACCTGCAGAGCGTACGCAGGACGACATTCAGCAGCATCCGTTATA

TGATCCGAAAAGAAGGTGTTGCCGTTATCCATGCCCCGACAGCTGCCACGGATCTTG

CTGCTATAAGTGATAACATGTTGATGGCCAGCTTTGTTATCACGGCCACGTCAAGTG

TABLE 1-continued

DNA and Amino Acid Sequences of µ-Conopeptides and Precursors

TCTAATGAATAAGTAAAACGATTGCAGT

Translation:

MMSKLGVLLTICLLLFPLTALPLDGDQPADQSAERPAERTQDDIQQHPLYDPKRRCCRY (SEQ ID NO:255)

PCPDSCHGSCCYK

Toxin Sequence:

Arg-Cys-Cys-Arg-Xaa5-Xaa3-Cys-Xaa3-Asp-Ser-Cys-His-Gly-Ser-Cys-Cys-Xaa5-Lys-^ (SEQ ID NO:256)

Name: Wi3.1
Species: *wittigi*
Cloned: Yes

DNA Sequence:

GGATCCATGATGTCTAAACTGGGAGTCTTGTTGACCATCTGTCTGCTTCTGTTTCCCA (SEQ ID NO:257)

TTACTGCTCTTCCGGTGGGTGGAGATCAGCCTGCAGACCGACTTGCAGAGCGTATGC

AGGACGACACTTCATCTGAGCAGCATCCCTTTGAAAAGAGACTACCATCATGTTGC

GACTTTGAGAGGCTTTGCGTAGTACCAGCATGCATACGTCATCAGTGTTGCACAGGA

TAACGTGTTGATGACCAACTTTCTCGAG

Translation:

MMSKLGVLLTICLLLFPITALPVGGDQPADRLAERMQDDTSSEQHPFEKRLPSCCDFERL (SEQ ID NO:258)

CVVPACIRHQCCTG

Toxin Sequence:

Leu-Xaa3-Ser-Cys-Cys-Asp-Phe-Xaa1-Arg-Leu-Cys-Val-Val-Xaa3-Ala-Cys-Ile-Arg-His-Gln- (SEQ ID NO:259)

Cys-Cys-Thr-#

Name: bt3a
Species: *betulinus*
Isolated: Yes

Toxin Sequence:

Cys-Cys-Lys-Gln-Ser-Cys-Thr-Thr-Cys-Met-Xaa3-Cys-Cys-Xaa4-^ (SEQ ID NO:260)

Name: T3.2
Species: *tulipa*
Cloned: Yes

DNA Sequence:

GGATCCATGATGTCTAAACTGGGAGTCTTGTTGACAATCTGTCTGCTTCTGTTTCCCC (SEQ ID NO:261)

TTACTGCTCTGCCGATGGATGGAGATGAACCTGCAGACCGACCTGCAGAGCGTATG

CAGGACAACATTTCATCTGAGCAGCATCCCTTGTTTGAGGAGAGACACGGATGTTG

CGAGGGGCCGAAGGGATGCTCCTCCAGAGAATGCAGACCCCAACATTGTTGCGGTC

GACGATAACGTGTTGATGACCAACTNTCTCGAG

Translation:

MMSKLGVLLTICLLLFPLTALPMDGDEPADRAPAERMQDNISSEQHPLFEERHGCCEGPK (SEQ ID NO:262)

GCSSRECRPQHCCGRR

Toxin Sequence:

His-Gly-Cys-Cys-Xaa1-Gly-Xaa3-Lys-Gly-Cys-Ser-Ser-Arg-Xaa1-Cys-Arg-Xaa3-Gln-His- (SEQ ID NO:263)

Cys-Cys-#

TABLE 1-continued

DNA and Amino Acid Sequences of μ-Conopeptides and Precursors

Name: A3.5
Species: *aurisiacus*
Cloned: Yes

DNA Sequence:

GGATCCATGATGTCTAAACTGGGAGTCTTGTTGACCATCTGTCTACTTCTGTTTCCCC (SEQ ID NO:264)

TTACTGCTTTTCCGATGGATGGAGATCAACCTGCAGACCAACCTGCAGATCGTATGC

AGGACGACATTTCATCTGAGCAGTATCCCTTGTTTGATAAGAGACAAAGTGTTGCA

CTGGGAGGAAGGGGTCATGCTCCGGCAAAGCATGCAAAAATCTCAAATGTTGCTCT

GGACGATAACGTGTTGATGACCAACTTTCTCGAN

Translation:

MMSKLGVLLTICLLLFPLTAFPMDGDQPADQPADRMQDDISSEQYPLFDKRQKCCTGR (SEQ ID NO:265)

KGSCSGKACKNLKCCSGR

Toxin Sequence:

Xaa2-Lys-Cys-Cys-Thr-Gly-Arg-Lys-Gly-Ser-Cys-Ser-Gly-Lys-Ala-Cys-Lys-Asn-Leu-Lys- (SEQ ID NO:266)

Cys-Cys-Ser-#

Name: Bt3.5
Species: *betulinus*
Cloned: Yes

DNA Sequence:

GGATCCATGATGTCTAAACTGGGAGTCTTGTTGACCATCTGTCTGCTTCTGTTTCCCC (SEQ ID NO:267)

TTACTGCTGTTCCGTTGGATGGAGATCAACCTGCAGACCAACCTGCAGAGCGTATGC

AGAACGAGCAGCATCCCTCGTTTGATCAGAAAAGAAGGTGCTGCCGGTGGCCATGC

CCCAGTATATGCGGCATGGCTAGGTGTTGCTTCGTCATGATAACGTGTTGATGACCA

ACTTTCTCGAG

Translation:

MMSKLGVLLTICLLLFPLTAVPLDGDQPADQPAERMQNEQHPSFDQKRRCCRWPCPSIC (SEQ ID NO:268)

GMARCCFVMITC

Toxin Sequence:

Arg-Cys-Cys-Arg-Xaa4-Xaa3-Cys-Xaa3-Ser-Ile-Cys-Gly-Met-Ala-Arg-Cys-Cys-Phe-Val-Met- (SEQ ID NO:269)

IIe-Thr-Cys-^

Name: Bt3.6
Species: *betulinus*
Cloned: Yes

DNA Sequence:

GGATCCATGATGTCTAAACTGGGAGTCTTGTTGATCATCTGTCTGCTTCTGTTTCCCC (SEQ ID NO:270)

TTACTGCTGTTCCGCTGGATGGAGATCAGCCTGCAGAGCGTACGCAGATCGAGCAG

CATCCCTTGTTTGACCAGAAAAGAAGGTGTTGCCGGTGGCCATGCCCCAGTAGATG

CGGCATGGCTAGGTGTTGCTTCGTCATGATAACGTGTTGATGANCGACCTCTCNAG

Translation:

MMSKGVLLIICLLLFPLTAVPLDGDQPAERTQIEQHPLFDQKRRCCRWPCPSRCGMAR (SEQ ID NO:271)

CCFVMITC

TABLE 1-continued

DNA and Amino Acid Sequences of μ-Conopeptides and Precursors

Toxin Sequence:

Arg-Cys-Cys-Arg-Xaa4-Xaa3-Cys-Xaa3-Ser-Arg-Cys-Gly-Met-Ala-Arg-Cys-Cys-Phe-Val- (SEQ ID NO:272)

Met-Ile-Thr-Cys-^

Name: Pr3.1
Species: *parius*
Cloned: Yes

DNA Sequence:

GGATCCATGATGTCTAAACTGGGAGTCTTGTTGACCATCTGTCTGCTTCTGTTTCCCC (SEQ ID NO:273)

TTACTGCTCTTCCGATGGATGGTGATCAACCTGCAGACCGACTTGTAGAGCGTATGC

AGGACAACATTTCATCTGAGCAGCATCCCTTCTTTGAAAAGAGAAGAGGAGGCTGT

TGCACACCTCCGAAGAAATGCAAAGACCGAGCCTGCAAACCTGCACGTTGCTGCGG

CCCAGGATAACGTGTTGATGACCAACTTTCTCGCC

Translation:

MMSKLGVLLTICLLLFPLTALPMDGDQPADRLVERMQDNISSEQHPFFEKRRGGCCTPP (SEQ ID NO:274)

KKCKDRACKPARCCGPG

Toxin Sequence:

Arg-Gly-Gly-Cys-Cys-Thr-Xaa3-Xaa3-Lys-Lys-Cys-Lys-Asp-Arg-Ala-Cys-Lys-Xaa3-Ala-Arg- (SEQ ID NO:275)

Cys-Cys-Gly-Xaa3-#

Name: Pr3.2
Species: *parius*
Cloned: Yes

DNA Sequence:

GGATCCATGATGTCTAAACTGGGAGTCTTGTTGACCATCTGTCTGCTTCTGTTTCCCC (SEQ ID NO:276)

TTACTGCTCTTCCGATGGATGGTGATCAACCTGCAGACCGACTTGTAGAGCGTATGC

AGGACAACATTTCATCTGAGCAGCATCCCTTCTTTGAAAAGAGAAGAGGCTGTTGC

ACACCTCCGAGGAAATGCAAAGACCGAGCCTGCAAACCTGCACGTTGTTGCGGCCC

AGGATAACGTGTTGATGACCAACTTTCTCGAG

Translation:

MMSKLGVLLTICLLLFPLTALPMDGDQPADRLVERMQDNISSEQHPFFEKRRGCCTPPR (SEQ ID NO:277)

KCKDRACKPARCCGPG

Toxin Sequence:

Arg-Gly-Cys-Cys-Thr-Xaa3-Xaa3-Arg-Lys-Cys-Lys-Asp-Arg-Ala-Cys-Lys-Xaa3-Ala-Arg- (SEQ ID NO:278)

Cys-Cys-Gly-Xaa3-#

Name: Ct3.1
Species: *coronatus*
Cloned: Yes

DNA Sequence:

GGATCCATGATGTCTAAACTGGGAGTCTTGTTGACCATCTGTCTGCTTCTGTTTCCAA (SEQ ID NO:279)

TTACTGCCCTTCCGCTGGATGAAGATCAACCTGCAGACCGACCTGCAGAGCGTATGC

AGGACATTGCAACTGAACAGCATCCCTTGTTTGATCCCGTCAAACGGTGCTGCGATT

GGCCATGCATCCCAGGATGCACCCCTTGTTGCTTGCCTTGATAACGTGTTGATGACC

AACTTTCTCGAG

TABLE 1-continued

DNA and Amino Acid Sequences of µ-Conopeptides and Precursors

Translation:

MMSKLGVLLTICLLLFPITALPLDEDQPADRPAERMQDIATEQHPLFDPVKRCCDWPCIP (SEQ ID NO:280)

GCTPCCLP

Toxin Sequence:

Cys-Cys-Asp-Xaa4-Xaa3-Cys-Ile-Xaa3-Gly-Cys-Thr-Xaa3-Cys-Cys-Leu-Xaa3-^ (SEQ ID NO:281)

Name: Ms3.1
Species: *musicus*
Cloned: Yes

DNA Sequence:

GGATCCATGATGTCTAAACTGGGAGTCCTGTTGACCATCTGTCTGCTTCTGTTTCCTC (SEQ ID NO:282)

TTTCTGCTCTTCCGATGGATGAAGATCAACTTGCAGACCTACCTGCAGAGCGTATGC

GGGACACTGCAACTGTAGATCATCCCTCCTATGATCCTGACAAAGCGTGCTGCGAG

CAGAGCTGTACAACATGCTTTCCGTGCTGCTAGCCTTGAACACAGTAACGTGTTGAT

GACCAACTTTCTCGAG

Translation:

MMSKLGVLLTICLLLFPLSALPMDEDQLADLPAERMRDTATVDHPSYDPDKACCEQSC (SEQ ID NO:283)

TTCFPCC

Toxin Sequence:

Ala-Cys-Cys-Xaa1-Gln-Ser-Cys-Thr-Thr-Cys-Phe-Xaa3-Cys-Cys-^ (SEQ ID NO:284)

Name: bt3b
Species: *betulinus*
Isolated: Yes

Toxin Sequence:

Ala-Cys-Cys-Xaa1-Gln-Ser-Cys-Thr-Thr-Cys-Met-Xaa3-Cys-Cys-^ (SEQ ID NO:285)

Name: bt3c
Species: *betulinus*
Isolated: Yes

Toxin Sequence:

Cys-Cys-Xaa1-Gln-Ser-Cys-Thr-Thr-Cys-Met-Xaa3-Cys-Cys-Xaa4-# (SEQ ID NO:286)

Name: Pn3.2
Species: *pennaceus*
Cloned: Yes

DNA Sequence:

GGATCCATGATGTCTAAACTGGGAGTCTTGTTGACCATCTGTCTGCTTCTGTTTCCCC (SEQ ID NO:287)

TTACTGCTCTTCCGCTGGATGGAGATCAACCTGCATACCAAGCTGCAGAGCGTATGC

AGGCCGAGCATCATCCCTTGTTTGATCAGAAAAGACGGTGCTGCAAGTTTCCATGCC

CCGATAGTTGCAAATATTTGTGTTGCGGGTGATGATAACATGTTGATGACCAACTTT

CTTGAG

Translation:

MMSKLGVLLTICLLLFPLTALPLDGDQPAYQAAERMQAEHHPLFDQKRRCCKEPCPDS (SEQ ID NO:288)

CKYLCCG

Toxin Sequence:

Arg-Cys-Cys-Lys-Phe-Xaa3-Cys-Xaa3-Asp-Ser-Cys-Lys-Xaa5-Leu-Cys-Cys-# (SEQ ID NO:289)

TABLE 1-continued

DNA and Amino Acid Sequences of μ-Conopeptides and Precursors

Name: Pu3.2
Species: *pulicarius*
Cloned: Yes

DNA Sequence:

GGATCCATGATGTCTAAACTGGGAGTCTTGTTGACCATCTGTCTGCTTCTGTTTCCCC (SEQ ID NO:290)

TTACTGCTCTTCCGATGGATGGTGATCAACTTGCAGACCGACTTGTAGAGCGTATGC

AGGACAACATTTCATCTGAGCAGCATCCCTTCTTTGATCCCGTCAAACGGTGTTGCG

TCAGCTGTTACATGGGATGCATCCCTTGTTGCTTCTAGTAATAACGTGTTGATGACC

AACTTTCTCGAG

Translation:

MMSKLGVLLTICLLLFPLTALPMDGDQLADRLVERMQDNISSEQHPFFDPVKRCCVSCY (SEQ ID NO:291)

MGCIPCCF

Toxin Sequence:

Cys-Cys-Val-Ser-Cys-Xaa5-Met-Gly-Cys-Ile-Xaa3-Cys-Cys-Phe- (SEQ ID NO:292)

Name: Pu3.3
Species: *pulicarius*
Cloned: Yes

DNA Sequence:

GGATCCATGATGTCTAAACTGGGAGTCTTGTTGACCGTCTGTCTGCTTCTGTGTCCCC (SEQ ID NO:293)

TTACTGCTCTTCCACTGGATGAAGATCAACTTGCAGACCGACCTGCAGAGCGTATGC

AGGATGACACTTCAGCTGCACAGATTTTCGGGTTTGATCCCGTCAAACGGTGCTGCA

AATTGCTATGCTACTCGGGATGCACTCCTTGTTGCCATATTTGATAACGTGTTGATG

ACCAACTTTCTCGAG

Translation:

MMSKLGVLLTVCLLLCPLTALPLDEDQLADRPAERMQDDTSAAQIFGFDPVKRCCKLL (SEQ ID NO:294)

CYSGCTPCCHI

Toxin Sequence:

Cys-Cys-Lys-Leu-Leu-Cys-Xaa5-Ser-Gly-Cys-Thr-Xaa3-Cys-Cys-His-Ile- (SEQ ID NO:295)

Name: Ra3.2
Species: *rattus*
Cloned: Yes

DNA Sequence:

GGATCCATGATGTCTAAACTGGGAGTCTTGTTGACCATCTGTCTGCTTGTGTTTCCGC (SEQ ID NO:296)

TTACTGCTCTTCCGATGGATGGTGATCAACCTGCAGACCGACTTGTAGAGCGTATAC

AGGACAACATTTCATCTGAGCAGCATCCCTTCTTTGAAAAGAGAAGAGGCTGTTGC

GCACCTCCGAGGAAATGCAAAGACCGAGCCTGCAAACCTGCACGTTGCTGCGGCCC

AGGATAACGTGTTGATGACCAACTTTCTCGAG

Translation:

MMSKLGVLLTICLLVFPLTALPMDGDQPADRLVERQDNISSEQHPFFERGCCAAPPRK (SEQ ID NO:297)

CKDRACKPARCCGPG

Toxin Sequence:

Arg-Gly-Cys-Cys-Ala-Xaa3-Xaa3-Arg-Lys-Cys-Lys-Asp-Arg-Ala-Cys-Lys-Xaa3-Ala-Arg- (SEQ ID NO:298)

TABLE 1-continued

DNA and Amino Acid Sequences of μ-Conopeptides and Precursors

Cys-Cys-Gly-Xaa3-#

Name: Sm3.3
Species: *stercusmuscarum*
Cloned: Yes

DNA Sequence:

GGATCCATGATGTCTAAACTGGGAGTCTTGTTGACAATCTGTCTGCTTCTGTTTCCCC (SEQ ID NO:299)

TTATTGCTCTTCCGCTGGATGGAGATCAACCTGCAGACCGACCTGCAGAGCGTATGC

AGGACGACATTTCATCTGAGAAGCATCCCTTGTTTGATAAGAGACAACGGTGTTGC

AATGGGCGGAGGGGATGCTCCAGCAGATGGTGCAGAGATCACTCACGTTGTTGCGG

TCGACGATAACGTGTTGATGACCAACTTTCTCGAG

Translation:

MMSKLGVLLTICLLLFPLIALPLDGDQPADRPAERMQDDISSEKHPLFDKRQRCCNGRR (SEQ ID NO:300)

GCSSRWCRDHSRCCGRR

Toxin Sequence:

Xaa2-Arg-Cys-Cys-Asn-Gly-Arg-Arg-Gly-Cys-Ser-Ser-Arg-Xaa4-Cys-Arg-Asp-His-Ser-Arg- (SEQ ID NO:301)

Cys-Cys-#

Name: Eb3.1
Species: *ebraeus*
Cloned: Yes

DNA Sequence:

GGATCCATGATGTCTAAACTGGGAGTCTTGTTGACCATCTGTCTGCTTCTGTTTCCCC (SEQ ID NO:302)

TTACTGCTCTTCCACTGGATGAAGGTCAACCTGCAGACCTACCTGCAGAGCGTATGC

AGGACATTGCAACTGAACAGCATCCCTTGTTTGATCCTGTCAAACGGTGTTGCGAGC

AGCCATGCTACATGGGATGCATCCCTTGTTGC TCTAATAATAACGTGTTGATGACC

AACTTTCTCGAG

Translation:

MMSKLGVLLTICLLLFPLTALPLDEGQPADLPAERMQDIATEQHPLFDPVKRCCEQPCY (SEQ ID NO:303)

MGCIPCCF

Toxin Sequence:

Cys-Cys-Xaa1-Gln-Xaa3-Cys-Xaa5-Met-Gly-Cys-Ile-Xaa3-Cys-Cys-Phe-^ (SEQ ID NO:304)

Name: Eb3.2
Species: *ebraeus*
Cloned: Yes

DNA Sequence:

GGATCCATGATGTCTAAACTGGGAGTCTTGTTGACCATCTGTCTGCTTCTGTTTCCCC (SEQ ID NO:305)

TTACTGCTCTTCCACTGGATGAAGATCAACCTGCAGACCTACCTGCAGAGCGTATGC

AGGACATTGCAACTGAACAGCATCCCTTGTTTGATCCTGTCAAACGGTGCTGCGCGC

AGCCATGCTACATGGGATGCATCCCTTGTTGCTTCTAATAATAACGTGTTGATGACC

AACTTTCTCGAG

Translation:

MMSKLGVLLTICLLLFPLTALPLDEDQPADLPAERMQDIATEQHPLFDPVKRCCAQPCY (SEQ ID NO:306)

TABLE 1-continued

DNA and Amino Acid Sequences of μ-Conopeptides and Precursors

MGCIPCCF

Toxin Sequence:

Cys-Cys-Ala-Gln-Xaa3-Cys-Xaa5-Met-Gly-Cys-Ile-Xaa3-Cys-Cys-Phe-^ (SEQ ID NO:307)

Name: Fd3.2
Species: *flavidus*
Cloned: Yes

DNA Sequence:

GGATCCATGATGTCTAAACTGGGAGTCTTGTTGACCATCTGTCTGCTTCTGTTTCCCC (SEQ ID NO:308)

TTACTGCTGTTCCGTTGGATGGAGATCAACCTGCAGACCAGCCTGCAGAGCGTATGC

AGAACGAGCAGCATCCCTTGTTTGATCAGAAAAGAAGGTGCTGCCGGTGGCCATGC

CCCAGTATATGCGGCATGGCTAGGTGTTGCTCGTCATGATAACGTGTTGATGACCAA

CTTTCTCGAG

Translation:

MMSKLGVLLTICLLLFPLTAVPLDGDQPADQPAERMQNEQHPLFDQKRRCCRWPCPSIC (SEQ ID NO:309)

GMARCCSS

Toxin Sequence:

Arg-Cys-Cys-Arg-Xaa4-Xaa3-Cys-Xaa3-Ser-Ile-Cys-Gly-Met-Ala-Arg-Cys-Cys-Ser-Ser-^ (SEQ ID NO:310)

Name: Mf3.1
Species: *miliaris*
Cloned: Yes

DNA Sequence:

GGATCCATGATGTCTAAACTGGGAGTCTTGTTGACCATCTGTCTGCTTCTGTTTCCAA (SEQ ID NO:311)

TTACTGCCCTTCCACTGGATGAAGATCAACCTGCAGACCGACCTGCAGAGCGTATGC

AGGACATTGCAACTGAACAGCATCCCTTGTTTGATCCCGTCAAACGGTGTTGCGATT

GGCCATGCAGCGCAGGATGCTACCCTTGTTGCTTCCCTTAATAACGTGTTGATGACC

AACTNANGNAAAAAAA

Translation:

MMSKLGVLLTICLLLFPITALPLDEDQPADRPAERMQDIATEQHPLFDPVKRCCDWPCS (SEQ ID NO:312)

AGCYPCCFP

Toxin Sequence:

Cys-Cys-Asp-Xaa4-Xaa3-Cys-Ser-Ala-Gly-Cys-Xaa5-Xaa3-Cys-Cys-Phe-Xaa3-^ (SEQ ID NO:313)

Name: Mf3.2
Species: *miliaris*
Cloned: Yes
Notes:

DNA Sequence:

GGATCCATGATGTCTAAACTGGGAGTGGTGCCATTCGTCTTTCTGGTCCTGTTTCCCC (SEQ ID NO:314)

TGGCAACACTCCAACTGGATGCAGATCAACCTGCAGACCGACCTGCGCGTAAAAAG

GGCATTGCAACTAAACGGCATCCCTTGTCTGATCCTGTCAGAGGGTGTTGCCCTCCA

ATGTGCACACCATGCTTCCCTTGCTGTTTTCGTTAATAACGTGTTGATGNATGATGN

AN

TABLE 1-continued

DNA and Amino Acid Sequences of μ-Conopeptides and Precursors

Translation:

MMSKLGVVPFVFLVLFPLATLQLDADQPADRPARKKGIATKRHPLSDPVRGCCPPMCTPCFPCC (SEQ ID NO:315)

FR

Toxin Sequence:

Gly-Cys-Cys-Xaa3-Xaa3-Met-Cys-Thr-Xaa3-Cys-Phe-Xaa3-Cys-Cys-Phe-Arg-^ (SEQ ID NO:316)

Name: Af3.1
Species: *ammiralis*
Cloned: Yes

DNA Sequence:

CAAGAGGGATCGATAGCAGTTCATGATGTCTAAACTGGGAGTCTTGTTGACCATCTG (SEQ ID NO:317)

TCTGCTTCTGTTTCCCCTTACTGCTCTTCCGCTGGATGGAGATCAACCTGCAGACCA

AGCTGCAGAGCGTATGCAGGCCGAGCAGCATCCCTTGTTTGATCAGAAAAGACGGT

GTTGCAGGTTTCCATGCCCCGATACTTGCAGACATTTGTGTTGCGGGTGATGATAAC

GTGCTGATGACCCACTTTGTCATCACGGCTACGTCAAGTGTCTAATGAATAAGTAAA

ATGATTGCAGT

Translation:

MMSKLGVLLTICLLLFPLTALPLDGDQPADQAAERMQAEQHPLFDQKRRCCRFPCPDT (SEQ ID NO:318)

CRLHLCCG

Toxin Sequence:

Arg-Cys-Cys-Arg-Phe-Xaa3-Cys-Xaa3-Asp-Thr-Cys-Arg-His-Leu-Cys-Cys-# (SEQ ID NO:319)

Name: Af3.2
Species: *ammiralis*
Cloned: Yes

DNA Sequence:

CAAGAGGGATCGATAGCAGTTCATGATGTTTAAACTGGGAGTCTTGCTGACCATCTG (SEQ ID NO:320)

TCTACTTCTGTTTTCCCCTTAATGCTGTTCCGCTGGATGGAGATCAACCTGCAGACCA

ACCTGCAGAGCGTCTGCTGGACGACATTTCATCTGAAAATAATCCCTTTTATGATCC

CGCCAAACGGTGTTGCATGACTTGCTTCGGTTGCACACCTTGTTGTGGATGACCAGC

CTCATCAAGTGTCTAACGAATAAGTAAAACGATTGCAGT

Translation:

MMFKILGVLLTICLLLFSLNAVPLDGDQPADQPAERLLDDISSENNPFYDPAKRCCMTCF (SEQ ID NO:321)

GCTPCCG

Toxin Sequence:

Cys-Cys-Met-Thr-Cys-Phe-Gly-Cys-Thr-Xaa3-Cys-Cys-# (SEQ ID NO:322)

Name: Af3.3
Species: *ammiralis*
Cloned: Yes

DNA Sequence:

CAAGAAGGATCGATAGCAGTTCATGATGTCTAAACTGGGAGCCTTGTTGACCATCT (SEQ ID NO:323)

GTCTACTTCTGTTTTCCCTTACTGCTGTTCCGCTGGATGGAGATCAACATGCAGACC

AACCTGCAGAGCGTCTGCAGGACCGCCTTCCAACTGAAAATCATCCCTTATATGATC

CCGTCAAACGGTGTTGCGATGATTCGGAATGCGACTATTCTTGCTGGCCTTGCTGTA

TABLE 1-continued

DNA and Amino Acid Sequences of µ-Conopeptides and Precursors

TTTTTTCATAACCTTTGTTATCGCGGCCTCATCCTAGTGTCAAATGAATAAGTAAAA

CGATTGCAGT

Translation:

MMSKLGALLTICLLLFSLTAVPLDGDQHADQPAERLQDRLPTENHPLYDPVKRCCDDSE (SEQ ID NO:324)

CDYSCWPCCIFS

Toxin Sequence:

Cys-Cys-Asp-Asp-Ser-Xaa1-Cys-Asp-Xaa5-Ser-Cys-Xaa4-Xaa3-Cys-Cys-Ile-Phe-Ser-^ (SEQ ID NO:325)

Name: Af3.4
Species: *ammiralis*
Cloned: Yes

DNA Sequence:

CAAGAGGGATCGATAGCAGTTCATGATGTTTAAACTCGGAGTCTTGCTGACCATCTG (SEQ ID NO:326)

TCTACTTCTGTTTTCCCTAATtGCTGTTCCGCTGGATGGAGATCAACATGCAGACCAA

CCTGCAGAGCGTCTGCAGGACCGCCTTCCAACTGAAAATCATCCCTTATATGATCCC

GTCAAACGGTGTTGCAGGTTGTTATGCCTCAGTTGCAACCCTTGTTGTGGATGACCA

GCTTTGTTATCACGGCCTCATCAAGTGTCTAATGAATAAGTAAAACGATTGCAGT

Translation:

MMFKLGVLLTICLLLFSLIAVPLDGDQHADQPAERLQDRLPTENHPLYDPVKRCCRLLC (SEQ ID NO:327)

LSCNPCCG

Toxin Sequence:

Cys-Cys-Arg-Leu-Leu-Cys-Leu-Ser-Cys-Asn-Xaa3-Cys-Cys-# (SEQ ID NO:328)

Name: Af3.6
Species: *ammiralis*
Cloned: Yes

DNA Sequence:

CAAGAAGGATCGATAGCAGTTCATGATGTCTAAACTGGGAGCCTTGTTGACCATCT (SEQ ID NO:329)

GTCTACTTCTGTTTTCCCTTACTGCTGTTCCGCTGGATGGAGATCAACATGCAGACC

AACCTGCAGAGCGTCTGCAGGACCGCATTCCAACTGAAGATCATCCCTTATTTGATC

CCAACAAACGGTGTTGCGATGATTCGGAATGCGGCTATTCATGCTGGCCTTGCTGTT

ATGGATAAGCTTTGTTATCGCGGCCTCATCCAGTGTCAACGAATAAGTAAAACGATT

GCAGT

Translation:

MMSKLGALLTICLLLFSLTAVPLDGDQHADQPAERLQDRIPTEDHPLFDPNKRCCDDSE (SEQ ID NO:330)

CGYSCWPCCYG

Toxin Sequence:

Cys-Cys-Asp-Asp-Ser-Xaa1-Cys-Gly-Xaa5-Ser-Cys-Xaa4-Xaa3-Cys-Cys-Xaa5-# (SEQ ID NO:331)

Name: Sf3.1
Species: *spurius*
Cloned: Yes

DNA Sequence:

CAAGAAGGATCGATAGCAGTTCATGATGTCTAAACTGGGAGTCTTGCTGACCATCT (SEQ ID NO:332)

TABLE 1-continued

DNA and Amino Acid Sequences of μ-Conopeptides and Precursors

GTCTGCTTCTGTTTCCACGTACTTCTCTTCCGCTGGATGGAGATCAACCTGCAGTCCG

ATCTGCAAAGCGTATGCATTCATCTATACAGCGTCGTTTCTTTGATCCCGTCAAACG

GTGTTGCCCTAGATGCAGCGAGTGCAACCCTTGTTGTGGATGACCAGCTTTGTCATC

GCGGCCTCATTAAGTGTCTAATGAATAAGTAAAATGATTGCAGT

Translation:

MMSKLGVLLTICLLLFPRTSLPLDGDQPAVRSAKRMHSSIQRRFFDPVKRCCPRCSECNP (SEQ ID NO:333)

CCG

Toxin Sequence:

Cys-Cys-Xaa3-Arg-Cys-Ser-Xaa1-Cys-Asn-Xaa3-Cys-Cys-# (SEQ ID NO:334)

Name: Om3.1
Species: omaria
Cloned: Yes

DNA Sequence:

CAAGAGGGATCGATAGCAGTTCATGATGTCTAAACTGGGAGTCTCGTTGACCATCT (SEQ ID NO:335)

GTCTACTTCTATTTTCCCTTACTGCTGTTCCGCTTGATGGAGATCAACATGCAGACCA

ACCTGCAGAGCGTCTGCAGGGCGACATTTTATCTGAAAAGCATCCCTTATTTAATCC

CGTCAAACGGTGTTGCGATGAGGAAGAATGCAGCAGTGCATGCTGGCCTTGTTGTT

GGGGGTGATCAGCTTTGTTATCGCGGCCTCATCAAGTGTCTAATGAATAAGTAAAAT

GATTGCAGT

Translation:

MMSKLGVSLTICLLLFSLTAVPLDGDQHADQPAERLQGDILSEKHPLFNPVKRCCDEEE (SEQ ID NO:336)

CSSACWPCCWG

Toxin Sequence:

Cys-Cys-Asp-Xaa1-Xaa1-Xaa1-Cys-Ser-Ser-Ala-Cys-Xaa4-Xaa3-Cys-Cys-Xaa4-# (SEQ ID NO:337)

Name: Om3.2
Species: omaria
Cloned: Yes

DNA Sequence:

CAAGAAGGATCGATAGCAGTTCATGATGTCTAAACTGGGAGTCTTGTTGATCATCTG (SEQ ID NO:338)

TCTACTTCTGTGTCCCCTTACTGCTGTTCTGGAGGATGGAGATCAACCTGCAGACCG

ACCTGCAGAGCGTATGCAGGACGACATTTCAACTGAGCATCATCCCTTTTATGATCC

CGTCAAACGGTGTTGCAAGTACGGGTGGACATGCTTGCTAGGATGCACTCCTTGTGA

TTGTTGACCAGTTTTGTTATCGCGGCCTCGTCAAGTGTCTAATGAATAAGTAAAACG

ATTGCAGT

Translation:

MMSKLGVLLIICLLLCPLTAVLEDGDQPADRPAERMQDDISTEHHPFYDPVKRCCKYG (SEQ ID NO:339)

WTCLLGCTPCDC

Toxin Sequence:

Cys-Cys-Lys-Xaa5-Gly-Xaa4-Thr-Cys-Leu-Leu-Gly-Cys-Thr-Xaa3-Cys-Asp-Cys-^ (SEQ ID NO:340)

Name: Om3.3
Species: omaria
Cloned: Yes

TABLE 1-continued

DNA and Amino Acid Sequences of µ-Conopeptides and Precursors

DNA Sequence:

CAAGAGGGATCGATAGCAGTTCATGATGTCTATACTGGGAGTCTTGTTGATCATCTG (SEQ ID NO:341)

TCTACTTCTGTGTCCCCTTACTGCTGTTCTGGAGGATGGAGATCAACCTGCAGACCG

ACCTGCAGAGCGTATGCAGGACGGCATTTCATCTGAACATCATCCCTTTTTGGATCC

CGTCAAACGGTGTTGCCATCTATTGGCATGCCGCTTTGGATGCTCGCCTTGTTGTTG

GTGACCAGCTTTGTTATCGCGGCCTCATCAAGTGTCTAATGAATAAGTAAAACGATT

GCAGT

Translation:

MMSILGVLLIICLLLCPLTAVLEDGDQPADRPAERMQDGISSEHHPFLDPVKRCCHLLAC (SEQ ID NO:342)

RFGCSPCCW

Toxin Sequence:

Cys-Cys-His-Leu-Leu-Ala-Cys-Cys-Arg-Phe-Gly-Cys-Ser-Xaa3-Cys-Cys-Xaa4-^ (SEQ ID NO:343)

Name: Om3.4
Species: omaria
Cloned: Yes

DNA Sequence:

CAAGAAGGATCGATAGCAGTTCATGATGTCTAAACTGGGAGTCTTGTTGATCATCTG (SEQ ID NO:344)

TCTACTTCTTTGTCCCCTTACTGCTGTTCCGCAGGATGGAGATCAACCTGCAGACCG

ACCTGCAGAGCGTATGCAGGGCGGCATTTCATCTGAACATCATCCCTTTTTTGATCC

CGTCAAACGGTGTTGCAGGTACGGGTGGACATGCTGGCTAGGATGCACTCCCTGTG

GTTGTTGACCAGCTTTGTTATCGCGGCCTCATCAAGTGTCTAATGAATAAGTAAAAC

GATTGCAGT

Translation:

MMSKLGVLLIICLLLCPLTAVPQDGDQPADRPAERMQGGISSEHHPFFDPVKRCCRYGW (SEQ ID NO:345)

TCWLGCTPCGC

Toxin Sequence:

Cys-Cys-Arg-Xaa5-Gly-Xaa4-Thr-Cys-Xaa4-Leu-Gly-Cys-Thr-Xaa3-Cys-Gly-Cys-^ (SEQ ID NO:346)

Name: Ep3.1
Species: episcopatus
Cloned: Yes

DNA Sequence:

CAAGAAGGATCGATAGCAGTTCATGATGTCTAAACTGGGAGTCTTGTTGACCATCTG (SEQ ID NO:347)

TCTACTTCTGTTTTCCCTTATTGCTGTTCCGCTTGATGGAGATCAACATGCAGACCAA

CCTGCAGAGCGTCTGCAGGGCGACATTTTATCTGAAAAGCATCCCTTATTTATGCCT

GTCAAACGGTGTTGCGATGAGGACGAATGCAACAGTTCATGCTGGCCTTGTTGTTGG

GGGTGATCAGCTTTGTTATCGCGGCCTGATCAAGTGTATAATGAATAAGTAAAACG

ATTGCAGT

Translation:

MMSKLGVLLTICLLLFSLIAVPLDGDQHADQPAERLQGDILSEKHPLFMPVKRCCDEDE (SEQ ID NO:348)

CNSSCWPCCWG

TABLE 1-continued

DNA and Amino Acid Sequences of μ-Conopeptides and Precursors

Toxin Sequence:

Cys-Cys-Asp-Xaa1-Asp-Xaa1-Cys-Asn-Ser-Ser-Cys-Xaa4-Xaa3-Cys-Cys-Xaa4-# (SEQ ID NO:349)

Name: Ep3.2
Species: *episcopatus*
Cloned: Yes

DNA Sequence:

CAAGAGGGATCGATAGCAGTTCATGATGTCTAAACTGGGAGTCTTGTTGACCATCTG (SEQ ID NO:350)

TCTACTTCTGTTTTCCCTTATTGCTGTTCCGCTTGATGGAGATCAACATGCAGACCAA

CCTGCAGAGCGTCTGCAGGGCGACATTTTATCTGAAAAGCATCCCTTATTTATGCCT

GTCAAACGTGTTGCGATGAGGACGAATGCAGCAGTTCATGCTGGCCTTGTTGTTGG

GGATGAGCAGCTTTGTTATCGCGGCCTCATCAAGTGTCTAATGAATAAGTAAAACG

ATTGCAGT

Translation:

MMSKLGVLLTICLLLFSLIAVPLDGDQHADQPAERLQGDILSEKHPLFMPVKRCCDEDE (SEQ ID NO:351)

CSSSCWPCCWG

Toxin Sequence:

Cys-Cys-Asp-Xaa1-Asp-Xaa1-Cys-Ser-Ser-Ser-Cys-Xaa4-Xaa3-Cys-Cys-Xaa4-# (SEQ ID NO:352)

Name: Ep3.3
Species: *episcopatus*
Cloned: Yes

DNA Sequence:

CAAGAGGGATCGATAGCAGTTCATGATGTCTAAACTGGGAGTCTTGTTGACCATCTG (SEQ ID NO:353)

TCTACTTCTGTTTTCCCTTACTGCTGTTCCGCTTGATGGAGATCAACATGCAGACCAA

CCTGCAGAGCGTCTGCAGGGCGACATTTTATCTGAAAAGCATCCCTTATTTAATCCC

GTCAAACGTGTTGCCCGGCGGCGGCATGTGCCATGGGATGCAAGCCTTGTTGTGG

ATGAGCAGCTTTGTTATCGTGGCCTCATCAAGTGTCTAATGAATAAGTAAAACGATT

GCAGT

Translation:

MMSKLGVLLTICLLLFSLTAVPLDGDQHADQPAERLQGDILSEKHPLFNPVKRCCPAAA (SEQ ID NO:354)

CAMGCKPCCG

Toxin Sequence:

Cys-Cys-Xaa3-Ala-Ala-Ala-Cys-Ala-Met-Gly-Cys-Lys-Xaa3-Cys-Cys-# (SEQ ID NO:355)

Name: Au3.2
Species: *aulicus*
Cloned: Yes

DNA Sequence:

CAAGAGGGATCGATAGCAGTTCATGATGTCTAAACTGGGAGTCTTGTTGACCATCTG (SEQ ID NO:356)

TCTGCTTCTGTTTTCCGTTACTGCTCTTCCGCCGGATGGAGATCAACCTGCAGACCG

AGCTGCAGAGCGTAGGCAGGTCGAGCAGCATCCCGTGTTTGATCATGAAAGAGGGT

GTTGCTCGCCACCATGCCACAGTATTTGCGCTGCTTTCTGTTGCGGGTGATGATAAC

GTGTTGATGACCCACTTTGTCATCACGGCTGCGTCAAGTGTCTAATGAATAAGTAAA

ATGATTGCAGT

TABLE 1-continued

DNA and Amino Acid Sequences of µ-Conopeptides and Precursors

Translation:

MMSKLGVLLTICLLLFSVTALPPDGDQPADRAAERRQVEQHPVFDHERGCCSPPCHSIC (SEQ ID NO:357)

AAFCCG

Toxin Sequence:

Gly-Cys-Cys-Ser-Xaa3-Xaa3-Cys-His-Ser-Ile-Cys-Ala-Ala-Phe-Cys-Cys-# (SEQ ID NO:358)

Name: Au3.3
Species: *aulicus*
Cloned: Yes

DNA Sequence:

CAAGAGGGATCGATAGCAGTTCATGATGTCTAAACTGGGAGTCTTGTTGACCATCTG (SEQ ID NO:359)

TCTACTTCTGTTTTCCCTTACTGCTGTTCCGCTTGATGGAGATCAACATGCAGACCAA

CCTGCAGAGCGTCTGCAGGGCGACATTTTATCTGAAAAGCATCCCTTATTTAATCCC

GTCAAACGGTGTTGCCGACCGGTGGCATGTGCCATGGGATGCAAGCCTTGTTGTGG

ATGAGCAGCTTTGTTATCGTGGCCTCATCAAGTGTCTAATGAATAAGTAAAATGATT

GCAGT

Translation:

MMSKLGVLLTICLLLFSLTAVPLDGDQHADQPAERLQGDILSEKHPLFNPVKRCCRPVA (SEQ ID NO:360)

CAMGCKPCCG

Toxin Sequence:

Cys-Cys-Arg-Xaa3-Val-Ala-Cys-Ala-Met-Gly-Cys-Lys-Xaa3-Cys-Cys-# (SEQ ID NO:361)

Name: Au3.4
Species: *aulicus*
Cloned: Yes

DNA Sequence:

CAAGAGGGATCGATAGCAGTTCaTGATGTCTAAACTGGGAGTCTTGTTGATCATCTG (SEQ ID NO:362)

TCTACTTCTGTCTCCCCTTACTGCTGTTCCGCTGGATGGAGATCAACCTGCAGACCG

ACCTGCAGAGCGTATGCAGGACGACATTTCATCTGAACATCAACCCATGTTTGATGC

CATCAGACAGTGTTGCCCGGCGGTGGCATGCGCCATGGGATGCGAGCCTTGTTGTG

GATGACCAGCTTTGTTATCGCGGCCTCATCAAGTGTCTAATGAATAAGTAAAATGAT

TGCAGT

Translation:

MMSKLGVLLIICLLLSPLTAVPLDGDQPADRPAERMQDDISSEHQPMFDAIRQCCPAVA (SEQ ID NO:363)

CAMGCEPCCG

Toxin Sequence:

Xaa2-Cys-Cys-Xaa3-Ala-Val-Ala-Cys-Ala-Met-Gly-Cys-Xaa1-Xaa3-Cys-Cys-# (SEQ ID NO:364)

Name: Ae3.1
Species: *aureus*
Cloned: Yes

DNA Sequence:

CAAGAAGGATCGATAGCAGTTCATGATGTCTAAACTGGGAGCCTTGTTGACCATCT (SEQ ID NO:365)

GTCTACTTCTGTTTTCCCTTACTGCTGTTCCGCTGGATGGAGATCAACATGCAGACC

TABLE 1-continued

DNA and Amino Acid Sequences of μ-Conopeptides and Precursors

AACATGCAGAGCGTCTGCATGACCGCCTTCCAACTGAAAATCATCCCTTATATGATC

CCGTCAAACGGTGTTGCGATGATTCGGAATGCGACTATTCTTGCTGGCCTTGCTGTA

TTTTTGGATAACCTTTGTTATCGCGGCCTCATCAAGTGTCAAATGAATAAGTAAAAC

GATTGCAGT

Translation:

MMSKLGALLTICLLLFSLTAVPLDGDQHADQHAERLHDRLPTENHPLYDPVKRCCDDS (SEQ ID NO:366)

ECDYSCWPCCIFG

Toxin Sequence:

Cys-Cys-Asp-Asp-Ser-Xaa1-Cys-Asp-Xaa5-Ser-Cys-Xaa4-Xaa3-Cys-Cys-Ile-Phe-# (SEQ ID NO:367)

Name: Ae3.2
Species: *aureus*
Cloned: Yes

DNA Sequence:

CAAGAGGGATCGATAGCAGTTCATGATGTCTAAACTGGGAGCCTTGTTGACCATCT (SEQ ID NO:368)

GTCTACTTCTGTTTTCCCTAACTGCTGTTCCGCTGGATGGAGATCAACATGCAGACC

AACCTGCAGAGCGTCTGCAGGACCGCATTCCAACTGAAAATCATCCCTTATTTGATC

CGAACAAACGGTGTTGCAATGATTGGGAATGCGACGATTCATGCTGGCCTTGCTGTT

ATGGATAACCTTTGTTATCGCGGCCTCATCAAGTGTCAAATGAATAAGTAAAACGAT

TGCAGT

Translation:

MMSKLGALLTICLLLFSLTAVPLDGDQHADQPAERLQDRIPTENHPLFDPNKRCCNPWE (SEQ ID NO:369)

CDDSCWPCCYG

Toxin Sequence:

Cys-Cys-Asn-Asp-Xaa4-Xaa1-Cys-Asp-Asp-Ser-Cys-Xaa4-Xaa3-Cys-Cys-Xaa5-# (SEQ ID NO:370)

Name: Cn3.1
Species: *consors*
Cloned: Yes

DNA Sequence:

CAAGAGGGATCGATAGCAGTTCATGATGTCTAAACTGGGAGTCTTGTTGACCATCTG (SEQ ID NO:371)

TTTGCTTCTGTTTCCCCTTACTGCTCTTCCAATGGATGGAGATCAATCTGTAGACCGA

CCTGCAGAGCGTATGCAGGACGACATTTCATCTGAGCTGCATCCCTTGTTCAATCAG

AAAAGAATGTGTTGCGGCGAAGGTGCGCCATGCCCCAGCTATTTCAGAAACAGTCA

GATTTGTCATTGTTGTTAAATGACAACGTGTCGATGACCAACTTCGTTATCACGACT

AATGAATAAGTAAAATGATTGCAGT

Translation:

MMSKLGVLLTICLLLFPLTALPMDGDQSVDRPAERMQDDISSELHPLFNQKRMCCGEG (SEQ ID NO:372)

APCPSYFRNSQICHCC

Toxin Sequence:

Met-Cys-Cys-Gly-Xaa1-Gly-Ala-Xaa3-Cys-Xaa3-Ser-Xaa5-Phe-Arg-Asn-Ser-Gln-Ile-Cys-His- (SEQ ID NO:373)

Cys-Cys-^

TABLE 1-continued

DNA and Amino Acid Sequences of µ-Conopeptides and Precursors

Name: Cn3.3
Species: *consors*
Cloned: Yes

DNA Sequence:

TAAGAGGGATCGATAGCAGTTCATGATGTCTAAACTGGGAGTCTTGTTGACCATCTG (SEQ ID NO:374)

TCTGCTTCTGTTTCCCCTTATTGCTCTTCCAATGGATGGAGATCAACCTGCAGACCGA

CCTGCAGAGCGTATGCAgGACGACATTTCATCTCAGCAGCATCCCTTGTTTGATAAG

AGAGGCCGCTGTTGCGATGTGCCGAACGCATGCTCCGGCAGATGGTGCAGAGATCA

CGCACAATGTTGCGGATGACGATAACGTGTTGATGACCAACTTTGTGATCACGGCTA

CATCAAGTGAATAAGTAAAACGATTGCAGT

Translation:

MMSKLGVLLTICLLLFPLIALPMDGDQPADRPAERMQDDISSQQHPLFDKRGRCCDVPN (SEQ ID NO:375)

ACSGRWCRDHAQCCG

Toxin Sequence:

Gly-Arg-Cys-Cys-Asp-Val-Xaa3-Asn-Ala-Cys-Ser-Gly-Arg-Xaa4-Cys-Arg-Asp-His-Ala-Gln- (SEQ ID NO:376)

Cys-Cys-#

Name: Cn3.4
Species: *consors*
Cloned: Yes

DNA Sequence:

CAAGAGGGATCGATAGCAGTTCATGATGTCTAAACTGGGAGTCTTGTTGACTGTCTG (SEQ ID NO:377)

TTTGCTTCTGTTTCCCCTTACTGCTCTTCCGATGGATGGAGATCAACCTGCAGACCAA

CCTGCAGAGCGTATGCAGGACGACATTTCATCTGAGCAGCATCCCTTGTTTGATAAG

AGACAAAGGTGTTGCACTGGGAAGAAGGGGTCATGCTCCGGTAAAGCATGCAAAA

GTCTCAAATGTTGCTCTGGACGATAACGTGTTGATGACCAACTTTGTTATCACGGCT

ACGTCAAGTGTCTAGTGAATAAGTAAAACGATTGCAGT

Translation:

MMSKLGVLLTVCLLLFPLTALPMDGDQPADQPAERMQDDISSEQHPLFDKRQRCCTGK (SEQ ID NO:378)

KGSCSGKACKSLKCCSGR

Toxin Sequence:

Xaa2-Arg-Cys-Cys-Thr-Gly-Lys-Lys-Gly-Ser-Cys-Ser-Gly-Lys-Ala-Cys-Lys-Ser-Leu-Lys-Cys- (SEQ ID NO:379)

Cys-Ser-#

Name: Em3.1
Species: *emaciatus*
Cloned: Yes

DNA Sequence:

CAAGAGGGATCGATAGCAGTTCATGATGTCTAAACTGGGAGTCTTGCTGACCATCTGTCTGCTTCTGTT (SEQ ID NO:380)

TCCCCTTACTGTTCTTCCGATGGATGGAGATCAACCTGCAGACCTACCTGCATTGCGTGCGCAGTTCTT

TGCAGGTGAACATAGTCCCCGGTTGACCCCGTCAAACGGTGCTGCTCGCGGGATTGCAGTGTTTGCAT

CCCTTGTTGCCCGTATGGATCACCTTGATTATTGCGGCCACGTCAAGTGTCTAATGAATAAGTAAAATG

ATTGCAGT

TABLE 1-continued

DNA and Amino Acid Sequences of μ-Conopeptides and Precursors

Translation:

MMSKLGVLLTICLLLFPLTVLPMDGDQPADLPALRAQFFAPEHSPRFDPVKRCCSRDCSVCIPCCPYGSP    (SEQ ID NO:381)

Toxin Sequence:

Cys-Cys-Ser-Arg-Asp-Cys-Ser-Val-Cys-Ile-Xaa3-Cys-Cys-Xaa3-Xaa5-Gly-Ser-Xaa3-^    (SEQ ID NO:382)

Where:
- Xaa1 is Glu or γ-carboxy-Glu
- Xaa2 is Gln or pyro-Glu
- Xaa3 is Pro or hydroxy-Pro
- Xaa4 is Trp or bromo-Trp
- Xaa5 is Tyr, $^{125}$I-Tyr, mono-iodo-Tyr, di-iodo-Tyr, O-sulpho-Tyr or O-phospho-Tyr
- ^ is free carboxyl or amidated C-terminus, preferably free carboxyl
- # is free carboxyl or amidated C-terminus, preferably amidated
- ?=Status of C-term not known.

TABLE 2

Alignment of μ-Conopeptides (SEQ ID NO:)

TYPE 1

| | | |
|---|---|---|
| A3.4 (F283) | ---CCKVQ-CES--C----TPCC^ | (383) |
| Ak3.1 (F585) | ---CCELP-CGBGFC---VPCC^ | (384) |
| Ar3.1 | ---CCERP-CNIG-C---VPCC^ | (385) |
| Bn3.1 (F586) | ---CCNWP-CSMG-C---IPCCYY^ | (386) |
| Bt3.1 | ---CCELP-CH-G-C---VPCCWP^ | (387) |
| Bt3.2 | ---CCGLP-CN-G-C---VPCCWPS^ | (388) |
| Bt3.3 | ---CCSRN-CAV--C---IPCCPNWPA^ | (389) |
| bt3a | ---CCKQS-CTT--C---MPCCW^ | (390) |
| bt3b | --ACCXQS-CTT--C---MPCC^ | (391) |
| bt3c | ---CCEQS-CTT--C---MPCCW? | (392) |
| Ca3.3 | R--CCRYP-CPDS-C---HGSCCYK^ | (393) |
| Ca3.4 | ---CCPPVACNMG-C----KPCC# | (394) |
| Ca3.5 | ---CCDDSECDYS-C---WPCCMF# | (395) |
| Ca3.6 (P349) | ---CCRR--CYMG-C---IPCCF^ | (396) |
| Circling | ---CCPPVACNMG-C----KPCCG^ | (397) |
| Comatose/Death | SKQCCHLAACRFG-C----TOCCN^ | (398) |
| Cp3.1 (F594) | S--CCR--DCGED-C---VGCCR^ | (399) |
| Ct3.1 (Z726) | ---CCDWP-CIPG-C---TPCCLP^ | (400) |

TABLE 2-continued

Alignment of μ-Conopeptides (SEQ ID NO:)

| | | |
|---|---|---|
| Da3.1 | ---CCDDSECDYS-C---WPCCILS^ | (401) |
| Da3.2 | Z-QCCPPVACNMG-C---EPCC# | (402) |
| Da3.3 | ---CCNAGFCRFG-C---TPCCW^ | (403) |
| Di3.1 | Z--CCVHP-C-P--C---TPCCR^ | (404) |
| Fi3.1 | ---CCPWP-CNIG-C---VPCC^ | (405) |
| Fi3.2 | --CCSKN-CAV--C---IPCCP^ | (406) |
| Fi3.3 | ---CCRWP-CP-ARC---GSCCL^ | (407) |
| Fi3.4 | ---CCELSRCL-G-C---VPCCTS^ | (408) |
| Fi3.5 | ---CCELSKCH-G-C---VPCCIP^ | (409) |
| Ge3.1 (F590) | Z--CCTF--CNFG-C---QPCCVP^ | (410) |
| Ge3.2 (F343/Z734) | Z--CCTF--CNFG-C---QPCCLT^ | (411) |
| Ge3.3 (F590 | Z--CCTF--CNFG-C---QPCCVP^ | (412) |
| Gm3.1 | ---CCDDSECDYS-C---WPCCMF# | (413) |
| Gm3.2 | G--CCHLLACRFG-C----SPCCW^ | (414) |
| Gm3.3 | ---CCSWDVCDHPSC---T-CCG# | (415) |
| La3.1 | ---CCDWP-CS-G-C---IPCC^ | (416) |
| Lp3.1 (F340) | ZINCCPWP-CPST-C--RHQCCH^ | (417) |
| Lv3.1 (F341) | ZINCCPWP-CPDS-C--HYQCCH^ | (418) |
| Mr3.2 | ---CCRLS-CGLG-C---HPCC# | (419) |
| Mr3.3 | --ECCGSFACRFG-C---VPCCV^ | (420) |
| Mr3.4 | SKQCCHLPACRFG-C---TPCCW^ | (421) |
| Mr3.5 (F286) | -MGCCPFP-CKTS-C--TTLCC# | (422) |
| Ms3.1 (Z738) | --ACCEQS-CTT--C---FPCC^ | (423) |
| Nb3.1 (F87) | ---CCELP-CGPGFC---VPCC^ | (424) |
| Pu3.1 (F339) | ---CCN-S-CYMG-C---IPCCF^ | (425) |
| Qc3.1 (F342) | ZR-CCQWP-CPGS-C----RCCRT# | (426) |

TABLE 2-continued

Alignment of μ-Conopeptides (SEQ ID NO:)

| Name | Sequence | SEQ ID |
|---|---|---|
| Qc3.2 | ZR-CCRWP-CPGS-C----RCCRYR^ | (427) |
| Qc3.3 | R--CCRYP-CPDS-C--HGSCCYK^ | (428) |
| QcIIIA | ---CCSQD-CLV--C---IOCCPN# | (429) |
| QcIIIB | ---CCSRH-CWV--C---IOCCPN? | (430) |
| Ra3.1 (P351) | Z-TCCS-N-CGED-C---DGCCQ^ | (431) |
| Scratcher I | ---CCR-T-C-FG-C---TOCC# | (433) |
| Ts3.1 (F592) | ---CCH-K-CYMG-C---IPCCI^ | (434) |
| Ts3.2 (F345) | K--CCRPP-CAMS-C-GMARCCY^ | (435) |
| Bt3.5 (Z495) | R--CCRWP-CPSI-C-GMARCCFVMITC^ | (436) |
| Bt3.6 (Z497) | R--CCRWP-CP-SRC-GMARCCFVMITC^ | (437) |
| Tx3.1 | F--CCDSNWCHISDC----ECCY# | (438) |
| U014 | ---CCHWNWCDHL-C----SCCGS^ | (439) |
| U017 | --DCCOLPACPFG-C---NOCC# | (440) |
| U019 | ---CCAPSACRLG-C---ROCCR^ | (441) |
| U020 | ---CCAOSACRLG-C---ROCCR^ | (442) |
| U022 | ---CCAPSACRLG-C---RPCCR^ | (443) |
| U024 | --GCCGSFACRFG-C---VOCCV^ | (444) |
| U031 | ---CCSWDVCDHPSC----TCC# | (445) |
| U032 (F353) | R--CCKFP-CPDS-C--RYLCC# | (446) |
| Ae3.1 | ---CCDDSECDYS-C---WPCCIF# | (447) |
| Ae3.2 | ---CCNDWECDDS-C---WPCCY# | (448) |
| Af3.1 | R--CCR-FPCPDT-C---RHLCC# | (449) |
| Af3.2 | ---CC--MTC-FG-C---TPCC# | (450) |
| Af3.3 | ---CCDDSECDYS-C---WPCCIFS^ | (451) |
| Af3.4 | ---CCR-LLC-LS-C---NPCC# | (452) |
| Af3.6 | ---CCDDSECGYS-C---WPCCY# | (453) |
| Au3.2 | G--CCS-PPCHSI-C---AAFCC# | (454) |
| Au3.3 | ---CCRPVACAMG-C---KPCC# | (455) |
| Au3.4 | Z--CCPAVACAMG-C---EPCC# | (456) |
| Em3.1 | ---CCS-RDC-SV-C---IPCCPYGSP^ | (457) |
| Ep3.1 | ---CCDEDECNSS-C---WPCCW# | (458) |
| Ep3.2 | ---CCDEDECSSS-C---WPCCW# | (459) |
| Ep3.3 | ---CCPAAACAMG-C---KPCC# | (460) |
| Om3.1 | ---CCDEEECSSA-C---WPCCW# | (461) |
| Om3.3 | ---CCHLLACRFG-C---SPCCW^ | (462) |
| Sf3.1 | ---CC--PRC-SE-C---NPCC# | (463) |
| TYPE 2 | | |
| Pn3.2 (AA049) | -RCC--KFP-CPDS-C--KYLCC# | (464) |
| Fd3.2 (Z831) | -RCC--RWP-CPSI-C-GMARCCSS^ | (465) |
| Pu3.3 (AA405) | --CC--KLL-CYSG-C---TPCCHI^ | (466) |
| Eb3.1 (Z821) | --CC--EQP-CYMG-C---IPCCF^ | (467) |
| Eb3.2 (Z822) | --CC--AQP-CYMG-C---IPCCF^ | (468) |
| Pu3.2 (AA403) | --CC--V-S-CYMG-C---IPCCF^ | (469) |
| Mf3.1 (Z882) | --CC--DWP-CSAG-C---YPCCFP^ | (470) |
| Mf3.2 (Z885) | -GCC--PPM-C-TP-C---FPCCFR^ | (471) |
| Ra3.2 (AA414) | RGCCAPPRK-CKDRACK-PARCCGP# | (472) |
| Sm3.3 (AA419) | ZRCCNGRRG-CSSRWCRDHSRCC# | (473) |
| Cn3.3 | GRCCDVPNA-CSGRWCRDHAQCC# | (474) |
| Cn3.4 | ZRCCTGKKGSCSGKACKSL-KCCS# | (475) |
| TYPE 3 | | |
| A3.1 | -MCCGEGRKCPSYFRNSQICHCC^ | (476) |
| A3.2 (P84) | --CCR--WPCPRQIDGEY-CGCCL# | (477) |
| Bu3.5 | -RCCGEGLTCPRYWKNSQICACC^ | (478) |
| Ca3.1 | --CCGPGGSCPVYFRDNFICGCC^ | (479) |
| Cr3.1 | RKCCGKDGPCPKYFKDNFICGCC^ | (480) |
| E3.1 | --CCS--WPCPRYSNGKLVCFCCL# | (481) |
| M3.2 | --CCGPGGSCPVYFRDNFICGCC^ | (482) |
| M3.3 | -MCCGESAPCPSYFRNSQICHCC^ | (483) |
| M3.4 | ZKCCGPGGSCPVYFTDNFICGCC^ | (484) |
| M3.5 | ZKCCGPGGSCPVYFRDNFICGCC^ | (485) |
| S3.1 | ZKCCGEGSSCPKYFKNNFICGCC^ | (486) |
| U001 | ZKCCS-GGSCPLYFRDRLICPCC^ | (487) |
| U034 | ZKCCGPGASCPRYFKDNFICGCC^ | (488) |
| Cn3.1 | -MCCGEGAPCPSYFPNSQICHCC^ | (489) |
| TYPE 4 | | |
| A3.3 (F83) | ZK--CCTGK---KGSCSGKACKNL-KCCS# | (490) |
| A3.5 (Z488) | ZK--CCTGR---KGSCSGKACKNL-KCCS# | (491) |

TABLE 2-continued

Alignment of μ-Conopeptides (SEQ ID NO:)

| | | |
|---|---|---|
| Bu3.1 | VTDRCCK----GKREC-GRWCRDHSRCC# | (492) |
| Bu3.1A | VGDRCCK----GKRGC-GRWCRDHSRCC# | (493) |
| Bu3.2 | VGERCCK---NGKRGC-GRWCRDHSRCC# | (494) |
| Bu3.3 | IVDRCCN-KGNGKRGC-SRWCRDHSRCC# | (495) |
| Bu3.4 | VGLYCCRPKPNGQMMC-DRWCEKNSRCC# | (496) |
| Ca3.2 | -RD-CCTPP---KK-CKDRQCKPQ-RCCA# | (497) |
| L3.1 | GRD-CCTPP---RK-CRDRACKPQ-RCCG# | (498) |
| L3.2 | ZRL-CCGFP---KS-CRSRQCKPH--RCC# | (499) |
| La3.2 | -RD-CCTPP---KK-CRDRQCKPA-RCCG# | (500) |
| La3.3 | RPP-CCTYD---GS-CLKESCMRK-ACC# | (501) |
| La3.3A | RPP-CCTYD---GS-CLKESCKRK-ACC# | (502) |
| μ-GIIIA | -RD-CCTOO---KK-CKDRQCKOQ-RCCA# | (503) |
| μ-GIIIB | -RD-CCTOO---RK-CKDRRCKOM-KCCA# | (504) |
| μ-GIIIC | -RD-CCTOO---KK-CKDRRCKOL-KCCA# | (505) |
| μ-PIIIA | ZRL-CCGFO---KS-CRSRQCKOH-RCC# | (506) |
| M3.1 | -RD-CCTPP---KK--CKDRQCKPQ-RCCA# | (507) |
| Mr3.1 | RGG-CCTPP---RK-CKDPACKPA-RCCGP# | (508) |
| Nb3.2 (F582) | ZK--CCTGK---KGSCSGKACKNL-KCCS# | (509) |
| Pr3.1 (Z500) | RGG-CCTPP---KK-CKDPACKPA-RCCGP# | (510) |
| Pr3.2 (Z501) | -RG-CCTPP---RK-CKDRACKPA-RCCGP# | (511) |
| R3.1 | LOS-CCSLN---LRLCOVOACKRN-OCCT# | (512) |
| R3.2 | ZQR-CCTVK----RICOVOACRSK-OCCKŜ | (513) |
| R3.3 | RGG-CCTPP---RK-CKDPACKPA-RCCGP# | (514) |
| Sm3.1 | ZK--CCTGK---KGSCSGKACKNL-KCCS# | (515) |
| T3.1 | H-G-CCKGO---EG-CSSRECROQ-HCC# | (516) |
| T3.2 (Y088) | H-G-CCEGP---KG-CSSRECRPQ-HCC# | (517) |
| Wi3.1 (M548) | LPS-CCDFE----RLCVVPACTRH-QCCT# | (518) |
| Type 5 | | |
| Om3.2 | CCKYGWTCLLGCTPCDĈ | (519) |
| Om3.4 | CCRYGWTCWLGCTPCGĈ | (520) |
| Type 6 | | |
| S3.2 (F352) | Z-NCCNGG-CSSKWCRDHARCC# | (432) |

Example 3

Effect of Intrathecal Administration of μ-Conopeptides

Male C57 black mice (20–25 g) are obtained from Charles River Laboratories. These mice and the animals are housed in a temperature controlled (23°±3° C.) room with a 12 hour light-dark cycle with free access to food and water. All animals are euthanized in accordance with Public Health Service policies on the humane care of laboratory animals.

Intrathecal (it) drug injections are performed as described (Hylden and Wilcox, 1980). A μ-conopeptide or vehicle is administered in a volume of 5 μl. Duration of hind-limb paralysis is assessed. This experiment reveals that injection of μ-conopeptides into the intrathecal space of C57 black mice produced a paralysis of the animal. The animals in this experiment recovered fully.

Example 4

Effect of μ-Conopeptides as a Local Anesthetic

Male Hartley guinea pigs (retired breeders) are obtained form Charles River Laboratories. The local anesthetic test is performed essentially as described (Bulbring and Wajda, 1945). On the day prior to test day, a patch on the back of the guinea pig is denuded of hair, first by shaving with electric clippers and subsequently with depilatory cream (Nair®). Depilatory cream is applied for five minutes and removed with a warm washcloth. The guinea pigs are dried and returned to their cages. On the following day, intradermal injections (0.1 ml vols) of lidocaine, bupivacaine, a μ-conopeptide or vehicle (0.5% cyclodextran) are made into the denuded patch. The injection produced a raised wheal on the surface of the skin which is circled with a felt-tipped pen. Typically, four injections are made on the back of each guinea pig. In some cases, guinea pigs are reused following at least one week of recovery and injecting into an unused portion of the skin. The stimulus consists of mild pin pricks (not hard enough to break the skin) with a 26 G needle. The response is a localized skin twitch caused by contraction of cutaneous muscles. A unit test consisted of six uniform pin pricks, 3–5 seconds apart, within the injected area. Unit scores range from 0 (complete anesthesia) to 6 (no anesthesia). For potency experiments, the unit test is repeated at each site at five minute intervals for 30 minutes, and unit test scores summed (with 36 representing no anesthesia to 0 representing complete anesthesia). For duration experiments, unit tests are performed as described over the course of several hours to days.

μ-Conopeptides of the present invention produce a potent and long lasting local anesthetic effect in the intracutaneous wheal test in the guinea pig. As expected, bupivacaine has a slightly longer duration thatn lidocaine, consistent with clinical observations.

Example 5

Muscle Relaxant Effect of μ-Conopeptides in Anesthetized Monkeys

μ-Conopeptides are dissolved 0.9 percent saline at a concentration of 2 mg/ml. Rhesus monkeys are anesthetized with halothane, nitrous oxide and oxygen. The maintenance concentration of halothane is 1.0%. Arterial and venous catheters are placed in the femoral vessels for drug administration and recording of the arterial pressure. Controlled ventilation is accomplished via an endotrachael tube. Twitch and tetanic contractions of the tibialis arterior muscle are elicited indirectly via the sciatic nerve. Recordings of arterial pressure electrocardiogram (lead I), heart rate, and muscle function are made simultaneously. Four to six animals received each listed compound. Four additional animals received succinylcholine chloride or d-tubocurarine chloride as controls. It is seen that the tested μ-conopeptides generally provide similar or better results than those seen for succinylcholine chloride or d-tubocurarine chloride.

Example 6

In vivo Activity of μ-Conopeptides in Pain Models

The anti-pain activity of μ-conopeptides is shown in several animal models. These models include the nerve injury model (Chaplan, et al., 1997), the nocioceptive response to s.c. formalin injection in rats (Codene, 1993) and an NMDA-induced persistent pain model (Liu, et al., 1997). In each of these models it is seen that the μ-conopeptides and μ-conopeptides derivatives have analgesic properties.

More specifically, this study evaluates the effect of intrathecal administration of μ-conopeptides in mice models of nocioceptive and neuropathic pain. For nocioceptive pain, the effect of the μ-conopeptides is studied in two different tests of inflammatory pain. The first is the formalin test, ideal because it produces a relatively short-lived, but reliable pain behavior that is readily quantified. There are two phases of pain behavior, the second of which is presumed to result largely from formalin-evoked inflammation of the hind paw. A μ-conopeptide is administered 10 minutes prior to injection of formalin. The number of flinches and/or the duration of licking produced by the injection is monitored. Since the first phase is presumed to be due to direct activation of primary afferents, and thus less dependent on long term changes in the spinal cord, μ-conopeptides are presumed to have greatest effect on the magnitude of pain behavior in the second phase.

The mechanical and thermal thresholds in animals that received an injection of complete Freund's adjuvant into the hind paw are also studied. This produces a localized inflammation including swelling of the hind paw and a profound decrease in mechanical and thermal thresholds, that are detected within 24 hours after injection. The changes in thresholds in rats that receive μ-conopeptides are compared with those of rats that receive vehicle intrathecal injections.

An important issue is whether the drugs are effective when administered after the pain model has been established, or whether they are effective only if used as a pretreatment. Clearly, the clinical need is for drugs that are effective after the pain has developed. To address this issue, animals are studied in which μ-conopeptides are administered repeatedly, after the inflammation (CFA) or nerve injury has been established. In these experiments, a μ-conopeptide is injected daily by the intrathecal (i.t.) route. The mechanical and thermal thresholds (measured, respectively, with von Frey hairs in freely moving animals and with the Hargreave's test, also in freely moving animals) are repeated for a 2 to 4 week period after the injury is induced and the changes in pain measured monitored over time.

Example 7

Effect of μ-Conotoxins in a Pain Model

Analgesic activity of μ-conotoxins is also tested in pain models as follows.

Persistent pain (formalin test). Intrathecal (it) drug injections are performed as described by Hylden and Wilcox (1980). An μ-conopeptide or vehicle is administered in a volume of 5 μl. Fifteen minutes after the i.t. injection, the right hindpaw is injected with 20 μl of 5% formalin. Animals are placed in clear plexiglass cylinders backed by mirrors to facilitate observation. Animals are closely observed for 2 minutes per 5 minute period, and the amount of time the animal spent licking the injected paw is recorded in this manner for a total of 45–50 minutes. Results are expressed as licking time in seconds per five minutes. At the end of the experiment, all animals are placed on an accelerating rotorod and the latency to first fall was recorded. μ-Conopeptides are found to be active in this model which is predictive of efficacy for treating neuropathic pain.

Acute pain (tail-flick). A μ-conopeptide or saline is administered intrathecally (i.t.) according to the method of Hylden and Wilcox (1980) in a constant volume of 5 μl. Mice are gently wrapped in a towel with the tail exposed. At various time-points following the i.t. injection, the tail is dipped in a water bath maintained at 54° C. and the time to a vigorous tail withdrawal is recorded. If there is no withdrawal by 8 seconds, the tail is removed to avoid tissue damage.

Neuropathic vain. The partial sciatic nerve ligation model is used to assess the efficacy of μ-conopeptides in neuropathic pain. Nerve injury is produced according to the methods of Malmberg and Basbaum (1998). Animals are anesthetized with a ketamine/xylazine solution, the sciatic nerve is exposed and tightly ligated with 8-0 silk suture around ⅓ to ½ of the nerve. In sham-operated mice the nerve is exposed, but not ligated. Animals are allowed to recover for at least 1 week before testing is performed. On the testing day, mice are placed in plexiglass cylinders on a wire mesh frame and allowed to habituate for at least 60 minutes. Mechanical allodynia is assessed with calibrated von Frey filaments using the up-down method as described by Chaplan et al. (1994), and the 50% withdrawal threshold is calculated. Animals that did not respond to any of the filaments in the series are assigned a maximal value of 3.6 grams, which is the filament that typically lifted the hindlimb without bending, and corresponds to approximately 1/10 the animal's body weight.

The data obtained demonstrate that μ-conopeptides have potent analgesic properties in three commonly used models of pain: acute, persistent/inflammatory and neuropathic pain models.

Example 8

Activity of μ-Conopeptide S3.2 on Neuronal Sodium Channels

μ-Conopeptide S3.2 was tested for activity on sodium channels as follows. S3.2 was administered to mice by intracerbroventricular (ICV) injection. Administration of S3.2 in this manner caused mice to show a spectrum of activity that is charcteristic of all sodium channel blockers, including rapid loss of righting reflex, coma-like inactivity and spastic uncontrolled limb movement. Following intrathecal (it) administration to mice, S3.2 causes rapid hindlimb paralysis that spreads to include the entire body over a course of 10–20 minutes followed by death, presumably due to respiratory paralysis. However, unlike classic μ-conopeptides, S3.2 has no significant activity following intravenous administration (iv) to mice. Classic μ-conopeptides, such as GIIIA and PIIIA, cause rapid paralysis and death following iv administration, indicating their activity at skeletal muscle sodium channels. To confirm the selectivity of S3.2, 80 nmol was administered iv to rats. The effect of S3.2 was measured on skeletal muscle contraction, blood pressure and heart rate. S3.2 was found to have no effect on any of these parameters. Controls were performed using classical μ-conopeptides, including Sm3.1, Sm3.3 and Bu3.1 described herein, also administered iv at 80 mmol. These control peptides caused a dramatic decrease in skeletal muscle contractility, as well as a significant drop in systemic blood pressure. Thus, μ-conopeptide S3.2 suprisingly is selective for neuronal sodium channels. The most obvious difference between the S3.2 sequence and the sequences of these other peptides is a shortened first loop (the first loop between cysteine residues) which lacks a charged amino acid.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

BIBLIOGRAPHY

Abiko, H. et al. (1986). *Brain Res.* 38:328–335.
Aldrete, J. A. et al. (1979). *Crit. Care Med.* 7:466–470.
Barnay, G. et al. (2000). *J. Med. Chem.*
Bitan, G. et al. (1997). *J. Peptide Res.* 49:421–426.
Bodansky et al. (1966). *Chem. Ind.* 38:1597–98.
Bulbring, W. and Wajda, J. (1945). *J. Pharmacol. Exp. Ther.* 85:78–84.
Cartier, G. E. et al. (1996). *J. Biol. Chem.* 271:7522–7528.
Chandler, P. et al. (1993). *J. Biol. Chem.* 268:17173–17178.
Chaplan S. R. (1994). *J Neuroscience Methods* 53:55–63.
Chaplan S. R. (1997). *J Pharmacol. Exp. Ther.* 280:829–838.
Clark, C. et al. (1981). *Toxicon* 19:691–699.
Codere, T. J. (1993). *Eur. J. Neurosci.* 5:390–393.
Craik, D. J. et al. (1991). *Toxicon* 39:43–60.
Cruz, L. J. at al. (1976). *Verliger* 18:302–308.
Ettinger, L. J. et al. (1978). *Cancer* 41:1270–1273.
*Goodman and Gilman's The Pharmacological Basis of Therapeutics*, Seventh Ed., Gilman, A. G. et al., eds., Macmillan Publishing Co., New York (1985).
Hammerland et al. (1992). *Eur. J. Pharmacol.* 226:239–244.
Heading, C. (1999). *Curr. Opin. CPNS Invest. Drugs* 1:153–166
Horiki, K. et al. (1978). *Chemistry Letters* 165–68.
Hubry, V. et al. (1994). *Reactive Polymers* 22:231–241.
Hylden, J. L. K. and Wilcox, G. (1980). *Eur. J. Pharmacol.* 67:313–316.
Kaiser et al. (1970). *Anal. Biochem.* 34:595.
Kapoor (1970). *J. Pharm. Sci.* 59:1–27.
Kornreich, W. D. et al. (1986). U.S. Pat. No. 4,569,967.
Luer, M. S. & Hatton, J. (1993). *Annals Pharmcotherapy* 27:912–921.
Liu, H. et al. (1997). *Nature* 386:721–724.
Malmberg, A. B. and Basbaum, A. I. (1998). *Pain* 76:215–222.
Martinez, J. S. et al. (1995). *Biochem.* 34:14519–14526.
McIntosh, J. M. et al. (1998). *Methods Enzymol.* 294:605–624.
*The Merck Manual of Diagnosis and Therapy*, 16 Ed., Berkow, R. et al., eds., Merck Research Laboratories, Rahway, N.J., pp. 1436–1445 (1992).
*Methoden der Organischen Chemie (Houben-Weyl): Synthese von Peptiden*, E. Wunsch (Ed.), Georg Thieme Verlag, Stuttgart, Ger. (1974).
Nehlig, A. et al. (1990). Effects of phenobarbital in the developing rat brain. In *Neonatal Seizures*, Wasterlain, C. G. and Vertt, P. (eds.), Raven Press, New York, pp. 285–194.
Nishiuchi, Y. et al. (1993). *Int. J. Pept. Protein Res.* 42:533–538.
Olivera, B. M. et al. (1984). U.S. Pat. No. 4,447,356.
Olivera, B. M. et al. (1985). *Science* 230:1338–1343.
Olivera, B. M. et al. (1990). *Science* 249:257–263.
Olivera, B. M. et al. (1996). U.S. Pat. No. 5,514,774.
Ornstein, et al. (1993). *Biorganic Medicinal Chemistry Letters* 3:43–48.
*Remington's Pharmaceutical Sciences*, 18th Ed. (1990, Mack Publishing Co., Easton, Pa.).
Rivier, J. R. et al. (1978). *Biopolymers* 17:1927–38.
Rivier, J. R. et al. (1987). *Biochem.* 26:8508–8512.
Sambrook, J. et al. (1989). *Molecular Cloning: A Laboratory Manual*, 2nd Ed., Cold Spring Harbor Laboratory, Cold Spring Harbor, N.Y.
Shon, K. J. et al. (1994). *Biochemistry* 33:11420–11425.
Stewart and Young, *Solid-Phase Peptide Synthesis*, Freeman & Co., San Francisco, Calif. (1969).
Vale et al. (1978). U.S. Pat. No. 4,105,603.
Troupin, A. S. et al. (1986). MK-801. In *New Anticonvulsant Drugs, Current Problems in Epilepsy* 4, Meldrum, B. S. and Porter, R. J. (eds.), John Libbey, London, pp. 191–202.
Van de Steen, P. et al. (1998). *Critical Rev. in Biochem. and Mol. Biol.* 33:151–208.
White, H. S., et al. (1992). *Epilepsy Res.* 12:217–226.
White, H. S., et al. (1995). Experimental Selection, Quantification, and Evaluation of Antiepileptic Drugs. In *Antiepileptic Drugs*, 4th Ed., Levy, R. H., eds., Raven Press, N.Y., pp. 99–110.
Wong, E. H. P. et al. (1986). *Proc. Natl. Acad. Sci. USA* 83:7104–7108.
Zhou L. M., et al. (1996). *J. Neurochem.* 66:620–628.
Zimm, S. et al. (1984). *Cancer Res.* 44:1698–1701.
U.S. Pat. No. 3,842,067.
U.S. Pat. No. 3,862,925.
U.S. Pat. No. 3,972,859.
U.S. Pat. No. 5,514,774.
U.S. Pat. No. 5,550,050.
U.S. Pat. No. 5,670,622.
U.S. Pat. No. 5,719,264.
U.S. Pat. No. 5,844,077 (1998).
Published PCT Application WO 92/19195.
Published PCT Application WO 94/25503.
Published PCT Application WO 95/01203.
Published PCT Application WO 95/05452.
Published PCT Application WO 96/02286.
Published PCT Application WO 96/02646.
Published PCT Application WO 96/40871.
Published PCT Application WO 96/40959.
Published PCT Application WO 97/12635.
Published PCT Application WO 98/03189.
Published PCT Application WO 00/23092.

What is claimed is:

1. An isolated peptide comprising the amino acid sequence Xaa—Asn—Cys—Cys—Asn—Gly—Gly—Cys—Ser—Ser—Lys—Xaa—Cys—Arg—Asp—His—Ala—Arg—Cys—Cys (SEQ ID NO:211), wherein Xaa at position 1 is Gln or pyro-Glu and Xaa at position 12 is Trp or bromo-Trp.

2. The isolated peptide of claim 1, wherein Xaa at position 1 is pyro-Glu and Xaa at position 12 is Trp.

3. An isolated μ-conopeptide propeptide comprising the amino acid sequence Gly-Ser-Met-Met-Ser-Lys-Leu-Gly-Val-Leu-Leu-Thr-Val-Cys-Leu-Leu- Leu-Phe-Pro-Leu-Thr-Ala-Leu-Pro-Leu-Asp-Gly-Asp-Gln-Pro-Ala-Asp-Arg-Pro-Ala-Glu-Arg-Met- Gln-Asp-ASp-Ile-Ser-Ser-Asp-Glu-His-Pro-Leu-Phe-Asp-Lys-Arg-Gln-Asn-Cys-Cys-Asn-Gly-Gly- Cys-Ser-Ser-Lys-Trp-Cys-Arg-Asp-His-Ala-Arg-Cys-Cys-Gly-Arg (SEQ ID NO:210).

4. A method for treating or preventing disorders associated with voltage gated neuronal sodium channel disorders in which comprises administering to a patient in need thereof a therapeutically effective amount of a peptide of claim 1 or a pharmaceutically acceptable salt thereof.

5. The method of claim 4, wherein said disorder is a neurologic disorder.

6. The method of claim 5, wherein said neurologic disorder is Amytrophic Lateral Sclerosis.

7. The method of claim 5, wherein said neurologic disorder is head trauma.

8. The method of claim 5, wherein said neurologic disorder is epilepsy.

9. The method of claim 5, wherein said neurologic disorder is a neurotoxic injury associated with conditions of hypoxia, anoxia or ischemia.

10. The method of claim 9, wherein said neurotoxic injury is associated with stroke, cerebrovascular accident, brain or spinal cord trauma, myocardial infarct, physical trauma, drownings, suffocation, perinatal asphyxia, or hypoglycemic events.

11. The method of claim 4, wherein said disorder is pain.

12. The method of claim 11, wherein said pain is migraine, acute pain, persistent pain, chronic pain, neuropathic pain or nociceptive pain.

13. The method of claim 12, wherein the pain is phantom limb pain, neuroma pain or pain associated with trigeminal neuralgia, diabetic neuropathy, and post-herpetic neuralgia.

14. The method of claim 11, wherein said pain is burn pain.

15. The method of claim 4, wherein said disorder is myofacial pain syndrome, chronic muscle spasm, or spasticity.

16. A method of alleviating pain which comprises administering to a mammal that is either exhibiting pain or is about to be subjected to a pain-causing event a pain-alleviating amount of a peptide of claim 1 or a pharmaceutically acceptable salt thereof.

17. The method of claim 16, wherein the peptide is administered as a local anesthetic.

18. The method of claim 16, wherein the peptide is administered as an occular anesthetic.

* * * * *